US010208059B2

(12) United States Patent
Jones et al.

(10) Patent No.: US 10,208,059 B2
(45) Date of Patent: *Feb. 19, 2019

(54) HETEROCYCLIC MODULATORS OF HIF ACTIVITY FOR TREATMENT OF DISEASE

(71) Applicant: Board of Regents, University of Texas System, Austin, TX (US)

(72) Inventors: Philip Jones, Houston, TX (US); Maria Emilia Di Francesco, Houston, TX (US); Alessia Petrocchi, Houston, TX (US); Christopher L. Carroll, Houston, TX (US); Joe Marszalek, Houston, TX (US); Barbara Czako, Houston, TX (US); Ryan Johnson, Houston, TX (US); Jay Theroff, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/285,177

(22) Filed: Oct. 4, 2016

(65) Prior Publication Data
US 2017/0121342 A1 May 4, 2017

Related U.S. Application Data

(63) Continuation of application No. 14/645,591, filed on Mar. 12, 2015, now Pat. No. 9,481,692, which is a continuation of application No. 13/974,258, filed on Aug. 23, 2013, now Pat. No. 9,018,380.

(60) Provisional application No. 61/743,131, filed on Aug. 24, 2012.

(51) Int. Cl.
C07D 413/14 (2006.01)
C07D 495/04 (2006.01)
C07D 413/04 (2006.01)
C07D 417/14 (2006.01)
C07D 417/04 (2006.01)
A61K 45/06 (2006.01)
A61K 31/496 (2006.01)
A61K 31/454 (2006.01)
C07D 471/04 (2006.01)
C07D 513/04 (2006.01)
A61K 31/4245 (2006.01)
A61K 31/437 (2006.01)
A61K 31/4439 (2006.01)
A61K 31/4545 (2006.01)
A61K 31/519 (2006.01)
A61K 31/5377 (2006.01)
A61K 31/541 (2006.01)
C07D 405/14 (2006.01)
A61K 31/427 (2006.01)
A61K 31/4709 (2006.01)
A61K 31/497 (2006.01)
A61K 31/506 (2006.01)

(52) U.S. Cl.
CPC .......... C07D 495/04 (2013.01); A61K 31/427 (2013.01); A61K 31/4245 (2013.01); A61K 31/437 (2013.01); A61K 31/4439 (2013.01); A61K 31/454 (2013.01); A61K 31/4545 (2013.01); A61K 31/4709 (2013.01); A61K 31/496 (2013.01); A61K 31/497 (2013.01); A61K 31/506 (2013.01); A61K 31/519 (2013.01); A61K 31/5377 (2013.01); A61K 31/541 (2013.01); A61K 45/06 (2013.01); C07D 405/14 (2013.01); C07D 413/04 (2013.01); C07D 413/14 (2013.01); C07D 417/04 (2013.01); C07D 417/14 (2013.01); C07D 471/04 (2013.01); C07D 513/04 (2013.01)

(58) Field of Classification Search
CPC .. C07D 495/04; C07D 405/14; C07D 413/04; C07D 413/14; C07D 417/04; C07D 417/14; C07D 471/04; C07D 513/04; A61K 31/4245; A61K 31/427; A61K 31/437; A61K 31/4439; A61K 31/454; A61K 31/4545; A61K 31/4709; A61K 31/496; A61K 31/497; A61K 31/506; A61K 31/519; A61K 31/5377; A61K 31/541; A61K 45/06
See application file for complete search history.

(56) References Cited

U.S. PATENT DOCUMENTS

| 6,300,344 | B1 | 10/2001 | Taniguchi |
| 8,470,811 | B2 | 6/2013 | Haerter |
| 9,018,380 | B2 | 4/2015 | Jones |
| 9,115,120 | B2 | 8/2015 | Jones |
| 9,481,692 | B2 | 11/2016 | Jones |

(Continued)

FOREIGN PATENT DOCUMENTS

| EP | 2768826 A1 | 8/2014 |
| JP | 2008541014 | 11/2008 |

(Continued)

OTHER PUBLICATIONS

Yasuda et al. (Bioorg. Med. Chem. 23 (2015) 1776-1787).*

(Continued)

Primary Examiner — Robert H Havlin
(74) Attorney, Agent, or Firm — Dennis A. Bennett; Cynthia Hathaway; John Desper

(57) ABSTRACT

The present invention relates to compounds and methods which may be useful as inhibitors of HIF pathway activity for the treatment or prevention of cancer and other hypoxia-mediated diseases.

6 Claims, 11 Drawing Sheets

(56) References Cited

U.S. PATENT DOCUMENTS

| | | |
|---|---|---|
| 9,663,504 B2 | 5/2017 | Jones |
| 2004/0058964 A1 | 3/2004 | Devadas |
| 2006/0269942 A1 | 11/2006 | Kolb |
| 2007/0105900 A1 | 5/2007 | Berdini |
| 2010/0063104 A1 | 3/2010 | Nakai |
| 2010/0249085 A1 | 9/2010 | Boyer |
| 2011/0301122 A1 | 12/2011 | Haerter |
| 2011/0312930 A1 | 12/2011 | Haerter |
| 2012/0028950 A1 | 2/2012 | Haerter |
| 2013/0196964 A1 | 8/2013 | Haerter |
| 2014/0057914 A1 | 2/2014 | Jones |
| 2014/0066424 A1 | 3/2014 | Jones |
| 2014/0073634 A1 | 3/2014 | Jones |
| 2014/0329797 A1 | 11/2014 | Hrter |
| 2015/0239876 A1 | 8/2015 | Jones |
| 2015/0252058 A1 | 9/2015 | Jones |
| 2017/0216271 A1 | 8/2017 | Jones |

FOREIGN PATENT DOCUMENTS

| | | |
|---|---|---|
| JP | 2012508702 | 4/2012 |
| JP | 2012508703 | 4/2012 |
| WO | 1997003973 A1 | 2/1997 |
| WO | 2000016760 A2 | 3/2000 |
| WO | 2000027394 A1 | 5/2000 |
| WO | 2003068230 A1 | 8/2003 |
| WO | 2005002576 A2 | 1/2005 |
| WO | 2005018557 A2 | 3/2005 |
| WO | 2006070198 A1 | 7/2006 |
| WO | 2006116736 A2 | 11/2006 |
| WO | 2008005457 A2 | 1/2008 |
| WO | 2008141731 | 11/2008 |
| WO | 2008141731 A2 | 11/2008 |
| WO | 2008145243 A1 | 12/2008 |
| WO | 2009003861 | 1/2009 |
| WO | 2010039248 A1 | 4/2010 |
| WO | 2010054762 A1 | 5/2010 |
| WO | 2010054763 A1 | 5/2010 |
| WO | 2010054764 | 5/2010 |
| WO | 2010054764 A1 | 5/2010 |
| WO | 2011006903 | 1/2011 |
| WO | 2011141325 A1 | 11/2011 |
| WO | 2011141326 A1 | 11/2011 |
| WO | 2013057101 A1 | 4/2013 |
| WO | 2014031928 A2 | 2/2014 |
| WO | 2014031933 A2 | 2/2014 |
| WO | 2014031936 A2 | 2/2014 |
| WO | 2014031928 A3 | 4/2014 |
| WO | 2014031933 A3 | 4/2014 |
| WO | 2014031936 A3 | 4/2014 |
| WO | 2015130790 A2 | 9/2015 |
| WO | 2015130790 A3 | 12/2015 |

OTHER PUBLICATIONS

Patani et al. (Chem. Rev., 1996, vol. 96, No. 8, p. 3147-3176).*
Kubinyi (3D QSAR in Drug Design: Ligand-Protein Interactions and Molecular Similarity, vol. 2-3, Springer, 1998, 800 pp.). p. 243-244 provided.*
Wermuth, The Practice of Medicinal Chemsitry, 2d ed. (2003), 768 pages. Chs. 9-10 provided.*
U.S. Appl. No. 14/800,307, dated Jul. 2015, Jones.
U.S. Appl. No. 15/492,751, dated Apr. 2017, Jones.
Atkinson, Karen et al, N-Benzylimidazole Carboxamides as Potent, Orally Active StearoylCoA Desaturase-1 Inhibitors, Bioorganic & Medicinal Chemistry Letters, 2011, 21(6), p. 1621-1625.
Coqueron PY et al., Iterative oxazole assembly via alpha-chloroglycinates: total synthesis of (-)—muscoride A., Angew Chem Int Ed Engl. Mar. 28, 2003;42(12)1411-1414.
Ellinghaus P. et al., 'BAY 87/2243, a highly potent and selective inhibitor of hypoxia-induced gene activation has antitumor activities by inhibition of mitochondrial complex I,' Cancer Medicine 2(5): 611-24, Aug. 20, 2013.
Gatta, A. et al., "Synthesis of imidazo[1,2-c]pyrazolo[4,3-e]pyrimidines, 1-2pyrazolo[4,3-e]1,2,4-triazolo[1,5-c] pyrimidines and 1,2,4-triazolo[5,1-i]purines as adenosine A2 receptor antagonists," Eur. J. Med Chem, 1993, vol. 28, pp. 569-576.
Harter M et al., 'Inhibition of Hypoxia-Induced Gene Transcription by Substituted Pyrazolyl Oxadiazoles: Initial Lead Generation and Structure—Activity Relationships,' ChemMedChem 8:61-6, 2013.
Jones, Philip et al., Heterocyclic modulators of HIF activity for treatment of disease, Univ. Texas MD Anderson Cancer Center Institute, U.S. Pat. No. 9,018,380, Corrected Notice of Allowance, dated Mar. 3, 2015.
Jones, Philip et al., Heterocyclic modulators of HIF activity for treatment of disease, Univ. Texas MD Anderson Cancer Center Institute, U.S. Pat. No. 9,115,120, Notice of Allowance, dated Apr. 17, 2015.
Jones, Philip et al., Heterocyclic modulators of HIF activity for treatment of disease, Univ. Texas MD Anderson Cancer Center Institute, U.S. Pat. No. 2014/0073634A1, Final rejection, dated Oct. 22, 2015.
Jones, Philip et al., Heterocyclic modulators of HIF activity for treatment of disease, Univ. Texas MD Anderson Cancer Center Institute, U.S. Pat. No. 2014/0073634A1, Non-final rejection, dated Mar. 31, 2015.
Jones, Philip et al., Heterocyclic modulators of HIF activity for treatment of disease, Univ. Texas MD Anderson Cancer Center Institute, U.S. Pat. No. 9,018,380, Notice of Allowance, dated Jan. 9, 2015.
Jones, Philip et al., Heterocyclic modulators of HIF activity for treatment of disease, Univ. Texas MD Anderson Cancer Center Institute, U.S. Pat. No. 2015/0252058A1, Notice of Allowance, dated Mar. 8, 2016.
Jones, Philip et al., Heterocyclic modulators of HIF activity for treatment of disease, Univ. Texas MD Anderson Cancer Center Institute, WO 2014031928A1, International Preliminary Report on Patentability, publication date, Feb. 24, 2015.
Jones, Philip et al., Heterocyclic modulators of HIF activity for treatment of disease, Univ. Texas MD Anderson Cancer Center Institute, WO 2014031933A2, International Preliminary Report on Patentability, publication date, Feb. 24, 2015.
Jones, Philip et al., Heterocyclic modulators of HIF activity for treatment of disease, Univ. Texas MD Anderson Cancer Center Institute, WO 2014031936A2, International Preliminary Report on Patentability, publication date, Feb. 24, 2015.
Kalluraya et al., Studies on arylthiophene heterocycles. Part 1. Synthesis and biological activity of some 2-aryl/arylarnino-4-[5(p-nitrophenyl)-2-thieny1)] thiazoles, Oriental Journal of Chemistry (1996), 12(2), 141-144, CAS Accession No. 748862.
Nakai Hisao et al., Preparation of nitrogen-containing heterocyclic compounds as p38 MAP kinase inhibitors, STN record of WO2007040208, Acc No. 2007:410206, DN 146:421971, 2007.
U.S. Appl. No. 14/800,307, filed Jul. 15, 2015, Jones, Philip et al.
Giaccia, A. et al., HIF-1 as a Target for Drug Development, Nature Reviews Drug Discovery 2, 1-9, 2003.
International Application No. PCT/US2013/056338; International Search Report and Written Opinion of the International Search Authority; dated Mar. 31, 2014; 19 pages
International Application No. PCT/US2013/056343; International Search Report and Written Opinion of the International Search Authority; dated Mar. 31, 2014; 16 pages.
International Application No. PCT/US2013/056346; International Search Report and Writen Opinion of the International Search Authority; dated Apr. 1, 2014; 19 pages.
International Application No. PCT/US2015/017533; International Preliminary Report on Patentability; dated Aug. 30, 2016; 4 pages.
International Application No. PCT/US2015/017533; International Search Report and Written Opinion of the International Search Authority; dated Dec. 3, 2015; 06 pages.
U.S. Appl. No. 15/492,751; Non-Final Office Action dated Jan. 5, 2018; 17 pages.
U.S. Appl. No. 13/974,258; Notice of Allowance dated Mar. 3, 2015; 04 pages.
U.S. Appl. No. 13/974,258; Notice of Allowance dated Jan. 9, 2015; 07 pages.

(56) References Cited

OTHER PUBLICATIONS

U.S. Appl. No. 13/974,261; Examiner Initiated Interview Summary dated Apr. 17, 2015; 13 pages.
U.S. Appl. No. 13/974,261; Notice of Allowance dated Apr. 17, 2015; 13 pages.
U.S. Appl. No. 13/974,261; Office Action Appendix dated Apr. 17, 2015; 11 pages.
U.S. Appl. No. 14/631,454; Examiner Initiated Intervuew Summary dated Jan. 20, 2017; 02 pages.
U.S. Appl. No. 14/631,454; Final Office Action dated Sep. 23, 2016; 09 pages.
U.S. Appl. No. 14/631,454; Non-Final Office Action dated Feb. 5, 2016; 18 pages.
U.S. Appl. No. 14/631,454; Notice of Allowance dated Jan. 20, 2017; 07 pages.
U.S. Appl. No. 14/645,591; Notice of Allowance dated Jul. 1, 2016; 07 pages.
U.S. Appl. No. 14/645,591; Notice of Allowance dated Mar. 8, 2016; 07 pages.
U.S. Appl. No. 15/492,751; Examiner Initiated Interview Summary dated Aug. 2, 2018; 2 pages.
U.S. Appl. No. 15/492,751; Notice of Allowance dated Aug. 2, 2018; 12 pages.

\* cited by examiner

FIGURE 2
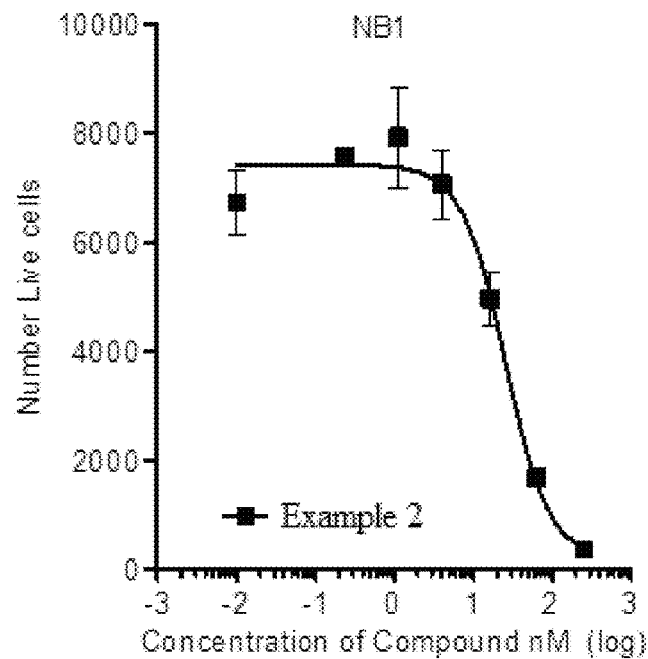
Figure 2a
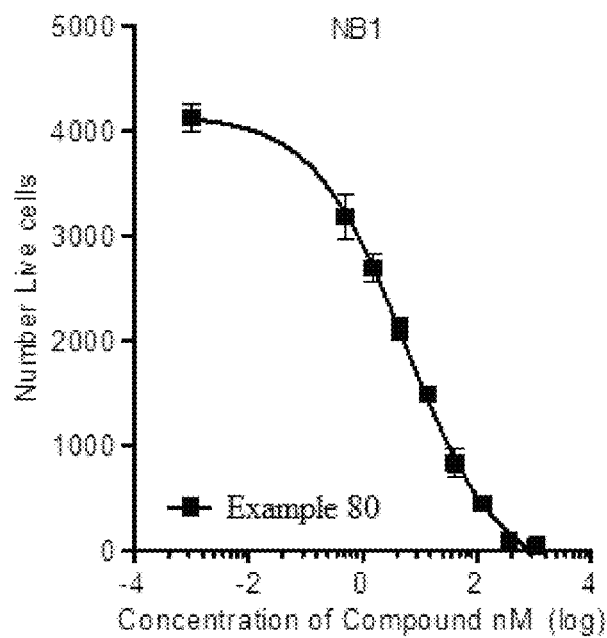
Figure 2b

FIGURE 4
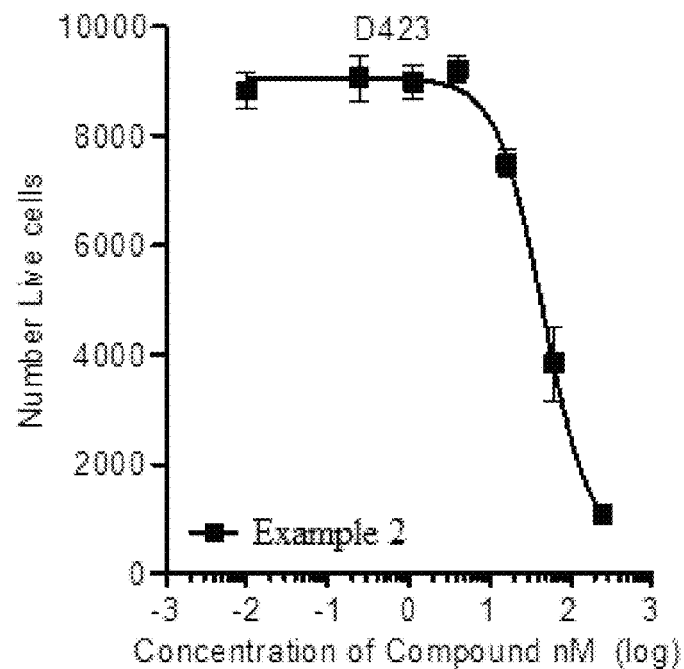
Figure 4a
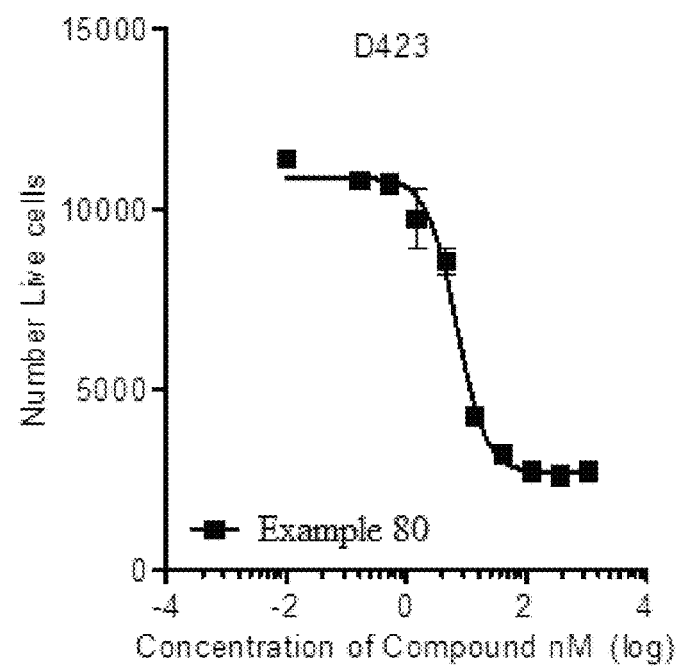
Figure 4b

HETEROCYCLIC MODULATORS OF HIF ACTIVITY FOR TREATMENT OF DISEASE

This application is a continuation of U.S. application Ser. No. 14/645,591, filed Mar. 12, 2015, now U.S. Pat. No. 9,481,692, issued Nov. 1, 2016, which is a continuation of U.S. application Ser. No. 13/974,258, filed Aug. 23, 2013, now U.S. Pat. No. 9,018,380, issued Apr. 28, 2015, which claims the benefit of priority of U.S. provisional application No. 61/743,131 filed Aug. 24, 2012, the disclosures of which are expressly incorporated by reference as if written herein in their entireties.

Disclosed herein are new heterocyclic compounds, compositions and their application as a pharmaceutical for the treatment of disease. Methods to inhibit HIF pathway activity through the degradation of the HIFα protein subunits in a human or animal subject are also provided for the treatment of diseases mediated by HIF pathway activity.

The heterodimeric HIF transcription factor is composed of a stable HIF1β (aka ARNT) and an oxygen regulatable HIFα subunit (HIF1α or EPAS1 (aka HIF2α) (Semenza, 2012b). Under normal physiological conditions, the capacity of the cell to degrade the HIFα subunits exceeds the amount of HIFα protein that is being synthesized. The HIFα subunit is regulated by hydroxylation at two key proline residues (ie. $Pro^{402}$ and $Pro^{564}$ in HIF1α) by a family of proline hydroxylases (PHD1, PHD2 and PHD3), that utilize α-ketoglutarate and oxygen as substrates to generate hydroxylated HIFα, succinate and $CO_2$ (Kaelin and Ratcliffe, 2008). Hydroxylation of HIFα makes it a substrate for the VHL ubiquitin ligase complex, which promotes HIFα polyubiquitination, thus targeting HIFα for proteosomal degradation. This process is very rapid at normal oxygen levels, with a <5 minute half-life of HIFα protein, thus enabling rapid regulation of the complex and HIF activity in response to changes in oxygen levels (Maxwell et al., 1999).

Frequently in disease, the HIF pathway is activated by either reduced oxygen levels or genetic alterations that increase the amount of stabilized HIFα subunit (Semenza, 2012a). Increased HIFα levels occur through several mechanisms that include increased in HIFα subunit mRNA expression, HIFα protein translation, or through a decrease in HIFα protein degradation. Increased HIF leads to several biological pathways being activated through HIF mediated transcription of genes that promote stem cell maintenance, metabolic reprogramming, endothelial to mesenchymal transition (EMT), survival, proliferation, migration, pH regulation and angiogenesis.

A substantial body of preclinical experimentation and clinical evidence has implicated HIF as an important therapeutic target that is essential for the maintenance of a subset of tumors and a potential major contributor to therapeutic resistance and residual disease (Kaelin, 2011; Kaelin and Ratcliffe, 2008; Li et al., 2005; Semenza, 2012a; Semenza, 2012b). In numerous clinical studies, tumor hypoxia has been reported to correlate with poor prognosis and incomplete response to current therapeutic agents, including various chemotherapies as well as radiotherapy (Harada et al., 2012; Rohwer and Cramer, 2011; Wilson and Hay, 2011). This is most likely due to HIF regulation of procancerous mechanisms, including increased proliferation, activation of survival pathways such as autophagy, enhanced glycolysis as part of a metabolic reprogramming shift away from oxidative phosphorylation, increased migration/invasion promoting metastasis, maintenance of pluripotent "stem cell" population and stimulation of angiogenesis through the synthesis and secretion of pro-angiogenic growth factors.

The loss of any of several tumor suppressors (i.e. VHL, SDH, FH, TSC and others) and/or dysregulation of several oncogenic pathways (i.e. RAS and Pi3K) activate the HIF pathway and its downstream effector pathways, but do so in the presence of oxygen creating a "pseudohypoxic" state. These subsets of tumors become dependent on the HIF pathway for their continued growth. An example of a genetically driven HIF tumor indication is renal cell carcinoma (RCC), in which the tumor suppressor VHL is inactivated by mutation, deletion or promoter hypermethylation in 70% of tumors (Kim and Kaelin, 2004). VHL inactivation results in HIFα stabilization that is independent of oxygen concentration. In another example, tumors where either fumarate hydratase (FH) or a subunit in the succinate dehydrogenase (SDH) complex is inactivated, HIFα accumulation occurs due to inhibition of PHDs by succinate and fumarate (Bardella et al., 2011; Gill, 2012; Isaacs et al., 2005; Pollard et al., 2005). The lack of HIFα hydroxylation prevents VHL mediated degradation.

In other tumors, the Pi3K pathway is frequently mutated (ie., PTEN loss, AKT, PIK3CA, TSC1/2, LKB1 and others) ultimately leading to an increase in the activity of mammalian target of rapaycin (mTOR), which results in an increase in HIFα protein translation to the point where it overwhelms the degradation pathway. Therefore, in tumors with active Pi3K pathway, HIF pathway activity is frequently increased (Wouters and Koritzinsky, 2008). Taken together, in tumors where the HIF pathway is driven by specific genetic changes, therapeutic interventions that inactivate the HIF pathway in genetically driven HIF dependent tumors may provide substantial therapeutic benefit as monotherapy or as part of a combination therapy.

In addition to the activation of HIF through genetic alterations, HIF is also activated in hypoxia that results from the tumor outgrowing the vasculature as well as a result of therapeutic intervention. HIF mediated survival of cells in hypoxia is a major contributor to resistance to therapies, lack of durable response and the foundation of residual disease. When tumor cells become hypoxic, several HIF dependent mechanisms prolong the survival of the cells in the harsh nutrient and oxygen deprived environment. These include genomic instability to promote adaptation (Klein and Glazer, 2010; Koi and Boland, 2011), metabolic reprogramming, induction of autophagy to recycle energy (Mazure and Pouyssegur, 2010), secretion of pro-angiogenic factors to promote neovascularization and cessation of pro-growth pathways. Severe hypoxia mediates innate resistance to radiotherapy and chemotherapy, which require oxygen and proliferation, respectively, as part of their mechanisms of action. Alternatively, resistance can be adaptive as in the case of anti-angiogenic therapies, such as anti-VEGF therapies, that create hypoxic niches due to the destruction of the vasculature, which creates more intratumoral hypoxia thus activating HIF and promoting its milieu of procancerous pathways. Multiple reports in a mouse models of cancer show that treatment with an anti-VEGF therapy promoted metastasis, most likely through HIF mediated activation of tumor cell migration/invasion (Ebos et al., 2009; Paez-Ribes et al., 2009). Hypoxia has also been proposed to promote genomic alteration by increasing DNA damage, including impairment of mismatch repair, nucleotide excision repair, double strand break repair and homologous recombination repair. The introduction of point mutations, frameshifts, insertions, deletions, amplifications and translocations give rise to tumor heterogeneity and evolution that provide the genetic alterations that enable adaptive resistance of tumors.

In most tumor types, inhibition of the HIF pathway activity will sensitize tumors to standard of care therapies such as anti-angiogenic therapies, radiotherapies, chemotherapies and targeted therapies by either improving the perfusion of drug and oxygen throughout the tumor via normalization of vascular function (Carmeliet and Jain, 2011; Chauhan et al., 2012) and by directly targeting the resistant HIF activated tumor cells to inhibit HIF mediated survival pathways.

In addition to cancer, inactivation of HIF pathway activate would be beneficial for conditions where activation of HIF promotes the disease state through aberrant survival or through promotion of neovascularization. These include traumatic shock, pulmonary arterial hypertension, obstructive sleep apnea, cardiovascular diseases such as cardiac arrhythmia and heart failure, diseases that involve neoangiogenesis such as ocular macular degeneration and rheumatoid arthritis, sepsis and inflammation and diseases of the lung and kidney where fibrosis occurs due HIF mediated EMT (Arjamaa et al., 2009; Semenza, 2012a; Westra et al., 2010).

To date, numerous small molecules have been reported that downregulate the HIF pathway via several direct and indirect mechanisms which target various HIF intervention points (Jones and Harris, 2012; Poon et al., 2009; Semenza, 2012b). These include reducing HIFα mRNA, reducing HIFα protein translation, reducing reactive oxygen species (ROS), increasing HIFα degradation, disrupting HIFα/HIF1β dimerization or the HIFα interaction with p300, a co-factor for HIF translation. Genetic and pharmacological inhibition of the HIF pathway utilizing RNAi, genetic ablation or via small molecule inhibitors have been reported to reduce the growth of tumors in preclinical models clearly establishing that the HIF pathway performs a critical function in tumor growth and maintenance (Onnis et al., 2009). Promoting HIFα degradation as part of a therapeutic intervention regime would be highly beneficial to patients. Herein we describe a series of selective small molecule inhibitors of HIF pathway activity that promote VHL and PHD mediated degradation of HIF.

Novel compounds and pharmaceutical compositions, certain of which have been found to inhibit HIF pathway activity have been discovered, together with methods of synthesizing and using the compounds including methods for the treatment of HIF pathway-mediated diseases in a patient by administering the compounds.

In certain embodiments of the present invention, compounds have structural Formula I:

$$(R_1)_n\text{-A-}Y_1\text{-B-D-E-}(R_3)_p \quad (I)$$

or a salt thereof, wherein:
n is 0, 1, or 2;
p is 0, 1, or 2;
q is 0, 1, 2, 3, or 4;
u is 0, 1, or 2;
A is selected from the group consisting of aryl and heteroaryl;
B is selected from the group consisting of

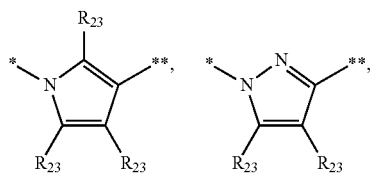

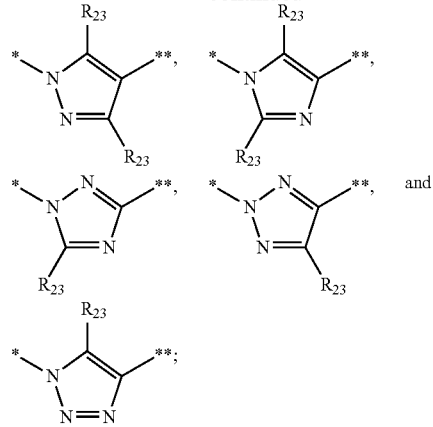

D is selected from the group consisting of alkyl, heteroalkyl, alkoxy, alkylthio, carbonyl, alkylcarbonyl, carboxyl, oxy, thio, sulfinyl, sulfonyl, sulfonamido, amino, amido, alkylamino, and heteroaryl, any of which can be optionally substituted with one or more substituents selected from the group consisting of hydrogen, deuterium, halogen, alkyl, haloalkyl, perhaloalkyl, heteroalkyl, hydroxyalkyl, acyl, cyano, hydroxy, alkoxy, haloalkoxy, perhaloalkoxy, cycloalkyl, aryl, heterocycloalkyl, heteroaryl, and oxo, any of which may be optionally substituted;

E is selected from the group consisting of aryl and heteroaryl;

G is selected from the group consisting of saturated 3- to 7-membered cycloalkyl and saturated 3- to 7-membered heterocycloalkyl;

$R_1$ is selected from the group consisting of —$Y_2$-alkyl-$N(R_4)R_5$, hydrogen, deuterium, halogen, alkyl, alkenyl, alkynyl, haloalkyl, perhaloalkyl, heteroalkyl, hydroxyalkyl, aminoalkyl, acyl, carboxylalkyl, carbonyl, carboxyl, cyano, hydroxy, alkoxy, haloalkoxy, perhaloalkoxy, oxo, alkylthio, thiolalkyl, mercaptyl, thiol, sulfonate, sulfonamido, alkylsulfonyl, amino, amido, alkylamino, dialkylamino, carbamate, nitro, cycloalkyl, aryl, heterocycloalkyl, heteroaryl, cycloalkyloxy, aryloxy, heterocycloalkyloxy, heteroaryloxy,

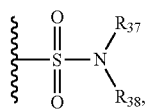

cycloalkylcarbonyl, arylcarbonyl, heterocycloalkylcarbonyl, heteroarylcarbonyl, cycloalkylalkyl, arylalkyl, heterocycloalkylalkyl, heterocycloalkylcarbonylalkyl, and heteroarylalkyl, any of which can be optionally substituted with one or more substituents selected from the group consisting of hydrogen, deuterium, halogen, alkyl, alkenyl, alkynyl, haloalkyl, perhaloalkyl, heteroalkyl, hydroxyalkyl, amidoalkyl, acyl, carbonyl, carboxyl, carboxylalkyl, alkylcarbonyl, heteroalkylcarbonyl, hydroxyalkylcarbonyl, aminoalkylcarbonyl, alkylaminoalkylcarbonyl, alkenylcarbonyl, alkynylcarbonyl, alkoxyalkyl, carboxyl, cyano, hydroxy, alkoxy, haloalkoxy, perhaloalkoxy, oxo, alkylthio, thiol, acylthio, sulfonamido, alkylsulfonyl, amino, amido, carbamate, nitro, cycloalkyl, aryl, heterocycloalkyl, heteroaryl, alkylheterocycloalkyl, any of which may be optionally substituted;

$R_3$ is selected from the group consisting of hydrogen, deuterium, halogen, alkyl, haloalkyl, perhaloalkyl, heteroalkyl, hydroxyalkyl, alkoxyalkyl, aminoalkyl, acyl, carbonyl, carboxyl, cyano, cyanoalkyl, hydroxy, alkoxy, haloalkoxy, perhaloalkoxy, alkoxyalkoxy, hydroxyalkoxy, oxo, alkylthio, mercaptyl, thiol, haloalkylthio, perhaloalkylthio, cyanoalkylthio, haloalkylsulfonyl, alkylsulfonyl, alkoxyalkylsulfonyl, cyanoalkylsulfonyl, sulfonate, sulfonamido, amino, amido, alkylamino, dialkylamino, carbamate, nitro, cycloalkyl, aryl, heterocycloalkyl, heteroaryl, cycloalkyloxy, aryloxy, heterocycloalkyloxy, heteroaryloxy, cycloalkylalkyl, arylalkyl, heterocycloalkylalkyl, and heteroarylalkyl, trisubstituted silyl, —SF$_5$, —(C(R$_{31}$)(R$_{32}$))$_q$—O-alkyl, —(C(R$_{31}$)(R$_{32}$))$_q$—O-cycloalkyl, —S(O)$_u$-alkyl, —S(O)$_u$-cycloalkyl, cycloalkylthio, —CF$_3$, —OCF$_3$, —(C(R$_{31}$)(R$_{32}$))$_q$—OCF$_3$, saturated heterocycloalkyloxy, —(C(R$_{31}$)(R$_{32}$))$_q$—O-saturated heterocycloalkyl, —(C(R$_{31}$)(R$_{32}$))$_q$— saturated heterocycloalkyl, saturated heterocycloalkylthio, —S(O)$_u$-saturated heterocycloalkyl, —(C(R$_{31}$)(R$_{32}$))$_q$—OCF$_3$

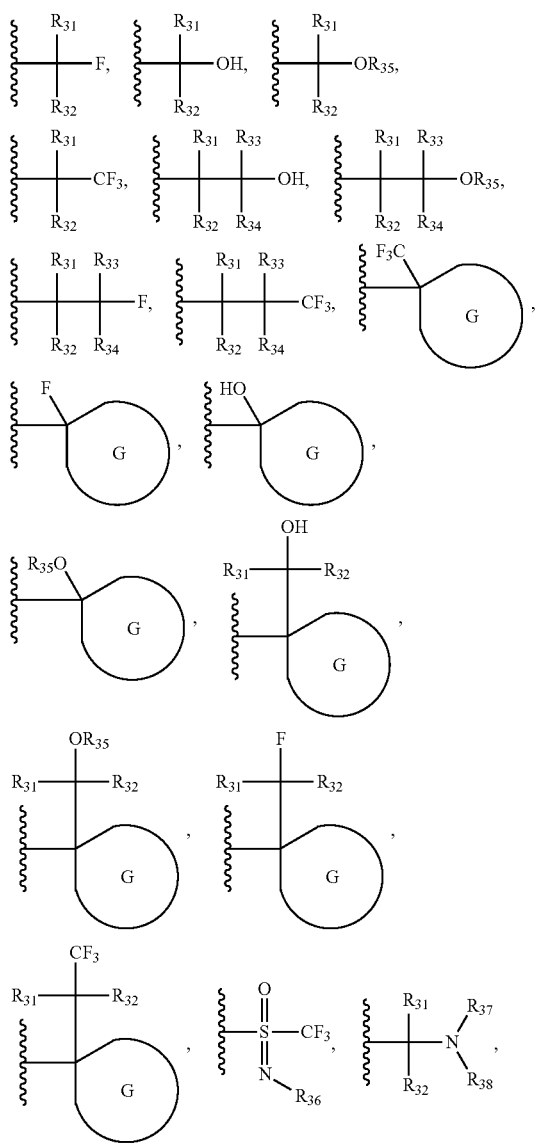

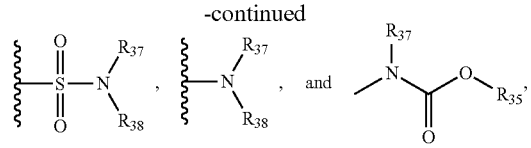

any of which may be optionally substituted;

$R_4$ and $R_5$ are independently selected from the group consisting of hydrogen, deuterium, alkyl, alkenyl, alkynyl, haloalkyl, perhaloalkyl, heteroalkyl, hydroxyalkyl, acyl, carbonyl, carboxyl, alkoxy, haloalkoxy, perhaloalkoxy, alkylsulfonyl, sulfonamido, amido, cycloalkyl, aryl, heterocycloalkyl, heteroaryl, cycloalkylalkyl, arylalkyl, heterocycloalkylalkyl, and heteroarylalkyl, or $R_4$ and $R_5$, taken together, form a heterocycloalkyl or heteroaryl, any of which can be optionally substituted with one or more substituents selected from the group consisting of hydrogen, deuterium, halogen, alkyl, alkenyl, alkynyl, haloalkyl, perhaloalkyl, heteroalkyl, hydroxyalkyl, acyl, carbonyl, carboxyl, cyano, hydroxy, alkoxy, haloalkoxy, perhaloalkoxy, oxo, alkylthio, mercaptyl, thiol, sulfonate, sulfonamido, amino, amido, alkylamino, dialkylamino, carbamate, nitro, cycloalkyl, aryl, heterocycloalkyl, heteroaryl, cycloalkyloxy, aryloxy, heterocycloalkyloxy, heteroaryloxy, cycloalkylalkyl, arylalkyl, heterocycloalkylalkyl, and heteroarylalkyl, any of which may be optionally substituted;

each $R_{23}$ is independently selected from the group consisting of hydrogen, deuterium, halogen, alkyl, haloalkyl, perhaloalkyl, heteroalkyl, hydroxyalkyl, aminoalkyl, acyl, carbonyl, carboxyl, cyano, hydroxy, alkoxy, haloalkoxy, perhaloalkoxy, oxo, alkylthio, amino, alkylamino, dialkylamino, nitro, cycloalkyl, aryl, and heteroaryl, any of which may be optionally substituted;

$R_{31}$, $R_{32}$, $R_{33}$, $R_{34}$, and $R_{36}$ are independently selected from the group consisting of hydrogen, deuterium, alkyl, and perfluoroalkyl, any of which can be optionally substituted;

$R_{35}$ is selected from the group consisting of hydrogen, deuterium, alkyl, perfluoroalkyl, cycloalkyl, and saturated heterocycloalkyl, any of which can be optionally substituted;

$R_{37}$ and $R_{38}$ are independently selected from the group consisting of alkyl and perfluoroalkyl, or $R_{37}$ and $R_{38}$, taken together, form a heterocycloalkyl, any of which can be optionally substituted;

$Y_1$ is selected from the group consisting of alkyl, alkenyl, alkynyl, heteroalkyl, alkoxy, alkylthio, carbonyl, alkylcarbonyl, carboxyl, oxy, thio, sulfinyl, sulfonyl, sulfonamido, amino, amido, alkylamino, and carbamate, any of which can be optionally substituted with one or more substituents selected from the group consisting of hydrogen, deuterium, halogen, alkyl, haloalkyl, perhaloalkyl, heteroalkyl, hydroxyalkyl, aminoalkyl, acyl, carbonyl, carboxyl, cyano, hydroxy, alkoxy, haloalkoxy, perhaloalkoxy, oxo, alkylthio, amino, alkylamino, dialkylamino, and cycloalkyl, any of which may be optionally substituted; and $Y_2$ is selected from the group consisting of a bond, carbonyl, alkylcarbonyl, carboxyl, oxy, thio, sulfinyl, sulfonyl, sulfonamido, amino, amido, alkylamino, and carbamate, any of which can be optionally substituted with one or more substituents selected from the group consisting of hydrogen, deuterium, halogen, alkyl, alkenyl, alkynyl, haloalkyl, perhaloalkyl, heteroalkyl, hydroxyalkyl, acyl, carbonyl, carboxyl, cyano, hydroxy, alkoxy, haloalkoxy, perhaloalkoxy, oxo, alkylthio, mercaptyl, thiol, sulfonate, sulfonamido, amino, amido, alkylamino, dialkylamino, carbamate, cycloalkyl, aryl, heterocycloalkyl, heteroaryl, cycloalkyloxy, aryloxy, heterocycloalkyloxy, heteroaryloxy, cycloalkylalkyl, arylalkyl, heterocycloalkylalkyl, and heteroarylalkyl, any of which may be optionally substituted.

Certain compounds disclosed herein may possess useful HIF pathway inhibiting activity, and may be used in the treatment or prophylaxis of a disease or condition in which the HIF pathway plays an active role. Thus, in broad aspect, certain embodiments also provide pharmaceutical compositions comprising one or more compounds disclosed herein together with a pharmaceutically acceptable carrier, as well as methods of making and using the compounds and compositions. Certain embodiments provide methods for inhibiting the HIF pathway. Other embodiments provide methods for treating a HIF pathway-mediated disorder in a patient in need of such treatment, comprising administering to said patient a therapeutically effective amount of a compound or composition according to the present invention. Also provided is the use of certain compounds disclosed herein for use in the manufacture of a medicament for the treatment of a disease or condition ameliorated by the inhibition of the HIF pathway.

In certain embodiments,
if A is phenyl, B is not

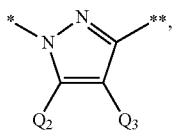

wherein $Q_2$ and $Q_3$ are freely substituted;
if A is phenyl or pyridyl, $Y_1$ is $CH_2$, B is

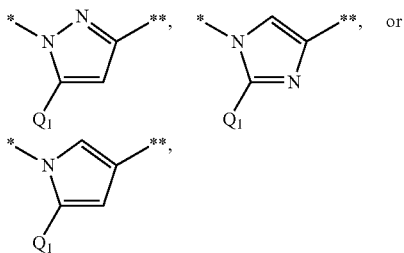

and $Q_1$ is methyl, ethyl, or trifluoromethyl, then D is not

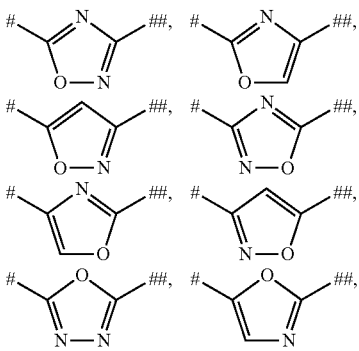

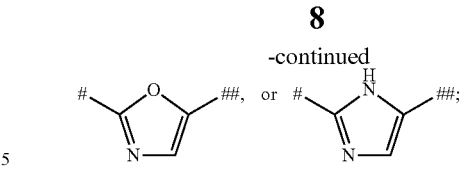

and
wherein * represents the point of attachment to $Y_1$ and ** represents the point of attachment to D, and # represents the point of attachment to B and ## represents the point of attachment to E.

In further embodiments,
A is selected from the group consisting of aryl and mono- or bicyclic heteroaryl;
B is selected from the group consisting of

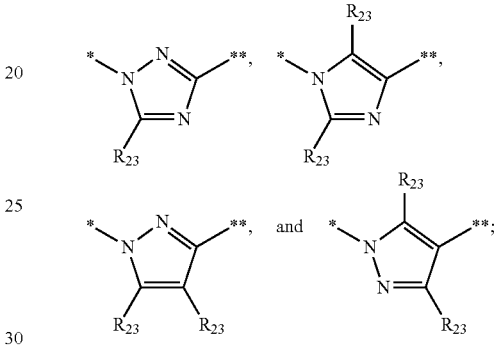

D is selected from the group consisting of amido, 5-membered heteroaryl, and 6-membered heteroaryl, any of which can be optionally substituted with one or more substituents selected from the group consisting of hydrogen, deuterium, halogen, alkyl, haloalkyl, perhaloalkyl, heteroalkyl, hydroxyalkyl, acyl, cyano, hydroxy, alkoxy, haloalkoxy, perhaloalkoxy, cycloalkyl, aryl, heterocycloalkyl, heteroaryl, and oxo, any of which may be optionally substituted;
E is selected from the group consisting of phenyl, 5-membered heteroaryl, 6-membered heteroaryl, and 9-membered bicyclic heteroaryl;
$R_4$ and $R_5$ are independently selected from the group consisting of hydrogen, deuterium, alkyl, alkenyl, alkynyl, haloalkyl, perhaloalkyl, heteroalkyl, hydroxyalkyl, acyl, carbonyl, carboxyl, alkoxy, haloalkoxy, perhaloalkoxy, alkylsulfonyl, sulfonamido, amido, cycloalkyl, aryl, heterocycloalkyl, heteroaryl, cycloalkylalkyl, arylalkyl, heterocycloalkylalkyl, and heteroarylalkyl, or $R_4$ and $R_5$, taken together, form a heterocycloalkyl or heteroaryl, any of which can be optionally substituted with one or more substituents selected from the group consisting of hydrogen, deuterium, halogen, alkyl, haloalkyl, perhaloalkyl, heteroalkyl, hydroxyalkyl, acyl, carbonyl, carboxyl, cyano, hydroxy, alkoxy, haloalkoxy, perhaloalkoxy, oxo, alkylthio, mercaptyl, thiol, sulfonamido, amino, amido, alkylamino, dialkylamino, carbamate, and cycloalkyl, any of which may be optionally substituted;
$R_{23}$ is selected from the group consisting of hydrogen, deuterium, halogen, alkyl, haloalkyl, perhaloalkyl, heteroalkyl, hydroxyalkyl, cyano, hydroxy, alkoxy, haloalkoxy, perhaloalkoxy, alkylthio, amino, alkylamino, dialkylamino, cycloalkyl, aryl, and heteroaryl;
$Y_1$ is alkyl, which can be optionally substituted with one or more substituents selected from the group consisting of hydrogen, deuterium, alkyl, cycloalkyl, and halogen; and Y₂ is selected from the group consisting of a bond, carbonyl, alkylcarbonyl, carboxyl, oxy, thio, sulfinyl, sulfonyl, sulfonamido, amino, amido, alkylamino, and carbamate, any of which can be optionally substituted with one or more substituents selected from the group consisting of hydrogen, deuterium, halogen, alkyl, haloalkyl, perhaloalkyl, heteroalkyl, hydroxyalkyl, acyl, carbonyl, carboxyl, cyano, hydroxy, alkoxy, haloalkoxy, perhaloalkoxy, oxo, alkylthio, mercaptyl, thiol, sulfonamido, amino, amido, alkylamino, dialkylamino, carbamate, and cycloalkyl, any of which may be optionally substituted.

In further embodiments, B is

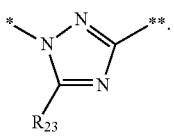

In further embodiments,

D is selected from the group consisting of —C(=O) NR₁₁—, 5-membered heteroaryl, and 6-membered heteroaryl;

E is selected from the group consisting of phenyl, pyrimidine, 1,3-benzodioxol, indole, and 1-benzofuran;

R₁ is selected from the group consisting of —Y₂-alkyl-N(R₄)R₅, hydrogen, deuterium, halogen, alkyl, alkenyl, haloalkyl, perhaloalkyl, heteroalkyl, hydroxyalkyl, aminoalkyl, acyl, carboxylalkyl, carbonyl, carboxyl, cyano, hydroxy, alkoxy, haloalkoxy, perhaloalkoxy, oxo, alkylthio, thiolalkyl, sulfonamido, alkylsulfonyl, amino, amido, alkylamino, dialkylamino, nitro, cycloalkyl, aryl, heterocycloalkyl, heteroaryl, cycloalkyloxy, aryloxy, heterocycloalkyloxy, heteroaryloxy,

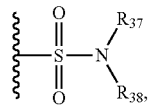

cycloalkylcarbonyl, arylcarbonyl, heterocycloalkylcarbonyl, and heterocycloalkylcarbonylalkyl, any of which can be optionally substituted with one or more substituents selected from the group consisting of hydrogen, deuterium, halogen, alkyl, alkenyl, alkynyl, amidoalkyl, acyl, carboxylalkyl, alkylcarbonyl, heteroalkylcarbonyl, hydroxyalkylcarbonyl, aminoalkylcarbonyl, alkylaminoalkylcarbonyl, alkenylcarbonyl, alkynylcarbonyl, haloalkyl, perhaloalkyl, heteroalkyl, hydroxyalkyl, alkoxyalkyl, carboxyl, cyano, hydroxy, alkoxy, haloalkoxy, perhaloalkoxy, oxo, thiol, acylthio, sulfonamido, alkylsulfonyl, amino, amido, carbamate, alkylamino, dialkylamino, alkylaminoalkyl, dialkylaminoalkyl, trisubstituted silyl, trisubstituted siloxy, cycloalkyl, aryl, heterocycloalkyl, heteroaryl, alkylheterocycloalkyl, any of which may be optionally substituted;

R₃ is selected from the group consisting of hydrogen, deuterium, halogen, alkyl, haloalkyl, perhaloalkyl, heteroalkyl, hydroxyalkyl, alkoxyalkyl, aminoalkyl, dialkylamino, acyl, carbonyl, carboxyl, cyano, cyanoalkyl, hydroxy, alkoxy, haloalkoxy, perhaloalkoxy, alkoxyalkoxy, hydroxyalkoxy, oxo, alkylthio, haloalkylthio, perhaloalkylthio, cyanoalkylthio, alkylsulfonyl, alkoxyalkylsulfonyl, cyanoalkylsulfonyl, haloalkylsulfonyl, sulfonamido, alkylsulfonamido, amino, alkylamino, dialkylamino, amido, cycloalkyl, aryl, heterocycloalkyl, heteroaryl perhaloalkylcycloalkyl, hydroxyheterocycloalkyl, hydroxycycloalkyl, heterocycloalkylcarbonyl, and heterocycloalkylalkyl, any of which can be optionally substituted;

R₁₁ is selected from the group consisting of hydrogen, deuterium, alkyl, haloalkyl, perhaloalkyl, heteroalkyl, hydroxyalkyl, cycloalkyl, aryl, heterocycloalkyl, and heteroaryl, any of which may be optionally substituted;

Y₁ is —CH₂—; and

Y₂ is selected from the group consisting of a bond, carbonyl, amino, and alkylamino.

In further embodiments,

A is selected from the group consisting of phenyl, 5-membered heteroaryl, and 6-membered heteroaryl;

E is phenyl;

R₁ is selected from the group consisting of —Y₂-alkyl-N(R₄)R₅, hydrogen, deuterium, halogen, alkyl, alkenyl, haloalkyl, perhaloalkyl, heteroalkyl, hydroxyalkyl, acyl, carboxylalkyl, carboxyl, carbonyl, cyano, hydroxy, alkoxy, haloalkoxy, perhaloalkoxy, oxo, thiolalkyl, sulfonyl, sulfonamido, alkylsulfonyl, amino, amido, alkylamino, dialkylamino, nitro, heterocycloalkyl, heterocycloalkyloxy,

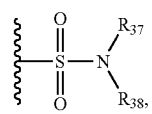

heterocycloalkylcarbonylalkyl, and heterocycloalkylcarbonyl, any of which can be optionally substituted with one or more substituents selected from the group consisting of hydrogen, deuterium, halogen, alkyl, alkenyl, amidoalkyl, acyl, carboxylalkyl, hydroxyalkylcarbonyl, alkynylcarbonyl, heteroalkyl, hydroxyalkyl, alkoxyalkyl, carboxyl, cyano, hydroxy, alkoxy, oxo, sulfonamido, alkylsulfonyl, amino, amido, carbamate, dialkylamino, dialkylaminoalkyl, trisubstituted siloxy, cycloalkyl, heterocycloalkyl, alkylheterocycloalkyl, any of which may be optionally substituted;

R₁₁ is selected from the group consisting of hydrogen, deuterium, alkyl, and cycloalkyl, any of which may be optionally substituted; and each R₂₃ is independently selected from the group consisting of hydrogen, deuterium, hydroxyl, alkyl, haloalkyl, perhaloalkyl, cyano, saturated 3- to 6-membered cycloalkyl, 4- to 6-membered heterocycloalkyl, and 5- to 6-membered heteroaryl.

In further embodiments of the present invention, n is 1; p is 1; and R₂₃ is selected from the group consisting of alkyl, haloalkyl, perhaloalkyl, hydroxy, and cyclopropyl.

In certain embodiments, disclosed herein are compounds having structural Formula II

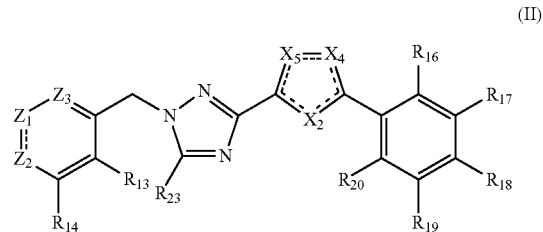

or a salt thereof, wherein:

$X_2$, $X_4$, and $X_5$ are independently selected from the group consisting of $CR_{21}$, N, O, and S, and wherein $X_2$, $X_4$, and $X_5$, taken together, form a 5-membered heteroaryl;

$Z_1$ and $Z_2$ are independently selected from the group consisting of N, $NR_1$, C=O, and $CR_1$;

$Z_3$ is selected from the group consisting of N, $NR_{12}$, C=O, and $CR_{12}$;

$R_1$ is selected from the group consisting of —$Y_2$-alkyl-$N(R_4)R_5$, hydrogen, deuterium, halogen, alkyl, alkenyl, haloalkyl, perhaloalkyl, heteroalkyl, hydroxyalkyl, aminoalkyl, acyl, carboxylalkyl, carbonyl, carboxyl, carbonyl, cyano, hydroxy, alkoxy, haloalkoxy, perhaloalkoxy, oxo, alkylthio, thiolalkyl, sulfonyl, sulfonamido, alkylsulfonyl, amino, amido, alkylamino, dialkylamino, nitro, cycloalkyl, aryl, heterocycloalkyl, heteroaryl, cycloalkyloxy, aryloxy, heterocycloalkyloxy, heteroaryloxy,

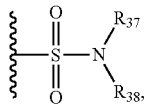

cycloalkylcarbonyl, arylcarbonyl, heterocycloalkylcarbonyl, and heterocycloalkylcarbonylalkyl, any of which can be optionally substituted with one or more substituents selected from the group consisting of hydrogen, deuterium, halogen, alkyl, alkenyl, alkynyl, amidoalkyl, acyl, carboxylalkyl, alkylcarbonyl, heteroalkylcarbonyl, hydroxyalkylcarbonyl, aminoalkylcarbonyl, alkylaminoalkylcarbonyl, alkenylcarbonyl, alkynylcarbonyl, haloalkyl, perhaloalkyl, heteroalkyl, hydroxyalkyl, alkoxyalkyl, carboxyl, cyano, hydroxy, alkoxy, haloalkoxy, perhaloalkoxy, oxo, thiol, acylthio, sulfonamido, alkylsulfonyl, amino, amido, carbamate, alkylamino, dialkylamino, alkylaminoalkyl, dialkylaminoalkyl, trisubstituted silyl, trisubstituted siloxy, cycloalkyl, aryl, heterocycloalkyl, heteroaryl, alkylheterocycloalkyl, any of which may be optionally substituted;

$R_{12}$, $R_{13}$, and $R_{14}$ are independently selected from the group consisting of hydrogen, deuterium, halogen, alkyl, haloalkyl, perhaloalkyl, cyano, hydroxy, alkoxy, haloalkoxy, perhaloalkoxy, alkylthio, amino, and saturated 3- to 7-membered cycloalkyl, any of which may be optionally substituted;

$R_{16}$, $R_{19}$, and $R_{20}$ are independently selected from the group consisting of hydrogen, deuterium, halogen, alkyl, haloalkyl, perhaloalkyl, cyano, hydroxy, alkoxy, haloalkoxy, perhaloalkoxy, alkylthio, amino, and cycloalkyl, any of which may be optionally substituted;

$R_{17}$ and $R_{18}$ are independently selected from the group consisting of hydrogen, deuterium, halogen, alkyl, haloalkyl, perhaloalkyl, heteroalkyl, hydroxyalkyl, alkoxyalkyl, aminoalkyl, dialkylamino, acyl, carbonyl, carboxyl, cyano, cyanoalkyl, hydroxy, alkoxy, haloalkoxy, perhaloalkoxy, alkoxyalkoxy, hydroxyalkoxy, oxo, alkylthio, haloalkylthio, perhaloalkylthio, cyanoalkylthio, alkylsulfonyl, alkoxyalkylsulfonyl, cyanoalkylsulfonyl, haloalkylsulfonyl, sulfonamido, alkylsulfonamido, amino, alkylamino, dialkylamino, amido, cycloalkyl, aryl, heterocycloalkyl, heteroaryl perhaloalkylcycloalkyl, hydroxyheterocycloalkyl, hydroxycycloalkyl, heterocycloalkylcarbonyl, and heterocycloalkylalkyl, any of which can be optionally substituted;

$R_{21}$ is selected from the group consisting of null, hydrogen, deuterium, halogen, alkyl, haloalkyl, perhaloalkyl, heteroalkyl, hydroxyalkyl, cyano, hydroxy, alkoxy, haloalkoxy, perhaloalkoxy, alkylthio, amino, alkylamino, and dialkylamino; and $R_{23}$ is selected from the group consisting of hydrogen, deuterium, hydroxyl, alkyl, haloalkyl, perhaloalkyl, cyano, saturated 3- to 6-membered cycloalkyl, 4- to 6-membered heterocycloalkyl, and 5- to 6-membered heteroaryl.

In further embodiments, two of $X_2$, $X_4$, and $X_5$ are N; and one of $X_2$, $X_4$, and $X_5$ is O; or one of $X_2$, $X_4$, and $X_5$ is N; one of $X_2$, $X_4$, and $X_5$ is O; and one of $X_2$, $X_4$, and $X_5$ is CH; and $R_{23}$ is selected from the group consisting of hydrogen, deuterium, hydroxyl, alkyl, haloalkyl, perhaloalkyl, cyano, and saturated 3- to 6-membered cycloalkyl.

In further embodiments, at least one of $Z_1$ or $Z_2$ is $CR_1$;

$R_1$ is selected from the group consisting of —$Y_2$-alkyl-$N(R_4)R_5$, hydrogen, deuterium, halogen, alkyl, alkenyl, haloalkyl, perhaloalkyl, heteroalkyl, hydroxyalkyl, acyl, carboxylalkyl, carboxyl, carbonyl, cyano, hydroxy, alkoxy, haloalkoxy, perhaloalkoxy, oxo, thiolalkyl, sulfonyl, sulfonamido, alkylsulfonyl, amino, amido, alkylamino, dialkylamino, nitro, heterocycloalkyl, heterocycloalkyloxy,

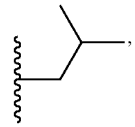

heterocycloalkylcarbonylalkyl, and heterocycloalkylcarbonyl, any of which can be optionally substituted with one or more substituents selected from the group consisting of hydrogen, deuterium, halogen, alkyl, alkenyl, amidoalkyl, acyl, carboxylalkyl, hydroxyalkylcarbonyl, alkynylcarbonyl, heteroalkyl, hydroxyalkyl, alkoxyalkyl, carboxyl, cyano, hydroxy, alkoxy, oxo, sulfonamido, alkylsulfonyl, amino, amido, carbamate, dialkylamino, dialkylaminoalkyl, trisubstituted siloxy, cycloalkyl, heterocycloalkyl, alkylheterocycloalkyl, any of which may be optionally substituted;

$R_{12}$, $R_{13}$, and $R_{14}$ are hydrogen;

$R_{16}$, $R_{17}$, $R_{19}$, and $R_{20}$ are hydrogen;

$R_{21}$ is selected from the group consisting of null, hydrogen, deuterium, halogen, and alkyl; and $R_{23}$ is selected from the group consisting of hydrogen, deuterium, hydroxyl, alkyl, haloalkyl, perhaloalkyl, cyano, and saturated 3- to 6-membered cycloalkyl.

In further embodiments, $R_1$ is selected from the group consisting of hydrogen, deuterium, fluorine, bromine, cyano, methyl, isopropyl,

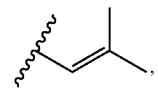 [SMILES: *C=C(C)C]

ethylene, trifluoromethyl, bromomethyl, hydroxymethyl, difluoromethoxy, methoxy, ethoxy, isopropoxy, hydroxy, nitro, acetyl, carboxyl, —CO$_2$CH$_3$,
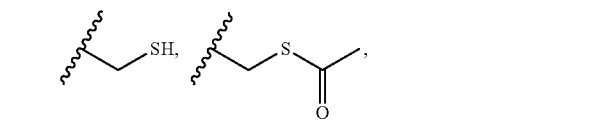
—SO$_2$CH$_3$, —SO$_2$CH$_2$CH$_3$, SO$_2$CH$_2$CH$_2$CH$_3$, —SO$_2$NH$_2$,
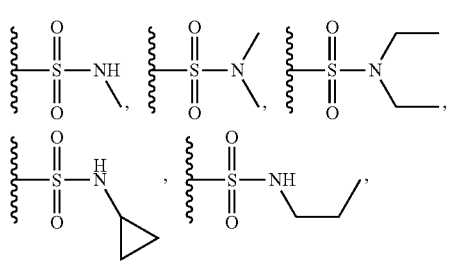
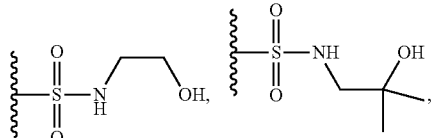
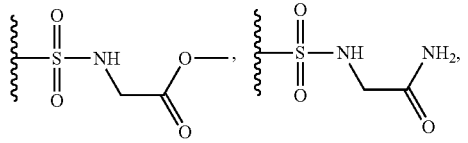
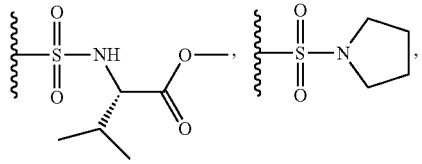
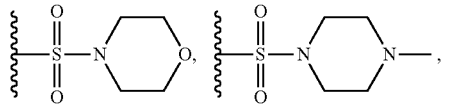
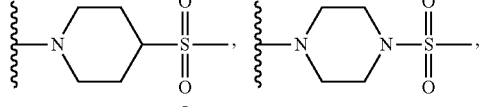
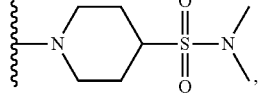
amino, methylamino, dimethylamino,
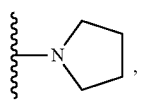
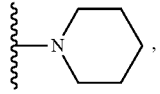
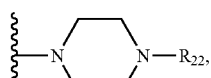
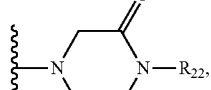
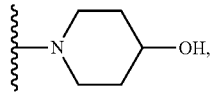
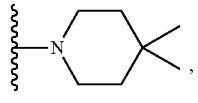
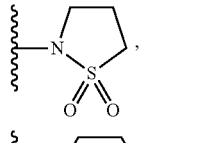
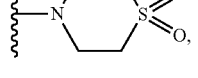
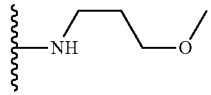
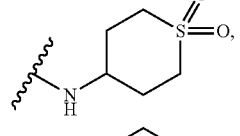
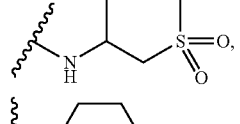
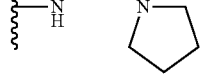
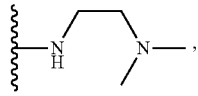
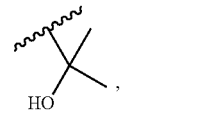

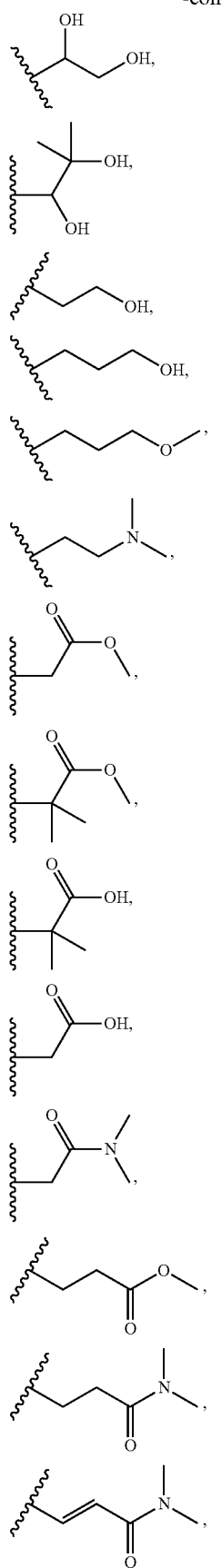
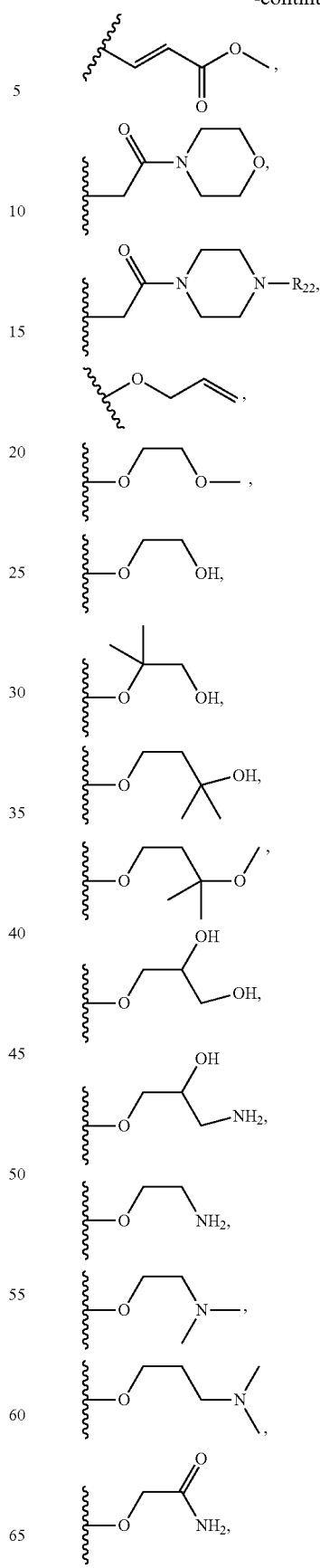

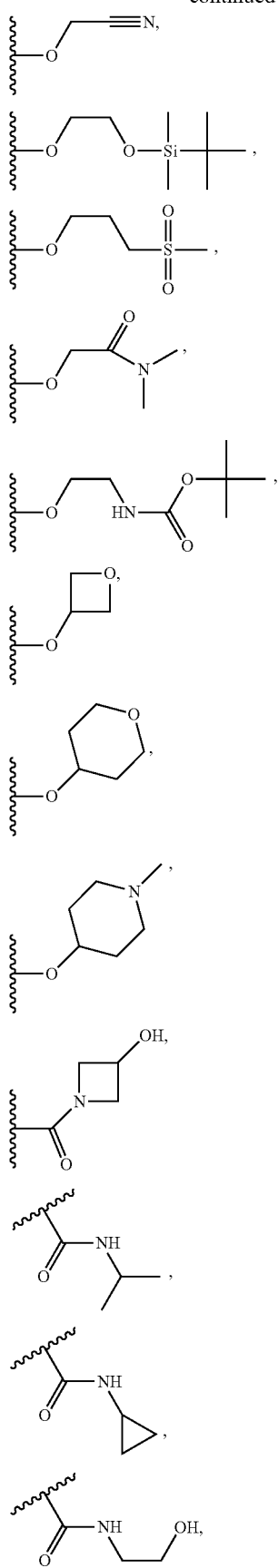
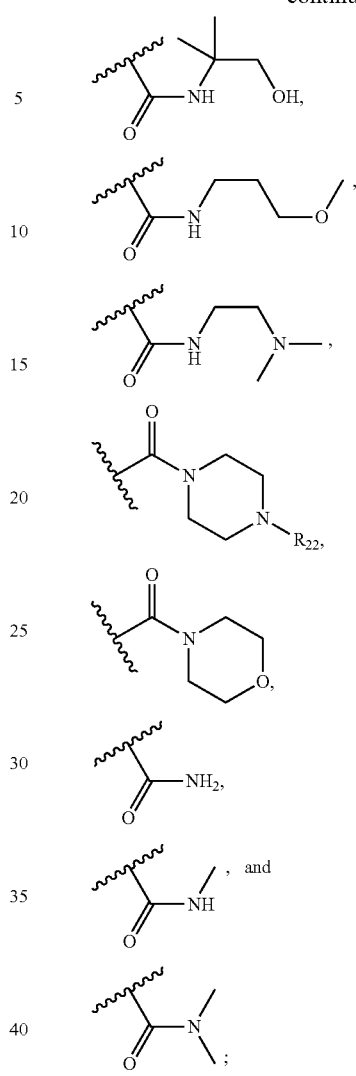
$R_{18}$ is selected from the group consisting of hydrogen, deuterium, halogen, methyl, isopropyl, tert-butyl, cyclopropyl, cyclohexyl, acetyl, hydroxymethyl, methoxymethyl, methoxy, isopropoxy, methylamino, dimethylamino, methylthio, cyanomethyl, cyanomethylthio, cyano, —SO$_2$CH$_3$, —SO$_2$CH(CH$_3$)$_2$, —SO$_2$CH$_2$CH(CH$_3$)$_2$, —SO$_2$NHCH$_2$CH$_2$CH$_3$, —SO$_2$CHF$_2$, —SO$_2$CF$_3$,
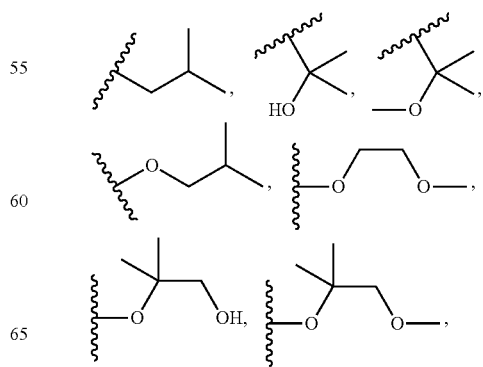

-continued

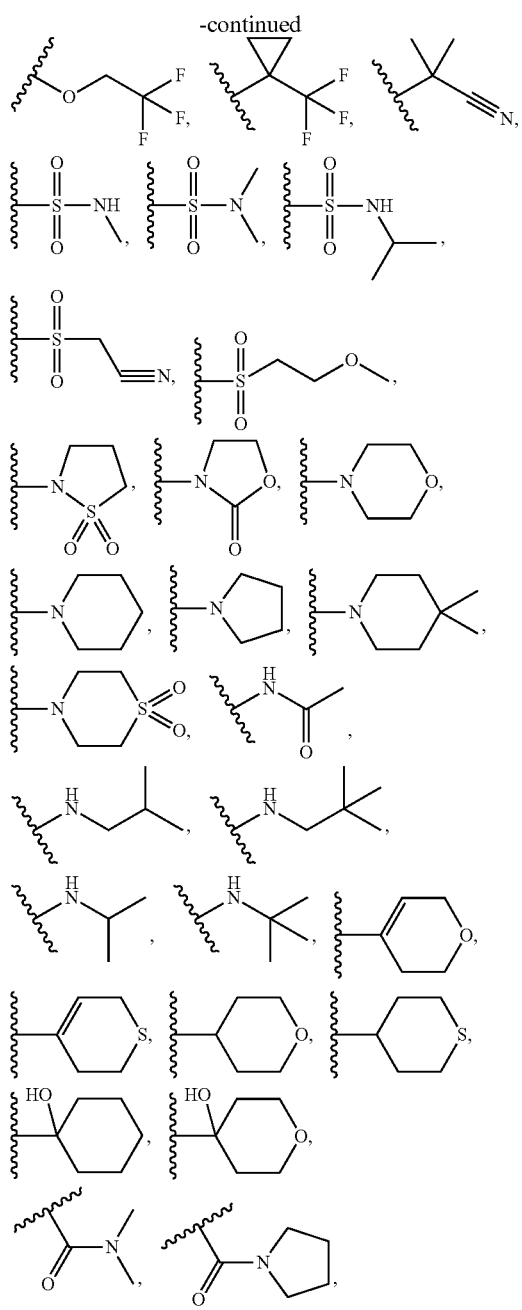

trifluoromethyl, trifluoromethylthio, difluoromethoxy, and trifluoromethoxy;

$R_{22}$ is selected from the group consisting of hydrogen, deuterium, methyl, acetyl,

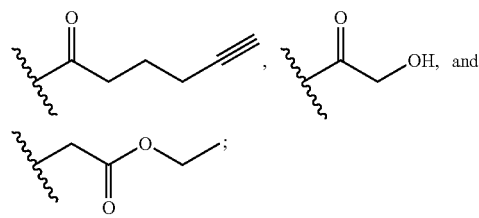

and $R_{23}$ is selected from the group consisting of hydrogen, deuterium, methyl, ethyl, 3-pyridyl, and cyclopropyl.

In further embodiments, $R_1$ is selected from the group consisting of hydrogen, halogen, cyano, methyl, isopropyl,

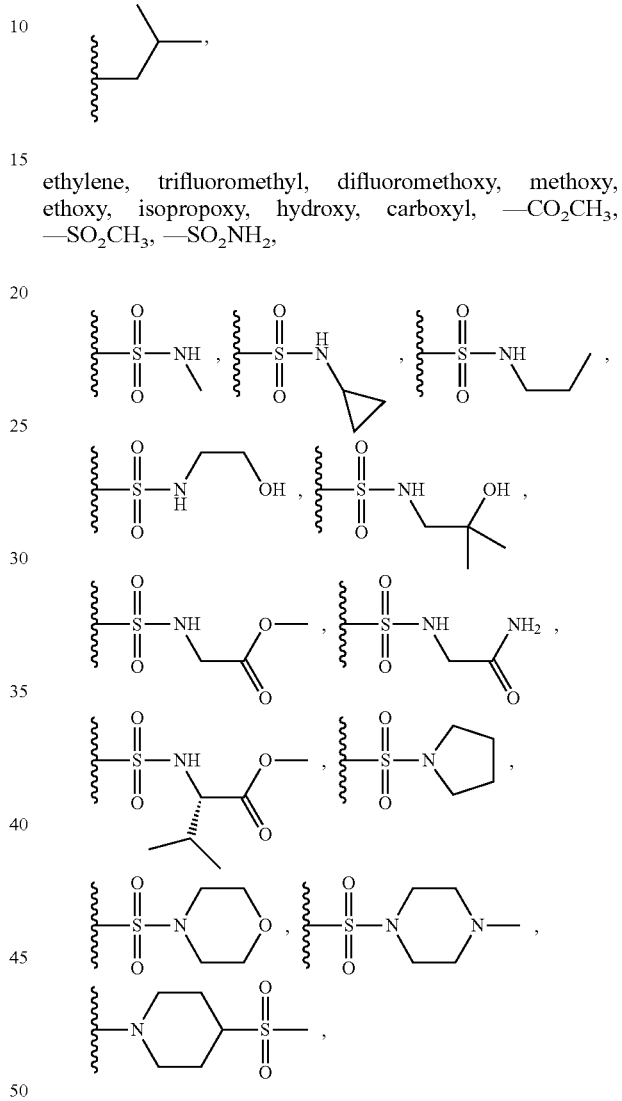

ethylene, trifluoromethyl, difluoromethoxy, methoxy, ethoxy, isopropoxy, hydroxy, carboxyl, —CO$_2$CH$_3$, —SO$_2$CH$_3$, —SO$_2$NH$_2$, amino, methylamino, dimethylamino,

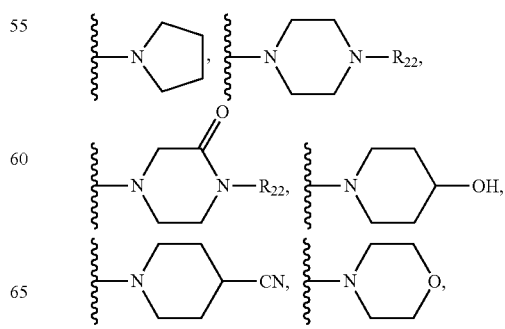

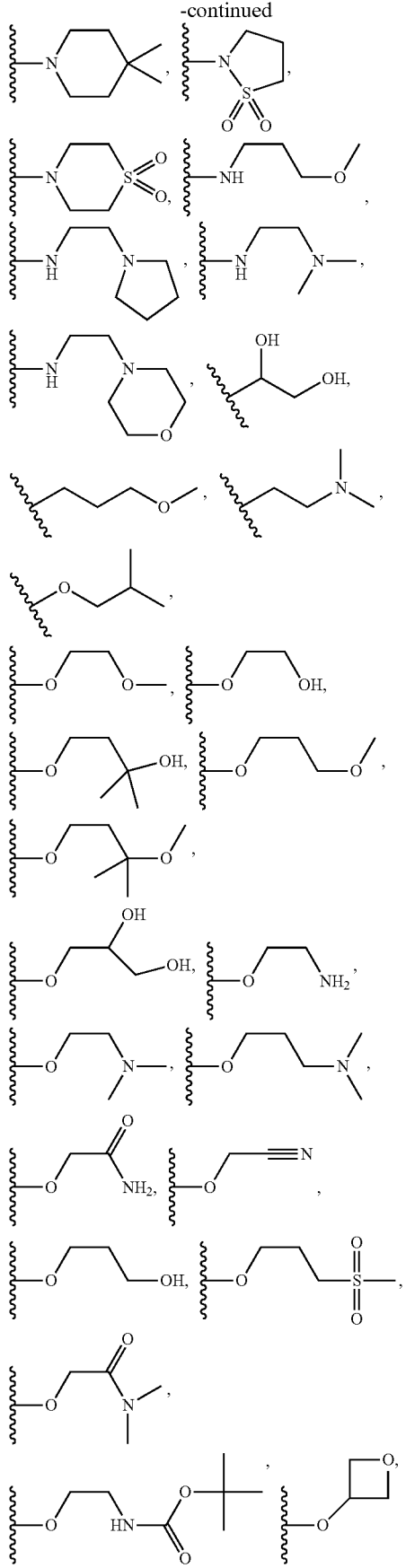

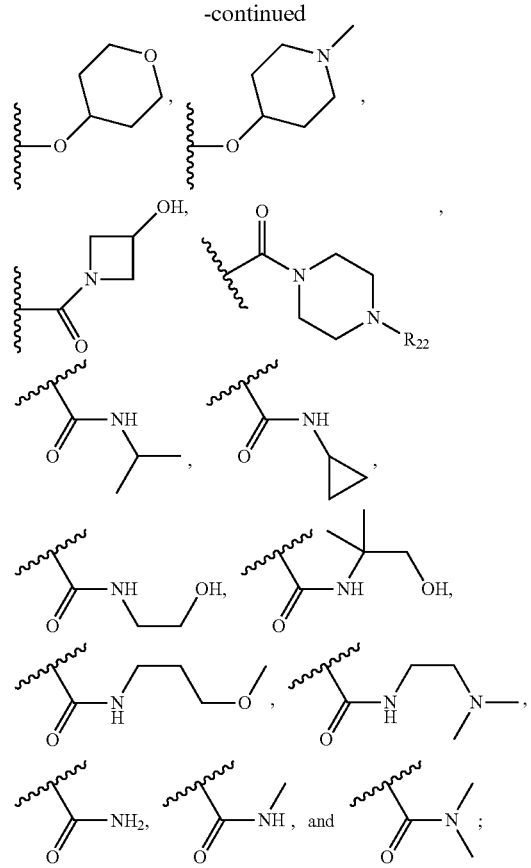

and
R₂₃ is methyl.

In further embodiments, two of $X_2$, $X_4$, and $X_5$ are N; and one of $X_2$, $X_4$, and $X_5$ is O.

In further embodiments, one of $X_2$, $X_4$, and $X_5$ is N; one of $X_2$, $X_4$, and $X_5$ is O; and one of $X_2$, $X_4$, and $X_5$ is CH.

In certain embodiments, disclosed herein are compounds having structural Formula III:

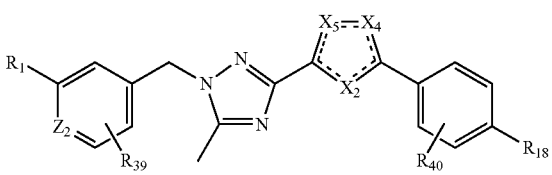

(III)

or a salt thereof, wherein:
$X_2$ and $X_4$ are N and $X_5$ is O; $X_4$ and $X_5$ are N and $X_2$ is O; $X_2$ and $X_5$ are N and $X_4$ is O; $X_2$ is CH, $X_4$ is N, and $X_5$ is O; or $X_2$ is CH, $X_4$ is O, and $X_5$ is N;

$Z_2$ is selected from the group consisting of N and $CR_{14}$;

$R_1$ is selected from the group consisting of heterocycloalkyl, alkoxyalkoxy, alkylsulfonylalkoxy, heterocycloalkyloxy, heterocycloalkylcarbonyl, alkoxyalkylamido, heterocycloalkylsulfonyl, alkoxyalkylsulfonamido, wherein said heterocycloalkyl, heterocycloalkyloxy, heterocycloalkylcarbonyl, and heterocycloalkylsulfonyl can be optionally substituted with one or more substituents selected from the group consisting hydrogen, alkyl, and oxo;

$R_{14}$, $R_{39}$, and $R_{40}$ are independently selected from the group consisting of hydrogen, deuterium, halogen, alkyl, haloalkyl, perhaloalkyl, cyano, hydroxy, alkoxy, haloalkoxy, perhaloalkoxy, alkylthio, amino, and saturated 3- to 7-membered cycloalkyl, any of which may be optionally substituted; and $R_{18}$ is selected from the group consisting of alkyl, haloalkyl, perhaloalkyl, alkoxy, haloalkoxy, perhaloalkoxy, alkylthio, haloalkylthio, and perhaloalkylthio.

In further embodiments, $R_1$ is selected from the group consisting of

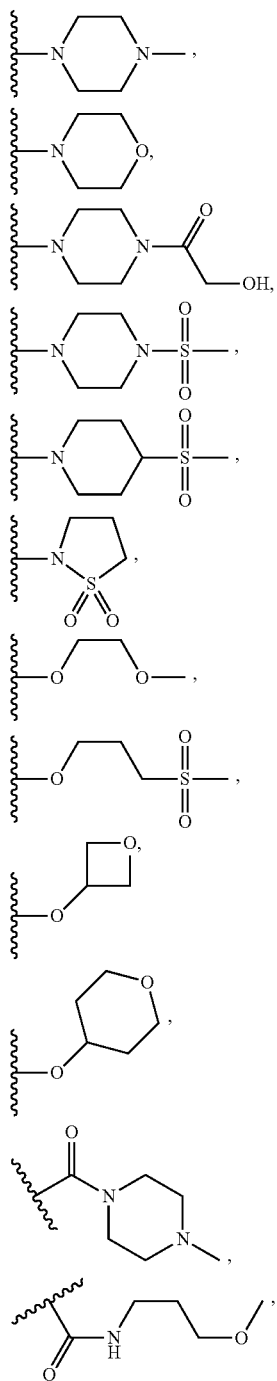

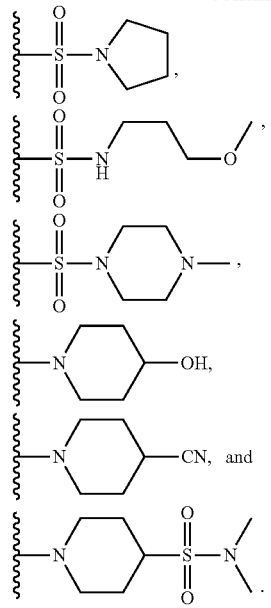

In further embodiments, $R_{18}$ is selected from the group consisting of isopropyl, tert-butyl, —CF$_3$, —OCF$_3$, —OCHF$_2$, and —SCF$_3$.

In further embodiments, $R_1$ is selected from the group consisting of

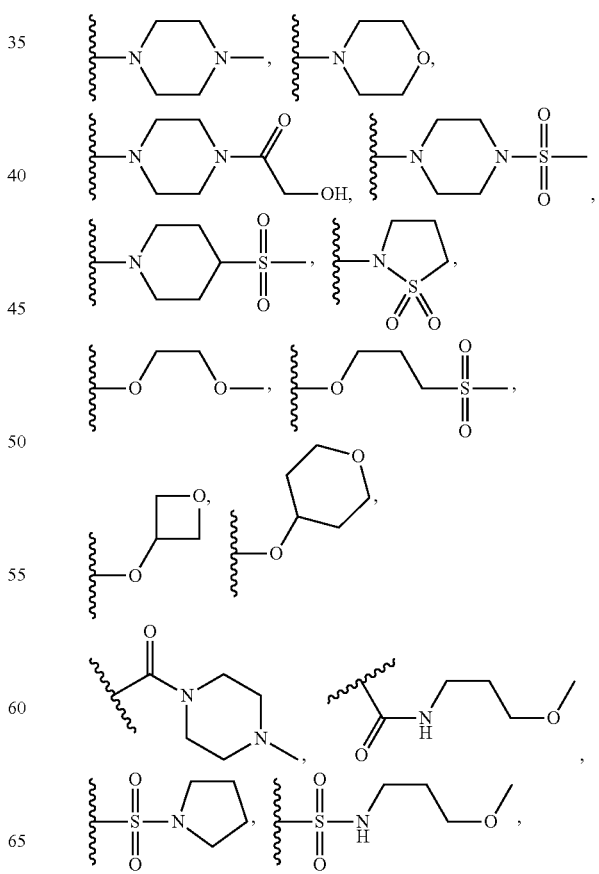

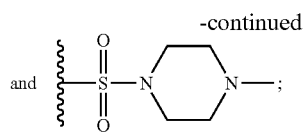

$R_{13}$, $R_{14}$, $R_{16}$, $R_{17}$, and $R_{19}$ are hydrogen; and $R_{18}$ is selected from the group consisting of isopropyl, tert-butyl, —CF$_3$, —OCF$_3$, —OCHF$_2$, and —SCF$_3$.

In certain embodiments, disclosed herein are compounds having structural Formula IV:

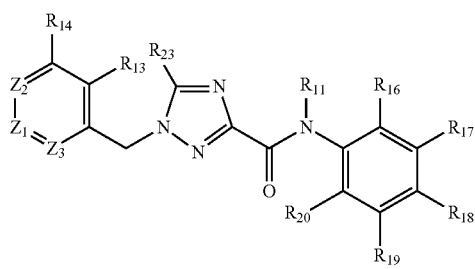

or a salt thereof, wherein:

$Z_1$ and $Z_2$ are independently selected from the group consisting of N, NR$_1$, C=O, and CR$_1$;

$Z_3$ is selected from the group consisting of N, NR$_{12}$, C=O, and CR$_{12}$; R$_1$ is selected from the group consisting of —Y$_2$-alkyl-N(R$_4$)R$_5$, hydrogen, deuterium, halogen, alkyl, alkenyl, haloalkyl, perhaloalkyl, heteroalkyl, hydroxyalkyl, aminoalkyl, acyl, carboxylalkyl, carbonyl, carboxyl, carbonyl, cyano, hydroxy, alkoxy, haloalkoxy, perhaloalkoxy, oxo, alkylthio, thiolalkyl, sulfonyl, sulfonamido, alkylsulfonyl, amino, amido, alkylamino, dialkylamino, nitro, cycloalkyl, aryl, heterocycloalkyl, heteroaryl, cycloalkyloxy, aryloxy, heterocycloalkyloxy, heteroaryloxy,

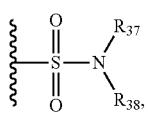

cycloalkylcarbonyl, arylcarbonyl, heterocycloalkylcarbonyl, and heterocycloalkylcarbonylalkyl, any of which can be optionally substituted with one or more substituents selected from the group consisting of hydrogen, deuterium, halogen, alkyl, alkenyl, alkynyl, amidoalkyl, acyl, carboxylalkyl, alkylcarbonyl, heteroalkylcarbonyl, hydroxyalkylcarbonyl, aminoalkylcarbonyl, alkylaminoalkylcarbonyl, alkenylcarbonyl, alkynylcarbonyl, haloalkyl, perhaloalkyl, heteroalkyl, hydroxyalkyl, alkoxyalkyl, carboxyl, cyano, hydroxy, alkoxy, haloalkoxy, perhaloalkoxy, oxo, thiol, acylthio, sulfonamido, alkylsulfonyl, amino, amido, carbamate, alkylamino, dialkylamino, alkylaminoalkyl, dialkylaminoalkyl, trisubstituted silyl, trisubstituted siloxy, cycloalkyl, aryl, heterocycloalkyl, heteroaryl, alkylheterocycloalkyl, any of which may be optionally substituted;

$R_{11}$ is selected from the group consisting of hydrogen, deuterium, alkyl, haloalkyl, perhaloalkyl, heteroalkyl, hydroxyalkyl, cycloalkyl, aryl, heterocycloalkyl, and heteroaryl;

$R_{12}$, $R_{13}$, and $R_{14}$ are independently selected from the group consisting of hydrogen, deuterium, halogen, alkyl, haloalkyl, perhaloalkyl, cyano, hydroxy, alkoxy, haloalkoxy, perhaloalkoxy, alkylthio, amino, and saturated 3- to 7-membered cycloalkyl, any of which may be optionally substituted;

$R_{16}$, $R_{19}$, and $R_{20}$ are independently selected from the group consisting of hydrogen, deuterium, halogen, alkyl, haloalkyl, perhaloalkyl, cyano, hydroxy, alkoxy, haloalkoxy, perhaloalkoxy, alkylthio, amino, and cycloalkyl, any of which may be optionally substituted;

$R_{17}$ and $R_{18}$ are independently selected from the group consisting of hydrogen, deuterium, halogen, alkyl, haloalkyl, perhaloalkyl, heteroalkyl, hydroxyalkyl, alkoxyalkyl, aminoalkyl, dialkylamino, acyl, carbonyl, carboxyl, cyano, cyanoalkyl, hydroxy, alkoxy, haloalkoxy, perhaloalkoxy, alkoxyalkoxy, hydroxyalkoxy, oxo, alkylthio, haloalkylthio, perhaloalkylthio, cyanoalkylthio, alkylsulfonyl, alkoxyalkylsulfonyl, cyanoalkylsulfonyl, haloalkylsulfonyl, sulfonamido, alkylsulfonamido, amino, alkylamino, dialkylamino, amido, cycloalkyl, aryl, heterocycloalkyl, heteroaryl perhaloalkylcycloalkyl, hydroxyheterocycloalkyl, hydroxycycloalkyl, heterocycloalkylcarbonyl, and heterocycloalkylalkyl, any of which can be optionally substituted; and $R_{23}$ is selected from the group consisting of hydrogen, deuterium, hydroxyl, alkyl, haloalkyl, perhaloalkyl, cyano, saturated 3- to 6-membered cycloalkyl, 4- to 6-membered heterocycloalkyl, and 5- to 6-membered heteroaryl.

In further embodiments, $R_{11}$ is hydrogen.

In further embodiments, at least one of $Z_1$ or $Z_2$ is CR$_1$;

$R_1$ is selected from the group consisting of —Y$_2$-alkyl-N(R$_4$)R$_5$, hydrogen, deuterium, halogen, alkyl, alkenyl, haloalkyl, perhaloalkyl, heteroalkyl, hydroxyalkyl, acyl, carboxylalkyl, carboxyl, carbonyl, cyano, hydroxy, alkoxy, haloalkoxy, perhaloalkoxy, oxo, thiolalkyl, sulfonyl, sulfonamido, alkylsulfonyl, amino, amido, alkylamino, dialkylamino, nitro, heterocycloalkyl, heterocycloalkyloxy,

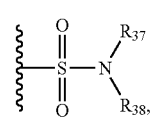

heterocycloalkylcarbonylalkyl, and heterocycloalkylcarbonyl, any of which can be optionally substituted with one or more substituents selected from the group consisting of hydrogen, deuterium, halogen, alkyl, alkenyl, amidoalkyl, acyl, carboxylalkyl, hydroxyalkylcarbonyl, alkynylcarbonyl, heteroalkyl, hydroxyalkyl, alkoxyalkyl, carboxyl, cyano, hydroxy, alkoxy, oxo, sulfonamido, alkylsulfonyl, amino, amido, carbamate, dialkylamino, dialkylaminoalkyl, trisubstituted siloxy, cycloalkyl, heterocycloalkyl, alkylheterocycloalkyl, any of which may be optionally substituted;

$R_{11}$ is selected from the group consisting of hydrogen, deuterium, alkyl, and cycloalkyl;

$R_{12}$, $R_{13}$, and $R_{14}$ are hydrogen;

$R_{16}$, $R_{17}$, $R_{19}$, and $R_{20}$ are hydrogen; and $R_{23}$ is selected from the group consisting of hydrogen, deuterium, hydroxyl, alkyl, haloalkyl, perhaloalkyl, cyano, and saturated 3- to 6-membered cycloalkyl.

In further embodiments, $R_1$ is selected from the group consisting of hydrogen, deuterium, fluorine, bromine, cyano, methyl, isopropyl,

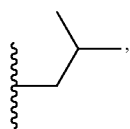 [SMILES: *CC(C)C]
ethylene,
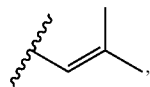 [SMILES: *C=C(C)C]
trifluoromethyl, bromomethyl, hydroxymethyl, difluoromethoxy, methoxy, ethoxy, isopropoxy, hydroxy, nitro, acetyl, carboxyl, —CO$_2$CH$_3$,
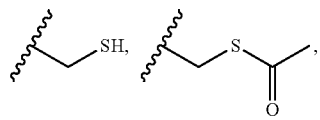
—SO$_2$CH$_3$, —SO$_2$CH$_2$CH$_3$, SO$_2$CH$_2$CH$_2$CH$_3$, —SO$_2$NH$_2$,
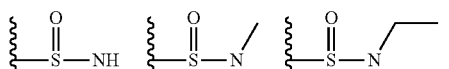
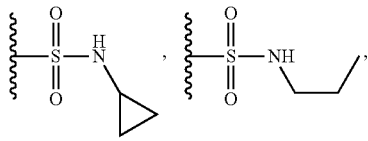
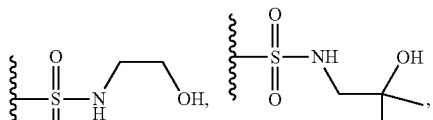
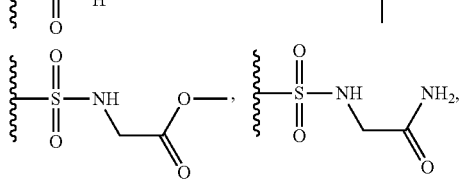
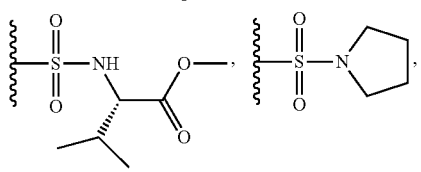
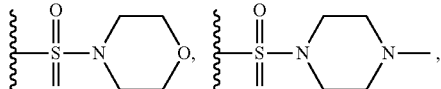
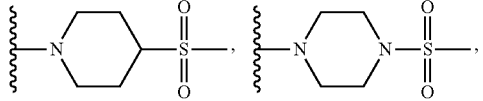
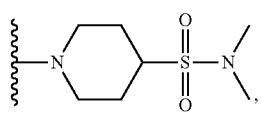
amino, methylamino, dimethylamino,
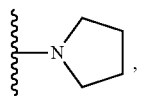
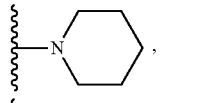
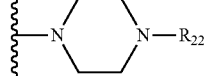
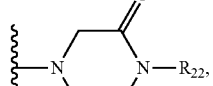
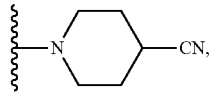
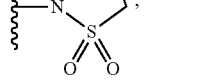
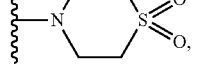
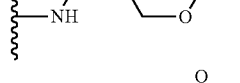
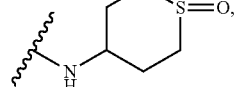
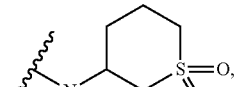
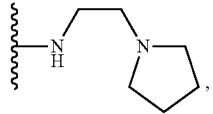

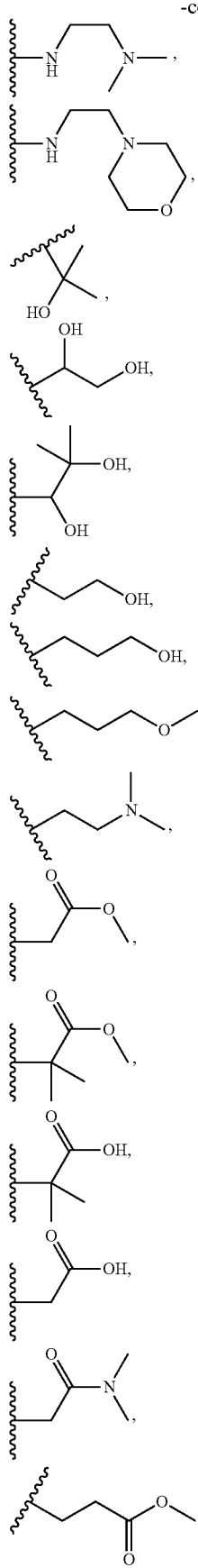
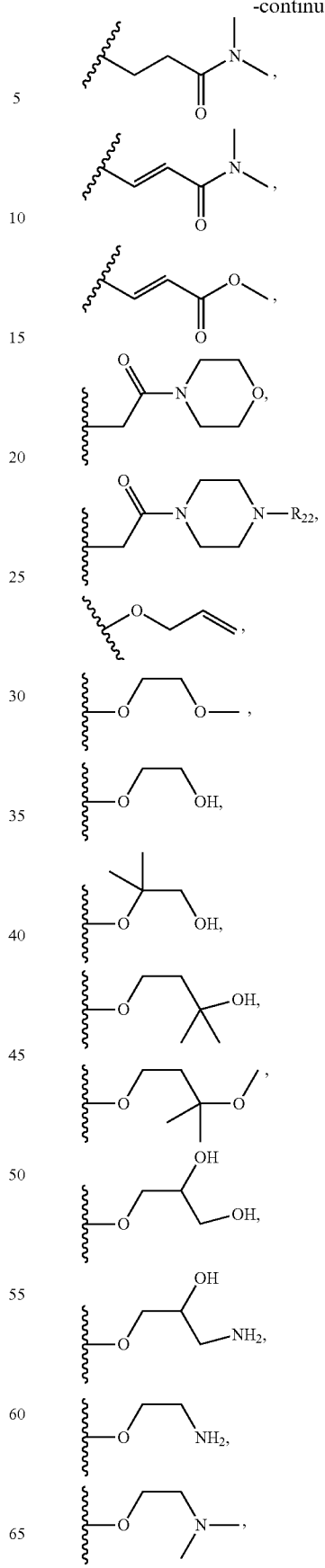

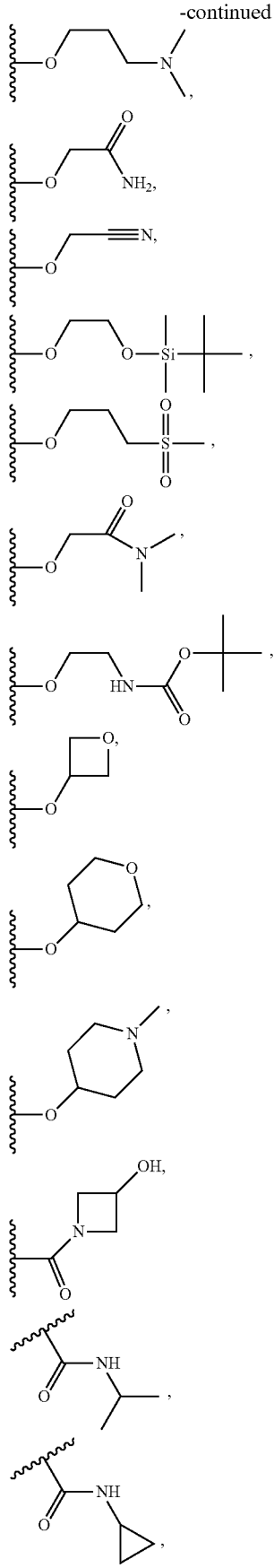
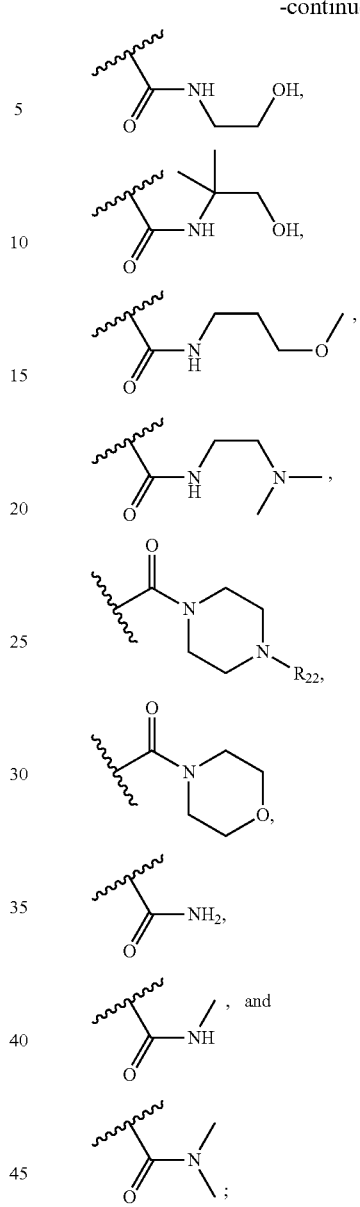
$R_{18}$ is selected from the group consisting of hydrogen, deuterium, halogen, methyl, isopropyl, tert-butyl, cyclopropyl, cyclohexyl, acetyl, hydroxymethyl, methoxymethyl, methoxy, isopropoxy, methylamino, dimethylamino, methylthio, cyanomethyl, cyanomethylthio, cyano, —SO$_2$CH$_3$, —SO$_2$CH(CH$_3$)$_2$, —SO$_2$CH$_2$CH(CH$_3$)$_2$, —SO$_2$NHCH$_2$CH$_2$CH$_3$, —SO$_2$CHF$_2$, —SO$_2$CF$_3$,
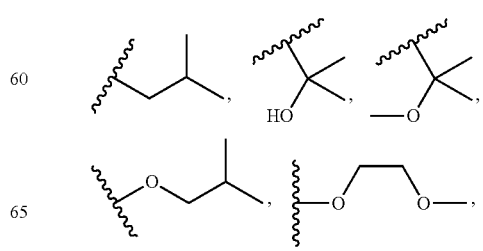

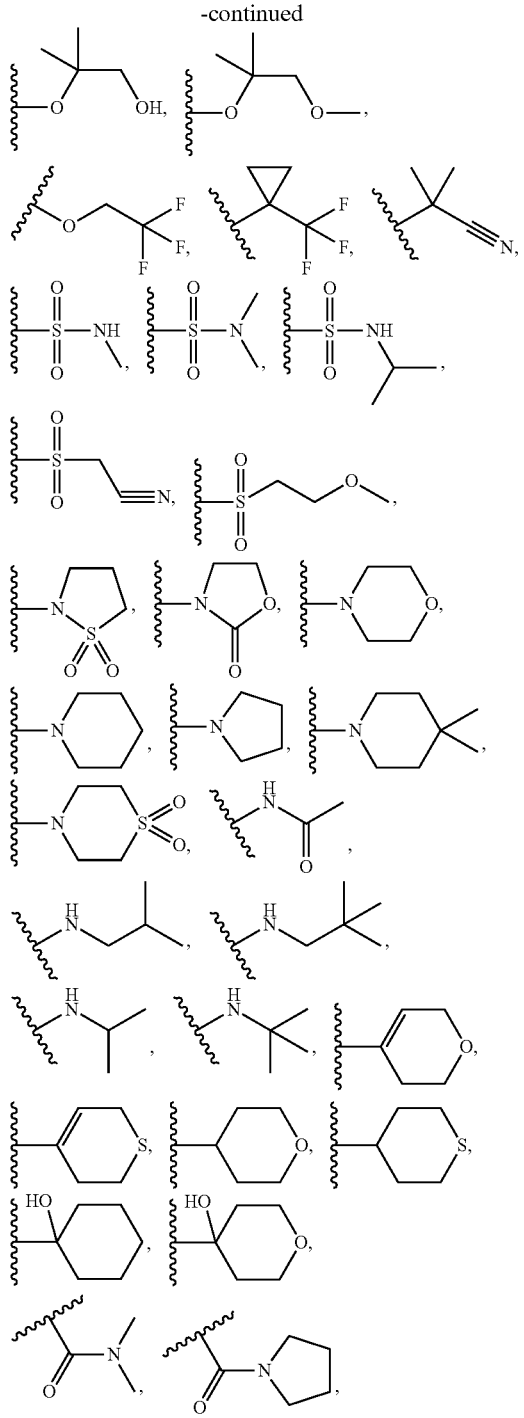
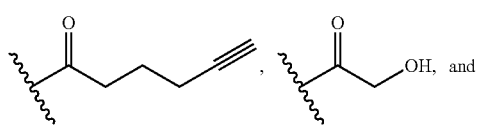

trifluoromethyl, trifluoromethylthio, difluoromethoxy, and trifluoromethoxy;

$R_{22}$ is selected from the group consisting of hydrogen, deuterium, methyl, acetyl,

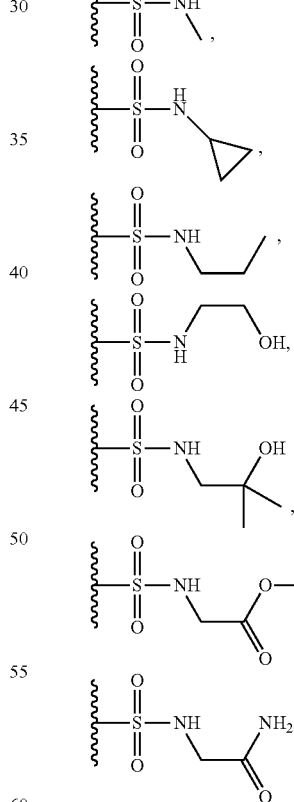

and $R_{23}$ is selected from the group consisting of hydrogen, deuterium, methyl, ethyl, 3-pyridyl, and cyclopropyl.

In further embodiments of the present invention, $R_1$ is selected from the group consisting of hydrogen, halogen, cyano, methyl, isopropyl,

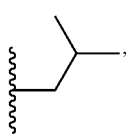 [SMILES: *CC(C)C]

ethylene, trifluoromethyl, difluoromethoxy, methoxy, ethoxy, isopropoxy, hydroxy, carboxyl, —CO$_2$CH$_3$, —SO$_2$CH$_3$, —SO$_2$NH$_2$,

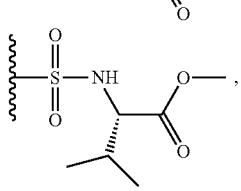

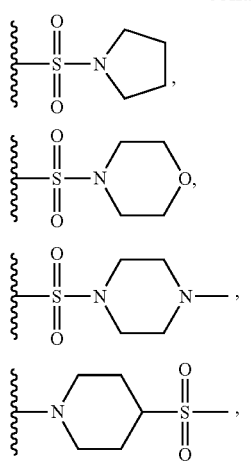
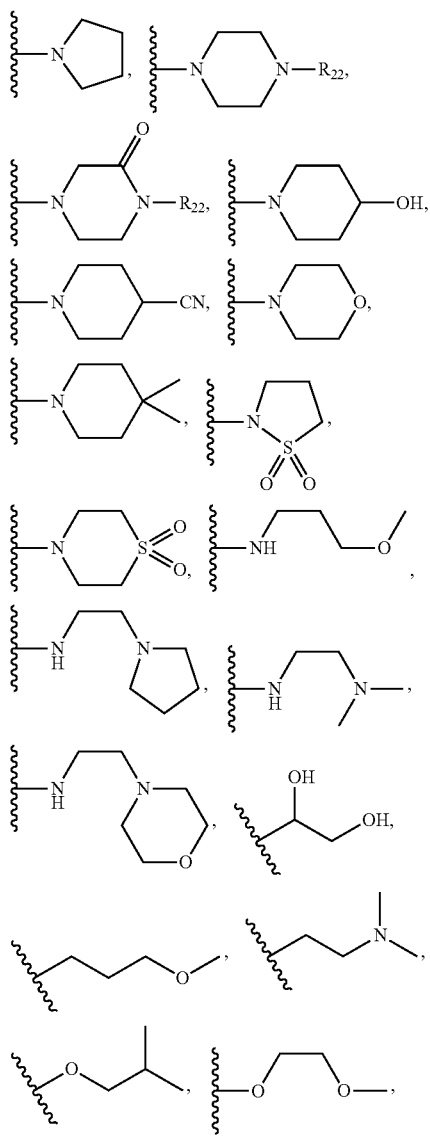
amino, methylamino, dimethylamino,
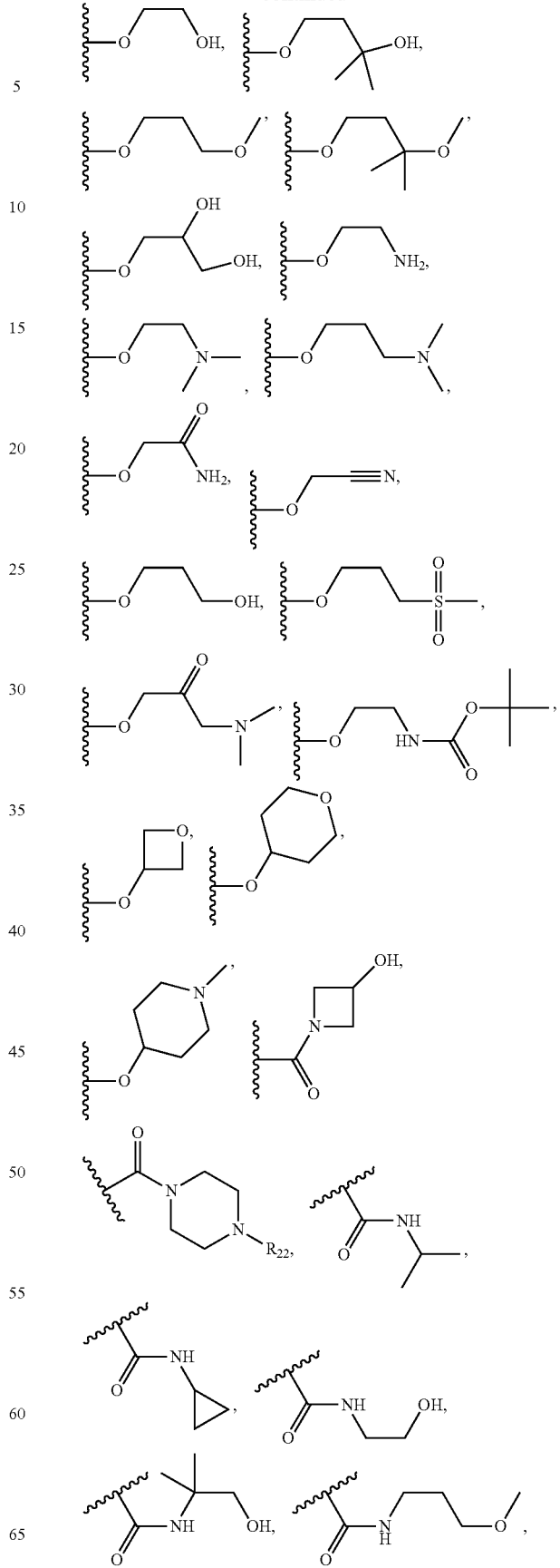

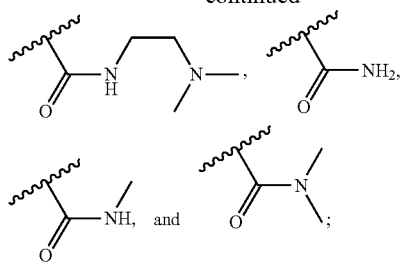

and

R$_{23}$ is methyl.

In further embodiments, R$_{11}$ is hydrogen.

In certain embodiments, disclosed herein are compounds having structural Formula V:

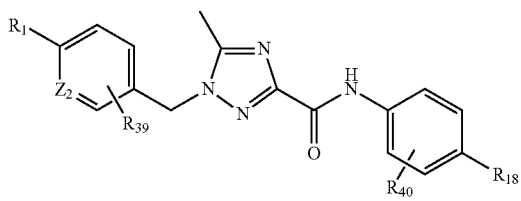

(V)

or a salt thereof, wherein:

Z$_2$ is selected from the group consisting of N and CR$_{14}$;

R$_1$ is selected from the group consisting of heterocycloalkyl, alkoxyalkoxy, alkylsulfonylalkoxy, heterocycloalkyloxy, heterocycloalkylcarbonyl, alkoxyalkylamido, heterocycloalkylsulfonyl, alkoxyalkylsulfonamido, wherein said heterocycloalkyl, heterocycloalkyloxy, heterocycloalkylcarbonyl, and heterocycloalkylsulfonyl can be optionally substituted with one or more substituents selected from the group consisting hydrogen, alkyl, and oxo;

R$_{14}$, R$_{39}$, and R$_{40}$ are independently selected from the group consisting of hydrogen, deuterium, halogen, alkyl, haloalkyl, perhaloalkyl, cyano, hydroxy, alkoxy, haloalkoxy, perhaloalkoxy, alkylthio, amino, and saturated 3- to 7-membered cycloalkyl, any of which may be optionally substituted; and R$_{18}$ is selected from the group consisting of alkyl, haloalkyl, perhaloalkyl, alkoxy, haloalkoxy, perhaloalkoxy, alkylthio, haloalkylthio, and perhaloalkylthio.

In further embodiments, R$_1$ is selected from the group consisting of

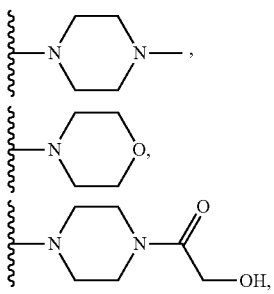

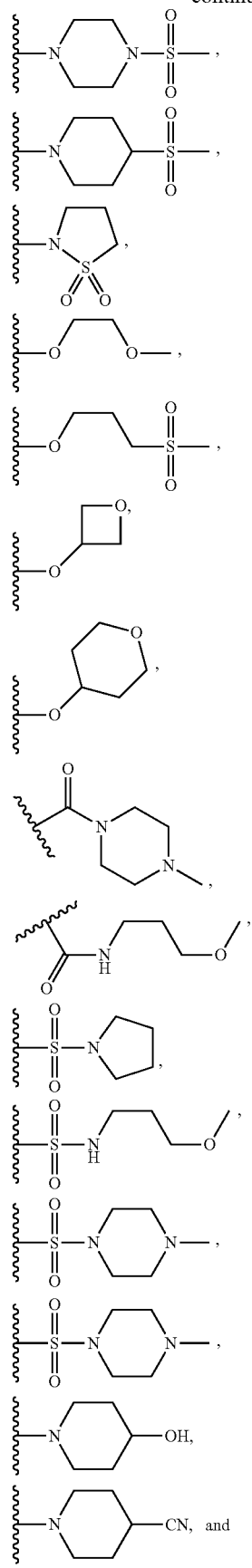

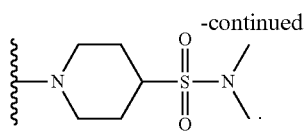

In further embodiments, $R_{18}$ is selected from the group consisting of isopropyl, tert-butyl, —$CF_3$, —$OCF_3$, —$OCHF_2$, and —$SCF_3$.

In further embodiments,
$R_1$ is selected from the group consisting of

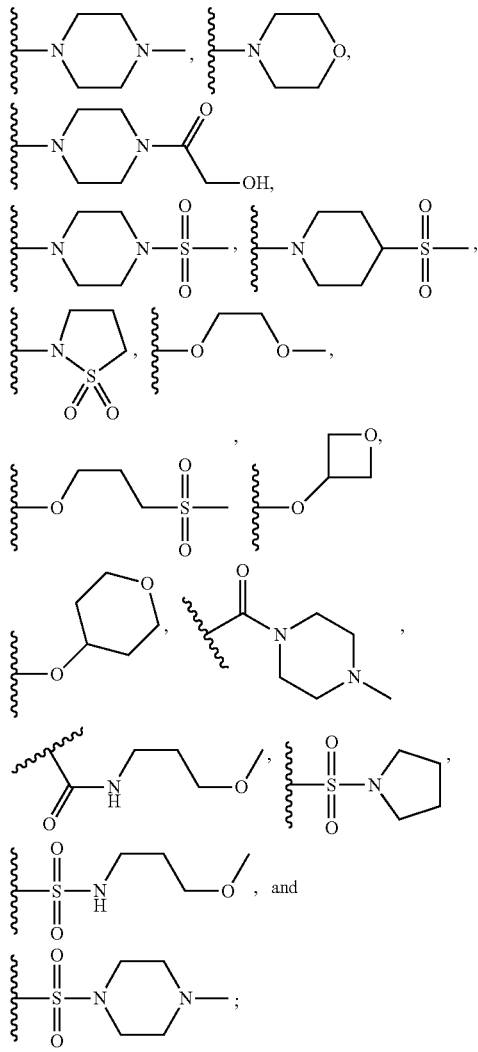

$R_{13}$, $R_{14}$, $R_{16}$, $R_{17}$, and $R_{19}$ are hydrogen; and
$R_{18}$ is selected from the group consisting of isopropyl, tert-butyl, —$CF_3$, —$OCF_3$, —$OCHF_2$, and —$SCF_3$.

In further embodiments, disclosed herein is a compound selected from the group consisting of Examples 1 to 163, or a salt thereof.

In further embodiments, disclosed herein is a pharmaceutical composition comprising a compound as disclosed herein together with a pharmaceutically acceptable carrier.

In further embodiments, disclosed herein is a method of treatment of a HIF pathway-mediated disease comprising the administration of a therapeutically effective amount of a compound as disclosed herein to a patient in need thereof.

In further embodiments, said disease is cancer.

In further embodiments, said cancer is selected from the group consisting of colon cancer, breast cancer, ovarian cancer, lung cancer, prostate cancer; cancers of the oral cavity and pharynx (lip, tongue, mouth, larynx, pharynx), esophagus, stomach, small intestine, large intestine, colon, rectum, liver and biliary passages; pancreas, bone, connective tissue, skin, cervix, uterus, corpus endometrium, testis, bladder, kidney and other urinary tissues, including renal cell carcinoma (RCC); cancers of the eye, brain, spinal cord, and other components of the central and peripheral nervous systems, as well as associated structures such as the meninges; cancers of the thyroid and other endocrine glands; Hodgkin's disease, non-Hodgkin's lymphomas, multiple myeloma, hematopoietic malignancies including leukemias (Chronic Lymphocytic Leukemia (CLL), Acute Lymphocytic Leukemia (ALL)) and lymphomas including lymphocytic, granulocytic and monocytic; adrenocarcinoma, angiosarcoma, astrocytoma, acoustic neuroma, anaplastic astrocytoma, basal cell carcinoma, blastoglioma, chondrosarcoma, choriocarcinoma, chordoma, craniopharyngioma, cutaneous melanoma, cystadenocarcinoma, endotheliosarcoma, embryonal carcinoma, ependymoma, Ewing's tumor, epithelial carcinoma, fibrosarcoma, gastric cancer, genitourinary tract cancers, glioblastoma multiforme, head and neck cancer, hemangioblastoma, hepatocellular carcinoma, hepatoma, Kaposi's sarcoma, large cell carcinoma, leiomyosarcoma, leukemias, liposarcoma, lymphatic system cancer, lymphomas, lymphangiosarcoma, lymphangioendotheliosarcoma, medullary thyroid carcinoma, medulloblastoma, meningioma mesothelioma, myelomas, myxosarcoma neuroblastoma, neurofibrosarcoma, oligodendroglioma, osteogenic sarcoma, epithelial ovarian cancer, papillary carcinoma, papillary adenocarcinomas, paraganglioma, parathyroid tumours, pheochromocytoma, pinealoma, plasmacytomas, retinoblastoma, rhabdomyosarcoma, sebaceous gland carcinoma, seminoma, skin cancers, melanoma, small cell lung carcinoma, non-small cell lung carcinoma, squamous cell carcinoma, sweat gland carcinoma, synovioma, thyroid cancer, uveal melanoma, and Wilm's tumor.

In further embodiments, disclosed herein is a method of treatment of a disease caused by abnormal cell proliferation comprising the administration of a therapeutically effective amount of a compound as disclosed herein to a patient in need thereof.

In further embodiments, disclosed herein is a method of treatment of a HIF pathway-mediated disease comprising the administration of:
a. a therapeutically effective amount of a compound as disclosed herein; and
b. another therapeutic agent.

In further embodiments, disclosed herein is a method for achieving an effect in a patient comprising the administration of a therapeutically effective amount of a compound as disclosed herein to a patient, wherein the effect is selected from the group consisting of preventing or reducing resistance to radiotherapy and chemotherapy, preventing or reducing tumor invasion and tumor metastasis, and preventing or reducing angiogenesis.

In certain embodiments, the compositions and methods disclosed herein may be used to inhibit HIF pathway activity, to downregulate HIF-1α (which is induced by hypoxia or genetic alterations, as well as in various disease states, e.g. in persons with certain genetic backgrounds), by increasing HIF-1α degradation, decreasing HIF heterodimer formation, increasing HIF-1α prolyl hydroxylation, and/or to reduce transcription of hypoxia response element (HRE) downstream elements.

In certain embodiments, the compositions and methods disclosed herein may be used to reduce tumor growth, to inhibit neoangiogenesis (e.g., by downregulating VEGF), to normalize tumor vasculature, to enhance radiotherapy and chemotherapy, to prevent metastasis, to reduce tumor stem cell numbers, and to prevent induction of anaerobic cellular metabolism.

In certain embodiments, the compositions and methods disclosed herein may be used to treat HIF-deregulated diseases with an inflammatory component, such as cancers, stroke, and rheumatoid arthritis.

In certain embodiments, the compositions and methods disclosed herein may be used to treat HIF-deregulated diseases cardiovascular diseases such as cardiac arrhythmia and heart failure.

In certain embodiments, the compositions and methods disclosed herein are useful for preventing or reducing resistance to radiotherapy and chemotherapy.

In certain embodiments, the compositions and methods disclosed herein are useful for preventing or reducing tumor invasion and tumor metastasis.

In certain embodiments, the compositions and methods disclosed herein are useful for preventing or reducing angiogenesis and disorders related to angiogenesis.

In certain embodiments, the compounds disclosed herein may be used as a medicament.

In further embodiments, said compounds which may be used as a medicament include the compounds of Formula I, II, III, IV, and V, optionally including any further limitation to the scope of said Formulas as defined above. In further embodiments, said compounds may be selected from the group consisting of Examples 1 to 163, or a salt thereof.

In certain embodiments, the disclosed are compounds for use in the treatment of a HIF pathway-mediated disease.

In further embodiments, said compounds which may be used in the treatment of a HIF pathway-mediated disease include the compounds of Formula I, II, III, IV, and V, optionally including any further limitation to the scope of said Formulas as defined above. In further embodiments, said compounds may be selected from the group consisting of Examples 1 to 163, or a salt thereof.

In further embodiments, said disease is cancer.

In further embodiments, said cancer is selected from the group consisting of colon cancer, breast cancer, ovarian cancer, lung cancer, prostrate cancer; cancers of the oral cavity and pharynx (lip, tongue, mouth, larynx, pharynx), esophagus, stomach, small intestine, large intestine, colon, rectum, liver and biliary passages; pancreas, bone, connective tissue, skin, cervix, uterus, corpus endometrium, testis, bladder, kidney and other urinary tissues, including renal cell carcinoma (RCC); cancers of the eye, brain, spinal cord, and other components of the central and peripheral nervous systems, as well as associated structures such as the meninges; cancers of the thyroid and other endocrine glands; Hodgkin's disease, non-Hodgkin's lymphomas, multiple myeloma, hematopoietic malignancies including leukemias (Chronic Lymphocytic Leukemia (CLL), Acute Lymphocytic Leukemia (ALL)) and lymphomas including lymphocytic, granulocytic and monocytic; adrenocarcinoma, angiosarcoma, astrocytoma, acoustic neuroma, anaplastic astrocytoma, basal cell carcinoma, blastoglioma, chondrosarcoma, choriocarcinoma, chordoma, craniopharyngioma, cutaneous melanoma, cystadenocarcinoma, endotheliosarcoma, embryonal carcinoma, ependymoma, Ewing's tumor, epithelial carcinoma, fibrosarcoma, gastric cancer, genitourinary tract cancers, glioblastoma multiforme, head and neck cancer, hemangioblastoma, hepatocellular carcinoma, hepatoma, Kaposi's sarcoma, large cell carcinoma, leiomyosarcoma, leukemias, liposarcoma, lymphatic system cancer, lymphomas, lymphangiosarcoma, lymphangioendotheliosarcoma, medullary thyroid carcinoma, medulloblastoma, meningioma mesothelioma, myelomas, myxosarcoma neuroblastoma, neurofibrosarcoma, oligodendroglioma, osteogenic sarcoma, epithelial ovarian cancer, papillary carcinoma, papillary adenocarcinomas, paraganglioma, parathyroid tumours, pheochromocytoma, pinealoma, plasmacytomas, retinoblastoma, rhabdomyosarcoma, sebaceous gland carcinoma, seminoma, skin cancers, melanoma, small cell lung carcinoma, non-small cell lung carcinoma, squamous cell carcinoma, sweat gland carcinoma, synovioma, thyroid cancer, uveal melanoma, and Wilm's tumor.

In certain embodiments, disclosed herein are compounds for use in the treatment of a disease caused by abnormal cell proliferation.

In certain embodiments, disclosed herein are compounds for use in the treatment of HIF-deregulated diseases with an inflammatory component, such as cancers, stroke, and rheumatoid arthritis.

In certain embodiments, disclosed herein are compounds for use in the treatment of HIF-deregulated cardiovascular diseases such as cardiac arrhythmia and heart failure.

In certain embodiments, disclosed herein are compounds for use in the treatment of preventing or reducing resistance to radiotherapy and chemotherapy.

In certain embodiments, disclosed herein are compounds for use in the prevention or reduction of tumor invasion and tumor metastasis.

In certain embodiments, disclosed herein are compounds for use in the prevention or reduction of angiogenesis and disorders related to angiogenesis.

In further embodiments, said compounds which may be used in the treatment of a disease caused by abnormal cell proliferation, HIF-deregulated diseases with an inflammatory component, such as cancers, stroke, and rheumatoid arthritis, HIF-deregulated cardiovascular diseases such as cardiac arrhythmia and heart failure, for use in preventing or reducing resistance to radiotherapy and chemotherapy, prevention or reduction of tumor invasion and tumor metastasis, or prevention or reduction of angiogenesis and disorders related to angiogenesis include the compounds of Formula I, II, III, IV, and V, optionally including any further limitation to the scope of said Formulas as defined above. In further embodiments, said compounds may be selected from the group consisting of Examples 1 to 163, or a salt thereof.

BRIEF DESCRIPTION OF THE DRAWINGS

FIG. 2—Compounds of this invention inhibit the growth of neuroblastoma NB-1 cells as shown by reduced number of viable cells following treatment with Examples 2 (FIG. 2A) and 80 (FIG. 2B).

FIG. 4—Compounds of this invention inhibit the growth of glioblastoma D423 cells as shown by reduced number of viable cells following treatment with Examples 2 (FIG. 4A) and 80 (FIG. 4B).

Figure 1:
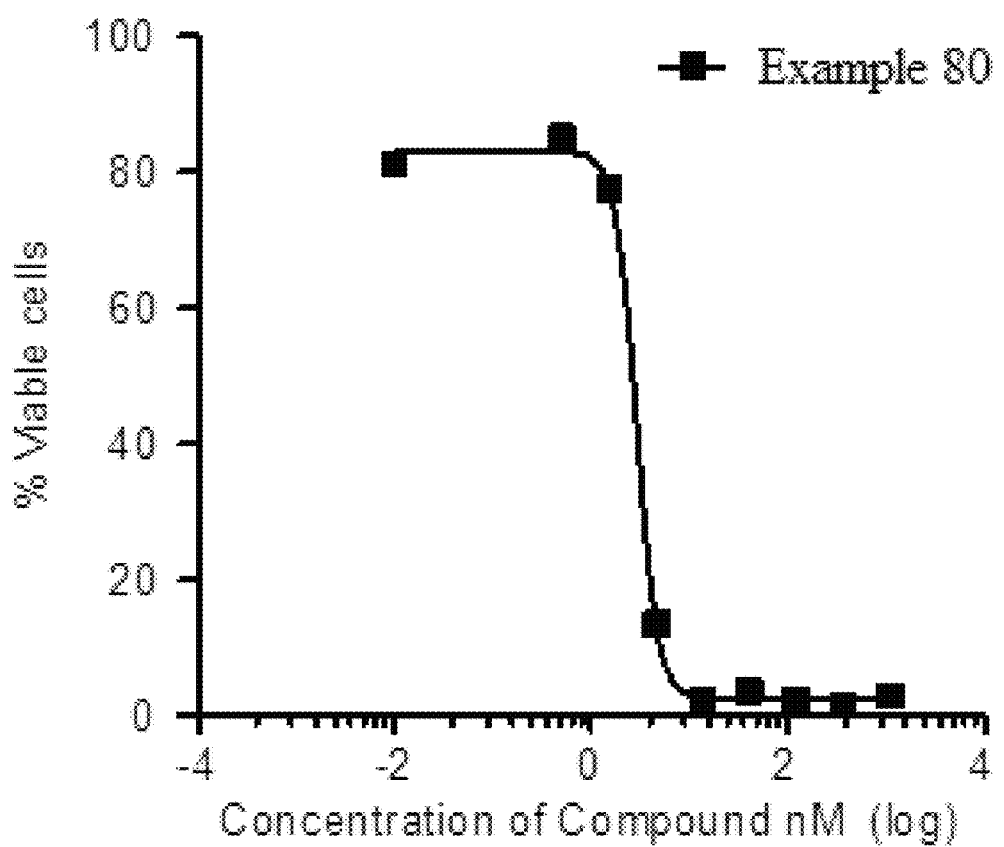
FIG. 1—Compounds of this invention inhibit the growth of diffuse large B-cell lymphoma TMD8 cells as shown by reduced number of viable cells following treatment with Example 80.

Unless otherwise defined, all technical and scientific terms used herein have the same meaning as commonly understood by one of ordinary skill in the art to which this invention belongs. When a conflict occurs, the meaning ascribed herein controls.

When ranges of values are disclosed, and the notation "from n1 . . . to n2" is used, where n1 and n2 are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a —C(O)CH$_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds and containing from 2 to 20 carbon atoms. In certain embodiments, said alkenyl will comprise from 2 to 6 carbon atoms. The term "alkenylene" refers to a carbon-carbon double bond system attached at two or more positions such as ethenylene [(—CH=CH—),(—C::C—)]. Examples of suitable alkenyl radicals include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to 20 carbon atoms. In certain embodiments, said alkyl will comprise from 1 to 10 carbon atoms. In further embodiments, said alkyl will comprise from 1 to 6 carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—CH$_2$—). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) radical wherein the term alkyl is as defined above and wherein the sulfur may be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon radical having one or more triple bonds and containing from 2 to 20 carbon atoms. In certain embodiments, said alkynyl comprises from 2 to 6 carbon atoms. In further embodiments, said alkynyl comprises from 2 to 4 carbon atoms. The term "alkynylene" refers to a carbon-carbon triple bond attached at two positions such as ethynylene (—C:::C—, —C≡C—). Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl," as used herein, alone or in combination, refer to an amino group as described below attached to the parent molecular moiety through a carbonyl group, or vice versa. The term "C-amido" as used herein, alone or in combination, refers to a —C(O)N(RR') group with R and R' as defined herein or as defined by the specifically enumerated "R" groups designated. The term "N-amido" as used herein, alone or in combination, refers to a RC(O)N(R')— group, with R and R' as defined herein or as defined by the specifically enumerated "R" groups designated. The term "acylamino" as used herein, alone or in combination, embraces an acyl group attached to the parent moiety through an amino group. An example of an "acylamino" group is acetylamino ($CH_3C(O)NH—$).

The term "amino," as used herein, alone or in combination, refers to NRR', wherein R and R' are independently selected from the group consisting of hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl radical derived from an aryl-substituted alkanecarboxylic acid such as benzoyl, napthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent radical $C_6H_4$=derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O-carbamyl" as used herein, alone or in combination, refers to a —OC(O)NRR', group—with R and R' as defined herein.

The term "N-carbamyl" as used herein, alone or in combination, refers to a ROC(O)NR'— group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, said cycloalkyl will comprise from 5 to 7 carbon atoms. Examples of such cycloalkyl groups include cyclopropyl, cyclobutyl, cyclopentyl, cyclohexyl, cycloheptyl, tetrahydronaphthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type, including spiro-ring fused systems. The bicyclic and tricyclic types of isomer are exemplified in general by, bicyclo[1,1,1]pentane, camphor, adamantane, bicyclo[3,2,1] octane, and [4,4.1]-bicyclononane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—$CF_2$—), chloromethylene (—CHCl—) and the like.

The term "heteroalkyl," as used herein, alone or in combination, refers to a stable straight or branched chain, or cyclic hydrocarbon radical, or combinations thereof, fully saturated or containing from 1 to 3 degrees of unsaturation, consisting of the stated number of carbon atoms and from one to three heteroatoms selected from the group consisting of O, N, and S, and wherein the nitrogen and sulfur atoms may optionally be oxidized and the nitrogen heteroatom may optionally be quaternized. The heteroatom(s) O, N and S may be placed at any interior position of the heteroalkyl group. Up to two heteroatoms may be consecutive, such as, for example, —$CH_2$—NH—$OCH_3$.

The term "heteroaryl," as used herein, alone or in combination, refers to a 3 to 15 membered unsaturated heteromonocyclic ring, or a fused monocyclic, bicyclic, or tricyclic ring system in which at least one of the fused rings is aromatic, which contains at least one atom selected from the group consisting of O, S, and N. In certain embodiments, said heteroaryl will comprise from 5 to 7 carbon atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated monocyclic, bicyclic, or tricyclic heterocyclic group containing at least one heteroatom as a ring member, wherein each said heteroatom may be independently selected from the group consisting of nitrogen, oxygen, and sulfur In certain embodiments, said heterocycloalkyl will comprise from 1 to 4 heteroatoms as ring members. In further embodiments, said heterocycloalkyl will comprise from 1 to 2 heteroatoms as ring members. In certain embodiments, said heterocycloalkyl will comprise from 3 to 8 ring members in each ring. In further embodiments, said heterocycloalkyl will comprise from 3 to 7 ring members in each ring. In yet further embodiments, said heterocycloalkyl will comprise from 5 to 6 ring members in each ring. "Heterocycloalkyl" and "heterocycle" are intended to include sulfones, cyclic sulfonamides, sulfoxides, N-oxides of tertiary nitrogen ring members, and carbocyclic fused, benzo fused, and spiro-ring fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihydropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, isothiazolidine, and the like. The heterocycle groups may be optionally substituted unless specifically prohibited.

The term "hydrogen," as used herein, refers to both protium ($^1$H) and deuterium ($^2$H). This definition extends to hydrogen atoms which appear in chemical structural drawings disclosed herein, including at sites where hydrogen atoms are not explicitly shown. For example, a chemical structure disclosed herein may include an ethyl group represented as

which includes five hydrogen atoms which are not explicitly drawn, any of which can be protium ($^1$H) or deuterium ($^2$H). This definition also extends to hydrogen atoms which form a part of a named chemical substituent disclosed herein. For example, a generic chemical structure disclosed herein may recite an aryl group, which encompasses specific embodiments such as a phenyl group, which comprises five hydrogen atoms, any of which can be protium ($^1$H) or deuterium ($^2$H).

The term "deuterium enrichment" refers to the percentage of incorporation of deuterium at a given position in a molecule in the place of hydrogen. For example, deuterium enrichment of 1% at a given position means that 1% of molecules in a given sample contain deuterium at the specified position. Because the naturally occurring distribution of deuterium is about 0.0156%, deuterium enrichment at any position in a compound synthesized using non-enriched starting materials is about 0.0156%. The deuterium enrichment can be determined using conventional analytical methods known to one of ordinary skill in the art, including mass spectrometry and nuclear magnetic resonance spectroscopy.

In certain embodiments, compounds disclosed herein are enriched with deuterium. Carbon-hydrogen bond strength is directly proportional to the absolute value of the ground-state vibrational energy of the bond. This vibrational energy depends on the mass of the atoms that form the bond, and increases as the mass of one or both of the atoms making the bond increases. Since deuterium (D) has twice the mass of protium ($^1$H), a C-D bond is stronger than the corresponding C—$^1$H bond. If a C—$^1$H bond is broken during a rate-determining step in a chemical reaction (i.e. the step with the highest transition state energy), then substituting a deuterium for that protium will cause a decrease in the reaction rate, including cases where a C—H bond is broken during metabolism of a compound disclosed herein. This phenomenon is known as the Deuterium Kinetic Isotope Effect (DKIE). The magnitude of the DKIE can be expressed as the ratio between the rates of a given reaction in which a C-$^1$H bond is broken, and the same reaction where deuterium is substituted for protium. The DKIE can range from about 1 (no isotope effect) to very large numbers, such as 50 or more. The deuteration approach has the potential to slow the metabolism of the compounds disclosed herein. Various deuteration patterns can be used to (a) reduce or eliminate unwanted metabolites, (b) increase the half-life of the parent drug, (c) decrease the number of doses needed to achieve a desired effect, (d) decrease the amount of a dose needed to achieve a desired effect, (e) increase the formation of active metabolites, if any are formed, (f) decrease the production of deleterious metabolites in specific tissues, and/or (g) create a more effective drug and/or a safer drug for polypharmacy, whether the polypharmacy be intentional or not. Deuterium can be introduced into a compound as disclosed herein by synthetic techniques that employ deuterated reagents, whereby incorporation rates are pre-determined; and/or by exchange techniques, wherein incorporation rates are determined by equilibrium conditions, and may be highly variable depending on the reaction conditions. Synthetic techniques where deuterium is directly and specifically inserted by a deuterated reagent of known isotopic content, can yield high deuterium abundance, but can be limited by the chemistry required. Exchange techniques, on the other hand, may yield lower deuterium incorporation, often with the isotope being distributed over many sites on the molecule.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N(OH) and =N—O—.

The phrase "in the main chain" refers to the longest contiguous or adjacent chain of carbon atoms starting at the point of attachment of a group to the compounds of any one of the formulas disclosed herein.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower," as used herein, alone or in a combination, where not otherwise specifically defined, means containing from 1 to and including 6 carbon atoms.

The term "lower aryl," as used herein, alone or in combination, means phenyl or naphthyl, either of which may be optionally substituted as provided.

The term "lower heteroaryl," as used herein, alone or in combination, means either 1) monocyclic heteroaryl comprising five or six ring members, of which between one and four said members may be heteroatoms selected from the group consisting of O, S, and N, or 2) bicyclic heteroaryl, wherein each of the fused rings comprises five or six ring members, comprising between them one to four heteroatoms selected from the group consisting of O, S, and N.

The term "lower cycloalkyl," as used herein, alone or in combination, means a monocyclic cycloalkyl having between three and six ring members. Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms selected from the group consisting of O, S, and N. Examples of lower heterocycloalkyls include pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to —NRR', wherein R and R' are independently selected from the group consisting of hydrogen, lower alkyl, and lower heteroalkyl, any of which may be optionally substituted. Additionally, the R and R' of a lower amino group may combine to form a five- or six-membered heterocycloalkyl, either of which may be optionally substituted.

The term "mercaptyl" as used herein, alone or in combination, refers to an RS— group, where R is as defined herein.

The term "nitro," as used herein, alone or in combination, refers to —NO$_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The terms "sulfonate," "sulfonic acid," and "sulfonic," as used herein, alone or in combination, refer the —SO$_3$H group and its anion as the sulfonic acid is used in salt formation.

The term "sulfanyl," as used herein, alone or in combination, refers to —S—.

The term "sulfinyl," as used herein, alone or in combination, refers to S(O)—.

The term "sulfonyl," as used herein, alone or in combination, refers to —S(O)$_2$—.

The term "N-sulfonamido" refers to a RS(=O)$_2$NR'— group with R and R' as defined herein.

The term "S-sulfonamido" refers to a —S(=O)$_2$NRR', group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR'— group, with R and R' as defined herein.

The term "O-thiocarbamyl" refers to a —OC(S)NRR', group with R and R' as defined herein.

The term "thiocyanato" refers to a —CNS group.

The term "trihalomethanesulfonamido" refers to a X$_3$CS(O)$_2$NR— group with X is a halogen and R as defined herein.

The term "trihalomethanesulfonyl" refers to a X$_3$CS(O)$_2$— group where X is a halogen.

The term "trihalomethoxy" refers to a X$_3$CO— group where X is a halogen.

The term "trisubstituted silyl," as used herein, alone or in combination, refers to a silicone group substituted at its three free valences with groups as listed herein under the definition of substituted amino. Examples include trimethylsilyl, tert-butyldimethylsilyl, triphenylsilyl and the like.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, N$_3$, SH, SCH₃, C(O)CH₃, CO₂CH₃, CO₂H, pyridinyl, thiophene, furanyl, lower carbamate, and lower urea. Two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —CH₂CH₃), fully substituted (e.g., —CF₂CF₃), monosubstituted (e.g., —CH₂CH₂F) or substituted at a level anywhere in-between fully substituted and monosubstituted (e.g., —CH₂CF₃). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety selected from the group consisting of hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and R'' where n=(1, 2, 3, ... n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. Thus, by way of example only, an unsymmetrical group such as —C(O)N(R)— may be attached to the parent moiety at either the carbon or the nitrogen.

Asymmetric centers exist in the compounds disclosed herein. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position. When a group in a chemical formula is designated to be "a bond," the group reduces to a linkage between the groups to which it is linked in the formula. By way of example, in Formula I, when $Y_2$ is a bond, it becomes a direct link between A and -alkyl-N(R₄)R₅, forming R₅(R₄)N-alkyl-A-Y₁—(B—(R₂)ₘ)-D-E-(R₃)ₚ.

As used herein, the term "modulate" means to increase or decrease the activity of a target or the amount of a substance.

As used herein, the term "increase" or the related terms "increased," "enhance" or "enhanced" refers to a statistically significant increase, and the terms "decreased," "suppressed," or "inhibited" to a statistically significant decrease. For the avoidance of doubt, an increase generally refers to at least a 10% increase in a given parameter, and can encompass at least a 20% increase, 30% increase, 40% increase, 50% increase, 60% increase, 70% increase, 80% increase, 90% increase, 95% increase, 97% increase, 99% or even a 100% increase over the control, baseline, or prior-in-time value. Inhibition generally refers to at least a 10% decrease in a given parameter, and can encompass at least a 20% decrease, 30% decrease, 40% decrease, 50% decrease, 60% decrease, 70% decrease, 80% decrease, 90% decrease, 95% decrease, 97% decrease, 99% or even a 100% decrease over the control value.

The term "disease" as used herein is intended to be generally synonymous, and is used interchangeably with, the terms "disorder" and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single formulation (e.g., a capsule or injection) having a fixed ratio of active ingredients or in multiple, separate dosage forms for each active ingredient. In addition, such administration also encompasses use of each type of therapeutic agent in a sequential manner. In either case, the treatment regimen will provide beneficial effects of the drug combination in treating the conditions or disorders described herein.

The phrase "therapeutically effective" is intended to qualify the amount of active ingredients used in the treatment of a disease or disorder. This amount will achieve the goal of reducing or eliminating the said disease or disorder.

The term "therapeutically acceptable" refers to those compounds (or salts, polymorphs, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, reference to "treatment" of a patient is intended to include prophylaxis.

In the present invention, the term "radiation" means ionizing radiation comprising particles or photons that have sufficient energy or can produce sufficient energy via nuclear interactions to produce ionization (gain or loss of electrons).

An exemplary and preferred ionizing radiation is an x-radiation. Means for delivering x-radiation to a target tissue or cell are well known in the art. The amount of ionizing radiation needed in a given cell generally depends on the nature of that cell. Means for determining an effective amount of radiation are well known in the art. Used herein, the term "an effective dose" of ionizing radiation means a dose of ionizing radiation that produces an increase in cell damage or death.

The term "radiation therapy" refers to the use of electromagnetic or particulate radiation in the treatment of neoplasia and includes the use of ionizing and non-ionizing radiation.

As used herein, the term "patient" means all mammals including humans. Examples of patients include humans, cows, dogs, cats, goats, sheep, pigs, and rabbits. Preferably, the patient is a human.

The term "prodrug" refers to a compound that is made more active in vivo. Certain compounds disclosed herein may also exist as prodrugs, as described in Hydrolysis in Drug and Prodrug Metabolism: Chemistry, Biochemistry, and Enzymology (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound and N-oxides of amines or heterocyclic groups such as pyridine.

The term "metabolite" refers to a compound produced through biological transformation of a compound following administration to a subject. In order to eliminate foreign substances such as therapeutic agents, the animal body expresses various enzymes, such as the cytochrome $P_{450}$ enzymes (CYPs), esterases, proteases, reductases, dehydrogenases, and monoamine oxidases, to react with and convert these foreign substances to more polar intermediates or metabolites for renal excretion. Such metabolic reactions frequently involve the oxidation of a carbon-hydrogen (C—H) bond to either a carbon-oxygen (C—O) or a carbon-carbon (C═C) □-bond, N-oxidation, or covalent bonding of a polar molecule or functional group (such as sulfate, glucuronic acid, glutathione, or glycine, to the therapeutic agent. The resultant metabolites may be stable or unstable under physiological conditions, and can have substantially different pharmacokinetic, pharmacodynamic, and acute and long-term toxicity profiles relative to the parent compounds. Certain compounds disclosed herein may, after administration to a subject result in formation of metabolites, which in some cases have biological activity as HIF pathway modulators or activity against other biological systems. In certain embodiments, metabolites of the compounds disclosed herein include N-oxides, particularly N-oxides of heterocyclic groups such as pyridine. In further embodiments, metabolites of compounds disclosed herein may themselves have substantial activity as HIF pathway inhibitors.

The compounds disclosed herein can exist as therapeutically acceptable salts. Suitable acid addition salts include those formed with both organic and inorganic acids, and will normally be pharmaceutically acceptable. However, salts of non-pharmaceutically acceptable salts may be of utility in the preparation and purification of the compound in question. Basic addition salts may also be formed and be pharmaceutically acceptable. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethanesulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylpropionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. For a more complete discussion of the preparation and selection of salts, refer to Pharmaceutical Salts: Properties, Selection, and Use (Stahl, P. Heinrich. Wiley-VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion.

Basic addition salts can be prepared during the final isolation and purification of the compounds, often by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium (e.g., NaOH), potassium (e.g., KOH), calcium (including $Ca(OH)_2$), magnesium (including $Mg(OH)_2$ and magnesium acetate), zinc, (including $Zn(OH)_2$ and zinc acetate) and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, piperazine, choline hydroxide, hydroxyethyl morpholine, hydroxyethyl pyrrolidone, imidazole, n-methyl-d-glucamine, N, N'-dibenzylethylenediamine, N, N'-diethylethanolamine, N, N'-dimethylethanolamine, triethanolamine, and tromethamine. Basic amino acids such as 1-glycine and 1-arginine, and amino acids which may be zwitterionic at neutral pH, such as betaine (N,N,N-trimethylglycine) are also contemplated.

Salts disclosed herein may combine in 1:1 molar ratios, and in fact this is often how they are initially synthesized. However, it will be recognized by one of skill in the art that the stoichiometry of one ion in a salt to the other may be otherwise. Salts shown herein may be, for the sake of convenience in notation, shown in a 1:1 ratio; all possible stoichiometric arrangements are encompassed by the scope of the present invention.

The terms, "polymorphs" and "polymorphic forms" and related terms herein refer to crystal forms of the same molecule, and different polymorphs may have different physical properties such as, for example, melting temperatures, heats of fusion, solubilities, dissolution rates and/or vibrational spectra as a result of the arrangement or conformation of the molecules in the crystal lattice. The differences in physical properties exhibited by polymorphs affect pharmaceutical parameters such as storage stability, compressibility and density (important in formulation and product manufacturing), and dissolution rates (an important factor in bioavailability). Differences in stability can result from changes in chemical reactivity (e.g. differential oxidation, such that a dosage form discolors more rapidly when comprised of one polymorph than when comprised of another polymorph) or mechanical changes (e.g. tablets crumble on storage as a kinetically favored polymorph converts to thermodynamically more stable polymorph) or both (e. g., tablets of one polymorph are more susceptible to breakdown at high humidity). As a result of solubility/dissolution differences, in the extreme case, some polymorphic transitions may result in lack of potency or, at the other extreme, toxicity. In addition, the physical properties of the crystal may be important in processing, for example, one polymorph might be more likely to form solvates or might be difficult to filter and wash free of impurities (i.e., particle shape and size distribution might be different between polymorphs).

Polymorphs of a molecule can be obtained by a number of methods, as known in the art. Such methods include, but are not limited to, melt recrystallization, melt cooling, solvent recrystallization, desolvation, rapid evaporation, rapid cooling, slow cooling, vapor diffusion and sublimation.

While it may be possible for the compounds and prodrugs disclosed herein to be administered as the raw chemical, it is also possible to present them as a pharmaceutical formulation. Accordingly, provided herein are pharmaceutical formulations which comprise one or more of certain compounds and prodrugs disclosed herein, or one or more pharmaceutically acceptable salts, esters, amides, or solvates thereof, together with one or more pharmaceutically acceptable carriers thereof and optionally one or more other therapeutic ingredients. The carrier(s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, intranasal, rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the subject invention or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the compounds and prodrugs disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds and prodrugs may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds and prodrugs may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds and prodrugs which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds and prodrugs to allow for the preparation of highly concentrated solutions.

In addition to the formulations described previously, a compound or prodrug as disclosed herein may also be formulated as a depot preparation. Such long acting formulations may be administered by implantation (for example subcutaneously or intramuscularly) or by intramuscular injection. Thus, for example, the compounds and prodrugs may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

The compounds and prodrugs may also be formulated in rectal compositions such as suppositories or retention enemas, e.g., containing conventional suppository bases such as cocoa butter, polyethylene glycol, or other glycerides.

Certain compounds and prodrugs disclosed herein may be administered topically, that is by non-systemic administration. This includes the application of a compound disclosed herein externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

For administration by inhalation, compounds and prodrugs may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds and prodrugs disclosed herein may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Intranasal delivery, in particular, may be useful for delivering compounds to the CNS. It had been shown that intranasal drug administration is a noninvasive method of bypassing the blood-brain barrier (BBB) to deliver neurotrophins and other therapeutic agents to the brain and spinal cord. Delivery from the nose to the CNS occurs within minutes along both the olfactory and trigeminal neural pathways. Intranasal delivery occurs by an extracellular route and does not require that drugs bind to any receptor or undergo axonal transport. Intranasal delivery also targets the nasal associated lymphatic tissues (NALT) and deep cervical lymph nodes. In addition, intranasally administered therapeutics are observed at high levels in the blood vessel walls and perivascular spaces of the cerebrovasculature. Using this intranasal method in animal models, researchers have successfully reduced stroke damage, reversed Alzheimer's neurodegeneration, reduced anxiety, improved memory, stimulated cerebral neurogenesis, and treated brain tumors. In humans, intranasal insulin has been shown to improve memory in normal adults and patients with Alzheimer's disease. Hanson L R and Frey W H, 2nd, J Neuroimmune Pharmacol. 2007 March; 2(1):81-6. Epub 2006 Sep. 15.

Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Compounds and prodrugs may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compound or prodrug which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds and prodrugs can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one of the compounds and prodrugs described herein (or a pharmaceutically acceptable salt or ester thereof) in combination with another therapeutic agent. By way of example only, if one of the side effects experienced by a patient upon receiving one of the compounds herein for the treatment of cancer is nausea, then it may be appropriate to administer an antiemetic agent in combination. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for cancer involving administration of one of the compounds described herein, increased therapeutic benefit may result by also providing the patient with another therapeutic agent for cancer. In any case, regardless of the disease, disorder or condition being treated, the overall benefit experienced by the patient may simply be additive of the two therapeutic agents or the patient may experience a synergistic benefit.

The compounds disclosed herein, including compounds of Formula I, are also useful as chemo- and radio-sensitizers for cancer treatment. They are useful for the treatment of mammals who have previously undergone or are presently undergoing or will be undergoing treatment for cancer. Such other treatments include chemotherapy, radiation therapy, surgery or immunotherapy, such as cancer vaccines.

The instant compounds are particularly useful in combination with therapeutic, anti-cancer and/or radiotherapeutic agents. Thus, the present invention provides a combination of the presently compounds of Formula I with therapeutic, anti-cancer and/or radiotherapeutic agents for simultaneous, separate or sequential administration. The compounds of this invention and the other anticancer agent can act additively or synergistically. A synergistic combination of the present compounds and another anticancer agent might allow the use of lower dosages of one or both of these agents and/or less frequent dosages of one or both of the instant compounds and other anticancer agents and/or to administer the agents less frequently can reduce any toxicity associated with the administration of the agents to a subject without reducing the efficacy of the agents in the treatment of cancer. In addition, a synergistic effect might result in the improved efficacy of these agents in the treatment of cancer and/or the reduction of any adverse or unwanted side effects associated with the use of either agent alone.

The therapeutic agent, anti-cancer agent and/or radiation therapy can be administered according to therapeutic protocols well known in the art. It will be apparent to those skilled in the art that the administration of the therapeutic agent, anti-cancer agent and/or radiation therapy can be varied depending on the disease being treated and the known effects of the anti-cancer agent and/or radiation therapy on that disease. Also, in accordance with the knowledge of the skilled clinician, the therapeutic protocols (e.g., dosage amounts and times of administration) can be varied in view of the observed effects of the administered therapeutic agents (i.e., anti-neoplastic agent or radiation) on the patient, and in view of the observed responses of the disease to the administered therapeutic agents, and observed adverse affects.

Dosage ranges for x-rays range from daily doses of 50 to 200 roentgens for prolonged periods of time (3 to 4 weeks), to single doses of 2000 to 6000 roentgens. Dosage ranges for radioisotopes vary widely, and depend on the half-life of the isotope, the strength and type of radiation emitted, and the uptake by the neoplastic cells.

Any suitable means for delivering radiation to a tissue may be employed in the present invention. Common means of delivering radiation to a tissue is by an ionizing radiation source external to the body being treated. Alternative methods for delivering radiation to a tissue include, for example, first delivering in vivo a radiolabeled antibody that immunoreacts with an antigen of the tumor, followed by delivering in vivo an effective amount of the radio labeled antibody to the tumor. In addition, radioisotopes may be used to deliver ionizing radiation to a tissue or cell. Additionally, the radiation may be delivered by means of a radiomimetic agent. As used herein a "radiomimetic agent" is a chemotherapeutic agent, for example melphalan, that causes the same type of cellular damage as radiation therapy, but without the application of radiation.

In one embodiment, the compounds of formula I can be administered in combination with one or more agent selected from aromatase inhibitors, anti-estrogens, anti-progesterons, anti-androgens, or gonadorelin agonists, anti-inflammatory agents, antihistamines, anti-cancer agent, inhibitors of angiogenesis, topoisomerase 1 and 2 inhibitors, microtubule active agents, alkylating agents, antineoplastic, antimetabolite, dacarbazine (DTIC), platinum containing compound, lipid or protein kinase targeting agents, protein or lipid phosphatase targeting agents, anti-angiogenic agents, agents that induce cell differentiation, bradykinin 1 receptor and angiotensin II antagonists, cyclooxygenase inhibitors, heparanase inhibitors, lymphokines or cytokine inhibitors, bisphosphanates, rapamycin derivatives, anti-apoptotic pathway inhibitors, apoptotic pathway agonists, PPAR agonists, HSP90 inhibitor, smoothened antagonist, inhibitors of Ras isoforms, telomerase inhibitors, protease inhibitors, metalloproteinase inhibitors, aminopeptidase inhibitors, imununomodulators, therapeutic antibody and a protein kinase inhibitor, e.g., a tyrosine kinase or serine/threonine kinase inhibitor.

In another embodiment is provided a combination of a compound of formula I and an anti-cancer agent for simultaneous, separate or sequential administration.

Examples of cancer agents or chemotherapeutic agents for use in combination with the compounds as disclosed herein can be found in *Cancer Principles and Practice of Oncology* by V. T. Devita and S. Hellman (editors), 6th edition (Feb. 15, 2001), Lippincott Williams & Wilkins Publishers, and WO 2006/061638. A person of ordinary skill in the art would be able to discern which combinations of agents would be useful based on the particular characteristics of the drugs and the cancer involved. Classes of such agents include the following: estrogen receptor modulators, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, HIV protease inhibitors, reverse transcriptase inhibitors, inhibitors of cell proliferation and survival signaling, bisphosphonates, aromatase inhibitors, siRNA therapeutics, γ-secretase inhibitors, agents that interfere with receptor tyrosine kinases (RTKs), agents that interfere with cell cycle checkpoints, PARP inhibitors, HDAC inhibitors, Smo antagonists (HH inhibitors), HSP90 inhibitors, CYP17 inhibitors, 3rd generation AR antagonists, JAK inhibitors e.g. Ruxolitinib (trade name Jakafi, and BTK kinase inhibitors.

Anticancer agents suitable for use in the combination therapy with compounds as disclosed herein include, but are not limited to:

1) alkaloids and natural product drugs, including, microtubule inhibitors (e.g., Vincristine, Vinblastine, and Vindesine, and vinorelbine etc.), microtubule stabilizers (e.g., Paclitaxel [Taxol], and Docetaxel, Taxotere, etc.), and chromatin function inhibitors, including, topoisomerase inhibitors, such as, epipodophyllotoxins (e.g., Etoposide [VP-161, and Teniposide [VM-261, etc.), and agents that target topoisomerase I (e.g., Camptothecin, topotecan (Hycamtin) and Irinotecan [CPT-11], rubitecan (Orathecin) etc.);

2) covalent DNA-binding agents [alkylating agents], including, nitrogen mustards (e.g., Mechloretharnine, chlormethine, Chlorambucil, Cyclophosphamide, estramustine (Emcyt, Estracit), ifosfamide, Ifosphamide, melphalan (Alkeran) etc.); alkyl sulfonates like Busulfan [Myleran], nitrosoureas (e.g., Carmustine or BCNU (bis-chloroethylnitrosourea), fotemustine Lomustine, and Semustine, streptozocin etc.), and other alkylating agents (e.g., Dacarbazine, procarbazine ethylenimine/methylmelamine, thriethylenemelamine (TEM), triethylene thiophosphoramide (thiotepa), hexamethylmelamine (HMM, altretamine), and Mitocycin, uramustine etc.) including Temozolomide (brand names Temodar and Temodal and Temcad), altretamine (also hexalen) and mitomycin;

3) noncovalent DNA-binding agents [antitumor antibiotics], including nucleic acid inhibitors (e.g., Dactinomycin [Actinomycin D1, etc.), anthracyclines (e.g., Daunorubicin [Daunomycin, and Cerubidine], Doxorubicin [Adrianycin], epirubicin (Ellence), and Idarubicin [Idamycin], valrubicin (Valstar) etc.), anthracenediones (e.g., anthracycline analogues, such as, [Mitoxantrone], etc.), bleomycins (Blenoxane), etc., amsacrine and plicamycin (Mithramycin), dactinomycin, mitomycin C:

4) antimetabolites, including, antifolates (e.g., Methotrexate, Folex, aminopterin, pemetrexed, raltitrexed and Mexate, trimetrexate etc.), purine antimetabolites (e.g., 6-Mercaptopurine [6-MP, Purinethol], cladribine, 6-Thioguanine [6-TG], clofarabine (Clolar, Evoltra), Azathioprine, Acyclovir, Fludarabine or fludarabine phosphate (Fludara) Ganciclovir, Chlorodeoxyadenosine, 2-Chlorodeoxyadenosine [CdA], and 2'-Deoxycoformycin [Pentostatin], etc.), pyrimidine antagonists (e.g., fluoropyrimidines [e.g., 5-fluorouracil (Adrucil), 5-fluorodeoxyuridine (FdUrd) (Floxuridine)], capecitabine Carmofur or HCFU (1-hexylcarbamoyl-5-fluorouracil), tegafur etc.), gemcitabine (Gemzar), and cytosine arabinosides (e.g., Cytarabine, or cytosine arabinoside, Cytosar [ara-C] and Fludarabine, 5-azacytidine, 2,2'-difluorodeoxycytidine etc.) and hydroxyurea (Hydrea and Droxia, hydroxycarbamide), plus lonidamine;

5) enzymes, including, L-asparaginase and derivatives such as pegaspargase (Oncaspar), and RNAse A;

7) hormones and antagonists, Examples of hormones and hormonal analogues believed to be useful in the treatment of neoplasms include, but are not limited to antiestrogens and selective estrogen receptor modulators (SERMs), such as tamoxifen, toremifene, raloxifene, iodoxyfene, droloxifene, 4-hydroxytamoxifen, trioxifene, keoxifene, onapristone; anti-androgens; such as enzalutamide (Xtandi®), flutamide, nilutamide, bicalutamide, leuprolide, and goserelin, and cyproterone acetate; adrenocorticosteroids such as prednisone and prednisolone; aminoglutethimide, finasteride and other aromatase inhibitors such as anastrozole, letrazole, vorazole, exemestane, formestanie, and fadrozole; Estrogen Receptor Downregulators (EROs) including Faslodex or fulvestrant, progestrins such as megestrol acetate; Sa-reductase inhibitors such as finasteride and dutasteride; and gonadotropin-releasing hormones (GnRH) and analogues thereof, such as Leutinizing Hormone-releasing Hormone (LHRH) agonists and antagonists such as goserelin luprolide, leuprorelin and buserelin.

8) platinum compounds (e.g., Cisplatin and Carboplatin, oxaliplatin, Triplatin tetranitrate (rINN; also known as BBR3464), eptaplatin, lobaplatin, nedaplatin, or satraplatin etc.);

9) retinoids such as bexarotene (Targretin).

10) proteasome inhibitors such as bortezomib and carfilzomib (Kyprolis®).

11) anti-mitotics in addition to diterpenoids and vinca alkaloids include polo-like kinase (PLK) inhibitors, mitotic kinesin spindle protein (KSP) inhibitors including SB-743921 and MK-833 and CenpE inhibitors.

12) monoclonal antibodies, including cancer immunotherapy monoclonal antibodies and humanized monoclonal antibodies. For example:

12-a) cancer immunotherapy monoclonal antibodies include agents selected from the group consisting of Trastuzumab (Herceptin®), an example of an anti-erbB2 antibody inhibitor of growth factor function; cetuximab (Erbitux™, C225), an example of an anti-erbB1 antibody inhibitor of growth factor function; bevacizumab (Avastin®), an example of a monoclonal antibody directed against VEGFR; rituximab, alemtuzumab, gemtuzumab, panitumumab, tositumomab, pertuzumab.

12-b) humanized monoclonal antibodies with therapeutic potential as chemotherapeutic agents in combination include: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, dacliuzmab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab (Perjeta®), pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab;

13) monoclonal antibodies conjugated with anticancer drugs, toxins, and/or radionuclides, etc. gemtuzumab ozogamicin (MYLOTARG), trastuzumab emtansine (T-DM1)/ado-trastuzumab emtansine (Kadcyla®);

14) biological response modifiers (e.g., interferons [e.g., IFN-.alpha., etc.] and interleukins [e.g., IL-2, etc.], denileukin diftitox (Ontak), G-CSF, GM-CSF: etc.);

15) adoptive immunotherapy; Immunotherapeutic regimens include ex-vivo and in-vivo approaches to increasing immunogenicity of patient tumor cells such as transfection with cytokines (eg. IL-2 or aldesleukin, IL-4, GMCFS), as well as IL-1, IL-3, IL-4, IL-5, IL-6, IL-7, IL-8, IL-9, IL-10, IL-11, IL-12, and active biological variants approaches to increase T-cell activity, approaches with transfected immune cells and approaches with antiidiotypic antibodies;

16) immunosuppressant selected from the group consisting of fingolimod, cyclosporine A, Azathioprine, dexamethasone, tacrolimus, sirolimus, pimecrolimus, mycophenolate salts, everolimus, basiliximab, daclizumab, anti-thymocyte globulin, anti-lymphocyte globulin, and tofacitinib. Agents capable of enhancing antitumor immune responses, such as CTLA4 (cytotoxic lymphocyte antigen 4) antibodies such as Ipilimumab (MDX-010 or MDX-101, Yervoy) and tremelimumab, and other agents capable of blocking CTLA4;

17) immune modulators, for use in conjunction with the compound as disclosed herein include staurospine and macrocyclic analogs thereof, including UCN-01, CEP-701 and midostaurin; squalamine; DA-9601; alemtuzumab; interferons (e.g. IFN-α, IFN-b etc.); altretamine (Hexalen®); SU 101 or leflunomide; imidazoquinolines such as resiquimod, imiquimod, anti-PD-1 human monoclonal antibodies MDX-1106 (also known as BMS-936558), MK3475, CT-011, and AMP-224, anti-PD-L1 monoclonal antibodies such as MDX-1105, anti-OX40 monoclonal antibodies, and LAG3 fusion proteins such as IMP321g, anti-B7-H3 monoclonal antibodies such as MGA271, anti-B7-H4 monoclonal antibodies, and anti-TIM3 monoclonal antibodies;

18) hematopoietic growth factors;

19) agents that induce tumor cell differentiation (e.g., tretinoin (all trans retinoic acid) (brand names Aberela, Airol, Renova, Atralin, Retin-A, Avita, Retacnyl, Refissa, or Stieva-A));

20) gene therapy techniques; such as gene therapy vaccines, for example, ALLOVECTIN®, LEUVECTIN®, and V AXID®;

21) antisense therapy techniques;

22) tumor vaccines; include Avicine®; oregovomab (OvaRex®); Theratope® (STn-KLH); Melanoma Vaccines; GI-4000 series (GI-4014, GI-4015, and GI-4016), which are directed to five mutations in the Ras protein; GlioVax-1; MelaVax; Advexin® or INGN-201; Sig/E7/LAMP-1, encoding HPV-16 E7; MAGE-3 Vaccine or M3TK; HER-2VAX; ACTIVE, which stimulates T-cells specific for tumors; GM-CSF cancer vaccine; and Listeria onocytogenes-based vaccines;

23) therapies directed against tumor metastases (e.g., Batimistat, etc.);

24) inhibitors of angiogenesis. Receptor kinase angiogenesis inhibitors may also find use in the present invention. Inhibitors of angiogenesis related to VEGFR and TIE-2. Other inhibitors may be used in combination with the compounds of the invention. For example, anti-VEGF antibodies, which do not recognize VEGFR (the receptor tyrosine kinase), but bind to the ligand; small molecule inhibitors of integrin (alphav beta3) that inhibit angiogenesis; endostatin and angiostatin (non-RT) may also prove useful in combination with the compounds of the invention. One example of a VEGFR antibody is bevacizumab (Avastin®). Other anti-angiogenic compounds include acitretin, fenretinide, thalidomide, zoledronic acid, angiostatin, aplidine, cilengtide, combretastatin A-4, endostatin, halofuginone, rebimastat, removab, Lenalidomid (Revlimid), squalamine, Vitaxin, and pomalidomide (Pomalyst®);

25) signal transduction pathway inhibitors. Signal transduction pathway inhibitors are those inhibitors which block or inhibit a chemical process which evokes an intracellular change. As used herein these changes include, but are not limited to, cell proliferation or differentiation or survival. Signal transduction pathway inhibitors useful in the present invention include, but are not limited to, inhibitors of receptor tyrosine kinases, non-receptor tyrosine kinases, SH2/SH3 domain blockers, serine/threonine kinases, phosphatidyl inositoi-3-0H kinases, myoinositol signaling, and Ras oncogenes. Signal transduction pathway inhibitors may be employed in combination with the compounds of the invention;

26) kinase inhibitors, including tyrosine kinases, serine/threonine kinases, kinases involved in the IGF-1 R signaling axis, PI3k/AKT/mTOR pathway inhibitors, and SH2/SH3 domain blockers. Examples of relevant kinases include:

26-a) tyrosine kinases. Several protein tyrosine kinases catalyze the phosphorylation of specific tyrosine residues in various proteins involved in the regulation of cell growth. Such protein tyrosine kinases can be broadly classified as receptor or non-receptor kinases. Receptor tyrosine kinase inhibitors which may be combined with the compounds of the invention include those involved in the regulation of cell growth, which receptor tyrosine kinases are sometimes referred to as "growth factor receptors." Examples of growth factor receptor inhibitors, include but are not limited to inhibitors of: insulin growth factor receptors (IGF-1 R, IR and IRR); epidermal growth factor family receptors (EGFR, ErbB2, and ErbB4); platelet derived growth factor receptors (PDGFRs), vascular endothelial growth factor receptors (VEGFRs), tyrosine kinase with immunoglobulin-like and epidermal growth factor homology domains (TIE-2), macrophage colony stimulating factor (c-FMS), c-KIT, cMET, fibroblast growth factor receptors (FGFRs), hepatocyte growth factor receptors (HGFRs), Trk receptors (TrkA, TrkB, and TrkC), ephrin (Eph) receptors, the RET protooncogene, and Human Epidermal Growth Factor Receptor 2 (HER-2). Examples of small molecule inhibitors of epidermal growth factor receptors include but are not limited to gefitinib, lapatinib (Tykerb®), erlotinib (Tarceva®), afatinib (Gilotrif®, Tomtovok®, and Tovok®), and. lmatinib (Gleevec®) is one example of a PDGFR inhibitor. Examples of VEGFR inhibitors include pazopanib (Votrient™), Vandetanib (ZD6474), AZD2171, vatalanib (PTK-787), Axitinib (AG013736; Inlyta®), dovitinib (CHIR-258), cabozantinib (Cometriq®), sunitinib, and sorafenib. Protein Kinase C (PKC) inhibitors, such as ruboxistaurin, AEB071 (Sotrastaurin) LY-317615 and perifosine. Examples of small molecule inhibitors of multiple tyrosine kinases include but are not limited to bosutinib (Bosulif®) and. Other kinase inhibitors include but are not limited to BIBF-1120, dasatinib (sprycel), pelitinib, nilotinib, and lestaurtinib (CEP-701). Tyrosine kinases that are not transmembrane growth factor receptor kinases are termed non-receptor, or intracellular tyrosine kinases. Inhibitors of non-receptor tyrosine kinases are sometimes referred to as "anti-metastatic agents" and are useful in the present invention. Targets or potential targets of anti-metastatic agents, include, but are not limited to, c-Src, Lck, Fyn, Yes, Jak, Abl kinase (c-Abl and Bcr-Abl), FAK (focal adhesion kinase) and Bruton's tyrosine kinase (BTK). Examples of small molecule inhibitors of Bcr-Abl include but are not limited to ponatinib (Iclusig®). Non-receptor kinases and agents, which inhibit non-receptor tyrosine kinase function, are described in Sinha, S. and Corey, S. J., *J. Hematother. Stem Cell Res.* (1999) 8 465-80; and Bolen, J. B. and Brugge, J. S., *Annu. Rev. of Immunol.* (1997) 15 371-404;

26-b) serine/threonine kinases. Inhibitors of serine/threonine kinases may also be used in combination with the compounds of the invention in any of the compositions and methods described above. Examples of serine/threonine kinase inhibitors that may also be used in combination with a compound of the present invention include, but are not limited to, polo-like kinase inhibitors (Pik family e.g., Plk1, Plk2, and Plk3), which play critical roles in regulating processes in the cell cycle including the entry into and the exit from mitosis; MAP kinase cascade blockers, which include other Ras/Raf kinase inhibitors, mitogen or extracellular regulated kinases (MEKs), and extracellular regulated kinases (ERKs); Aurora kinase inhibitors (including inhibitors of Aurora A and Aurora B); protein kinase C (PKC) family member blockers, including inhibitors of PKC subtypes (alpha, beta, gamma, epsilon, mu, lambda, iota, zeta); inhibitors of kappa-B (lkB) kinase family (IKK-alpha, IKK-beta); PKB/Akt kinase family inhibitors; and inhibitors of TGF-beta receptor kinases. Examples of Plk inhibitors are described in PCT Publication No. W004/014899 and W007/03036;

26-c) kinases involved in the IGF-1 R signaling axis. Inhibitors of kinases involved in the IGF-1 R signaling axis may also be useful in combination with the compounds of the present invention. Such inhibitors include but are not limited to inhibitors of JNK1/2/3, PI3K, AKT and MEK, and 14.3.3 signaling inhibitors;

26-d) PI3k/AKT/mTOR pathway inhibitors, including GDC-0941, XL-147, GSK690693 and temsirolimus, SF-1126 (PI3K inhibitor), BEZ-235 (PI3K inhibitor);

26-e) SH2/SH3 domain blockers. SH2/SH3 domain blockers are agents that disrupt SH2 or SH3 domain binding in a variety of enzymes or adaptor proteins including, but not limited to, PI3-K p85 subunit, Src family kinases, adaptor molecules (She, Crk, Nck, Grb2) and Ras-GAP. Examples of Src inhibitors include, but are not limited to, dasatinib and BMS-354825 (*J. Med. Chem.* (2004) 4 7 6658-6661);

27) inhibitors of Ras oncogenes. Inhibitors of Ras oncogene may also be useful in combination with the compounds of the present invention. Such inhibitors include, but are not limited to, inhibitors of farnesyltransferase, geranyl-geranyl transferase, and CAAX proteases as well as anti-sense oligonucleotides, ribozymes and immunotherapy. Such inhibitors have been shown to block Ras activation in cells containing mutant Ras, thereby acting as antiproliferative agents.

28) Raf/MEK/ERK pathway modulators. The Raf/MEK/ERK pathway is critical for cell survival, growth, proliferation and tumorigenesis. Li, Nanxin, et al. "B-Raf kinase inhibitors for cancer treatment." Current Opinion in Investigational Drugs. Vol. 8, No. 6 (2007): 452-456. Raf kinases exist as three isoforms, A-Raf, B-Raf and C-Raf. Among the three isoforms, studies have shown that B-Raf functions as the primary MEK activator. B-Raf is one of the most frequently mutated genes in human cancers. B-Raf kinase represents an excellent target for anticancer therapy based on preclinical target validation, epidemiology and drugability. Small molecule inhibitors of B-Raf are being developed for anticancer therapy. Examples of small molecule inhibitors of B-Raf include but are not limited to dabrafenib (Tafinlar®). Nexavar® (sorafenib tosylate) is a multikinase inhibitor, which includes inhibition of B-Raf, and is approved for the treatment of patients with advanced renal cell carcinoma and unresectable hepatocellular carcinoma. Other Raf inhibitors have also been disclosed or have entered clinical trials, for example GSK-2118436, RAF-265, vemurafenib (Zelboraf, PLX-4032), PLX3603 and XL-281. Examples of small molecule inhibitors of MEK include but are not limited to trametinib (Mekinist®), Other MEK inhibitors include ARRY-886 (AZD6244);

29) Cell cycle signaling inhibitors, including inhibitors of cyclin dependent kinases (CDKs) are also useful in combination with the compounds of the invention in the compositions and methods described above. Examples of cyclin dependent kinases, including CDK2, CDK4, and CDK6 and inhibitors for the same are described in, for instance, Rosania G. R. et al., *Exp. Opin. Ther. Patents* (2000) 10 215-230;

30) Inhibitors of phosphatidyl inositoi-3-0H kinase family members including blockers of PI3-kinase, ATM, DNA-PK, and Ku may also be useful in combination with the present invention;

31) Antagonists of smoothened receptor (SMO) may also be useful in combination with the present invention. Examples of antagonists of smoothened receptor include but are not limited to vismodegib (Erivedge®));

32) Inhibitors of protein translation may also be useful in combination with the present invention. Examples of inhibitors of protein translation include but are not limited to omacetaxine mepesuccinate (Synribo®)); and 33) anti-cancer agents with other mechanisms of action including miltefosine (Impavido and Miltex), masoprocol, mitoguazone, alitretinoin, mitotane, arsenic trioxide, celecoxib, and anagrelide.

Compounds disclosed herein may also be employed in conjunction with anti-emetic agents to treat nausea or emesis, including acute, delayed, late-phase, and anticipatory emesis, which may result from the use of a compound as disclosed herein, alone or with radiation therapy. For the prevention or treatment of emesis, a compound as disclosed herein may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In another embodiment, conjunctive therapy with an anti-emesis agent selected from a neurokinin-1 receptor antagonist, a 5HT3 receptor antagonist and a corticosteroid is disclosed for the treatment or prevention of emesis that may result upon administration of the instant compounds.

A compound as disclosed herein may also be administered with an agent useful in the treatment of anemia. Such an anemia treatment agent is, for example, a continuous eythropoiesis receptor activator (such as epoetin alfa).

A compound as disclosed herein may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound as disclosed herein may also be useful for treating or preventing cancer in combination with siRNA therapeutics.

A compound as disclosed herein may also be useful for treating cancer in combination with the following therapeutic agents: abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexalen®); amifostine (Ethyol®); anastrozole (Arimidex®); arsenic trioxide (Trisenox®); asparaginase (Elspar®); Axitinib (Inlyta®); azacitidine (Vidaza®); bevacuzimab (Avastin®); bexarotene capsules (Targretin®); bexarotene gel (Targretin®); bicalutamide (Casodex®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); dasatinib (Sprycel®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); doxorubicin liposomal (Doxil®); dromostanolone propionate (Dromostanolone®); dromostanolone propionate (Masterone Injection®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); flutamide (Eulexin®), fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); ipilimumab (Yervoy®), irinotecan (Camptosar®); lapatinib (TYKERB®), lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel proteinbound particles (Abraxane®); palifermin (Kepivance®); panitumumab (VECTIBIX®), pamidronate (Aredia®); Pazopanib (Votrient®), pegademase (Adagen (Pegademase Bovine)®); pegaspargase (Oncaspar®); Pegfilgrastim (Neulasta®); pemetrexed disodium (Alimta®); pentostatin (Nipent®); pertuzumab (OMNITARG®, 2C4), pipobroman (Vercyte®); plicamycin, mithramycin (Mithracin®); porfimer sodium (Photofrin®); procarbazine (Matulane®); quinacrine (Atabrine®); Rapamycin (Sirolimus, RAPAMUNE®), Rasburicase (Elitek®); Rituximab (Rituxan®); rubitecan (Orathecin), ruxolitinib (Jakafi®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); temsirolimus (Torisel®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vandetanib (ZACTIMA®), vemurafenib (Zelboraf®), vinblastine (Velban®); vincristine (Oncovin®); vinorelbine (Navelbine®); vorinostat (Zolinza®); zoledronate (Zometa®), nilotinib (Tasigna®); and dasatinib (Sprycel®). ARRY-886 (Mek inhibitor, AZD6244), SF-1126 (PI3K inhibitor), BEZ-235 (PI3K inhibitor), XL-147 (PI3K inhibitor), PTK787/ZK 222584, crizotinib (Xalkori®), and vemurafenib (Zelboraf®).

In any case, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in another aspect, certain embodiments provide methods for treating disorders and symptoms relating cancer in a human or animal subject in need of such treatment comprising administering to said subject an amount of a compound disclosed herein effective to reduce or prevent said disorder in the subject, in combination with at least one additional agent for the treatment of said disorder that is known in the art. In a related aspect, certain embodiments provide therapeutic compositions comprising at least one compound disclosed herein in combination with one or more additional agents for the treatment of disorders and symptoms relating to cancer.

The compounds, compositions, and methods disclosed herein are useful for the treatment of disease. In certain embodiments, the diseases is one of dysregulated cellular proliferation, including cancer. The cancer may be hormone-dependent or hormone-resistant, such as in the case of breast cancers. In certain embodiments, the cancer is a solid tumor. In other embodiments, the cancer is a lymphoma or leukemia. In certain embodiments, the cancer is and a drug resistant phenotype of a cancer disclosed herein or known in the art. Tumor invasion, tumor growth, tumor metastasis, and angiogenesis may also be treated using the compositions and methods disclosed herein. Precancerous neoplasias are also treated using the compositions and methods disclosed herein.

Cancers to be treated by the methods disclosed herein include colon cancer, breast cancer, ovarian cancer, lung cancer and prostrate cancer; cancers of the oral cavity and pharynx (lip, tongue, mouth, larynx, pharynx), esophagus, stomach, small intestine, large intestine, colon, rectum, liver and biliary passages; pancreas, bone, connective tissue, skin, cervix, uterus, corpus endometrium, testis, bladder, kidney and other urinary tissues, including renal cell carcinoma (RCC); cancers of the eye, brain, spinal cord, and other components of the central and peripheral nervous systems, as well as associated structures such as the meninges; and thyroid and other endocrine glands. The term "cancer" also encompasses cancers that do not necessarily form solid tumors, including Hodgkin's disease, non-Hodgkin's lymphomas, multiple myeloma and hematopoietic malignancies including leukemias (Chronic Lymphocytic Leukemia (CLL), Acute Lymphocytic Leukemia (ALL)) and lymphomas including lymphocytic, granulocytic and monocytic. Additional types of cancers which may be treated using the compounds and methods of the invention include, but are not limited to, adrenocarcinoma, angiosarcoma, astrocytoma, acoustic neuroma, anaplastic astrocytoma, basal cell carcinoma, blastoglioma, chondrosarcoma, choriocarcinoma, chordoma, craniopharyngioma, cutaneous melanoma, cystadenocarcinoma, endotheliosarcoma, embryonal carcinoma, ependymoma, Ewing's tumor, epithelial carcinoma, fibrosarcoma, gastric cancer, genitourinary tract cancers, glioblastoma multiforme, head and neck cancer, hemangioblastoma, hepatocellular carcinoma, hepatoma, Kaposi's sarcoma, large cell carcinoma, leiomyosarcoma, leukemias, liposarcoma, lymphatic system cancer, lymphomas, lymphangiosarcoma, lymphangioendotheliosarcoma, medullary thyroid carcinoma, medulloblastoma, meningioma mesothelioma, myelomas, myxosarcoma neuroblastoma, neurofibrosarcoma, oligodendroglioma, osteogenic sarcoma, epithelial ovarian cancer, papillary carcinoma, papillary adenocarcinomas, paraganglioma, parathyroid tumours, pheochromocytoma, pinealoma, plasmacytomas, retinoblastoma, rhabdomyosarcoma, sebaceous gland carcinoma, seminoma, skin cancers, melanoma, small cell lung carcinoma, non-small cell lung carcinoma, squamous cell carcinoma, sweat gland carcinoma, synovioma, thyroid cancer, uveal melanoma, and Wilm's tumor.

In certain embodiments, the compositions and methods disclosed herein are useful for preventing or reducing tumor invasion and tumor metastasis.

In certain embodiments, the compositions and methods disclosed herein are useful for preventing or reducing angiogenesis and disorders related to angiogenesis. Besides being useful for human treatment, certain compounds and formulations disclosed herein may also be useful for veterinary treatment of companion animals, exotic animals and farm animals, including mammals, rodents, and the like. More preferred animals include horses, dogs, and cats.

LIST OF ABBREVIATIONS $CHCl_3$=chloroform; i-PrOH=isopropanol; $H_2O$=water; DCM=dichloromethane; $Na_2SO_4$=sodium sulfate; $MgSO_4$=magnesium sulfate; EtOAc=ethyl acetate; EtOH=ethanol; $Et_2O$=diethyl ether; THF=tetrahydrofuran; NMP=N-Methyl-2-pyrrolidone; NaOH=sodium hydroxide; MeOH=methanol; $CDCl_3$=deuterated chloroform; HCl=hydrochloric acid; MeCN=acetonitrile; $Cs_2CO_3$=cesium carbonate; DMF=N,N-dimethylformamide; $CD_3OD$=deuterated methanol; $DMSO-d_6$=deuterated dimethyl sulfoxide; DMSO=dimethyl sulfoxide; TFA=trifluoroacetic acid; AcOH=acetic acid; HBr=hydrobromic acid; HCOOH=formic acid; $K_2CO_3$=potassium carbonate; DBU=1,8-diazabicyclo[5.4.0]undec-7-ene; $NaHCO_3$=sodium hydrogen carbonate; KCN=potassium cyanide; TEA=$Et_3N$=triethylamine; DMAP=4-dimethylaminopyridine; $NH_2OH.HCl$=hydroxylammonium chloride; DIEA=N,N-diisopropylethylamine; LiOH=lithium hydroxide; $NH_4HCO_3$=ammonium hydrogen carbonate; $NH_4OH$=ammonium hydroxide; $K_3PO_4$=potassium phosphate tribasic; NaOtBu=sodium t-butoxide; $CuBr_2$=copper (II) bromide; $CuCl_2$=copper (II) chloride; $CuCN(LiCl)_2$=Copper(I) cyanide di(lithium chloride) complex; EDC.HCl=1-Ethyl-3-(3-dimethylaminopropyl)carbodiimide hydrochloride; HOBT=1-hydroxybenzotriazole; PyBop=(Benzotriazol-1-yloxy)tripyrrolidinophosphonium hexafluorophosphate; LiCl=lithium chloride; NaI=sodium iodide; NaBr=sodium bromide; $N_2$=nitrogen; Ar=argon; $MnO_2$=manganese dioxide; HATU=2-(1H-7-Azabenzotriazol-1-yl)-1,1,3,3-tetramethyl uronium hexafluorophosphate methanaminium; $BH_3$-THF=borane tetrahydrofuran complex solution; $POCl_3$=phosphorus oxychloride; $Ac_2O$=acetic anhydride; $NH_2NH_2.H_2O$=hydrazine hydrate; $NaBH_4$=sodium borohydride; $NaBH_3CN$=sodium cyanoborohydride; n-BuLi=n-butyllithium; $CH_3I$=methyl iodide; $CS_2$=carbon disulfide; AIBN=azobisisobutyronitrile; KF=potassium fluoride; $Bu_3SnH$=tributyltin hydride; RuPhos=2-Dicyclohexylphosphino-2',6'-diisopropoxybiphenyl; XPhos=2-Dicyclohexylphosphino-2',4',6'-triisopropylbiphenyl; and $Pd_2(dba)_3$=tris(dibenzylideneacetone)dipalladium(0); $Pd(Ph_3)_4$=tetrakis(triphenylphosphine)palladium(0); NCS=N-chlorosuccinimide; DEAD=diethyl azodicarboxylate; $OsO_4$=osmium tetraoxide; DIBAL-H=di-iso-butyl aluminium hydride; t-BuOH=tert-butanol; Py=pyridine; NaOMe=sodium methoxide; prep-HPLC=preparative high-performance liquid chromatography.

General Methods for Preparing Compounds

The following schemes can be used to practice the present invention. Additional structural groups, including but not limited to those defined elsewhere in the specification and not shown in the compounds described in the schemes can incorporated to give various compounds disclosed herein, or intermediate compounds which can, after further manipulation using techniques known in the art, be converted to compounds of the present invention. For example, in certain embodiments the A, B, D, and E rings in the structures described in the schemes can be substituted with various groups as defined herein.

SCHEME 1:

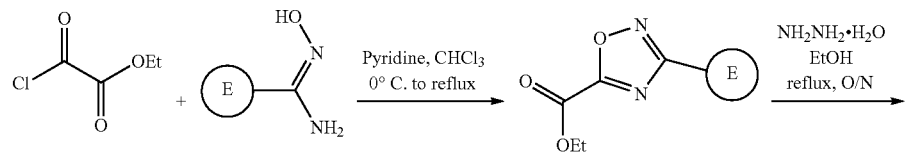

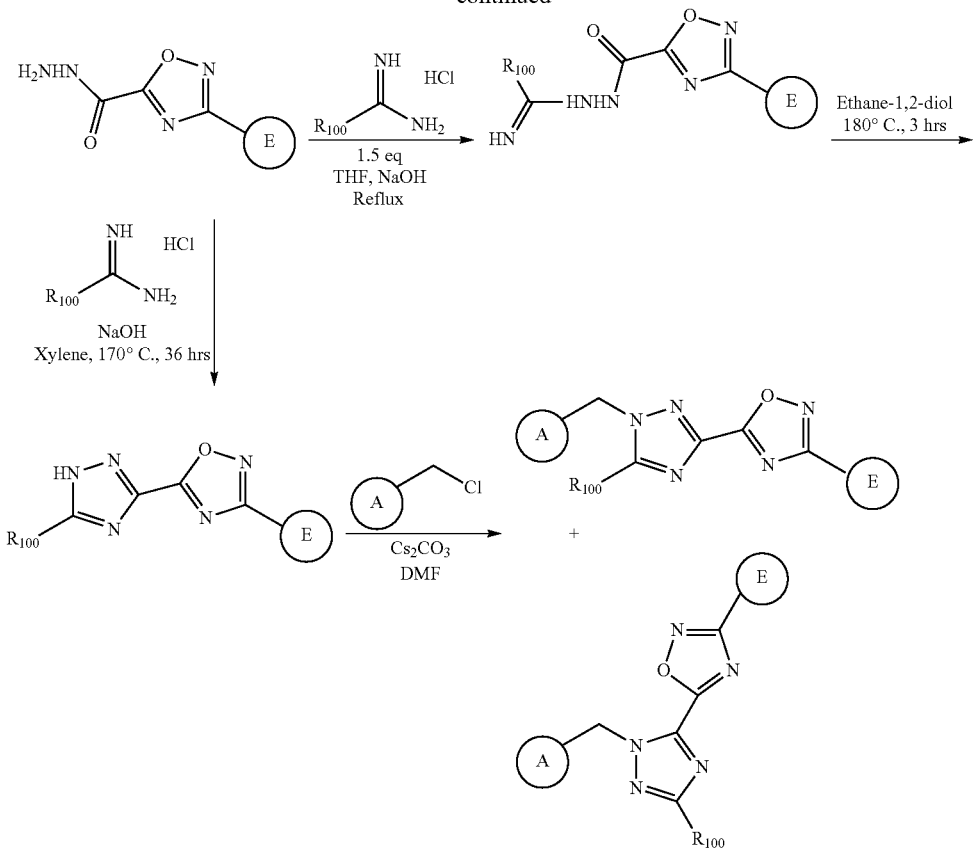

One route for preparation of compounds of the present invention is depicted in Scheme 1. Ethyl 2-chloro-2-oxoacetate can be condensed with a hydroxyamidine, and cyclized in refluxing pyridine to form a 1,2,4-oxadiazole. The resulting ester can be treated with hydrazine hydrate in refluxing ethanol to give the corresponding hydrazide. This can in turn be condensed with a substituted amidine in refluxing solvent such as THF to yield an intermediate, which after a solvent switch to ethane-1,2-diol and refluxing the reaction for several hours the desired 1,2,4-triazole can be prepared. Alternatively, the hydrazide can be mixed with the amidine hydrochloride salt in the presence of a base such as sodium hydroxide in a solvent such as xylene and the mixture stirred at 170° C. for 36 h to yield the 1,2,4-triazole directly. Alkylation of the triazole with an appropriately substituted benzyl halide, or heterocyclic methyl halide, or equivalent synthon yields a mixture of regioisomers. This transformation can be achieved using reagents such $Cs_2CO_3$ or $K_2CO_3$ in a polar solvent like DMF or DMSO, or $K_2CO_3$ in the presence of NaI in THF. These transformations can be accomplished at RT, although with some substrates it may be necessary to use elevated temperatures and/or microwave irradiation to drive the reaction to completion. The regioisomer can be separated at this stage, or later in the synthetic sequence by chromographic methods such as column chromatography or HPLC to yield compounds of this invention.

In a related manner, other heterocyclic carboxylic acids can be transformed to the corresponding hydrazide, for instance as depicted in Scheme 2 by coupling with Boc hydrazide, using a coupling reagent such as HATU in the presence of a base like $K_2CO_3$ in a solvent like DCM. Thereafter the Boc group can be removed using acid such as TFA in a solvent such as DCM. The resulting hydrazides can be coupled as described above with a substituted amidine to yield the corresponding 1,2,4-triazole, and alkylated as described in Scheme 1 above to yield the desired compound of this invention. These compounds can be further manipulated synthetically as described hereafter.

SCHEME 2:

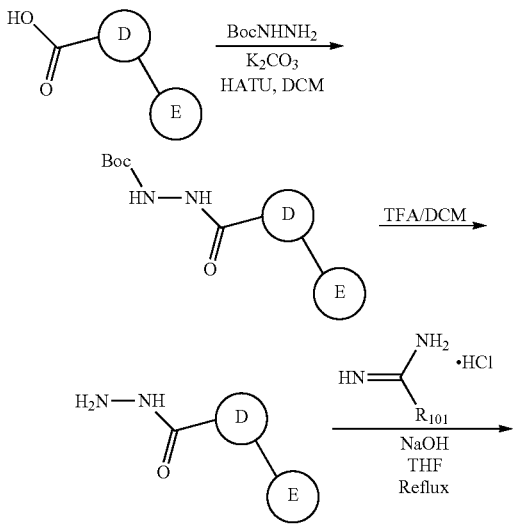

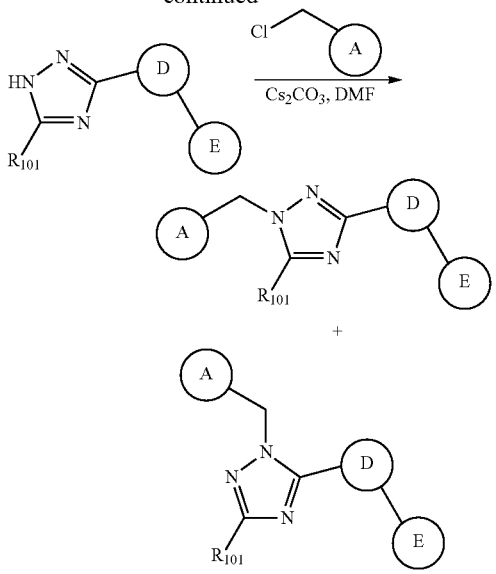

Compounds of the invention bearing 2-halopyridines, such as 2-chloropyridine, or heterocycles bearing a similarly reactive halogen substituents, for instance 2-chloropyrimidines or 2-chlorothiazoles, can be displaced with a variety of nucleophiles, such as primary and secondary amines [Scheme 3]. For example, by refluxing an excess of the amine at 120° C. overnight, using a solvent such as DMSO if required.

SCHEME 3:

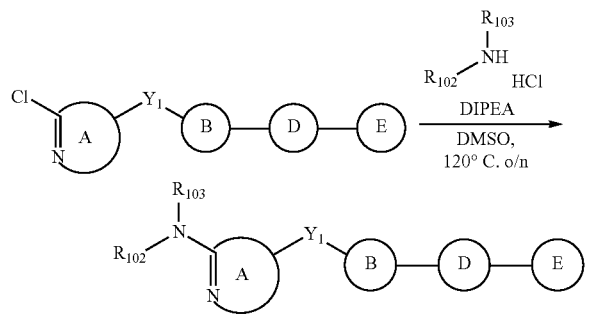

Alternatively, these heterocyclic halides or aromatic halides can be cross coupled with amines using palladium catalysis, using methods known to those trained in the art [Scheme 4]. For example, aromatic bromides can be coupled using a catalyst system comprising of dicyclohexyl(2',6'-diisopropoxy-[1,1'-biphenyl]-2-yl)phosphine and chloro-(2-dicyclohexylphosphino-2',6'-diisopropoxy-1,1'-biphenyl)[2-(2'-amino-1,1'-biphenyl)]palladium(II) in the presence of a base such as NaOtBu in THF at 65° C. for 2 h. Alternatively, a catalyst system comprising of X-Phos, $Pd_2(dba)_3$ and N',N'-dimethylethane-1,2-diamine in the presence of a base such as $Cs_2CO_3$ and be used for the transformation in a solvent such as dioxane. The reaction being conducted by microwave irradiation at 120° C. for 1 h. In addition, this transformation can be conducted using a catalytic system comprising of X-Phos and $Pd_2(dba)_3$ in the presence of a base such as $Cs_2CO_3$ in a solvent such as toluene, by heating at 140° C. for 18 h.

SCHEME 4:

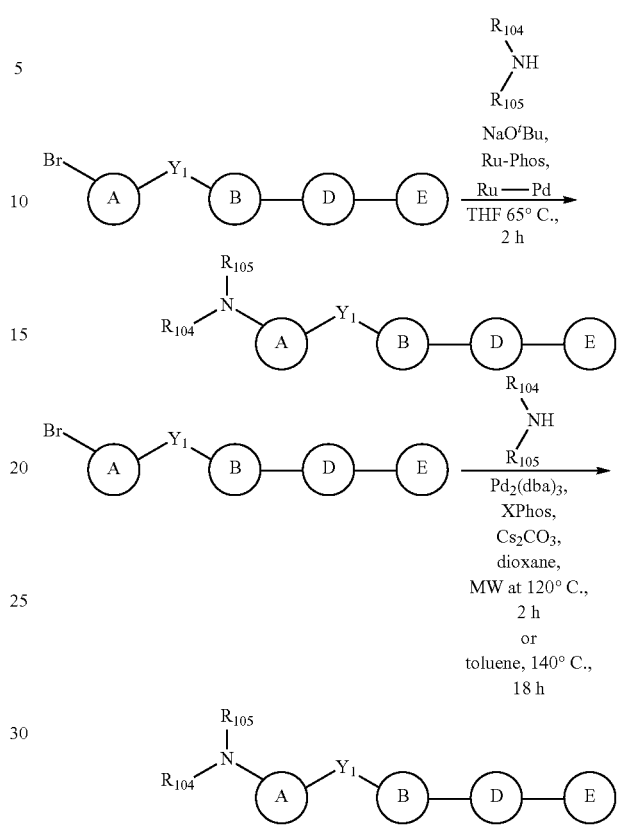

Furthermore, these heterocyclic halides or aromatic halides can be cross coupled with stannanes or boronates using palladium catalysis, applying methods known to those trained in the art [Scheme 5]. For example, aromatic bromides can be coupled with alkenyl stannanes using a catalyst system comprising of tetrakis(triphenylphosphine)palladium(0) in the presence of a base such as $K_2CO_3$ in a solvent such as dioxane, conducting the reaction thermally at 110° C. for 12 h.

SCHEME 5:

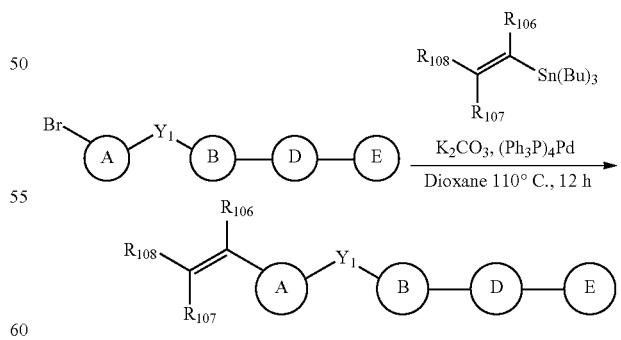

Compounds of the present invention can be further manipulated using synthetic transformation known to those trained in the art to yield alternative compounds also covered within the scope of this invention. For instance, as is depicted in Scheme 6, compounds bearing a protected amine can be deprotected using synthetic transformations known to those trained in the art, for example a Cbz-protecting group can be removed using HBr in AcOH/H$_2$O at temperatures around 40° C. The resulting primary or secondary amine can undergo a reductive amination reaction to yield higher substituted amines, for instance by reacting the amine with an aldehyde in the presence of a reducing agent such as NaBH$_3$(CN) in a alcoholic solvent.

SCHEME 6:

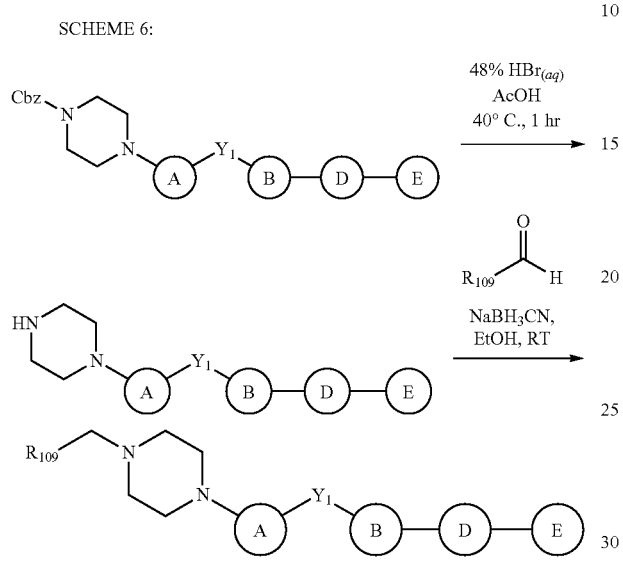

Alternatively, compounds of the present invention containing a primary or a secondary amine can be further manipulated by reaction with a carboxylic acid in the presence of coupling agents like EDCI or HATU, a carboxylic acid chloride, or a sulfonyl chloride in the presence of a base such as triethylamine in a suitable solvent, for example DCM, as depicted in Scheme 7.

SCHEME 7:

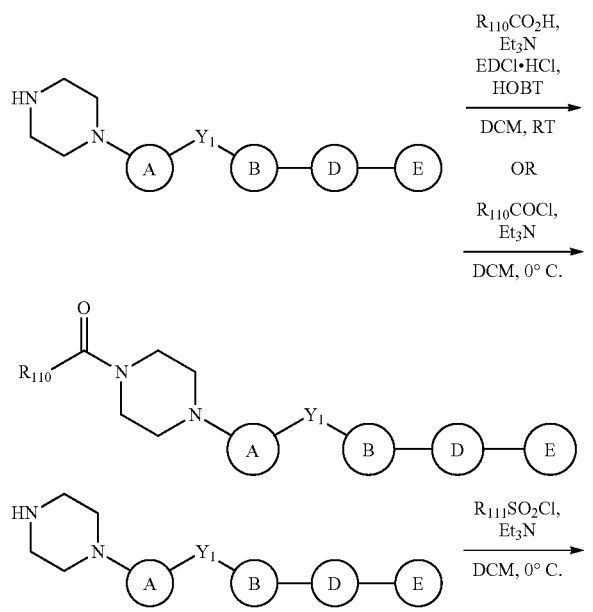

-continued

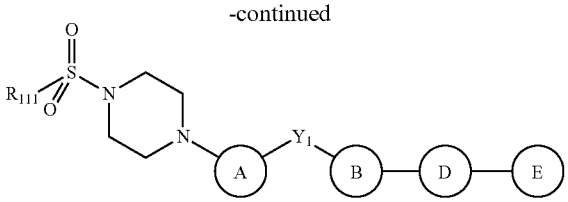

Another route for the preparation of compounds of the present invention is depicted in Scheme 8. Starting from compounds of the invention bearing a carboxylic ester, these can readily be transformed into amides. For example, a mixture of the ester can be reacted with the desired amine in the presence of 1,2,4-triazole and DBU, and heated to 70-100° C. overnight.

SCHEME 8:

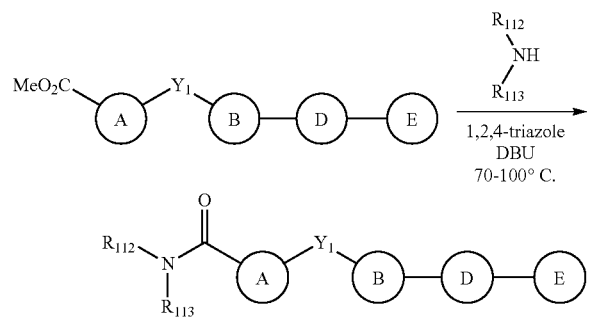

Compounds of the invention bearing a phenol moiety can be further manipulated by reaction with a variety of alkylating reagents such as alkyl-, benzyl- or allyl-halides, in the presence of a base such as K$_2$CO$_3$ or CsCO$_3$ in a suitable solvent like DMF, occasionally heating the reaction if necessary [Scheme 9a]. In addition, if such transformations are carried out with compounds of the invention bearing 2-hydroxypyridines, the products of N-alkylation can be obtained as well as the products of O-alkylation. An additional way to functionalize the compounds of this invention bearing a phenol moiety is described in Scheme 9b, and consists in reacting a suitable alcohol in the presence of an azodicarboxylate reagent, like diethyl azodicarboxylate (DEAD) and a phosphine, for example Ph$_3$P, according to the methodology described by Mistunobu et al. (Synthesis 1981, 1-28) or any modification thereof known to those trained in the art.

Scheme 9:

Scheme 9a

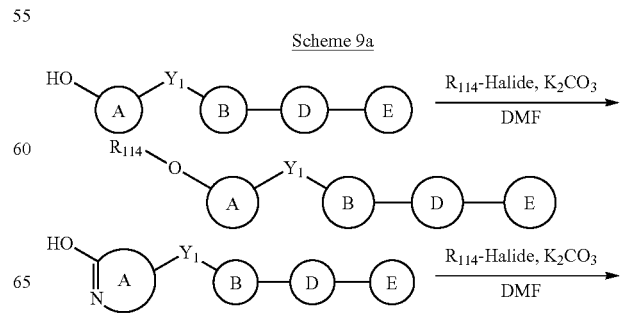

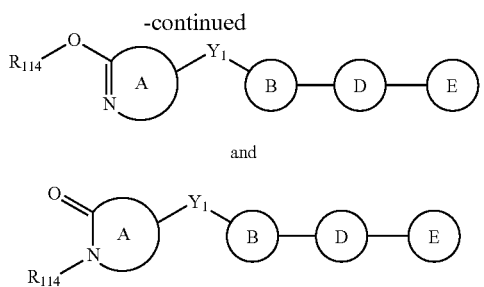

and

Scheme 9b

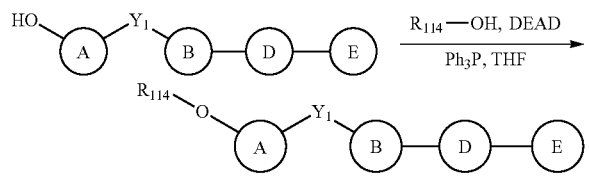

An additional route to prepare the compounds of this invention is described in Scheme 10. Compounds bearing an alkenyl group can be further manipulated by oxidative transformations. For example, they can undergo di-hydroxylation by applying methods known to those trained in the art, including using a catalytic amount of $OsO_4$ in the presence of N-methylmorpholine-oxide in a suitable solvent such as tert-butanol. Alternatively, the double bond can be converted into the corresponding epoxide by a suitable oxidizing reagent, for example 3-chloro-benzoperoxy acid, and the epoxide species could in turn be further functionalized by reaction with a suitable nucleophilic reagent such an amine [Scheme 10].

SCHEME 10:

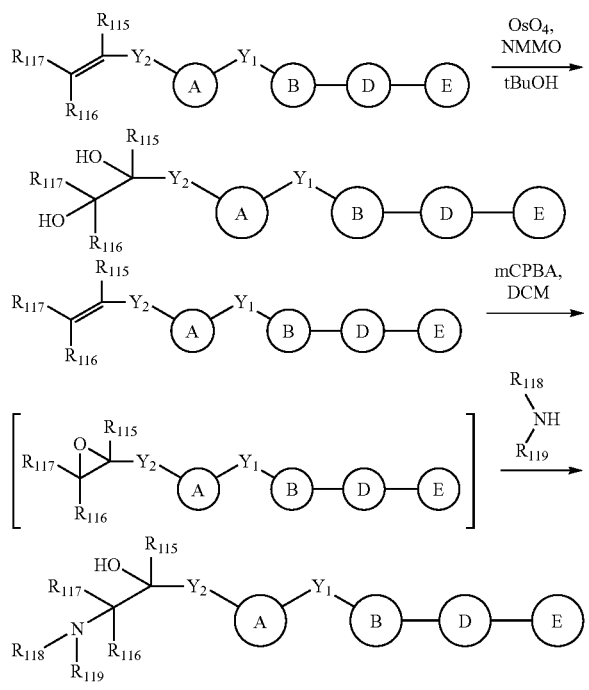

Furthermore, compounds described in this invention bearing an unsubstituted aniline group can be further manipulated by methods known to those skilled in the art and converted into compounds bearing a sulfonamide moiety, as depicted in Scheme 11. For example, treatment of unsubstituted anilines with sodium nitrite in the presence of suitable acidifying reagents, such as acetic acid and hydrochloric acid, followed by treatment with sulfur dioxide in the presence of a suitable inorganic salt such as $CuCl_2$, results in the formation of the corresponding sulfonyl chloride. The latter could then be further progressed to a sulfonamide by reaction with an amine in the presence of a base such as pyridine, in a suitable solvent, for example DCM.

SCHEME 11:

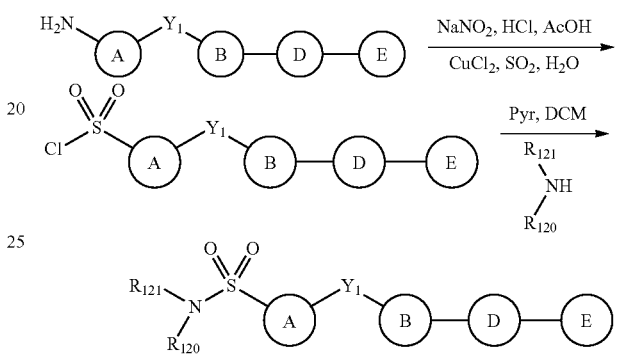

Another route for the preparation of compounds of the present invention is depicted in Scheme 12, where in 1,3,4-oxadiazoles can be prepared using synthetic procedures known to those trained in the art. Starting from a suitable triazole carboxylic acid ester, this can be alkylated to give the desired substituted benzyl triazole, or heteromethyltriazole. This synthetic sequence may give regioisomers which can be separated at various points along the synthetic sequence using chromaographical techniques. In turn, the resulting ester product is reacted with hydrazine hydrate in an alcoholic solvent to give the corresponding hydrazide. This can be coupled with an appropriately substituted benzoic or heterocyclic acid using reagents such as phosphorous oxychloride at elevated temperatures to synthesize the desired 1,3,4-oxadiazoles of this invention. As described above these can be transformed into other compounds described in this invention using protocols described above and below.

SCHEME 12:

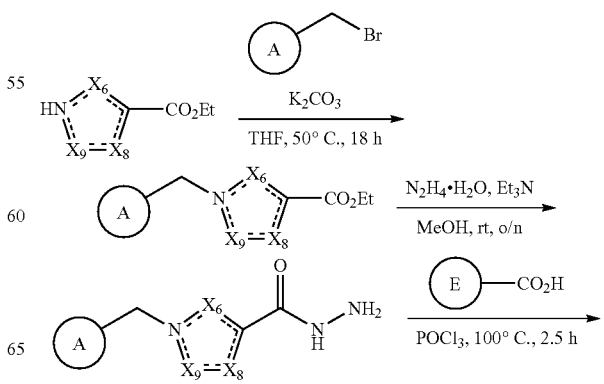

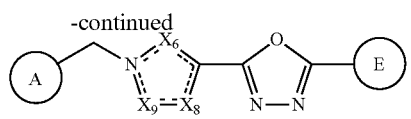

Another route for the preparation of compounds of the present invention is depicted in Scheme 13 for targeting isomeric oxadiazoles. Substituted triazole esters are converted to the corresponding primary amides, for instance by using methanolic ammonia solution at elevated temperature. These amides are alkylated with suitable functionalized alkyl halides and tosylates, for example using a base such as $Cs_2CO_3$ or $K_2CO_3$ in a solvent such as DMF or THF to yield isomeric N-substituted triazoles which can be separated using chromographic techniques such as column chromatography on silica. The primary amide can then be dehydrated to the corresponding nitrile, for example by using trifluoroacetic anhydride and triethylamine in a solvent such as DCM or other methods known to those trained in the art. Fictionalization on the periphery of the molecule can then be undertaken if required using methods described above and below. The nitrile can then be transformed into the hydroxyamidine through treatment with hydroxylamine hydrochloride in the presence of a tertiary amine base, in a alcohol solvent at elevated temperature. Coupling with a carboxylic acids, using coupling reagents such as carbonyl diimidazole in a solvent like DCM leads to a cyclization precursor which can be dehydrated to compounds of this invention at elevated temperature, such as heating at 135° C. in a solvent like DMF.

SCHEME 13:

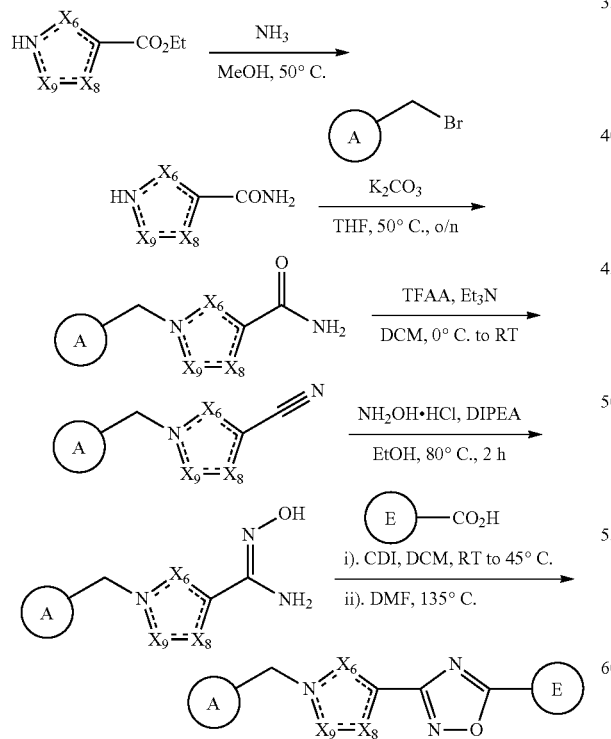

Compounds described in this invention containing a thiazole ring can be prepared by those skilled in the art according to a synthetic route like the one described in Scheme 14. A suitable alpha-bromo acetophenone can be converted to a thiazole 2-carboxylate by reaction with an amino-2-thioxoacetate heating at reflux in a solvent such as EtOH. The thiazole 2-carboxylate can then be progressed to the corresponding hydrazide by stirring in a suitable solvent, such as MeOH, in the presence of hydrazine hydrate. Reaction with a suitable amidine followed by thermal cyclization, for example in a high boiling solvent such as ethylene glycol, can be used to access a thiazole-containing tricyclic intermediate. The latter can in turn be alkylated as previously described in Scheme 1, and substituent A could be further manipulated as described in Schemes 3 to 11.

SCHEME 14:

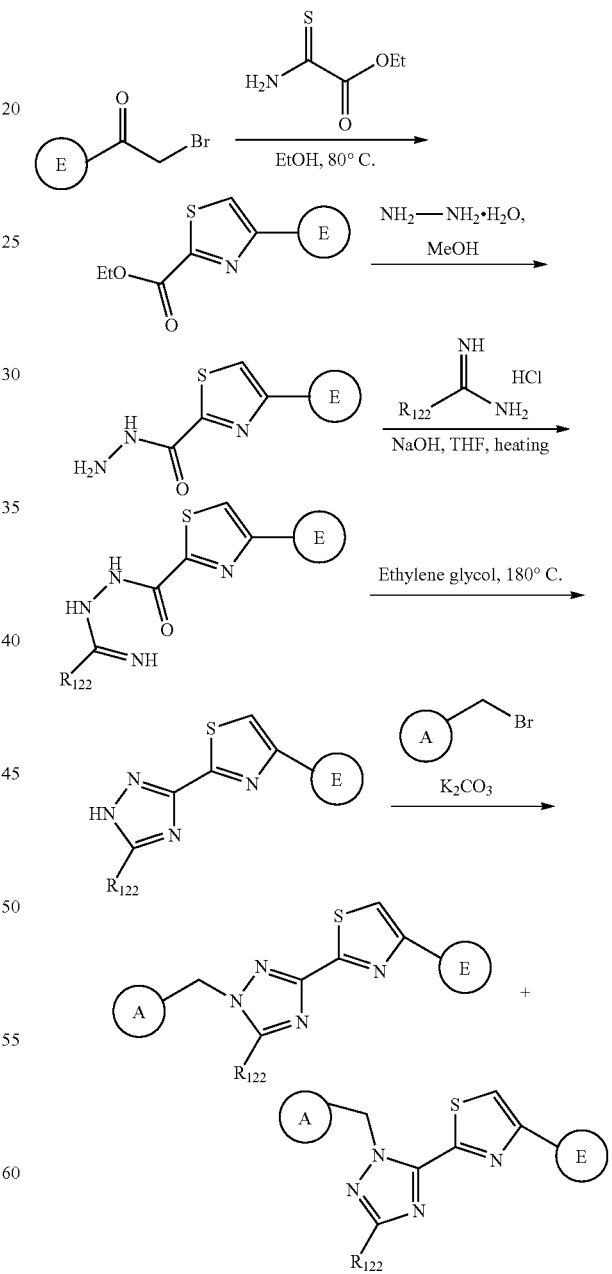

Additionally, compounds described in this invention containing an oxazole ring can be prepared by those skilled in the art according to a synthetic route like the one described in Scheme 15. A suitable alpha-amino acetophenone can be acylated with a 2-chloro-2-oxo-acetate in the presence of a base such as triethylamine in a solvent such as including DCM, NMP, MeCN. The resulting alpha-ketoamide product can then be cyclized to the corresponding oxazole-2-carboxylate by heating in the presence of a condensing agent such as POCl$_3$, and the resulting product can in turn be converted to the carbohydrazide by stirring in a solvent such as MeOH or EtOH in the presence of hydrazine hydrate. In analogous manner to the synthetic route previously described in Scheme 14, reaction with a suitable amidine followed by condensation in a solvent such as ethylene glycol or THF affords the desired oxazole-containing tricyclic intermediate. The latter can in turn be alkylated as previously described in Scheme 1, and substituent A could be further manipulated as described in Schemes 3 to 11.

SCHEME 15:

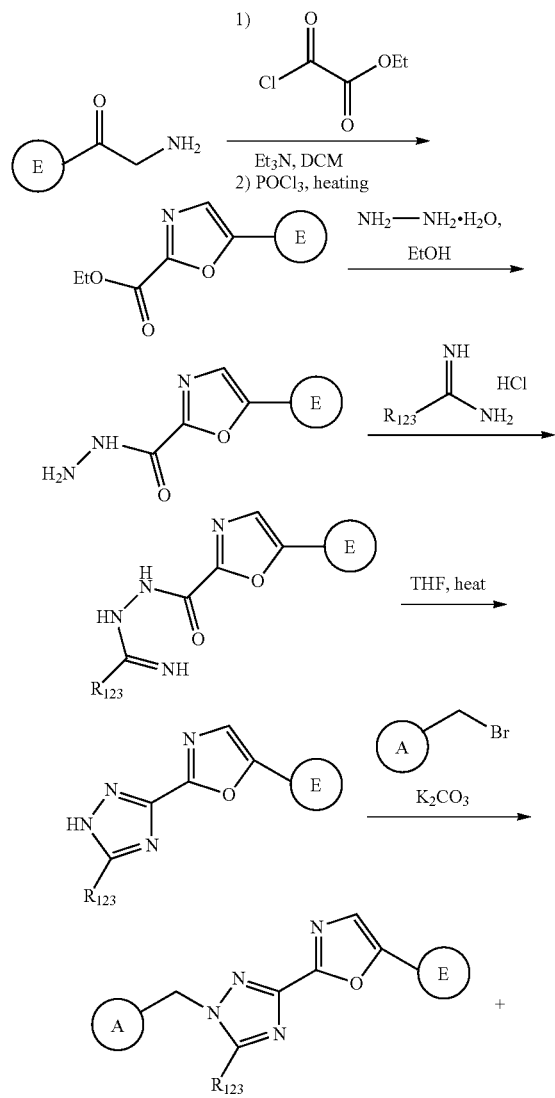

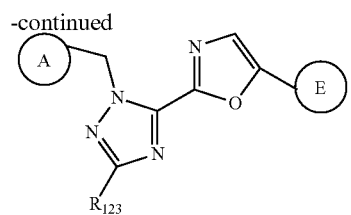

Compounds described in the present invention that contain an isoxazole ring can be prepared in a regiospecific manner by synthetic routes such those described in Scheme 16. In one case (Scheme 16a) a suitable benzaldehyde can be converted in the corresponding chloro-oxime by condensation with hydroxalamine in a solvent such as MeOH at elevated temperature, followed by treatment with a suitable chlorinating agent, for example N-chlorosuccinimide, in a solvent such as DMF. Thermal cycloaddition with methyl-propiolate in the presence of a suitable base, for example triethylamine, in a solvent such as toluene gives the isoxazole-5-carboxylate intermediates. Functional group manipulations similar to those described in Schemes 14 and 15 can be used to progress the latter intermediates to the fully functionalized isoxazole derivatives described here in, and substituent A could be further manipulated as described in Schemes 3 to 11. In a similar fashion, isoxazole-3-carboxylate intermediates can be prepared by condensation of a suitable acetophenone with an oxalate in the presence of a strong base, such as NaOMe in MeOH, followed by cyclization of the derived diketo ester in the presence of hydroxylamine [Scheme 16b]. Functional group manipulations previously described in Schemes 14 and 15 can then be employed to access the fully functionalized isomeric isoxazole intermediates, substituent A could be further manipulated as described in Schemes 3 to 11.

Scheme 16:

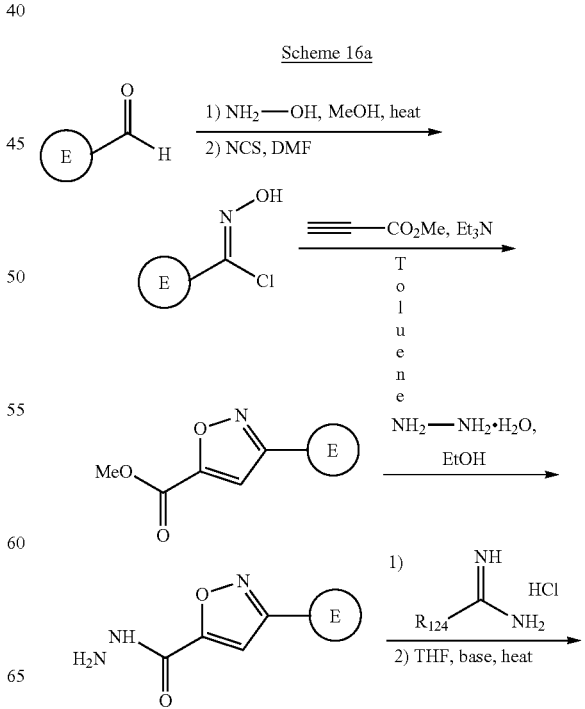

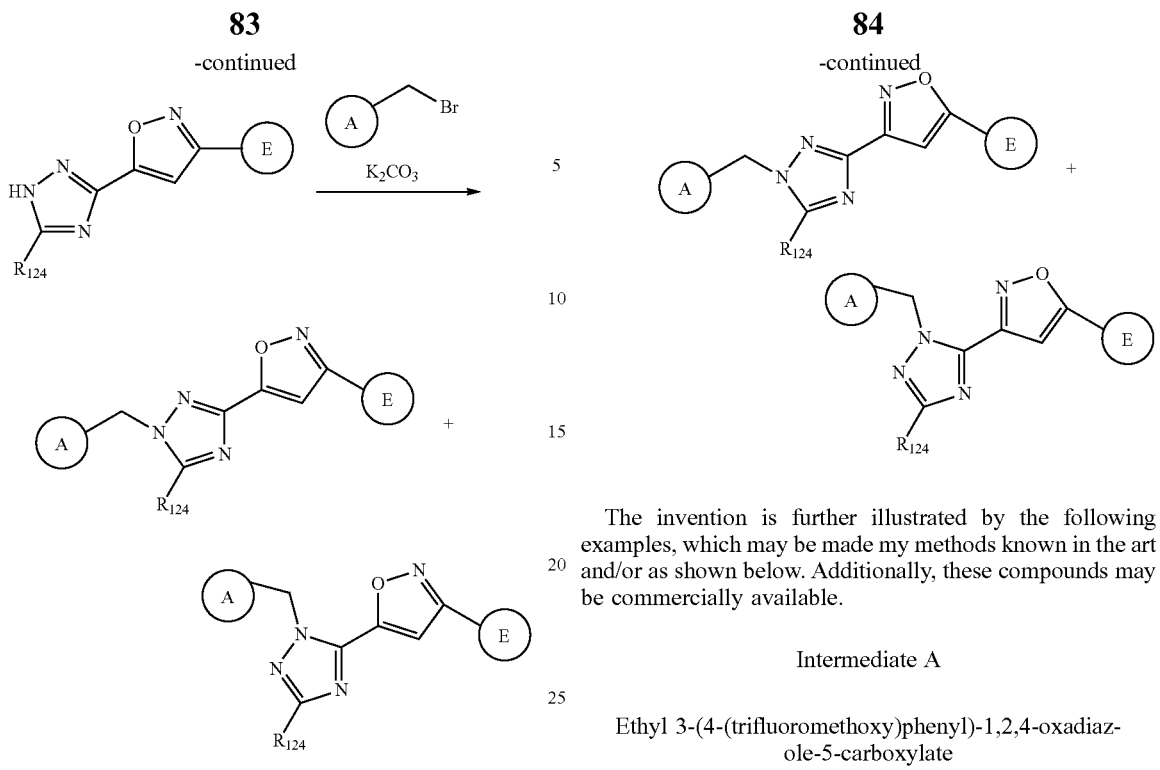

The invention is further illustrated by the following examples, which may be made my methods known in the art and/or as shown below. Additionally, these compounds may be commercially available.

Intermediate A

Ethyl 3-(4-(trifluoromethoxy)phenyl)-1,2,4-oxadiazole-5-carboxylate

Step 1

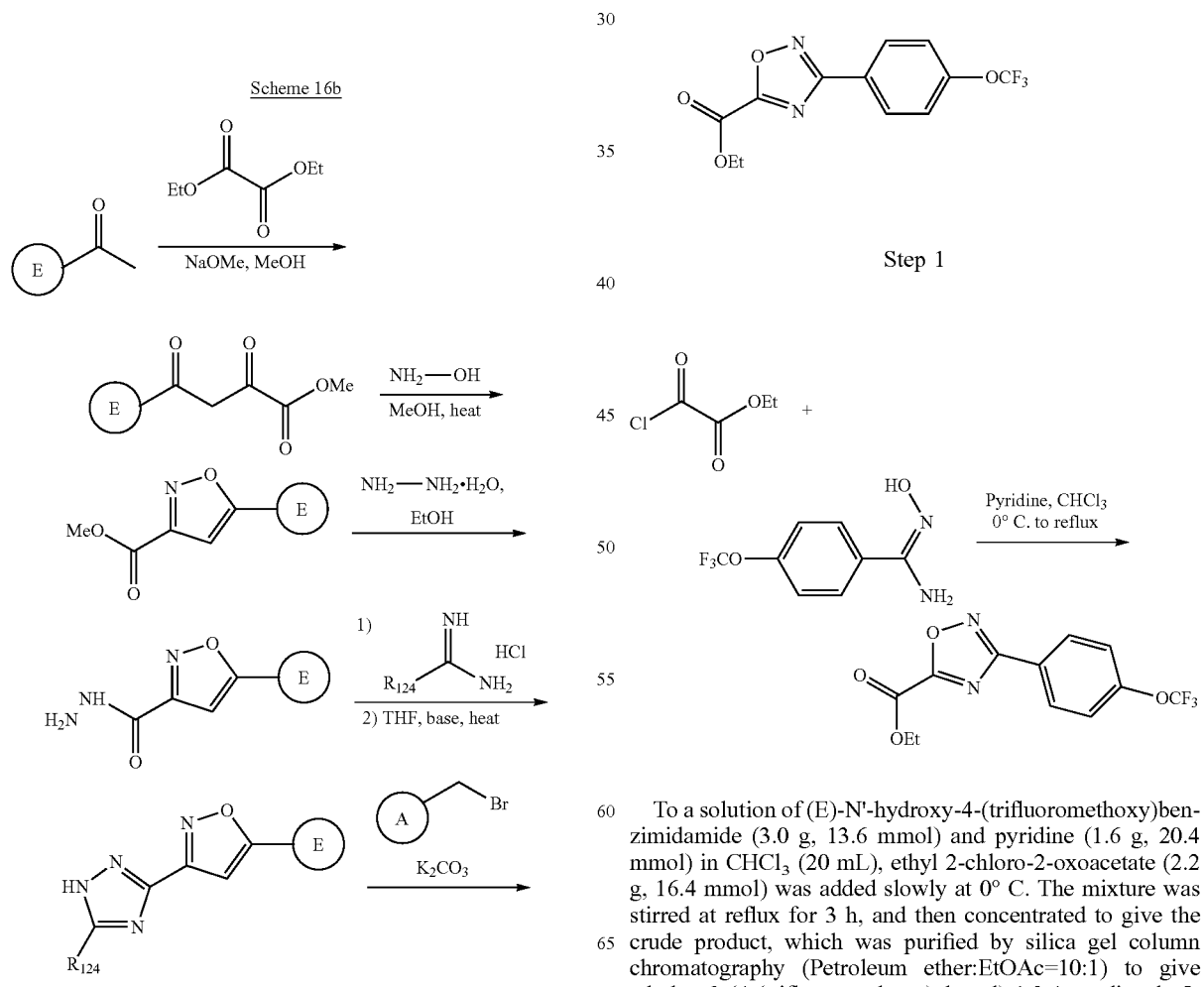

To a solution of (E)-N'-hydroxy-4-(trifluoromethoxy)benzimidamide (3.0 g, 13.6 mmol) and pyridine (1.6 g, 20.4 mmol) in CHCl₃ (20 mL), ethyl 2-chloro-2-oxoacetate (2.2 g, 16.4 mmol) was added slowly at 0° C. The mixture was stirred at reflux for 3 h, and then concentrated to give the crude product, which was purified by silica gel column chromatography (Petroleum ether:EtOAc=10:1) to give ethyl 3-(4-(trifluoromethoxy)phenyl)-1,2,4-oxadiazole-5- carboxylate as a white solid (4.5 g, 82%). MS (ES+) $C_{12}H_9F_3N_2O_4$ requires: 302, found: 303[M+H]$^+$.

Intermediate B 5-(5-Methyl-1H-1,2,4-triazol-3-yl)-3-(4-(trifluoromethoxy)phenyl)-1,2,4-oxadiazole

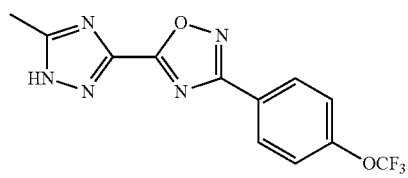 [SMILES: Cc1nc(-c2nc(-c3ccc(OC(F)(F)F)cc3)no2)n[nH]1]

Step 1

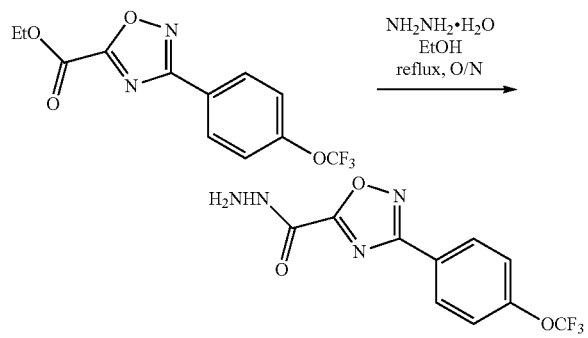

3-(4-(Trifluoromethoxy)phenyl)-1,2,4-oxadiazole-5-carbohydrazide

To the solution of ethyl 3-(4-(trifluoromethoxy)phenyl)-1,2,4-oxadiazole-5-carboxylate (13.6 g, 45.0 mmol) in EtOH (200 mL), NH$_2$NH$_2$.H$_2$O (80%, 14 mL, 225 mmol) was added. The reaction mixture was stirred at RT overnight. The desired compound precipitated from the reaction mixture, filtered and washed with EtOH (50 mL) to afford 3-(4-(trifluoromethoxy)phenyl)-1,2,4-oxadiazole-5-carbohydrazide as a light yellow solid (9.7 g, 75%). MS (ES+) $C_{10}H_7F_3N_4O_3$ requires: 288, found: 289 [M+H]$^+$.

Step 2

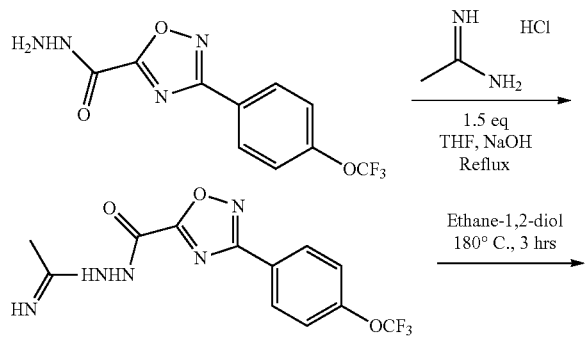

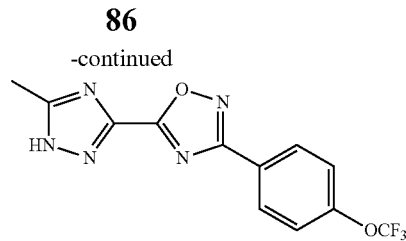

5-(5-Methyl-1H-1,2,4-triazol-3-yl)-3-(4-(trifluoromethoxy)phenyl)-1,2,4-oxadiazole To a solution of 3-(4-(trifluoromethoxy)phenyl)-1,2,4-oxadiazole-5-carbohydrazide (9.7 g, 33.7 mmol) and acetimidamide hydrochloride (4.8 g, 50.5 mmol) in dry THF (300 mL), NaOH (2.0 g, 50.5 mmol) was added at RT. The mixture was refluxed overnight. The solution was cooled, concentrated and ethane-1,2-diol (100 mL) was added. The resulting mixture was heated at 180° C. for 3 h, cooled to RT, diluted with H$_2$O (800 mL), and extracted with EtOAc (3×400 mL). The combined organic layers were washed with H$_2$O (300 mL) and brine (100 mL), dried over Na$_2$SO$_4$, filtered, and concentrated under reduced pressure to afford the crude solid product, which was treated with EtOAc (150 mL). The resulting suspension was stirred at RT for 15 min, and then filtered to afford 4.8 g of the pure desired compound. The remaining filtrate was concentrated and purified by silica gel column chromatography (Petroleum ether: EtOAc=1:1) to afford 1.4 g of another batch of 5-(5-methyl-1H-1,2,4-triazol-3-yl)-3-(4-(trifluoromethoxy)phenyl)-1,2,4-oxadiazole as a white solid-overall 6.2 g, yield 59%. MS (ES+) $C_{12}H_8F_3N_5O_2$ requires: 311, found: 312 [M+H]$^+$.

The invention is further illustrated by the following examples, which may be made my methods known in the art and/or as shown below. Additionally, these compounds may be commercially available.

EXAMPLE 1

4-(4-((5-Methyl-3-(3-(4-(trifluoromethoxy)phenyl)-1,2,4-oxadiazol-5-yl)-1H-1,2,4-triazol-1-yl)methyl)pyridin-2-yl)piperazin-1-ium trifluoroacetate

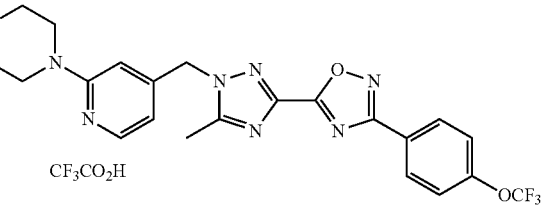

Step 1

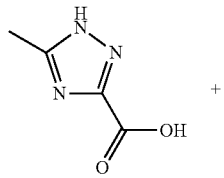

+

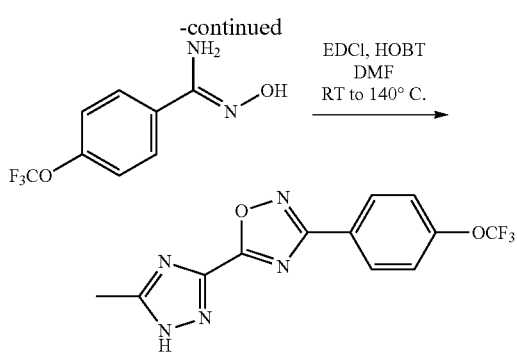

5-(5-Methyl-1H-1,2,4-triazol-3-yl)-3-(4-(trifluoromethoxy)phenyl)-1,2,4-oxadiazole To a solution of N'-hydroxy-4-(trifluoromethoxy)benzimidamide (1.3 g, 5.1 mmol) and 5-methyl-1H-1,2,4-triazole-3-carboxylic acid (650 mg, 5.1 mmol) in DMF (15 mL), EDC.HCl (980 mg, 5.1 mmol) and HOBT (690 mg, 5.1 mmol) were added at RT. The mixture was stirred at RT for 1 h, and then heated to 140° C. for 3 h. The resulting mixture was cooled, diluted with H₂O (20 mL) and extracted with EtOAc (4×40 mL). The combined organic layers were washed with H₂O (10 mL) and brine (10 mL), dried over Na₂SO₄, filtered and concentrated under reduced pressure, and the residue was purified by Combiflash reverse phase chromatography (50%~60% MeCN/H₂O containing 0.01% trifluoroacetic acid) to give 5-(5-methyl-1H-1,2,4-triazol-3-yl)-3-(4-(trifluoromethoxy)phenyl)-1,2,4-oxadiazole as a white solid (590 mg, 37%). MS (ES+) C₁₂H₈F₃N₅O₂ requires: 311, found: 312[M+H]⁺.

Step 2

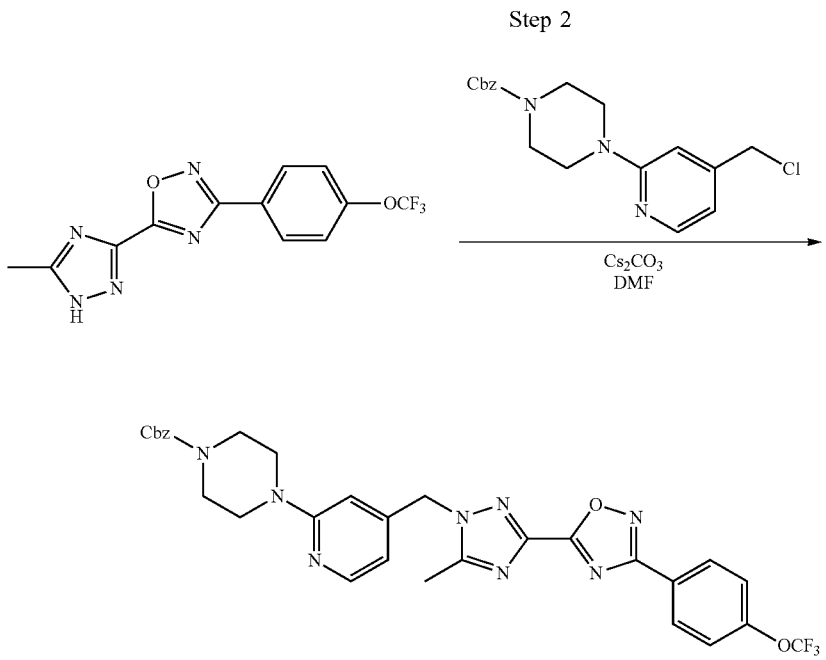

Benzyl 4-(4-((5-methyl-3-(3-(4-(trifluoromethoxy)phenyl)-1,2,4-oxadiazol-5-yl)-1H-1,2,4-triazol-1-yl)methyl)pyridin-2-yl)piperazine-1-carboxylate To a solution of 5-(5-methyl-1H-1,2,4-triazol-3-yl)-3-(4-(trifluoromethoxy)phenyl)-1,2,4-oxadiazole (311 mg, 1.0 mmol) and benzyl 4-(4-(chloromethyl)pyridin-2-yl)piperazine-1-carboxylate (690 mg, 2.0 mmol) in DMF (15 mL), Cs₂CO₃ (820 mg, 2.5 mmol) was added at RT. The mixture was stirred at RT overnight, then diluted with H₂O (50 mL), and extracted with EtOAc (3×50 mL). The combined organic layers were washed with H₂O (20 mL) and brine (20 mL), dried over Na₂SO₄, filtered and concentrated under reduced pressure, and the residue was purified by silica gel column chromatography (Petroleum ether:EtOAc=1:2) to give benzyl 4-(4-((5-methyl-3-(3-(4-(trifluoromethoxy)phenyl)-1,2,4-oxadiazol-5-yl)-1H-1,2,4-triazol-1-yl)methyl)pyridin-2-yl)piperazine-1-carboxylate (350 mg, 56%) as a yellow oil and benzyl 4-(4-((3-methyl-5-(3-(4-(trifluoromethoxy)phenyl)-1,2,4-oxadiazol-5-yl)-1H-1,2,4-triazol-1-yl)methyl)pyridin-2-yl)piperazine-1-carboxylate as a white solid (50 mg, 8%). MS (ES+) C₃₀H₂₇F₃N₈O₄ requires: 620, found: 621[M+H]⁺.

Step 3

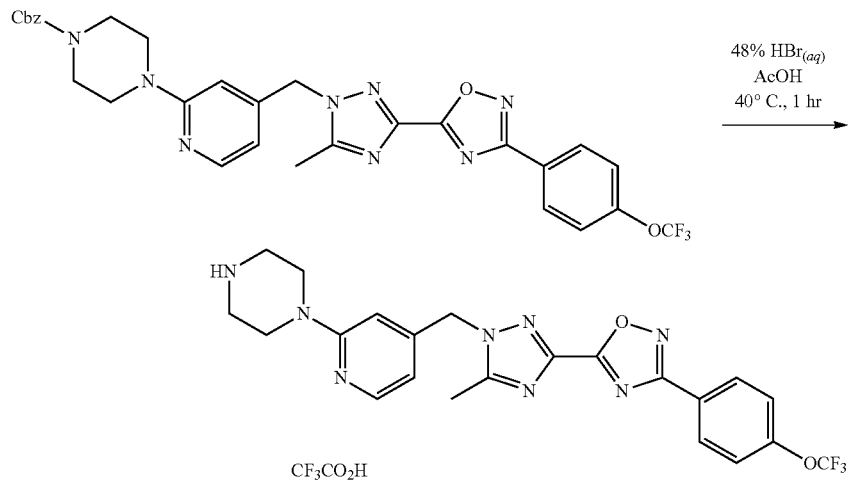

4-(4-((5-Methyl-3-(3-(4-(trifluoromethoxy)phenyl)-1,2,4-oxadiazol-5-yl)-1H-1,2,4-triazol-1-yl)methyl)pyridin-2-yl)piperazin-1-ium trifluoroacetate To a solution of benzyl 4-(4-((5-methyl-3-(3-(4-(trifluoromethoxy)phenyl)-1,2,4-oxadiazol-5-yl)-1H-1,2,4-triazol-1-yl)methyl)pyridin-2-yl)piperazine-1-carboxylate (200 mg, 0.30 mmol) in AcOH (1 mL), HBr (2 mL, 48% in H$_2$O) was added at RT. The mixture was stirred at 40° C. for 1 h, and then concentrated under reduced pressure to give the crude product, which was purified by prep-HPLC (Mobile phase: A=0.01% TFA/H$_2$O, B=MeCN; Gradient: B=60%-95% in 18 min; Column: XBridge C18, 5 um, 30 mm×150 mm) to afford 4-(4-((5-methyl-3-(3-(4-(trifluoromethoxy)phenyl)-1,2,4-oxadiazol-5-yl)-1H-1,2,4-triazol-1-yl)methyl)pyridin-2-yl)piperazin-1-ium 2,2,2-trifluoroacetate as a white solid (130 mg, 84%). MS (ES+) C$_{22}$H$_{21}$F$_3$N$_8$O$_2$ requires: 486, found: 487 [M+H]$^+$; $^1$H NMR (500 MHz, DMSO-d$_6$) δ 8.98 (s, 2H), 8.22 (d, J=8.5 Hz, 2H), 8.15 (d, J=5.0 Hz, 1H), 7.61 (d, J=8.5 Hz, 2H), 6.87 (s, 1H), 6.57 (d, J=5.0 Hz, 1H), 5.54 (s, 2H), 3.73-3.71 (m, 4H), 3.22-3.19 (m, 4H), 2.59 (s, 3H).

EXAMPLE 2

5-(5-Methyl-1-((2-(4-methylpiperazin-1-yl)pyridin-4-yl)methyl)-1H-1,2,4-triazol-3-yl)-3-(4-(trifluoromethoxy)phenyl)-1,2,4-oxadiazole

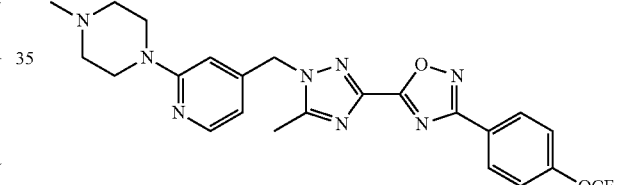

Step 1

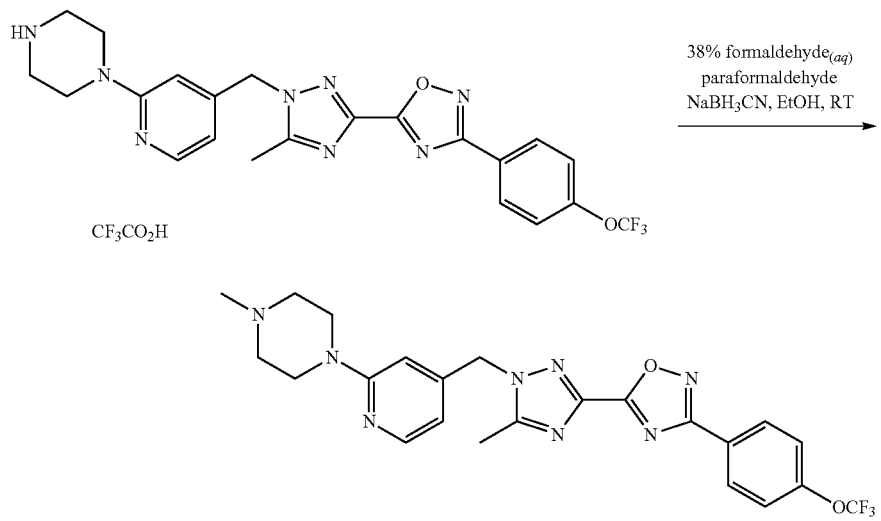

5-(5-Methyl-1-((2-(4-methylpiperazin-1-yl)pyridin-4-yl)methyl)-1H-1,2,4-triazol-3-yl)-3-(4-(trifluoromethoxy)phenyl)-1,2,4-oxadiazole The mixture of 4-(4-((5-methyl-3-(3-(4-(trifluoromethoxy)phenyl)-1,2,4-oxadiazol-5-yl)-1H-1,2,4-triazol-1-yl)methyl)pyridin-2-yl)piperazin-1-ium trifluoroacetate (100 mg, 0.2 mmol), formaldehyde (0.5 mL, 6.0 mmol, 38% in H$_2$O) and paraformaldehyde (100 mg, 3.3 mmol) in EtOH (1 mL) was stirred at RT, then treated with NaBH$_3$CN (63 mg, 1.0 mmol) in one portion. The mixture was stirred at RT for 3 h, and then concentrated under reduced pressure to give the crude product, which was purified by pre-HPLC (Mobile phase: A=10 mM NH$_4$HCO$_3$/H$_2$O, B=MeCN; Gradient: B=60%-95% in 18 min; Column: XBridge C18, 5 um, 30 mm×150 mm) to afford 5-(5-methyl-1-((2-(4-methylpiperazin-1-yl)pyridin-4-yl) methyl)-1H-1,2,4-triazol-3-yl)-3-(4-(trifluoromethoxy)phenyl)-1,2,4-oxadiazole as a white solid (45 mg, 45%). MS (ES+) C$_{23}$H$_{23}$F$_3$N$_8$O$_2$ requires: 500, found: 501 [M+H]$^+$; $^1$H NMR (500 MHz, DMSO-d$_6$) δ 8.22 (d, J=8.3 Hz, 2H), 8.08 (d, J=5.3 Hz, 1H), 7.60 (d, J=8.2 Hz, 2H), 6.77 (s, 1H), 6.42 (d, J=5.3 Hz, 1H), 5.50 (s, 2H), 3.50-3.48 (m, 4H), 2.58 (s, 3H), 2.41-2.32 (m, 4H), 2.20 (s, 3H).

EXAMPLE 3

1-Methyl-4-(4-(4-((5-methyl-3-(5-phenylfuran-2-yl)-1H-1,2,4-triazol-1-yl)methyl)pyridin-2-yl)piperazine

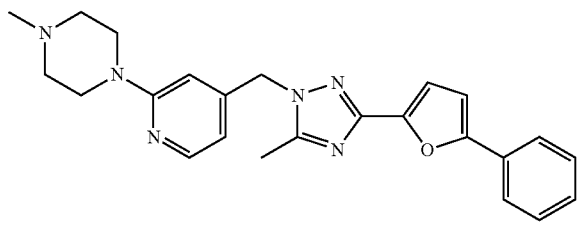 [SMILES: Cc1nc(-c2ccc(-c3ccccc3)o2)nn1Cc1ccnc(N2CCN(C)CC2)c1]

Step 1

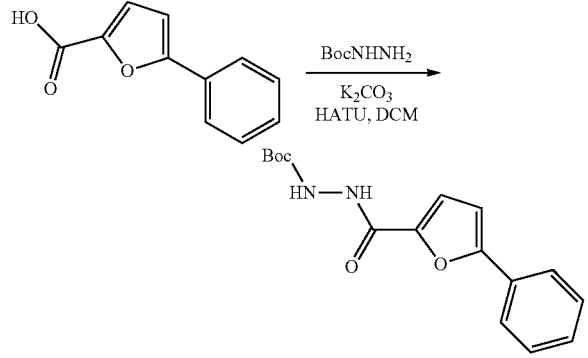

tert-Butyl 2-(5-phenylfuran-2-carbonyl)hydrazinecarboxylate

To a stirred suspension of 5-phenylfuran-2-carboxylic acid (200 mg, 1.06 mmol), tert-butyl hydrazinecarboxylate (140 mg, 1.06 mmol) and K$_2$CO$_3$ (440 mg, 3.19 mmol) in DCM (20 mL), HATU (404 mg, 1.06 mmol) was added. The mixture was stirred at RT for 3 h, then filtered to give the crude tert-butyl 2-(5-phenylfuran-2-carbonyl)hydrazinecarboxylate as a white solid (300 mg, 93%), which was directly used for next step without further purification. MS (ES+) C$_{16}$H$_{18}$N$_2$O$_4$ requires: 302, found: 247 [M+H-56]$^+$.

Step 2

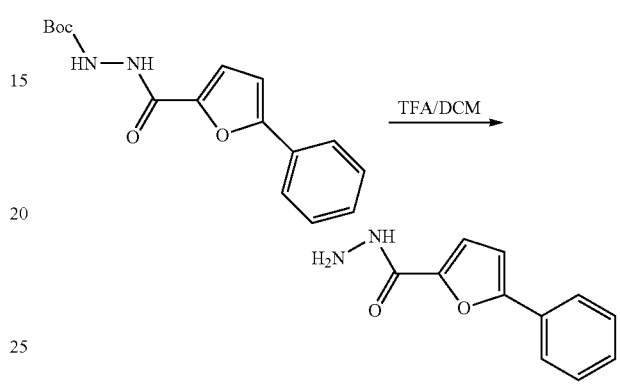

5-Phenylfuran-2-carbohydrazide

To a solution of tert-butyl 2-(5-phenylfuran-2-carbonyl)hydrazinecarboxylate (300 mg, 1 mmol) in DCM (10 mL), TFA (4.85 g, 50 mmol) was added dropwise. The mixture was stirred at RT overnight, then concentrated under reduced pressure and purified by silica gel column chromatography (EtOAc:Petroleum ether:TEA=50:50:1) to afford 5-phenylfuran-2-carbohydrazide as a light yellow solid (150 mg, 74%). MS (ES+) C$_{11}$H$_{10}$N$_2$O$_2$ requires: 202, found: 203 [M+H]$^+$.

Step 3

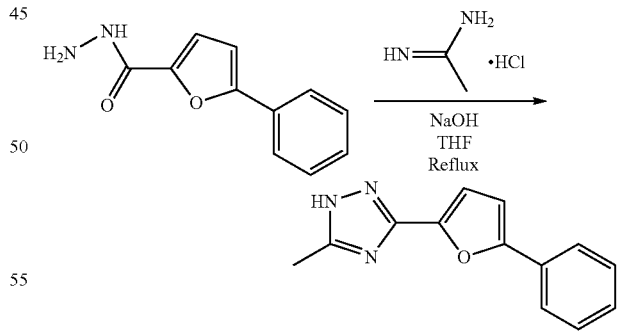

5-Methyl-3-(5-phenylfuran-2-yl)-1H-1,2,4-triazole

To a suspension of 5-phenylfuran-2-carbohydrazide (100 mg, 0.5 mmol) and acetamidine hydrochloride (141 mg, 1.49 mmol) in THF (20 mL), NaOH (59 mg, 1.49 mmol) was added. The mixture was refluxed overnight, cooled, then treated with H$_2$O (30 ml) and extracted with EtOAc (3×20 mL). The combined organic layers were washed with H$_2$O (1×10 mL) and brine (1×10 mL), dried over Na₂SO₄, filtered, concentrated under reduced pressure and purified by silica gel column chromatography (EtOAc:Petroleum ether=1:1) to afford 5-methyl-3-(5-phenylfuran-2-yl)-1H-1,2,4-triazole as a white solid (15 mg, 13%). MS (ES+) $C_{13}H_{11}N_3O$ requires: 225, found: 226 [M+H]⁺.

Step 4

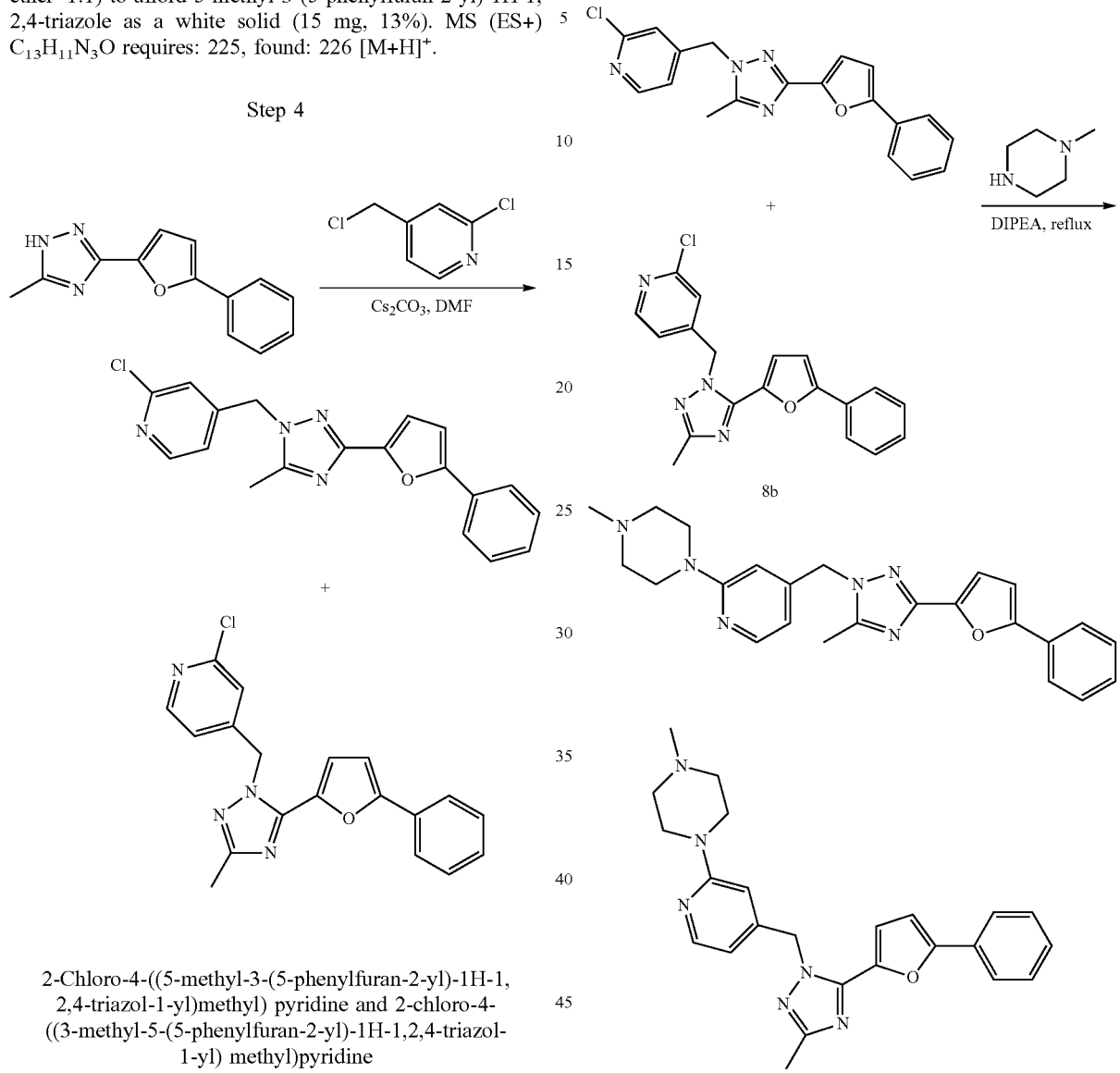

2-Chloro-4-((5-methyl-3-(5-phenylfuran-2-yl)-1H-1,2,4-triazol-1-yl)methyl) pyridine and 2-chloro-4-((3-methyl-5-(5-phenylfuran-2-yl)-1H-1,2,4-triazol-1-yl) methyl)pyridine To a solution of 5-methyl-3-(5-phenylfuran-2-yl)-1H-1,2,4-triazole (15 mg, 0.07 mmol) and 2-chloro-4-(chloromethyl)pyridine (13 mg, 0.08 mmol) in DMF (5 mL), Cs₂CO₃ (33 mg, 0.1 mmol) was added. The mixture was stirred at RT overnight, then treated with H₂O (30 mL), and extracted with EtOAc (3×30 mL). The combined organic layers were washed with H₂O (1×10 mL) and brine (1×10 mL), dried over Na₂SO₄, filtered, and concentrated under reduced pressure to afford the crude product, which was purified by silica gel column chromatography (EtOAc:Petroleum ether=100:20) to give the mixture of 2-chloro-4-((5-methyl-3-(5-phenylfuran-2-yl)-1H-1,2,4-triazol-1-yl)methyl)pyridine and 2-chloro-4-((3-methyl-5-(5-phenylfuran-2-yl)-1H-1,2,4-triazol-1-yl)methyl)pyridine as a yellow solid (10 mg, 42%). MS (ES+) $C_{19}H_{15}ClN_4O$ requires: 350, found: 351 [M+H]⁺.

Step 5

1-Methyl-4-(4-((5-methyl-3-(5-phenylfuran-2-yl)-1H-1,2,4-triazol-1-yl)methyl)pyridin-2-yl)piperazine A mixture of 2-chloro-4-((5-methyl-3-(5-phenylfuran-2-yl)-1H-1,2,4-triazol-1-yl) methyl)pyridine and 2-chloro-4-((3-methyl-5-(5-phenylfuran-2-yl)-1H-1,2,4-triazol-1-yl) methyl)pyridine (100 mg, 0.3 mmol) was treated with 1-methylpiperazine (280 mg, 3 mmol) in DIEA (10 ml), and refluxed overnight. The mixture was cooled, concentrated, treated with H₂O (30 mL) and extracted with EtOAc (3×30 mL). The combined organic layers were washed with H₂O (1×10 mL) and brine (1×10 mL), dried over Na₂SO₄, filtered, and concentrated to afford the crude product, which was purified by prep-HPLC (Mobile phase: A=0.1% NH₄OH/H₂O, B=MeCN; Gradient: B=60%-95% in 18 min; Column: XBridge (C18, 5 um, 30 mm×150 mm) to give 1-methyl-4-(4-((5-methyl-3-(5-phenylfuran-2-yl)-1H-1,2,4- triazol-1-yl)methyl)pyridin-2-yl)piperazine as a yellow solid (66 mg, 53%) and 1-methyl-4-(4-((3-methyl-5-(5-phenylfuran-2-yl)-1H-1,2,4-triazol-1-yl)methyl)pyridin-2-yl)piperazine as a yellow solid (42 mg, 34%).

For 1-methyl-4-(4-((5-methyl-3-(5-phenylfuran-2-yl)-1H-1,2,4-triazol-1-yl)methyl) pyridin-2-yl)piperazine: MS (ES+) $C_{24}H_{26}N_6O$ requires: 414, found: 415 [M+H]$^+$. $^1$H NMR (500 MHz, CDCl$_3$) δ 8.14 (d, J=5.1 Hz, 1H), 7.89-7.72 (m, 2H), 7.39 (t, J=7.8 Hz, 2H), 7.28 (td, J=7.4, 1.3 Hz, 1H), 7.04 (d, J=3.5 Hz, 1H), 6.76 (d, J=3.5 Hz, 1H), 6.44-6.26 (m, 2H), 5.26 (s, 2H), 3.53 (t, J=5.0 Hz, 4H), 2.48 (t, J=5.1 Hz, 4H), 2.44 (s, 3H), 2.32 (s, 3H).

For 1-methyl-4-(4-((3-methyl-5-(5-phenylfuran-2-yl)-1H-1,2,4-triazol-1-yl)methyl) pyridin-2-yl)piperazine: MS (ES+) $C_{24}H_{26}N_6O$ requires: 414, found: 415 [M+H]$^+$. $^1$H NMR (500 MHz, CDCl$_3$) δ 8.12 (d, J=5.1 Hz, 1H), 7.63-7.55 (m, 2H), 7.38 (t, J=7.6 Hz, 2H), 7.30 (dd, J=14.4, 6.9 Hz, 1H), 7.11 (d, J=3.5 Hz, 1H), 6.77 (d, J=3.6 Hz, 1H), 6.51-6.40 (m, 2H), 5.60 (s, 2H), 3.46 (t, J=5.1 Hz, 4H), 2.45 (s, 3H), 2.43 (t, J=5.1 Hz, 4H), 2.30 (s, 3H).

EXAMPLE 4

3-(1-Benzyl-3-(3-(4-(trifluoromethoxy)phenyl)-1,2,4-oxadiazol-5-yl)-1H-1,2,4-triazol-5-yl)pyridin-1-ium trifluoroacetate

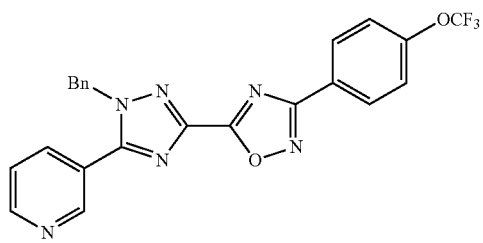 [SMILES: FC(F)(F)Oc1ccc(-c2noc(-c3nc(-c4cccnc4)n(Cc4ccccc4)n3)n2)cc1]

Step 1

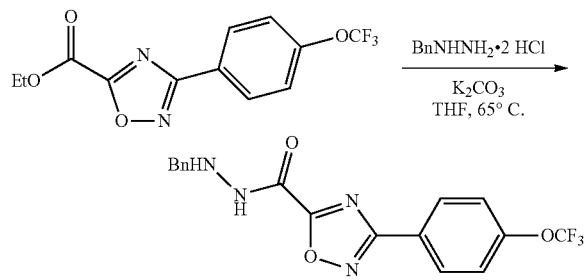

N'-benzyl-3-(4-(trifluoromethoxy)phenyl)-1,2,4-oxadiazole-5-carbohydrazide

To a suspension of ethyl 3-(4-(trifluoromethoxy)phenyl)-1,2,4-oxadiazole-5-carboxylate (Intermediate A) (1.0 g, 3.3 mmol) and K$_2$CO$_3$ (1.1 g, 13 mmol) in THF (17 mL) was added benzylhydrazine dihydrochloride (780 mg, 5.0 mmol). The mixture was heated to 70° C. for 3 h. The mixture was cooled to RT, filtered (Celite), and concentrated under reduced pressure. The crude oil was purified by Biotage (5% EtOAc/Hexane-60% EtOAc) to provide a white solid (500 mg, 40%): MS (ES+) $C_{17}H_{13}F_3N_4O_3$ requires: 378, found: 379 [M+H]+.

Step 2

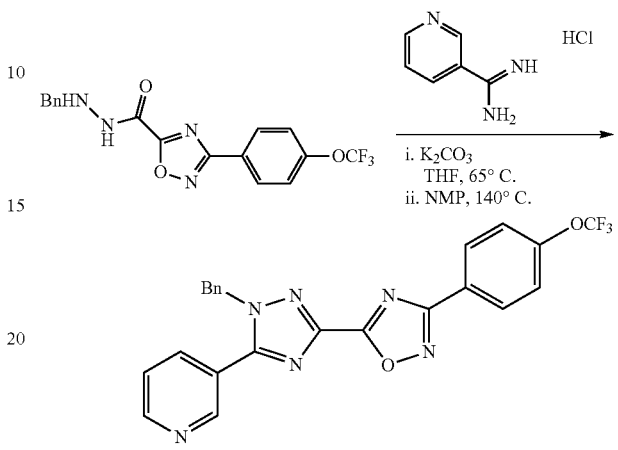

3-(1-Benzyl-3-(3-(4-(trifluoromethoxy)phenyl)-1,2,4-oxadiazol-5-yl)-1H-1,2,4-triazol-5-yl)pyridin-1-ium trifluoroacetate A mixture of N'-benzyl-3-(4-(trifluoromethoxy)phenyl)-1,2,4-oxadiazole-5-carbohydrazide (40 mg, 0.11 mmol) and nicotinimidamide hydrochloride (33 mg, 0.21 mmol) in 2N NaOH ethanol solution (1.1 mL, 0.21 mmol) was heated to 65° C. for 30 min. The mixture was cooled to RT and concentrated under reduced pressure. The crude mixture was taken up in NMP (0.5 mL) and heated to 140° C. for 2 h. The mixture was cooled to RT and partitioned between H$_2$O (0.5 mL) and EtOAc (0.5 mL). The aqueous layer was extracted with EtOAc (3×0.5 mL). The combined organic layers were washed with H$_2$O (3×0.5 mL) and brine (0.5 mL), dried (Na$_2$SO$_4$), filtered and concentrated under reduced pressure. The crude oil was purified by reverse-phase HPLC to provide the TFA salt as a white solid (1.8 mg, 3%): $^1$H NMR (600 MHz, CDCl$_3$) δ ppm 8.93 (s, 1H), 8.79 (d, J=4.8 Hz, 1H), 8.29 (d, J=8.1 Hz, 2H), 8.08 (d, J=8.0 Hz, 1H), 7.52 (app. dd, J=7.5 Hz, 5.5 Hz, 1H), 7.37-7.30 (m, 5H), 7.20 (d, J=7.3 Hz, 2H), 5.62 (s, 2H); MS (ES+) $C_{23}H_{15}F_3N_6O_2$ requires: 464, found: 465 [M+H]+.

EXAMPLE 5

2-(4,4-Dimethylpiperidin-1-yl)-4-((5-methyl-3-(5-phenyl-1,3,4-oxadiazol-2-yl)-1H-1,2,4-triazol-1-yl)methyl)pyridin-1-ium trifluoroacetate

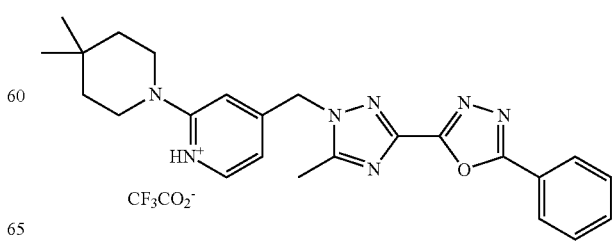

Step 1

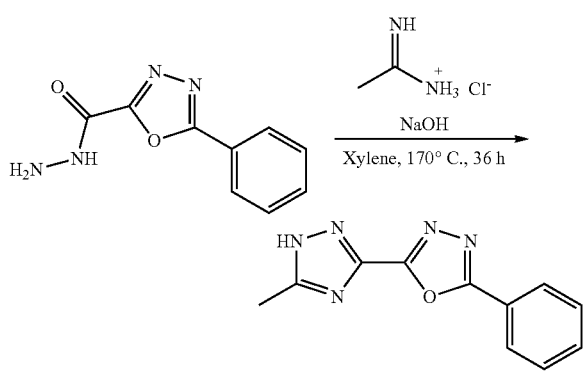

2-(5-Methyl-1H-1,2,4-triazol-3-yl)-5-phenyl-1,3,4-oxadiazole

To a solution of 5-phenyl-1,3,4-oxadiazole-2-carbohydrazide (400 mg, 1.96 mmol) and acetamidine hydrochloride (573 mg, 6.07 mmol) in xylene (20 mL) NaOH (243 mg, 6.07 mmol) was added. The mixture was stirred at 170° C. for 36 h, and then the reaction was cooled to RT, washed with H$_2$O (20 mL), extracted with 4:1 CHCl$_3$:i-PrOH (5×50 mL), dried with MgSO$_4$ and concentrated. The crude product was purified on a Biotage pre-packed silica gel column (MeOH:DCM 2% to 20% MeOH) to afford 2-(5-methyl-1H-1,2,4-triazol-3-yl)-5-phenyl-1,3,4-oxadiazole (100 mg, 22%) as a white powder. MS (ES+) C$_{11}$H$_9$N$_5$O requires: 227 found: 228 [M+H]$^+$.

Step 2

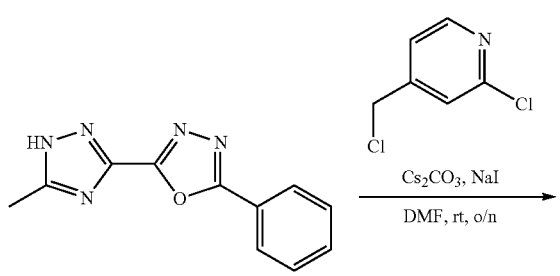

2-(1-((2-Chloropyridin-4-yl)methyl)-5-methyl-1H-1,2,4-triazol-3-yl)-5-phenyl-1,3,4-oxadiazole To a solution of 2-(5-methyl-1H-1,2,4-triazol-3-yl)-5-phenyl-1,3,4-oxadiazole (1.00 mg, 0.44 mmol) in DMF (3 mL) Cs$_2$CO$_3$ (430 mg, 1.32 mmol), NaI (78 mg, 0.52 mmol) and 2-chloro-4-(chloromethyl)pyridine (78 mg, 0.48 mmol) were added. The reaction was allowed to stir overnight at RT and then diluted with H$_2$O (10 mL), extracted with EtOAc (3×10 mL), 4:1 CHCl$_3$:i-PrOH (5×10 mL), dried with MgSO$_4$ and concentrated. The crude product was purified on a Biotage pre-packed silica gel column (EtOAc:Hexane 12% to 100% EtOAc) to afford 2-(1-((2-chloropyridin-4-yl)methyl)-5-methyl-1H-1,2,4-triazol-3-yl)-5-phenyl-1,3,4-oxadiazole (88 mg, 57%) as an off-white powder. MS (ES+) C$_{17}$H$_{13}$ClN$_6$O requires: 352 found: 353 [M+H]$^+$.

Step 3

2-(4,4-Dimethylpiperidin-1-yl)-4-((5-methyl-3-(5-phenyl-1,3,4-oxadiazol-2-yl)-1H-1,2,4-triazol-1-yl)methyl)pyridin-1-ium trifluoroacetate A mixture of 2-(1-((2-chloropyridin-4-yl)methyl)-5-methyl-1H-1,2,4-triazol-3-yl)-5-phenyl-1,3,4-oxadiazole (25 mg, 0.07 mmol), 4,4-dimethyl piperidine hydrochloride (104 mg, 0.7 mmol) and DIEA (122 μL, 0.7 mmol) in DMSO (0.5 mL) was stirred at 120° C. overnight. The crude reaction mixture was purified by pre-HPLC (Mobile phase: A=H$_2$O, B=MeCN containing 0.1% TFA; Gradient: B=20%-50% in 12 min; Column: Waters C18) to afford 2-(4,4-dimethylpiperidin-1-yl)-4-((5-methyl-3-(5-phenyl-1,3,4-oxadiazol-2-yl)-1H-1,2,4-triazol-1-yl)methyl)pyridin-1-ium trifluoroacetate (10.3 mg, 27%) as a white solid. MS (ES+) C$_{24}$H$_{27}$N$_7$O requires: 429, found: 430 [M+H]$^+$; $^1$H-NMR (500 MHz, CD$_3$OD) δ ppm 8.13 (d, J=7.5 Hz, 2H), 7.88 (d, J=6.7 Hz, 1H), 7.60 (m, 3H), 7.33 (s, 1H), 6.75 (d, J=6.9 Hz, 1H), 5.62 (s, 2H), 3.68 (t, J=5.0 Hz, 4H), 2.63 (s, 3H), 1.58 (t, J=5.0 Hz, 4H), 1.06 (s, 6H).

EXAMPLE 6

1-Methyl-4-(3-((5-methyl-3-(5-(4-(trifluoromethoxy)phenyl)-1,3,4-oxadiazol-2-yl)-1H-1,2,4-triazol-1-yl)methyl)phenyl)piperazin-1-ium trifluoroacetate

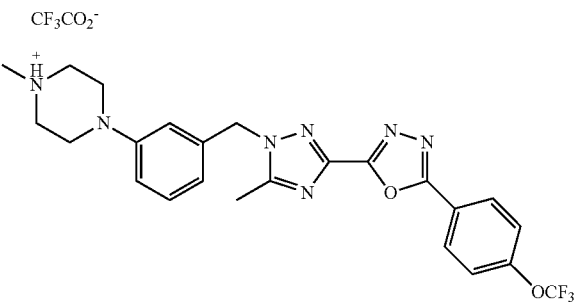

Step 1

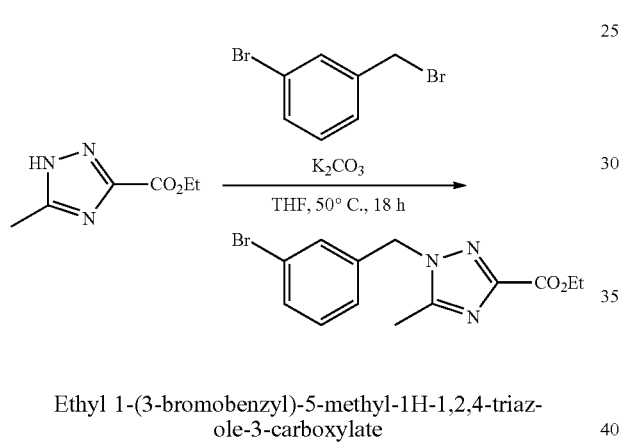

Ethyl 1-(3-bromobenzyl)-5-methyl-1H-1,2,4-triazole-3-carboxylate

To a solution of ethyl 5-methyl-1H-1,2,4-triazole-3-carboxylate (1.0 g, 6.44 mmol) and 1-bromo-3-(bromomethyl)benzene (1.77 g, 7.08 mmol) in THF (32 mL), $K_2CO_3$ (1.78 g, 12.88 mmol) was added. The mixture was stirred at 50° C. for 18 h, and then the reaction was filtered under vacuum. The solvent was removed under reduced pressure and the crude product was purified on a Biotage pre-packed silica gel column (EtOAc:Hexane 12% to 100% EtOAc) to afford ethyl 1-(3-bromobenzyl)-5-methyl-1H-1,2,4-triazole-3-carboxylate (1.25 g, 60%) as a viscous oil. MS (ES+) $C_{13}H_{14}BrN_3O_2$ requires: 323, 325 found: 324, 326 [M+H]$^+$ (1:1).

Step 2

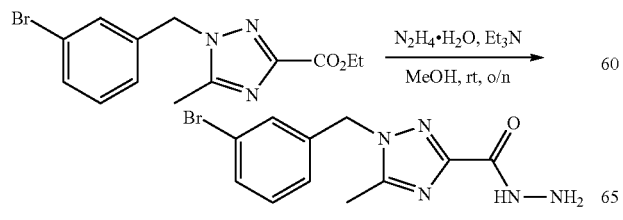

1-(3-Bromobenzyl)-5-methyl-1H-1,2,4-triazole-3-carbohydrazide

To a solution of ethyl 1-(3-bromobenzyl)-5-methyl-1H-1,2,4-triazole-3-carboxylate (1.28 g, 3.92 mmol) in MeOH (19 mL) $NH_2NH_2.H_2O$ (784 µL, 7.84 mmol) and TEA (2.47 mL, 17.6 mmol) were added. The reaction was allowed to stir overnight at RT. The solvent was then removed under reduced pressure and the crude material was spun down from toluene (3×) to give a white solid, which was used directly for the next step without further purification. MS (ES+) $C_{11}H_{12}BrN_5O$ requires: 309, 311 found: 310, 312 [M+H]$^+$ (1:1).

Step 3

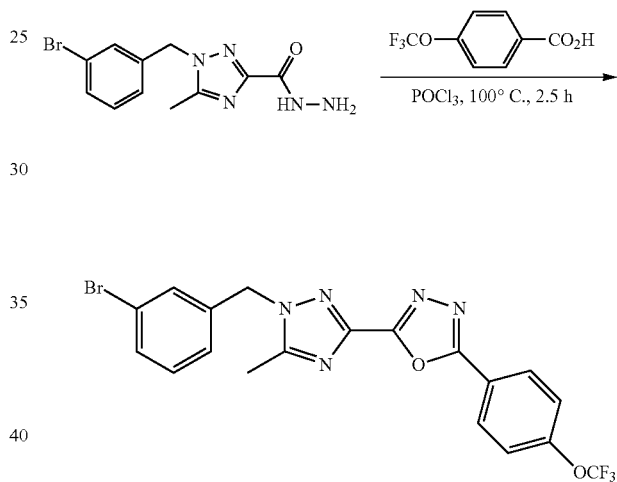

2-(1-(3-Bromobenzyl)-5-methyl-1H-1,2,4-triazol-3-yl)-5-(4-(trifluoromethoxy)phenyl)-1,3,4-oxadiazole To a solution of 1-(3-bromobenzyl)-5-methyl-1H-1,2,4-triazole-3-carbohydrazide (682 mg, 2.19 mmol), dissolved in POCl$_3$ (6 mL), 4-(trifluoromethoxy)benzoic acid (453 mg, 2.19 mmol) was added. The reaction was heated to 100° C. for 2.5 h. The solvent was removed under reduced pressure and the crude material was taken up in EtOAc. The organic layer was then washed with NaHCO$_3$ (3×40 mL) and brine (1×40 mL), dried over Na$_2$SO$_4$, filtered, concentrated under reduced pressure and purified on a Biotage pre-packed silica gel column (MeOH:DCM 2% to 40% MeOH) to afford 2-(1-(3-bromobenzyl)-5-methyl-1H-1,2,4-triazol-3-yl)-5-(4-(trifluoromethoxy)phenyl)-1,3,4-oxadiazole (443 mg, 42%). MS (ES+) $C_{19}H_{13}BrF_3N_5O_2$ requires: 479, 481 found: 480, 482 [M+H]$^+$ (1:1).

Step 4

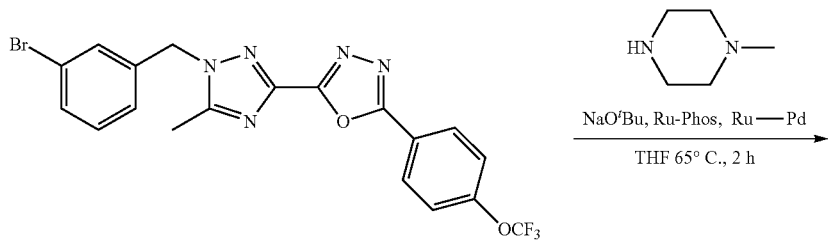

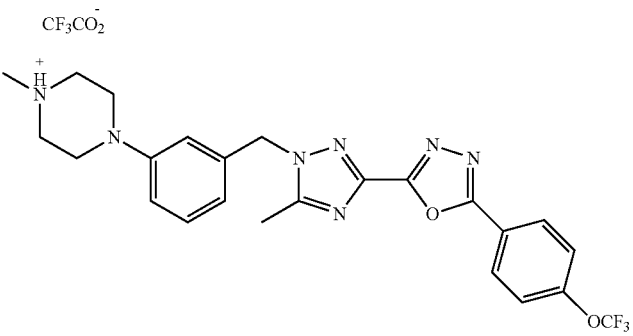

1-Methyl-4-(3-((5-methyl-3-(5-(4-(trifluoromethoxy)phenyl)-1,3,4-oxadiazol-2-yl)-1H-1,2,4-triazol-1-yl)methyl)phenyl)piperazin-1-ium trifluoroacetate A mixture of 2-(1-(3-bromobenzyl)-5-methyl-1H-1,2,4-triazol-3-yl)-5-(4-(trifluoromethoxy) phenyl)-1,3,4-oxadiazole (84 mg, 0.176 mmol), 1-methylpiperazine (28 μL, 0.26 mmol), NaOtBu (36.4 mg, 0.38 mmol), dicyclohexyl(2',6'-diisopropoxy-[1,1'-biphenyl]-2-yl)phosphine (8.2 mg, 0.0176 mmol) and chloro-(2-dicyclohexylphosphino-2',6'-diisopropoxy-1,1'-biphenyl)[2-(2'-amino-1,1'-biphenyl)]palladium(II) (13.6 mg, 0.0176 mmol) in THF (1 mL) was degassed (freeze-pump-thaw, under $N_2$). The reaction mixture was stirred at 65° C. for 2 h, and then the solvent was removed under reduced pressure. The crude reaction mixture was dissolved in DMSO and purified by pre-HPLC (Mobile phase: A=$H_2O$, B=MeCN containing 0.1% TFA; Gradient: B=20%-50% in 12 min; Column: Waters C18) to afford 1-methyl-4-(3-((5-methyl-3-(5-(4-(trifluoromethoxy)phenyl)-1,3,4-oxadiazol-2-yl)-1H-1,2,4-triazol-1-yl)methyl) phenyl)piperazin-1-ium trifluoroacetate (1 mg, 1.1%) as a white solid. MS (ES$^+$) $C_{24}H_{24}F_3N_7O_2$ requires: 499, found: 500 [M+H]$^+$; $^1$H-NMR (500 MHz, CD$_3$OD) δ ppm 8.26 (d, J=8.9 Hz, 2H), 7.53 (d, J=8.9 Hz, 2H), 7.32 (t, J=7.6 Hz, 1H), 7.02-7.00 (m, 2H), 6.88 (d, J=7.4 Hz, 1H), 5.47 (s, 2H), 3.89-3.79 (m, 2H), 3.60-3.52 (m, 2H), 3.35-3.33 (m, 4H), 2.94 (s, 3H), 2.57 (s, 3H).

EXAMPLE 7

1-Methyl-4-(4-((5-methyl-3-(5-(4-(trifluoromethoxy)phenyl)-1,3,4-oxadiazol-2-yl)-1H-1,2,4-triazol-1-yl)methyl)pyridin-1-ium-2-yl)piperazin-1-ium trifluoroacetate

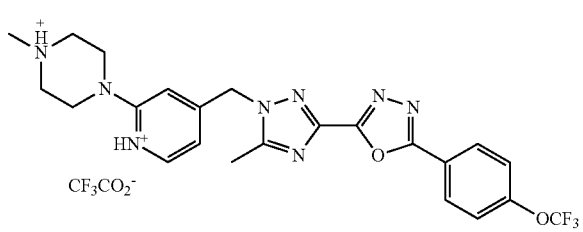

Step 1

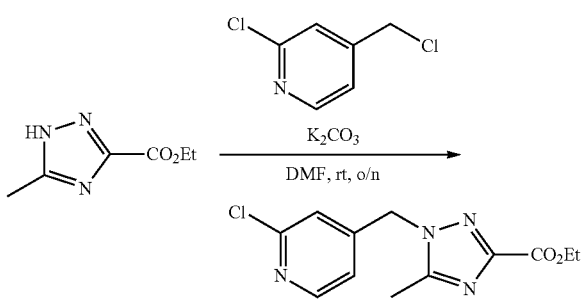

Ethyl 1-((2-chloropyridin-4-yl)methyl)-5-methyl-1H-1,2,4-triazole-3-carboxylate

To a solution of ethyl 5-methyl-1H-1,2,4-triazole-3-carboxylate (50 mg, 0.28 mmol) and 2-chloro-4-(chloromethyl)pyridine (50 mg, 0.31 mmol) in DMF (2 mL), $K_2CO_3$ (116 mg, 0.84 mmol) was added. The mixture was stirred at RT overnight, and was then diluted with $H_2O$ (20 mL), extracted with EtOAc (3×20 mL), 4:1 $CHCl_3$:iPrOH (3×20 mL), dried with $MgSO_4$ and concentrated under reduced pressure. The crude product was purified on a Biotage pre-packed silica gel column (EtOAc:Hexane 12% to 100% EtOAc) to afford ethyl 1-((2-chloropyridin-4-yl)methyl)-5-methyl-1H-1,2,4-triazole-3-carboxylate (29 mg, 40%) as a white solid. MS (ES+) $C_{12}H_{13}ClN_4O_2$ requires: 280 found: 281[M+H]$^+$.

Step 2

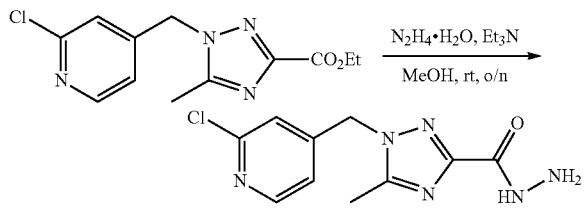

1-((2-Chloropyridin-4-yl)methyl)-5-methyl-1H-1,2,4-triazole-3-carbohydrazide

To a solution of ethyl 1-((2-chloropyridin-4-yl)methyl)-5-methyl-1H-1,2,4-triazole-3-carboxylate (218 mg, 0.81 mmol) in MeOH (4.5 mL) was added $NH_2NH_2 \cdot H_2O$ (122 µL, 1.22 mmol) and TEA (511 µL, 3.6 mmol). The reaction was allowed to stir overnight at RT. The solvent was then removed under reduced pressure and the crude material was spun down from toluene (3×) to give 1-((2-chloropyridin-4-yl)methyl)-5-methyl-1H-1,2,4-triazole-3-carbohydrazide as a white solid, which was used directly for the next step without further purification. MS (ES+) $C_{10}H_{11}ClN_6O$ requires: 266 found: 267[M+H]$^+$.

Step 3

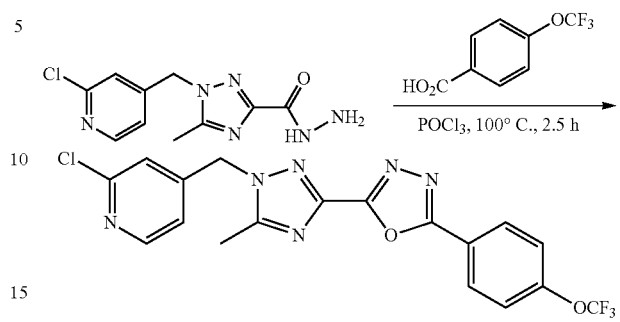

2-(1-((2-Chloropyridin-4-yl)methyl)-5-methyl-1H-1,2,4-triazol-3-yl)-5-(4-(trifluoromethoxy)phenyl)-1,3,4-oxadiazole To a solution of 1-((2-chloropyridin-4-yl)methyl)-5-methyl-1H-1,2,4-triazole-3-carbohydrazide (140 mg, 0.53 mmol) dissolved in $POCl_3$ (2.5 mL) 4-(trifluoromethoxy)benzoic acid (109 mg, 0.53 mmol) was added. The reaction was heated to 100° C. for 2.5 h. The solvent was removed under reduced pressure and the crude material was taken up in EtOAc. The organic layer was then washed with $NaHCO_3$ (3×40 mL) and brine (1×40 mL), dried over $Na_2SO_4$, filtered, concentrated under reduced pressure and purified on a Biotage pre-packed silica gel column (MeOH:DCM 0% to 20% MeOH) to afford 2-(1-((2-chloropyridin-4-yl)methyl)-5-methyl-1H-1,2,4-triazol-3-yl)-5-(4-(trifluoromethoxy)phenyl)-1,3,4-oxadiazole (45 mg, 19%) as a light brown solid. MS (ES+) $C_{18}H_{12}ClF_3N_6O_2$ requires: 436 found: 437[M+H]$^+$.

Step 4

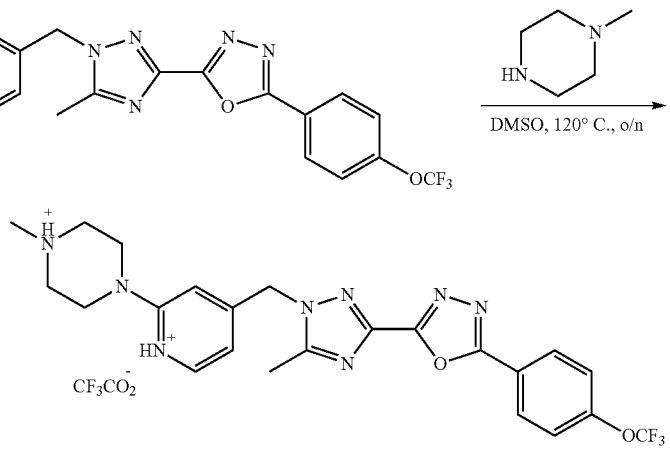

1-Methyl-4-(4-((5-methyl-3-(5-(4-(trifluoromethoxy)phenyl)-1,3,4-oxadiazol-2-yl)-1H-1,2,4-triazol-1-yl)methyl)pyridin-1-ium-2-yl)piperazin-1-ium trifluoroacetate A mixture of 2-(1-((2-chloropyridin-4-yl)methyl)-5-methyl-1H-1,2,4-triazol-3-yl)-5-(4-(trifluoromethoxy)phenyl)-1,3,4-oxadiazole (20 mg, 0.046 mmol) and 1-methylpiperazine (76 µL, 0.687 mmol) in DMSO (0.5 mL) was stirred at 120° C. overnight. The crude reaction mixture was purified by pre-HPLC (Mobile phase: A=H₂O, B=MeCN containing 0.1% TFA; Gradient: B=10%-40% in 12 min; Column: Waters C18) to afford 1-methyl-4-(4-((5-methyl-3-(5-(4-(trifluoromethoxy)phenyl)-1,3,4-oxadiazol-2-yl)-1H-1,2,4-triazol-1-yl)methyl)pyridin-1-ium-2-yl)piperazin-1-ium 2,2,2-trifluoroacetate (3 mg, 13%) as a white solid. MS (ES+) C₂₃H₂₃F₃N₈O₂ requires: 500, found: 501 [M+H]⁺; ¹H-NMR (500 MHz, CD₃OD) δ ppm 8.26 (d, J=8.9 Hz, 2H), 8.15 (d, J=5.4 Hz, 1H), 7.53 (d, J=8.5 Hz, 2H), 6.82 (s, 1H), 6.65 (d, J=5.7 Hz, 1H), 5.47 (s, 2H), 4.51-4.43 (m, 2H), 3.60-3.52 (m, 2H), 3.18-3.12 (m, 4H), 2.94 (s, 3H), 2.57 (s, 3H).

EXAMPLE 8

2-(4-(tert-Butyl)phenyl)-5-(5-methyl-1-(3-(4-methyl-piperazin-1-yl)benzyl)-1H-1,2,4-triazol-3-yl)-1,3,4-oxadiazole

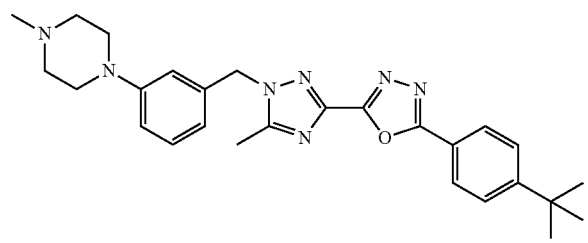 [SMILES: Cc1nc(-c2nnc(-c3ccc(C(C)(C)C)cc3)o2)nn1Cc1cccc(N2CCN(C)CC2)c1]

Step 1

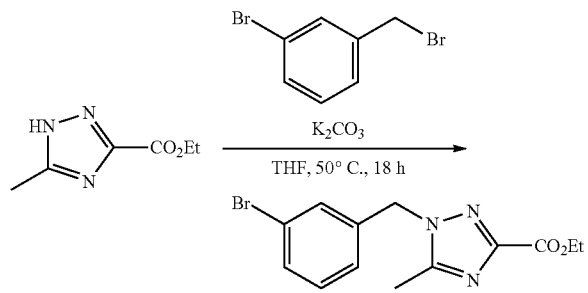

Ethyl 1-(3-bromobenzyl)-5-methyl-1H-1,2,4-triazole-3-carboxylate

To a solution of ethyl 5-methyl-1H-1,2,4-triazole-3-carboxylate (1.0 g, 6.44 mmol) and 1-bromo-3-(bromomethyl)benzene (1.77 g, 7.08 mmol) in THF (32 mL), K₂CO₃ (1.78 g, 12.88 mmol) was added. The mixture was stirred at 50° C. for 18 h then filtered. The filtrate was concentrated under reduced pressure and the crude product was purified on a Biotage pre-packed silica gel column with a gradient of 12% to 100% EtOAc:Hexanes to afford ethyl 1-(3-bromobenzyl)-5-methyl-1H-1,2,4-triazole-3-carboxylate (1.25 g, 60%) as a viscous oil. MS (ES+) C₁₃H₁₄BrN₃O₂ requires: 323, 325 found: 324, 326 [M+H]⁺ (1:1).

Step 2

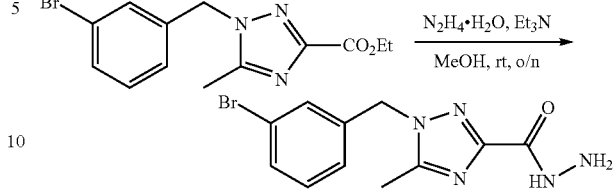

1-(3-Bromobenzyl)-5-methyl-1H-1,2,4-triazole-3-carbohydrazide

To a solution of ethyl 1-(3-bromobenzyl)-5-methyl-1H-1,2,4-triazole-3-carboxylate (1.28 g, 3.92 mmol) in MeOH (19 mL) was added hydrazine hydrate (784 μL, 7.84 mmol) and NEt₃ (2.47 mL, 17.6 mmol). The reaction was allowed to stir overnight at RT. The solvent was then removed under reduced pressure and the crude material was spun down from toluene (3×) to give a white solid, which was used directly for the next step without further purification. MS (ES+) C₁₁H₁₂BrN₅O requires: 309, 311 found: 310, 312 [M+H]⁺ (1:1).

Step 3

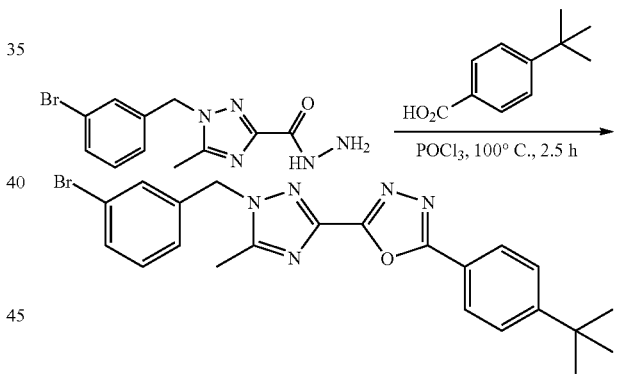

2-(1-(3-Bromobenzyl)-5-methyl-1H-1,2,4-triazol-3-yl)-5-(4-(tert-butyl)phenyl)-1,3,4-oxadiazole To a solution of 1-(3-bromobenzyl)-5-methyl-1H-1,2,4-triazole-3-carbohydrazide (2.22 g, 7.16 mmol) dissolved in POCl₃ (6 mL) was added 4-(tert-butyl)benzoic acid (1.27 g, 7.16 mmol). The reaction was heated to 100° C. for 2.5 h. The solvent was removed under reduced pressure and the crude material was taken up in EtOAc. The organic layer was then washed with NaHCO₃ (3×40 mL) and brine (1×40 mL), dried over Na₂SO₄, filtered, concentrated under reduced pressure and purified on a Biotage pre-packed silica gel column with a gradient of 12% to 100% EtOAc:Hexanes to afford 2-(1-(3-bromobenzyl)-5-methyl-1H-1,2,4-triazol-3-yl)-5-(4-(tert-butyl)phenyl)-1,3,4-oxadiazole (1.05 g, 32%). MS (ES+) C₂₂H₂₂BrN₅O requires: 451, 453 found: 452, 454 [M+H]⁺ (1:1).

Step 4

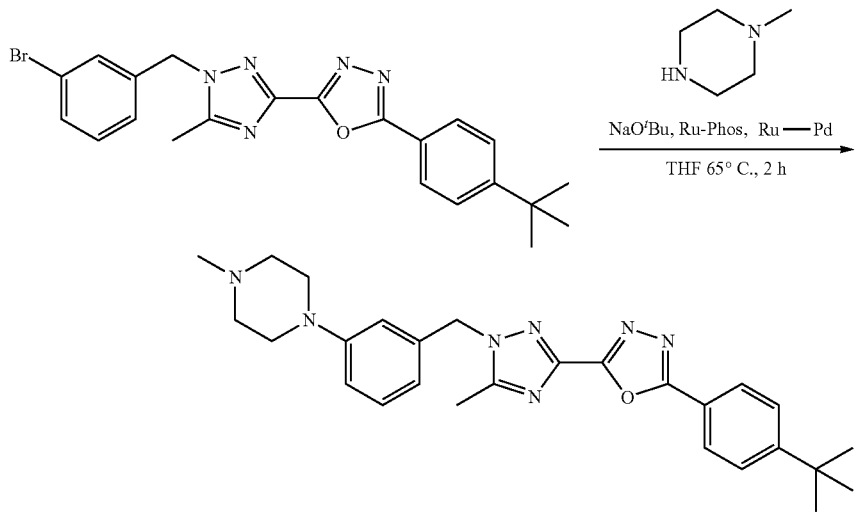

2-(4-(tert-Butyl)phenyl)-5-(5-methyl-1-(3-(4-methyl-piperazin-1-yl)benzyl)-1H-1,2,4-triazol-3-yl)-1,3,4-oxadiazole A mixture of 2-(1-(3-bromobenzyl)-5-methyl-1H-1,2,4-triazol-3-yl)-5-(4-(tert-butyl)phenyl)-1,3,4-oxadiazole (100 mg, 0.22 mmol), 1-methylpiperazine (37 µL, 0.33 mmol), NaOtBu (46.7 mg, 0.48 mmol), dicyclohexyl(2',6'-diiso-propoxy-[1,1'-biphenyl]-2-yl)phosphine (10.3 mg, 0.022 mmol) and chloro-(2-dicyclohexylphosphino-2',6'-diiso-propoxy-1,1'-biphenyl)[2-(2'-amino-1,1'-biphenyl)]palladium(II) (17.7 mg, 0.022 mmol) in THF (1 mL) was degassed (freeze-pump-thaw, under $N_2$). The reaction mixture was stirred at 65° C. for 2 h, and then the solvent was removed under reduced pressure. The crude reaction mixture was dissolved in DMSO and was purified by pre-HPLC (Mobile phase: A=0.1% $CF_3CO_2H/H_2O$, B=MeCN; Gradient: B=30%-70% in 12 min; Column: Waters C18) to afford 2-(4-(tert-butyl)phenyl)-5-(5-methyl-1-(3-(4-methylpiperazin-1-yl)benzyl)-1H-1,2,4-triazol-3-yl)-1,3,4-oxadiazole (4.5 mg, 4.3%) as a white solid. MS (ES+) $C_{27}H_{33}N_7O$ requires: 471, found: 472 [M+H]$^+$; $^1$H-NMR (500 MHz, $CDCl_3$) δ ppm 8.13 (d, J=8.2 Hz, 2H), 7.52 (d, J=8.6 Hz, 2H), 7.25 (d, J=7.9 Hz, 1H), 6.88 (d, J=8.5 Hz, 1H), 6.78 (t, J=2.0 Hz 1H), 6.70 (d, J=7.8 Hz, 1H), 5.38 (s, 2H), 3.27-3.20 (m, 4H), 2.67-2.58 (m, 4H), 2.51 (s, 3H), 2.40-2.37 (m, 3H), (1.36 (s, 9H).

EXAMPLE 9

3-(4-(tert-Butyl)phenyl)-5-(5-methyl-1-((2-(4-meth-ylpiperazin-1-yl)pyridin-4-yl)methyl)-1H-1,2,4-tri-azol-3-yl)-1,2,4-oxadiazole

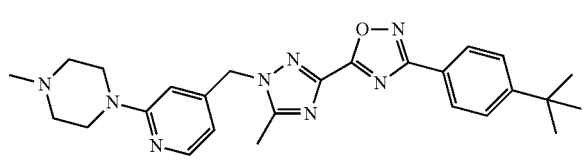 [SMILES: Cc1nc(-c2nc(-c3ccc(C(C)(C)C)cc3)no2)nn1Cc1ccnc(N2CCN(C)CC2)c1]

Step 1

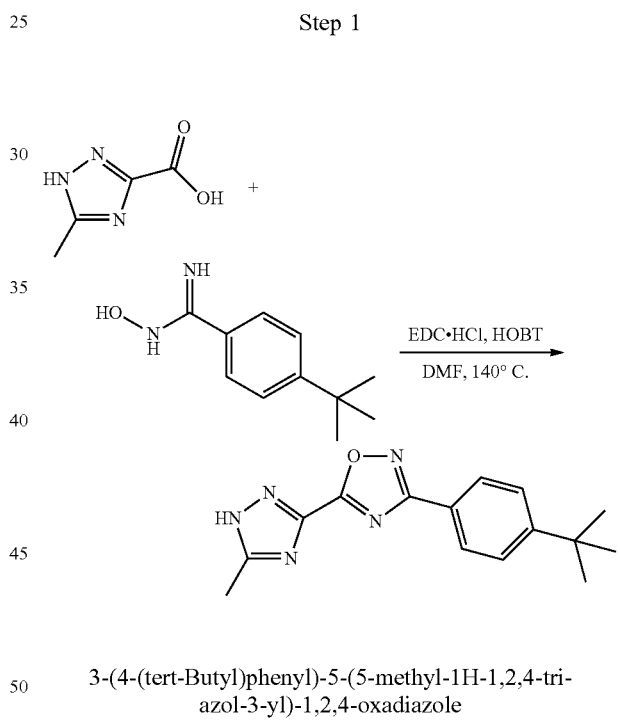

3-(4-(tert-Butyl)phenyl)-5-(5-methyl-1H-1,2,4-tri-azol-3-yl)-1,2,4-oxadiazole

5-Methyl-1H-1,2,4-triazole-3-carboxylic acid (200 mg, 1.57 mmol), EDC.HCl (360 mg, 1.89 mmol), and HOBT (255 mg, 1.89 mmol) were dissolved in DMF (15 mL) and the solution was stirred at RT for 30 min. 4-(tert-Butyl)-N-hydroxybenzimidamide (363 mg, 1.89 mmol) was added and the reaction was stirred at RT for 1 h and then at 140° C. for an additional 2 h. The reaction mixture was cooled to RT, and diluted with $H_2O$ (100 mL) and EtOAc (100 mL). The organic layer was separated, washed with $H_2O$ (2×50 mL) and brine (25 mL), dried over $Na_2SO_4$, filtered, and concentrated to afford the crude product which was purified by silica gel chromatography (EtOAc/Hexane 12%-100% EtOAc) to afford 3-(4-(tert-butyl)phenyl)-5-(5-methyl-1H-1,2,4-triazol-3-yl)-1,2,4-oxadiazole as a yellow solid (210 mg, 47%). MS (ES+) $C_{15}H_{17}N_5O$ requires: 283, found 284

[M+H]⁺; ¹H NMR (600 MHz, CDCl₃) δ 8.02 (d, J=8.4 Hz, 2H), 7.63 (d, J=8.4 Hz, 2H), 2.50 (s, 3H), 1.34 (s, 9H).

Step 2

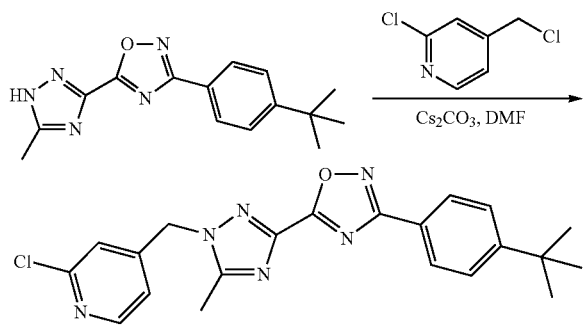

3-(4-(tert-Butyl)phenyl)-5-(1-((2-chloropyridin-4-yl)methyl)-5-methyl-1H-1,2,4-triazol-3-yl)-1,2,4-oxadiazole 3-(4-(tert-Butyl)phenyl)-5-(5-methyl-1H-1,2,4-triazol-3-yl)-1,2,4-oxadiazole (140 mg, 0.495 mmol) was placed in DMF (10 mL) and Cs₂CO₃ (193 mg, 0.594 mmol) was added. The reaction was stirred for 5 min and 2-chloro-4-(chloromethyl)pyridine (96 mg, 0.594 mmol) was added. The reaction was stirred at 45° C. overnight and was then partitioned between H₂O (25 mL) and EtOAc (25 mL). The organic layer was separated, washed with H₂O (2×25 mL) and brine (15 mL), dried over Na₂SO₄, filtered, and concentrated to afford the crude product which was purified by silica gel chromatography (EtOAc/Hexane 0%-100% EtOAc) to afford 3-(4-(tert-butyl)phenyl)-5-(1-((2-chloropyridin-4-yl)methyl)-5-methyl-1H-1,2,4-triazol-3-yl)-1,2,4-oxadiazole as a yellow solid (90 mg, 45%). MS (ES+) C₂₁H₂₁ClN₆O requires: 408, found 409 [M+H]⁺; ¹H NMR (600 MHz, CDCl₃) δ 8.42 (d, J=5.2 Hz, 1H), 8.16 (d, J=8.5 Hz, 2H), 7.52 (d, J=8.5 Hz, 2H), 7.16 (s, 1H), 7.05 (d, J=5.2 Hz, 1H), 5.46 (s, 2H), 2.57 (s, 3H), 1.37 (s, 9H).

Step 3

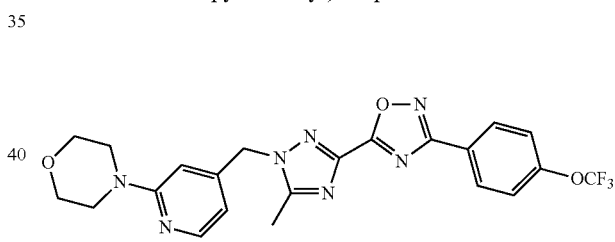

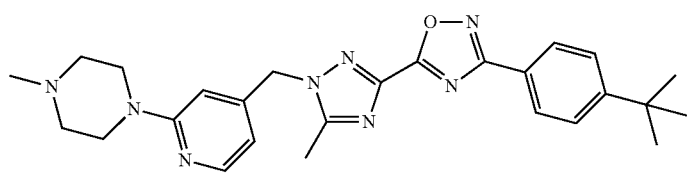

3-(4-(tert-Butyl)phenyl)-5-(5-methyl-1-((2-(4-methylpiperazin-1-yl)pyridin-4-yl)methyl)-1H-1,2,4-triazol-3-yl)-1,2,4-oxadiazole 3-(4-(tert-Butyl)phenyl)-5-(1-((2-chloropyridin-4-yl)methyl)-5-methyl-1H-1,2,4-triazol-3-yl)-1,2,4-oxadiazole (90 mg, 0.221 mmol) and 1-methylpiperazine (265 mg, 2.65 mmol) were dissolved in DMSO (3 mL) in a sealed tube reaction vessel. The reaction was heated at 140° C. overnight and then cooled to RT and partitioned between H₂O (25 mL) and EtOAc (25 mL). The organic layer was separated, washed with H₂O (2×25 mL) and brine (15 mL), dried over Na₂SO₄, filtered, and concentrated to afford the crude product which was purified by prep-HPLC (MeCN/H₂O 20%-60% MeCN, containing 0.1% TFA). The product was taken up in EtOAc (10 mL), washed with sat. NaHCO₃ (10 mL), dried over Na₂SO₄, filtered, and concentrated to afford 3-(4-(tert-butyl)phenyl)-5-(5-methyl-1-((2-(4-methylpiperazin-1-yl)pyridin-4-yl)methyl)-1H-1,2,4-triazol-3-yl)-1,2,4-oxadiazole as a yellow foam (23 mg, 22%). MS (ES+) C₂₆H₃₂N₈O requires: 472, found 473 [M+H]⁺; ¹H NMR (600 MHz, CDCl₃) δ 8.19-8.15 (m, 3H), 7.51 (d, J=8.4 Hz, 2H), 6.42 (d, J=4.9 Hz, 1H), 6.39 (s, 1H), 5.36 (s, 2H), 3.70-3.50 (m, 4H), 2.69-2.46 (bs, 3H), 2.54 (s, 3H), 2.46-2.30 (m, 4H), 1.37 (s, 9H).

EXAMPLE 10

4-(4-((5-Methyl-3-(3-(4-(trifluoromethoxy)phenyl)-1,2,4-oxadiazol-5-yl)-1H-1,2,4-triazol-1-yl)methyl)pyridin-2-yl)morpholine

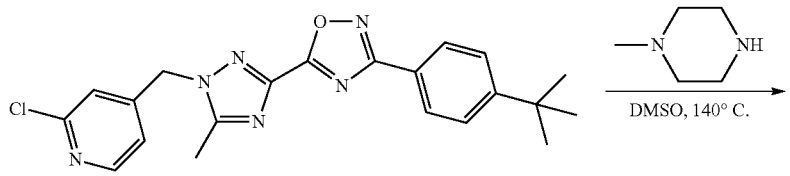

Step 1

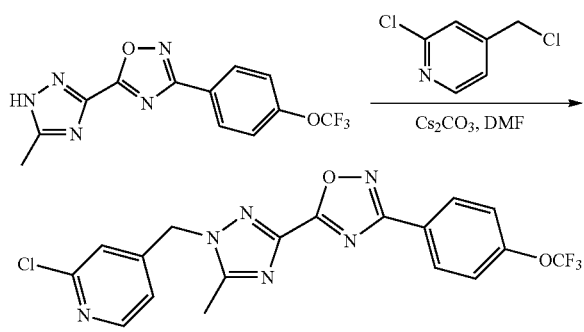

5-(1-((2-Chloropyridin-4-yl)methyl)-5-methyl-1H-1,2,4-triazol-3-yl)-3-(4-(trifluoromethoxy)phenyl)-1,2,4-oxadiazole 5-(5-methyl-1H-1,2,4-triazol-3-yl)-3-(4-(trifluoromethoxy)phenyl)-1,2,4-oxadiazole (500 mg, 1.61 mmol) was placed in DMF (20 mL) and Cs$_2$CO$_3$ (627 mg, 1.93 mmol) was added. The reaction was stirred for 5 min and 2-chloro-4-(chloromethyl)pyridine (312 mg, 1.93 mmol) was added. The reaction was stirred at 45° C. overnight and was then partitioned between H$_2$O (50 mL) and EtOAc (50 mL). The organic layer was separated, washed with H$_2$O (2×50 mL) and brine (30 mL), dried over Na$_2$SO$_4$, filtered, and concentrated to afford the crude product which was purified by silica gel chromatography (EtOAc/Hexane 10%-100% EtOAc) to afford 5-(1-((2-chloropyridin-4-yl)methyl)-5-methyl-1H-1,2,4-triazol-3-yl)-3-(4-(trifluoromethoxy)phenyl)-1,2,4-oxadiazole as a yellow solid (420 mg, 60%). MS (ES+) C$_{18}$H$_{12}$ClF$_3$N$_6$O$_2$ requires: 436, found 437 [M+H]$^+$; $^1$H NMR (600 MHz, CDCl$_3$) δ 8.42 (d, J=5.1 Hz, 1H), 8.28 (d, J=8.6 Hz, 2H), 7.34 (d, J=8.6 Hz, 2H), 7.16 (s, 1H), 7.05 (d, J=5.1 Hz, 1H), 5.46 (s, 2H), 2.58 (s, 3H).

Step 2

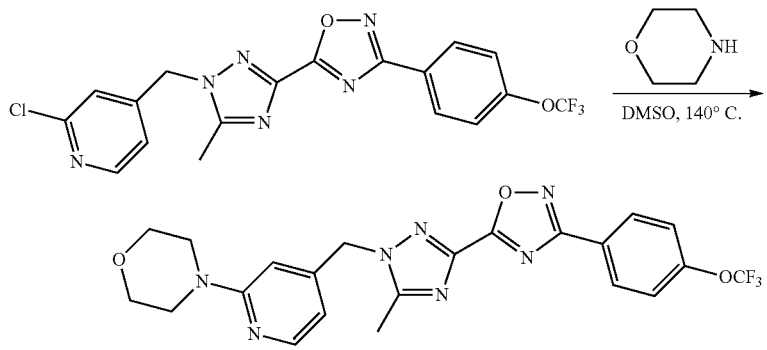

4-(4-((5-Methyl-3-(3-(4-(trifluoromethoxy)phenyl)-1,2,4-oxadiazol-5-yl)-1H-1,2,4-triazol-1-yl)methyl)pyridin-2-yl)morpholine 5-(1-((2-Chloropyridin-4-yl)methyl)-5-methyl-1H-1,2,4-triazol-3-yl)-3-(4-(trifluoromethoxy)phenyl)-1,2,4-oxadiazole (50 mg, 0.115 mmol) and morpholine (100 mg, 1.15 mmol) were dissolved in DMSO (0.5 mL) in a sealed tube reaction vessel. The reaction was heated at 130° C. overnight and then cooled to RT. The reaction was then filtered and purified by prep-HPLC (MeCN/H$_2$O 30%-MeCN 70% containing 0.1% TFA). The product was taken up in EtOAc (10 mL), washed with sat. NaHCO$_3$ (10 mL), dried over Na$_2$SO$_4$, filtered, and concentrated to afford 4-(4-((5-methyl-3-(3-(4-(trifluoromethoxy)phenyl)-1,2,4-oxadiazol-5-yl)-1H-1,2,4-triazol-1-yl)methyl)pyridin-2-yl)morpholine as a yellow solid (35 mg, 63%). MS (ES+) C$_{22}$H$_{20}$F$_3$N$_7$O$_3$ requires: 487, found 488 [M+H]$^+$; $^1$H NMR (600 MHz, CDCl$_3$) δ 8.28 (d, J=8.8 Hz, 2H), 8.18 (d, J=5.3 Hz, 1H), 7.34 (d, J=8.8 Hz, 2H), 6.44 (d, J=5.3 Hz, 1H), 6.37 (s, 1H), 5.37 (s, 2H), 3.82-3.77 (m, 4H), 3.51-3.45 (m, 4H), 2.55 (s, 3H).

EXAMPLE 11

N,N-Dimethyl-2-((3-((5-methyl-3-(3-(4-(trifluoromethoxy)phenyl)-1,2,4-oxadiazol-5-yl)-1H-1,2,4-triazol-1-yl)methyl)phenyl)amino)ethanaminium trifluoroacetate

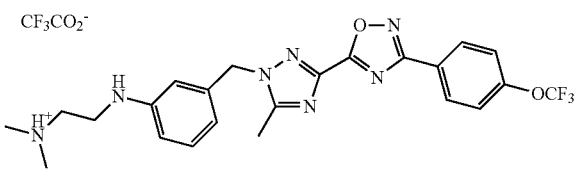

Step 1

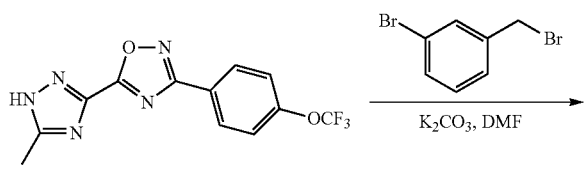

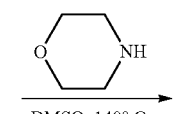

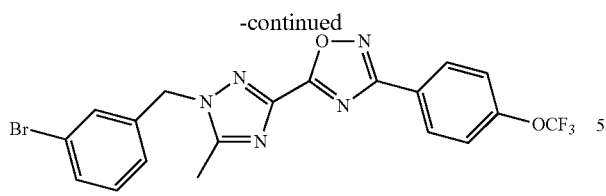

5-(1-(3-Bromobenzyl)-5-methyl-1H-1,2,4-triazol-3-yl)-3-(4-(trifluoromethoxy)phenyl)-1,2,4-oxadiazole 5-(5-Methyl-1H-1,2,4-triazol-3-yl)-3-(4-(trifluoromethoxy)phenyl)-1,2,4-oxadiazole (100 mg, 0.321 mmol) was placed in THF (3 mL) and K$_2$CO$_3$ (66 mg, 0.482 mmol) was added. The reaction was stirred for 5 min and 1-bromo-4-(bromomethyl)benzene (84 mg, 0.338 mmol) was added. The reaction was stirred at 50° C. overnight and was then partitioned between H$_2$O (15 mL) and EtOAc (15 mL). The organic layer was separated, washed with H$_2$O (2×10 mL) and brine (10 mL), dried over Na$_2$SO$_4$, filtered, and concentrated to afford the crude product which was purified by silica gel chromatography (EtOAc/Hexane 10%-100% EtOAc) to afford 5-(1-(3-bromobenzyl)-5-methyl-1H-1,2,4-triazol-3-yl)-3-(4-(trifluoromethoxy)phenyl)-1,2,4-oxadiazole as a white solid (82 mg, 53%). MS (ES+) C$_{19}$H$_{13}$BrF$_3$N$_5$O$_2$ requires: 479, 481 found 480 [M+H]$^+$, 482 [M+2+H]+ (1:1); $^1$H NMR (600 MHz, CDCl$_3$) δ 8.28 (d, J=8.8 Hz, 2H), 7.48 (d, J=7.9 Hz, 1H), 7.41 (s, 1H), 7.34 (d, J=8.8 Hz, 2H), 7.26 (d, J=7.6 Hz, 1H), 7.17 (d, J=7.9 Hz, 1H), 5.43 (s, 2H), 2.55 (s, 3H).

Step 2

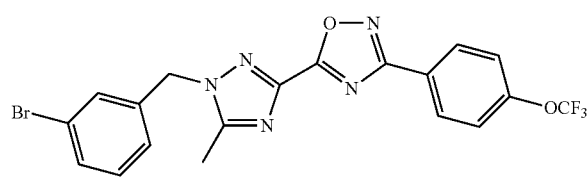 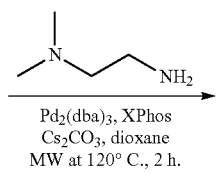

N,N-Dimethyl-2-((3-((5-methyl-3-(3-(4-(trifluoromethoxy)phenyl)-1,2,4-oxadiazol-5-yl)-1H-1,2,4-triazol-1-yl)methyl)phenyl)amino)ethanaminium trifluoroacetate 5-(1-(3-Bromobenzyl)-5-methyl-1H-1,2,4-triazol-3-yl)-3-(4-(trifluoromethoxy) phenyl)-1,2,4-oxadiazole (40 mg, 0.0833 mmol), Cs$_2$CO$_3$ (54 mg, 0.167 mmol), XPhos (16 mg, 0.0333 mmol), Pd$_2$(dba)$_3$ (15 mg, 0.0167 mmol), and N',N'-dimethylethane-1,2-diamine were placed in a microwave reaction vessel and dioxane (1 mL), which had been degassed by bubbling N$_2$ through it for 10 min, was added. The reaction was heated by microwave irradiation at 120° C. for 1 h. Purification by prep-HPLC (MeCN/H$_2$O 30%-70% MeCN containing 0.1% TFA) afforded N,N-dimethyl-2-((3-((5-methyl-3-(3-(4-(trifluoromethoxy)phenyl)-1,2,4-oxadiazol-5-yl)-1H-1,2,4-triazol-1-yl)methyl)phenyl)amino) ethanaminium trifluoroacetate as a thin film (1.5 mg, 4%). MS (ES+) C$_{23}$H$_{24}$F$_3$N$_7$O$_2$ requires: 487, found 488 [M+H]$^+$; $^1$H NMR (600 MHz, CDCl$_3$) δ 8.32-8.24 (m, 2H), 7.34 (d, J=8.1 Hz, 2H), 7.20-7.15 (m, 1H), 6.63-6.56 (m, 2H), 6.54-6.51 (m, 1H), 5.35 (s, 2H), 3.53 (t, J=5.4 Hz, 2H), 3.28 (t, J=5.4 Hz, 2H), 2.87 (s, 6H), 2.54 (s, 3H).

EXAMPLE 12

Methyl 3-((5-methyl-3-(3-(4-(trifluoromethoxy)phenyl)-1,2,4-oxadiazol-5-yl)-1H-1,2,4-triazol-1-yl)methyl)benzoate

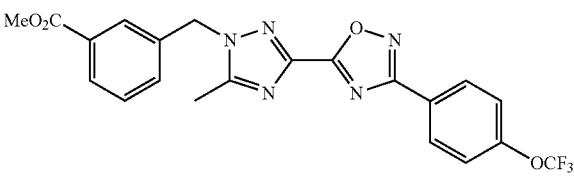 [SMILES: COC(=O)c1cccc(Cn2nc(-c3nc(-c4ccc(OC(F)(F)F)cc4)no3)nc2C)c1]

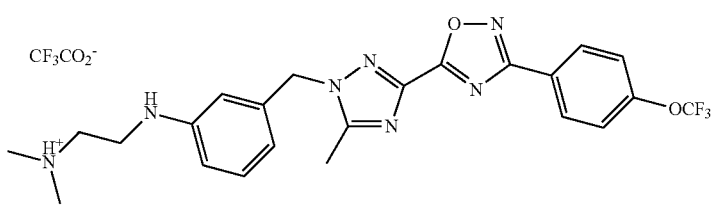

115
Step 1

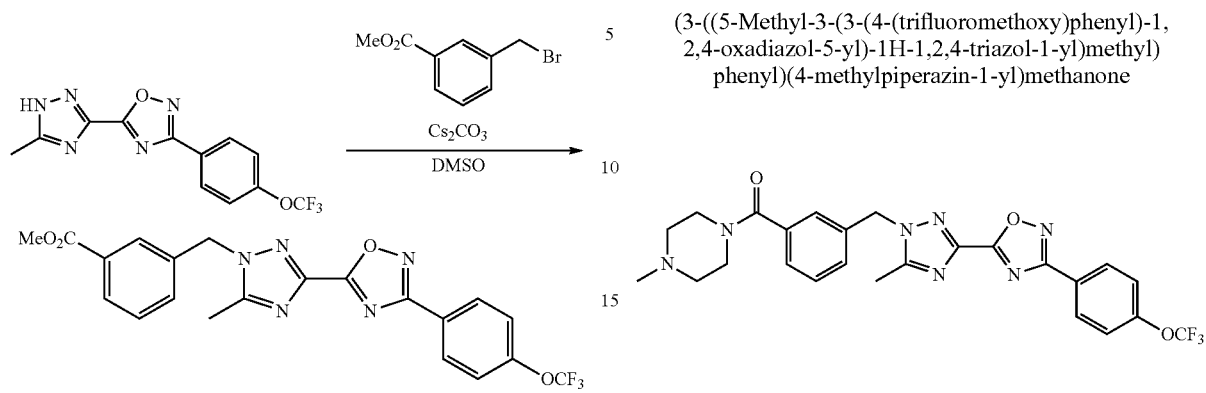

116
EXAMPLE 13

(3-((5-Methyl-3-(3-(4-(trifluoromethoxy)phenyl)-1,2,4-oxadiazol-5-yl)-1H-1,2,4-triazol-1-yl)methyl)phenyl)(4-methylpiperazin-1-yl)methanone

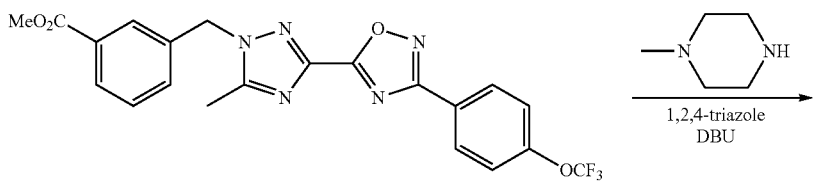

Step 1

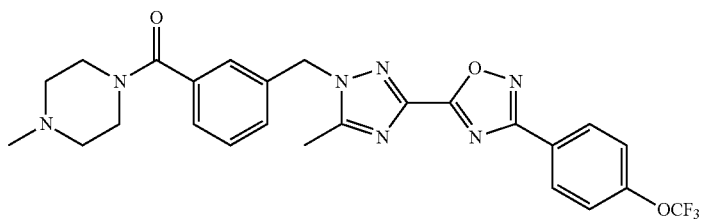

Methyl 3-((5-methyl-3-(3-(4-(trifluoromethoxy)phenyl)-1,2,4-oxadiazol-5-yl)-1H-1,2,4-triazol-1-yl)methyl)benzoate To a solution of 5-(5-methyl-1H-1,2,4-triazol-3-yl)-3-(4-(trifluoromethoxy)phenyl)-1,2,4-oxadiazole (311 mg, 1.0 mmol) in DMSO (5 mL), Cs$_2$CO$_3$ (652 mg, 2.0 mmol) and methyl 3-(bromomethyl)benzoate (252 mg, 1.1 mmol) were added at RT. The mixture was stirred at RT for 2 h. The resulting mixture was diluted with H$_2$O (20 mL) and extracted with EtOAc (4×40 mL). The combined organic layers were washed with H$_2$O (20 mL) and brine (2×20 mL), dried over Na$_2$SO$_4$, filtered and concentrated under reduced pressure, and the residue was purified by a silica gel chromatography (EtOAc/Hexane 10% to 60% EtOAc) to give methyl 3-((5-methyl-3-(3-(4-(trifluoromethoxy)phenyl)-1,2,4-oxadiazol-5-yl)-1H-1,2,4-triazol-1-yl)methyl)benzoate as a white solid (310 mg, 68%). MS (ES+) C$_{21}$H$_{16}$F$_3$N$_5$O$_4$ requires: 459, found: 460 [M+H]$^+$; $^1$H NMR (600 MHz, CDCl$_3$) δ 8.29 (d, J=8.8 Hz, 2H), 8.04 (d, J=7.4 Hz, 1H), 7.95 (s, 1H), 7.48 (t, J=7.5 Hz, 1H), 7.45 (d, J=7.8 Hz, 1H), 7.34 (d, J=8.3 Hz, 2H), 5.51 (s, 2H), 3.92 (s, 3H), 2.55 (s, 3H).

(3-((5-Methyl-3-(3-(4-(trifluoromethoxy)phenyl)-1,2,4-oxadiazol-5-yl)-1H-1,2,4-triazol-1-yl)methyl)phenyl)(4-methylpiperazin-1-yl)methanone A mixture of methyl 3-((5-methyl-3-(3-(4-(trifluoromethoxy)phenyl)-1,2,4-oxadiazol-5-yl)-1H-1,2,4-triazol-1-yl)methyl)benzoate (46 mg, 0.1 mmol) and 1-methylpiperazine (10 mg, 0.1 mmol) was treated with 1,2,4-triazole (1.4 mg, 0.02 mmol) and DBU (3 mg, 0.02 mmol)), and heated to 100° C. overnight. The crude product was purified by a silica gel column (MeOH/EtOAc 1% to 10% MeOH) to give (3-((5-Methyl-3-(3-(4-(trifluoromethoxy)phenyl)-1,2,4-oxadiazol-5-yl)-1H-1,2,4-triazol-1-yl)methyl)phenyl)(4-methylpiperazin-1-yl)methanone as a yellow solid (20 mg, 38%). MS (ES+) C$_{25}$H$_{24}$F$_3$N$_7$O$_3$ requires: 527, found: 528 [M+H]$^+$. $^1$H NMR (600 MHz, CDCl$_3$) δ8.28 (d, J=8.8 Hz, 2H), 7.43 (t, J=7.6 Hz, 1H), 7.39 (d, J=7.6 Hz, 1H), 7.35 (d, J=8.5 Hz, 2H), 7.32 (s, 1H), 7.29 (d, J=7.7 Hz, 1H), 5.48 (s, 2H), 3.82-3.74 (m, 2H), 3.42-3.36 (m, 2H), 2.57 (s, 3H), 2.51-2.44 (m, 2H), 2.35-2.30 (m, 2H), 2.29 (s, 3H).

EXAMPLE 14

N-(3-methoxypropyl)-3-((5-methyl-3-(3-(4-(trifluoromethoxy)phenyl)-1,2,4-oxadiazol-5-yl)-1H-1,2,4-triazol-1-yl)methyl)benzamide

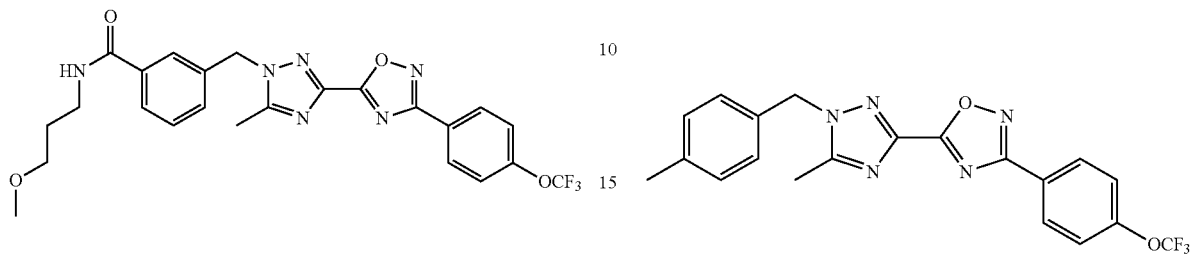

Step 1

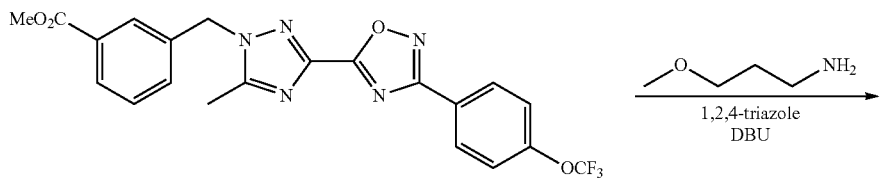

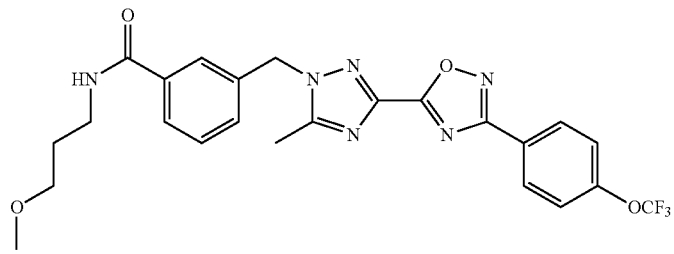

N-(3-methoxypropyl)-3-((5-methyl-3-(3-(4-(trifluoromethoxy)phenyl)-1,2,4-oxadiazol-5-yl)-1H-1,2,4-triazol-1-yl)methyl)benzamide A mixture of methyl 3-((5-methyl-3-(3-(4-(trifluoromethoxy)phenyl)-1,2,4-oxadiazol-5-yl)-1H-1,2,4-triazol-1-yl)methyl)benzoate (46 mg, 0.1 mmol) and 3-methoxypropylamine (27 mg, 0.3 mmol) was treated with 1,2,4-triazole (7 mg, 0.1 mmol) and DBU (15 mg, 0.1 mmol), and heated to 70° C. overnight. The crude product was purified by a silica gel column with EtOAc to give N-(3-methoxypropyl)-3-((5-methyl-3-(3-(4-(trifluoromethoxy)phenyl)-1,2,4-oxadiazol-5-yl)-1H-1,2,4-triazol-1-yl)methyl)benzamide as a white solid (45 mg, 87%). MS (ES+) $C_{24}H_{23}F_3N_6O_4$ requires: 516, found: 517 [M+H]$^+$. $^1$H NMR (600 MHz, CDCl$_3$) δ 8.28 (d, J=8.8 Hz, 2H), 7.77 (s, 1H), 7.68 (d, J=7.7 Hz, 1H), 7.45 (t, J=7.7 Hz, 1H), 7.37 (d, J=7.9 Hz, 1H), 7.35 (d, J=8.3 Hz, 2H), 5.50 (s, 2H), 3.60-3.55 (m, 4H), 3.38 (s, 3H), 2.55 (s, 3H), 1.91-1.86 (m, 2H).

EXAMPLE 15

5-(5-Methyl-1-(4-methylbenzyl)-1H-1,2,4-triazol-3-yl)-3-(4-(trifluoromethoxy)phenyl)-1,2,4-oxadiazole

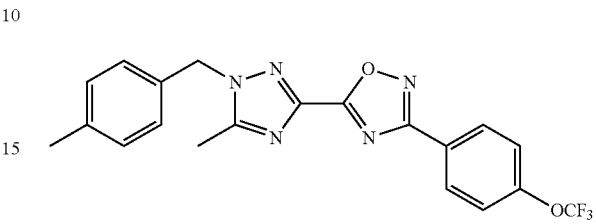

Step 1

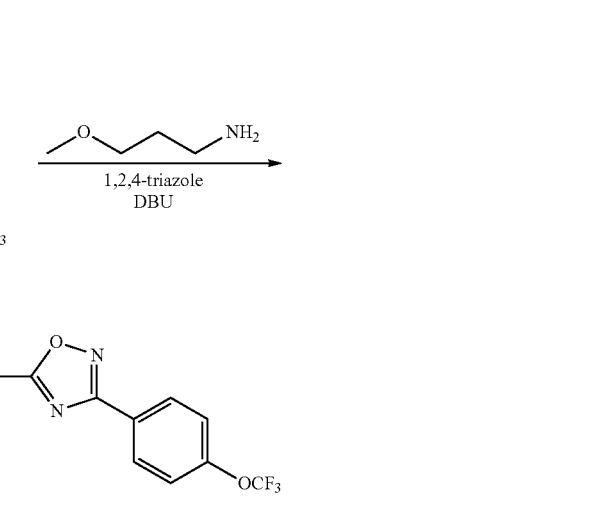

5-(5-Methyl-1-(4-methylbenzyl)-1H-1,2,4-triazol-3-yl)-3-(4-(trifluoromethoxy)phenyl)-1,2,4-oxadiazole To a solution of 5-(5-methyl-1H-1,2,4-triazol-3-yl)-3-(4-(trifluoromethoxy)phenyl)-1,2,4-oxadiazole (31 mg, 0.1 mmol) in DMSO (0.5 mL), Cs$_2$CO$_3$ (65 mg, 0.2 mmol) and α-bromo-p-xylene (20 mg, 0.11 mmol) were added at RT.

The mixture was stirred at RT overnight. The resulting crude product was purified by pre-HPLC (Mobile phase: A=0.01% TFA/H$_2$O, B=0.01% TFA/MeCN; Gradient: B=50%-90% in 12 min; Column: C18) and lyophilized to give 5-(5-methyl-1-(4-methylbenzyl)-1H-1,2,4-triazol-3-yl)-3-(4-(trifluoromethoxy)phenyl)-1,2,4-oxadiazole as a white solid (20 mg, 48%). MS (ES+) C$_{20}$H$_{16}$F$_3$N$_5$O$_2$ requires: 415, found: 416 [M+H]$^+$; $^1$H NMR (600 MHz, DMSO-d$_6$) δ 8.22 (d, J=8.8 Hz, 2H), 7.60 (d, J=8.3 Hz, 2H), 7.22 (d, J=8.3 Hz, 2H), 7.20 (d, J=8.3 Hz, 2H), 5.52 (s, 2H), 2.57 (s, 3H), 2.29 (s, 3H).

EXAMPLE 16

5-(1-(imidazo[1,2-a]pyridin-2-ylmethyl)-5-methyl-1H-1,2,4-triazol-3-yl)-3-(4-(trifluoromethoxy)phenyl)-1,2,4-oxadiazole

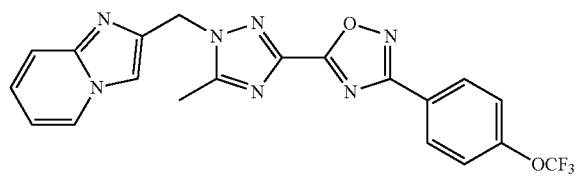 [SMILES: Cc1nc(-c2nc(-c3ccc(OC(F)(F)F)cc3)no2)nn1Cc1cn2ccccc2n1]

Step 1

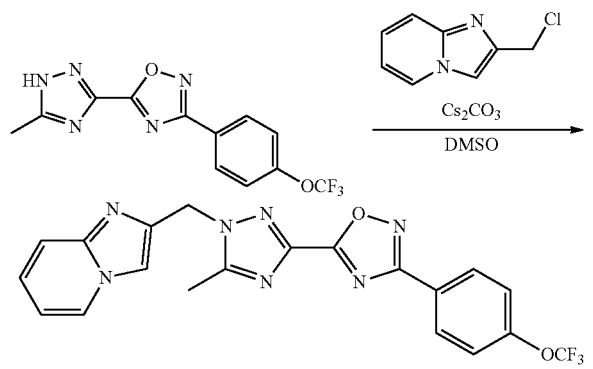

5-(1-(imidazo[1,2-a]pyridin-2-ylmethyl)-5-methyl-1H-1,2,4-triazol-3-yl)-3-(4-(trifluoromethoxy)phenyl)-1,2,4-oxadiazole To a solution of 5-(5-methyl-1H-1,2,4-triazol-3-yl)-3-(4-(trifluoromethoxy)phenyl)-1,2,4-oxadiazole (31 mg, 0.1 mmol) in DMSO (0.5 mL), Cs$_2$CO$_3$ (65 mg, 0.2 mmol) and 2-(chloromethyl)imidazo [1,2-a]pyridine (18 mg, 0.11 mmol) were added at RT. The mixture was stirred at RT overnight. The resulting crude product was purified by pre-HPLC (Mobile phase: A=0.01% TFA/H$_2$O, B=0.01% TFA/MeCN; Gradient: B=10%-50% in 20 min; Column: C18) and then a silica gel column with (EtOAc/Hexane 16% to 100% EtOAc) to give 5-(1-(imidazo[1,2-a]pyridin-2-ylmethyl)-5-methyl-1H-1,2,4-triazol-3-yl)-3-(4-(trifluoromethoxy)phenyl)-1,2,4-oxadiazole as a white solid (4 mg, 10%). MS (ES+) C$_{20}$H$_{14}$F$_3$N$_7$O$_2$ requires: 441, found: 442 [M+H]$^+$; $^1$H NMR (600 MHz, DMSO-d$_6$) δ 8.53 (d, J=6.8 Hz, 1H), 8.21 (d, J=8.8 Hz, 2H), 8.01 (s, 1H), 7.61 (d, J=8.5 Hz, 2H), 7.51 (d, J=9.1 Hz, 1H), 7.26 (dd, J=7.5, 8.2 Hz, 1H), 6.91 (t, J=6.8 Hz, 1H), 5.66 (s, 2H), 2.69 (s, 3H).

EXAMPLE 17

5-(1-((2-Chlorothiazol-5-yl)methyl)-5-methyl-1H-1,2,4-triazol-3-yl)-3-(4-(trifluoromethoxy)phenyl)-1,2,4-oxadiazole

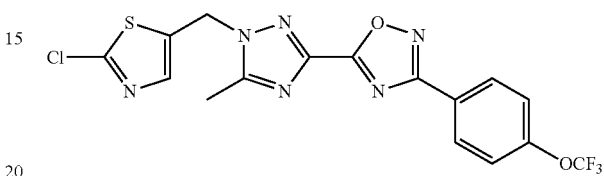

Step 1

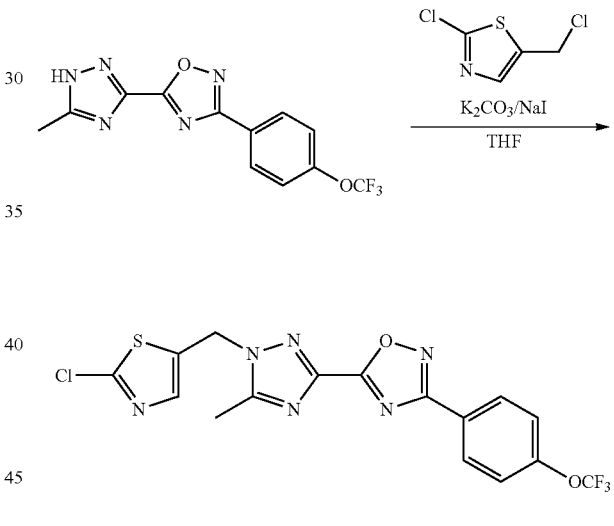

5-(1-((2-Chlorothiazol-5-yl)methyl)-5-methyl-1H-1,2,4-triazol-3-yl)-3-(4-(trifluoromethoxy)phenyl)-1,2,4-oxadiazole To a suspension of 5-(5-methyl-1H-1,2,4-triazol-3-yl)-3-(4-(trifluoromethoxy)phenyl)-1,2,4-oxadiazole (31 mg, 0.1 mmol) in THF (1 mL), K$_2$CO$_3$ (28 mg, 0.2 mmol), NaI (22 mg, 0.15 mmol), and 5-(chloromethyl)-2-chlorothiazole (25 mg, 0.15 mmol) were added at RT. The mixture was stirred at RT for 3 days. The resulting crude product was filtered and purified by a silica gel column with (EtOAc/Hexane 16% to 100% EtOAc) to give 5-(1-((2-chlorothiazol-5-yl)methyl)-5-methyl-1H-1,2,4-triazol-3-yl)-3-(4-(trifluoromethoxy)phenyl)-1,2,4-oxadiazole as a white solid (24 mg, 55%). MS (ES+) C$_{16}$H$_{10}$F$_3$N$_6$ClO$_2$S requires: 442, 444, found: 443, 445 [M+H]$^+$; $^1$H NMR (600 MHz, CDCl$_3$) δ 8.28 (d, J=8.9 Hz, 2H), 7.60 (s, 1H), 7.35 (d, J=8.2 Hz, 2H), 5.57 (s, 2H), 2.65 (s, 3H).

EXAMPLE 18

4-(5-((5-Methyl-3-(3-(4-(trifluoromethoxy)phenyl)-1,2,4-oxadiazol-5-yl)-1H-1,2,4-triazol-1-yl)methyl)thiazol-2-yl)morpholine

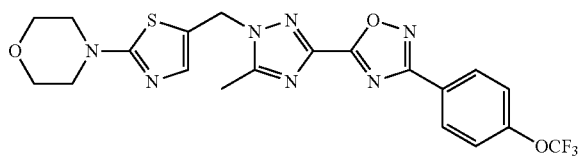 [SMILES: Cc1nc(-c2nc(-c3ccc(OC(F)(F)F)cc3)no2)nn1Cc1cnc(N2CCOCC2)s1]

Step 1

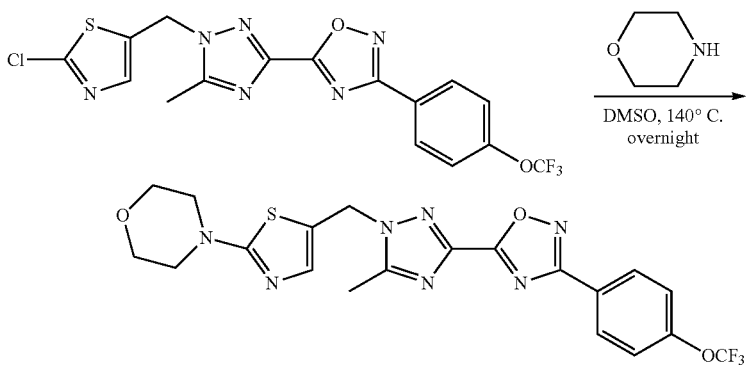

4-(5-((5-Methyl-3-(3-(4-(trifluoromethoxy)phenyl)-1,2,4-oxadiazol-5-yl)-1H-1,2,4-triazol-1-yl)methyl)thiazol-2-yl)morpholine 5-(1-((2-Chlorothiazol-5-yl)methyl)-5-methyl-1H-1,2,4-triazol-3-yl)-3-(4-(trifluoro methoxy)phenyl)-1,2,4-oxadiazole (45 mg, 0.1 mmol) was mixed with morpholine (87 mg, 1.0 mmol) in DMSO (0.5 mL). The mixture was heated to 140° C. overnight. The resulting crude product was purified by a silica gel column with (EtOAc/Hexane 50% to 100% EtOAc) to give 4-(5-((5-methyl-3-(3-(4-(trifluoromethoxy)phenyl)-1,2,4-oxadiazol-5-yl)-1H-1,2,4-triazol-1-yl)methyl)thiazol-2-yl)morpholine as a white solid (21 mg, 43%). MS (ES+) $C_{20}H_{18}F_3N_7O_3S$ requires: 493, found: 494[M+H]$^+$; $^1$H NMR (600 MHz, CDCl$_3$) δ 8.28 (d, J=8.8 Hz, 2H), 7.34 (d, J=8.4 Hz, 2H), 7.24 (s, 1H), 5.47 (s, 2H), 3.78 (t, J=4.9 Hz, 4H), 3.44 (t, J=4.9 Hz, 4H), 2.62 (s, 3H).

EXAMPLE 19

5-(1-((2-Chloropyrimidin-4-yl)methyl)-5-methyl-1H-1,2,4-triazol-3-yl)-3-(4-(trifluoromethoxy)phenyl)-1,2,4-oxadiazole

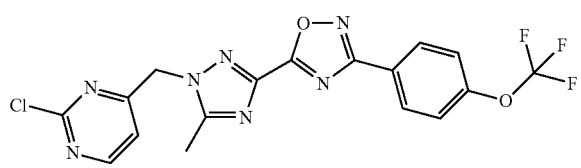 [SMILES: Cc1nc(-c2nc(-c3ccc(OC(F)(F)F)cc3)no2)nn1Cc1ccnc(Cl)n1]

5-(5-Methyl-1H-1,2,4-triazol-3-yl)-3-(4-(trifluoromethoxy)phenyl)-1,2,4-oxadiazole (200 mg, 0.643 mmol) was placed in DMF (5 ml) and Cs$_2$CO$_3$ (251 mg, 0.771 mmol) was added. The reaction was stirred for 5 min and 2-chloro-4-(chloromethyl)pyrimidine (126 mg, 0.771 mmol) was added. The reaction was stirred at 45° C. overnight and then partitioned between H$_2$O (50 mL) and EtOAc (50 mL). The organic layer was separated, washed with H$_2$O (2×50 mL) and brine (30 mL), dried over Na$_2$SO$_4$, filtered, and concentrated to afford the crude product which was purified by silica gel chromatography (EtOAc/Hexane 10%-100% EtOAc) to afford the desired compound as an orange solid (193 mg, 68%). MS (ES+) $C_{17}H_{11}ClF_3N_7O_2$ requires: 437, 439, found 438, 440 [M+H]$^+$; $^1$H NMR (600 MHz, DMSO-d$_6$) δ 8.81 (d, J=5.1 Hz, 1H), 8.21 (d, J=8.7 Hz, 2H), 7.61 (d, J=8.7 Hz, 2H), 7.52 (d, J=5.1 Hz, 1H), 5.81 (s, 2H), 2.59 (s, 3H).

EXAMPLE 20

5-(5-Methyl-1-((2-(4-methylpiperazin-1-yl)pyrimidin-4-yl)methyl)-1H-1,2,4-triazol-3-yl)-3-(4-(trifluoromethoxy)phenyl)-1,2,4-oxadiazole 5-(1-((2-Chloropyrimidin-4-yl)methyl)-5-methyl-1H-1,2,4-triazol-3-yl)-3-(4-(trifluoromethoxy)phenyl)-1,2,4-oxadiazole (50.0 mg, 0.114 mmol) was dissolved in DMSO (0.5 ml) and 1-methylpiperazine (0.127 ml, 1.142 mmol) was added. The reaction was heated at 130° C. overnight and purified by prep-HPLC (MeCN/H$_2$O 20%-50% MeCN, containing 0.1% TFA). The product was taken up in EtOAc (10 mL), washed with sat. NaHCO$_3$ (10 mL), dried over Na$_2$SO$_4$, filtered, and concentrated to afford the desired compound as a yellow solid (24 mg, 42%). MS (ES+) $C_{22}H_{22}F_3N_9O_2$ requires: 501, found 502 [M+H]$^+$; $^1$H NMR (600 MHz, CDCl$_3$) δ 8.33-8.24 (m, 3H), 7.33 (d, J=8.3 Hz, 2H), 6.32 (d, J=4.9 Hz, 1H), 5.33 (s, 2H), 3.84-3.70 (m, 4H), 2.64 (s, 3H), 2.47-2.38 (m, 4H), 2.32 (s, 3H).

EXAMPLE 21

1-Methyl-4-(4-((5-methyl-3-(3-(4-(methylsulfonyl)phenyl)-1,2,4-oxadiazol-5-yl)-1H-1,2,4-triazol-1-yl)methyl)pyridin-1-ium-2-yl)piperazin-1-ium bis-trifluoroacetate

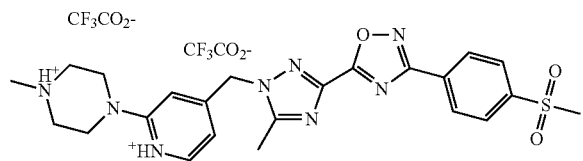

Prepared in an analogous manner to Example 9. Purification by prep-HPLC (MeCN/H$_2$O 10%-30% MeCN, containing 0.1% TFA) to afford the desired compound (20 mg, 57%). MS (ES+) C$_{23}$H$_{26}$N$_8$O$_3$S requires: 494, found 495 [M+H]$^+$; $^1$H NMR (600 MHz, DMSO-d$_6$) δ 8.34 (d, J=8.4 Hz, 2H), 8.18-8.13 (m, 3H), 6.88 (s, 1H), 6.57 (d, J=5.1 Hz, 1H), 5.52 (s, 2H), 4.41-4.37 (m, 2H), 3.53-3.46 (m, 2H), 3.32 (s, 3H), 3.20-3.01 (m, 4H), 2.84 (s, 3H), 2.59 (s, 3H).

EXAMPLE 22

1-Methyl-4-(4-((5-methyl-3-(3-(p-tolyl)-1,2,4-oxadiazol-5-yl)-1H-1,2,4-triazol-1-yl)methyl)pyridin-1-ium-2-yl)piperazin-1-ium bis-trifluoroacetate

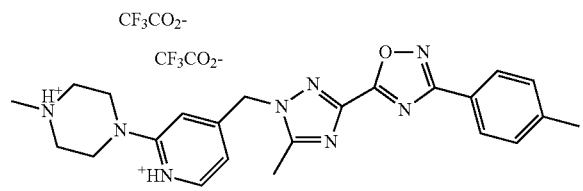

Prepared in an analogous manner to Example 9. Purification by prep-HPLC (MeCN/H$_2$O 20%-50% MeCN, containing 0.1% TFA) to afford the desired compound (9 mg, 11%). MS (ES+) C$_{23}$H$_{26}$N$_8$O requires: 430, found 431 [M+H]$^+$; $^1$H NMR (600 MHz, d$_6$-DMSO) δ 9.78 (bs, 1H), 8.14 (d, J=5.2 Hz, 1H), 7.96 (d, J=8.1 Hz, 2H), 7.41 (d, J=8.1 Hz, 2H), 6.87 (s, 1H), 6.57 (d, J=5.2 Hz, 1H), 5.51 (s, 2H), 4.43-4.34 (m, 2H), 3.60-3.40 (m, 2H), 3.16-3.01 (m, 4H), 2.84 (s, 3H), 2.58 (s, 3H), 2.40 (s, 3H).

EXAMPLE 23

4-(4-((3-(3-(4-(Difluoromethoxy)phenyl)-1,2,4-oxadiazol-5-yl)-5-methyl-1H-1,2,4-triazol-1-yl)methyl)pyridin-1-ium-2-yl)-1-methylpiperazin-1-ium bis-trifluoroacetate

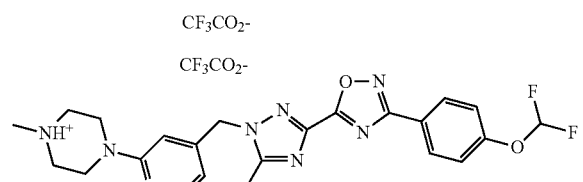

Prepared in an analogous manner to Example 9. Purification by prep-HPLC (MeCN/H$_2$O 20%-50% MeCN, containing 0.1% TFA) to afford the desired compound (2 mg, 4%). MS (ES+) C$_{23}$H$_{24}$F$_2$N$_8$O$_2$ requires: 482, found 483 [M+H]$^+$; $^1$H NMR (600 MHz, CDCl$_3$) δ 8.24 (d, J=8.7 Hz, 2H), 8.21 (d, J=5.2 Hz, 1H), 7.24 (d, J=8.7 Hz, 2H), 6.60 (t, J=73.3 Hz, 1H), 6.56 (d, J=5.2 Hz, 1H), 6.49 (s, 1H), 5.39 (s, 2H), 4.43-4.34 (m, 2H), 3.60-3.40 (m, 2H), 3.16-3.01 (m, 4H), 2.86 (s, 3H), 2.57 (s, 3H).

EXAMPLE 24

5-(1-Benzyl-5-methyl-1H-1,2,4-triazol-3-yl)-3-(4-(trifluoromethoxy)phenyl)-1,2,4-oxadiazole

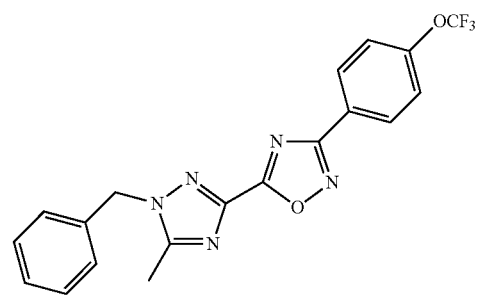 [SMILES: Cc1nc(-c2nc(-c3ccc(OC(F)(F)F)cc3)no2)nn1Cc1ccccc1]

Synthesized in an analogous method to Example 4 (2 mg, 4%): $^1$H NMR (600 MHz, DMSO-d$_6$) δppm 8.29 (d, J=8.8 Hz, 2H), 8.17 (d, J=8.8 Hz, 1H), 7.41-7.31 (m, 6H), 5.46 (s, 2H), 2.53 (s, 3H); MS (ES+) C$_{19}$H$_{14}$F$_3$N$_5$O$_2$ requires: 401, found: 402 [M+H]$^+$.

EXAMPLE 25

1-methyl-4-(3-((5-methyl-3-(3-(4-(trifluoromethoxy)phenyl)-1,2,4-oxadiazol-5-yl)-1H-1,2,4-triazol-1-yl)methyl)phenyl)piperazin-1-ium trifluoroacetate

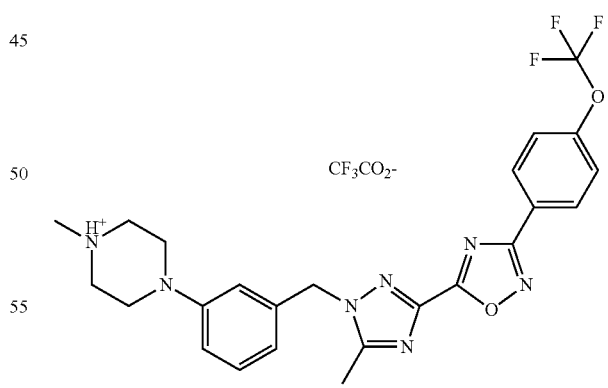

Synthesized in an analogous method to Example 11 to provide a white solid (12 mg, 24%): $^1$H NMR (600 MHz, DMSO-d$_6$) δ ppm 8.22 (d, J=8.7 Hz, 2H), 7.61 (d, J=8.4 Hz, 2H), 7.21 (t, J=7.9 Hz, 1H), 6.93 (s, 1H), 6.89 (app. dd, J=8.2 Hz, 1.9 Hz, 1H), 6.63 (d, J=7.6 Hz, 1H), 5.47 (s, 2H), 3.13 (t, J=4.9 Hz, 4H), 2.57 (s, 3H), 2.43 (t, J=4.9 Hz, 4H), 2.21 (s, 3H); MS (ES+) C$_{24}$H$_{24}$F$_3$N$_7$O$_2$ requires: 499, found: 500[M+H]$^+$.

EXAMPLE 26

1-(4-((5-Methyl-3-(3-(4-(trifluoromethoxy)phenyl)-1,2,4-oxadiazol-5-yl)-1H-1,2,4-triazol-1-yl)methyl)pyridin-2-yl)piperidin-4-ol

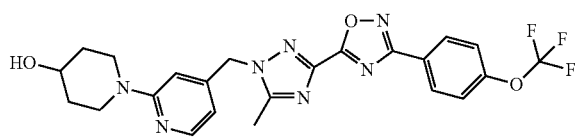 [SMILES: Cc1nc(-c2nc(-c3ccc(OC(F)(F)F)cc3)no2)nn1Cc1ccnc(N2CCC(O)CC2)c1]

Prepared in an analogous manner to Example 10. Purification by prep-HPLC (MeCN/H$_2$O 20%-60% MeCN, containing 0.1% TFA). The product was taken up in EtOAc (10 mL), washed with sat. NaHCO$_3$ (10 mL), dried over Na$_2$SO$_4$, filtered, and concentrated to afford the desired compound (25 mg, 43%). MS (ES+) C$_{23}$H$_{22}$F$_3$N$_7$O$_3$ requires: 501, found 502 [M+H]$^+$; $^1$H NMR (600 MHz, CDCl$_3$) δ 8.29 (d, J=8.8 Hz, 2H), 8.15 (d, J=5.2 Hz 1H), 7.34 (d, J=8.8 Hz, 2H), 6.41 (s, 1H), 6.36 (d, J=5.2 Hz, 1H), 5.35 (s, 2H), 4.05-3.97 (m, 2H), 3.97-3.89 (m, 1H), 3.21-3.13 (m, 2H), 2.54 (s, 3H), 1.99-1.91 (m, 2H), 1.61-1.52 (m, 2H).

EXAMPLE 27

1-(4-((5-Methyl-3-(3-(4-(trifluoromethoxy)phenyl)-1,2,4-oxadiazol-5-yl)-1H-1,2,4-triazol-1-yl)methyl)pyridin-2-yl)piperidine-4-carbonitrile

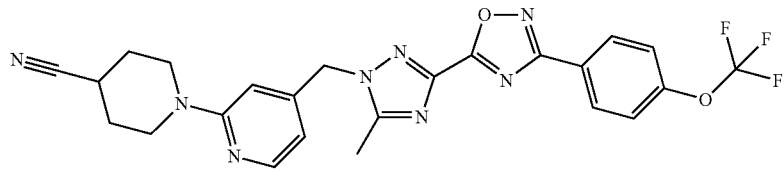 [SMILES: Cc1nc(-c2nc(-c3ccc(OC(F)(F)F)cc3)no2)nn1Cc1ccnc(N2CCC(C#N)CC2)c1]

Prepared in an analogous manner to Example 10. Purification by prep-HPLC (MeCN/H$_2$O 30%-70% MeCN, containing 0.1% TFA). The product was taken up in EtOAc (10 mL), washed with sat. NaHCO$_3$ (10 mL), dried over Na$_2$SO$_4$, filtered, and concentrated to afford the desired compound (42 mg, 71%). MS (ES+) C$_{24}$H$_{21}$F$_3$N$_8$O$_2$ requires: 510, found 511 [M+H]$^+$; $^1$H NMR (600 MHz, CDCl$_3$) δ 8.31 (d, J=8.6 Hz, 2H), 8.19 (d, J=5.0 Hz, 1H), 7.37 (d, 2H, J=8.6 Hz), 6.45 (d, J=5.0 Hz, 1H), 6.43 (s, 1H), 5.39 (s, 2H), 3.86-3.79 (m, 2H), 3.54-3.47 (m, 2H), 2.93-2.87 (m, 1H), 2.58 (s 3H), 2.05-1.97 (m, 2H), 1.97-1.88 (m, 2H).

EXAMPLE 28

5-(5-Methyl-1-((2-(pyrrolidin-1-yl)pyridin-4-yl)methyl)-1H-1,2,4-triazol-3-yl)-3-(4-(trifluoromethoxy)phenyl)-1,2,4-oxadiazole

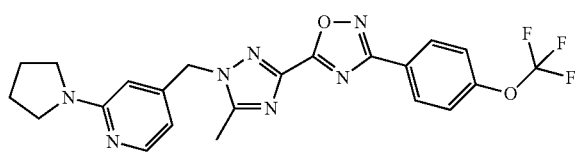 [SMILES: Cc1nc(-c2nc(-c3ccc(OC(F)(F)F)cc3)no2)nn1Cc1ccnc(N2CCCC2)c1]

Prepared in an analogous manner to Example 10. Purification by prep-HPLC (MeCN/H$_2$O 30%-70% MeCN, containing 0.1% TFA). The product was taken up in EtOAc (10 mL), washed with sat. NaHCO$_3$ (10 mL), dried over Na$_2$SO$_4$, filtered, and concentrated to afford the desired compound (20 mg, 37%). MS (ES+) C$_{22}$H$_{20}$F$_3$N$_7$O$_2$ requires: 471, found 472 [M+H]$^+$; $^1$H NMR (600 MHz, CDCl$_3$) δ 8.29 (d, J=8.8 Hz, 2H), 8.13 (d, J=5.4 Hz, 1H), 7.34 (d, J=8.8 Hz, 2H), 6.30 (d, J=5.4 Hz, 1H), 6.07 (s, 1H), 5.36 (s, 2H), 3.45-3.37 (m, 4H), 2.54 (s, 3H), 2.02-1.96 (m, 4H).

EXAMPLE 29

1-Methyl-4-(4-((5-methyl-3-(3-phenyl-1,2,4-oxadiazol-5-yl)-1H-1,2,4-triazol-1-yl)methyl)pyridin-1-ium-2-yl)piperazin-1-ium bis-trifluoroacetate

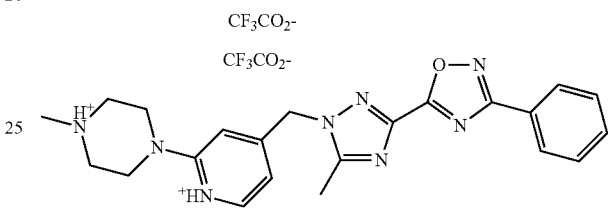

Prepared in an analogous manner to Example 10. Purification by prep-HPLC (MeCN/H$_2$O 10%-40% MeCN, containing 0.1% TFA) to afford the desired compound (45 mg, 49%). MS (ES+) C$_{22}$H$_{24}$N$_8$O requires: 416, found 417 [M+H]$^+$; $^1$H NMR (600 MHz, CDCl$_3$) δ 8.26-8.19 (m, 3H), 7.57-7.47 (m, 3H), 6.57 (d, J=5.2 Hz, 1H), 6.50 (s, 1H), 5.39 (s, 2H), 4.45-4.15 (m, 2H), 3.87-3.30 (m, 4H), 3.10-2.76 (m, 2H), 2.87 (s, 3H), 2.57 (s, 3H).

EXAMPLE 30

N-(2-(Dimethylamino)ethyl)-3-((5-methyl-3-(3-(4-(trifluoromethoxy)phenyl)-1,2,4-oxadiazol-5-yl)-1H-1,2,4-triazol-1-yl)methyl)benzamide

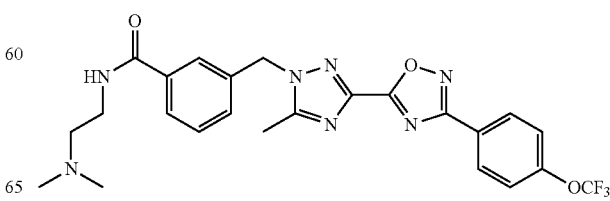

Step 1

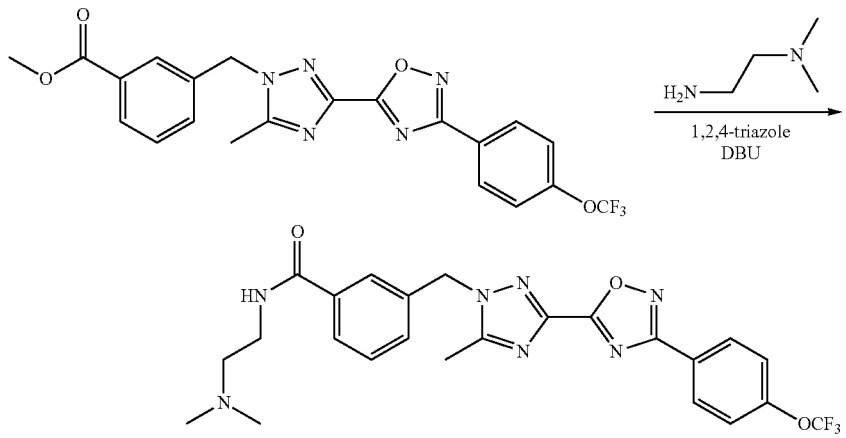

Synthesized in an analogous method to Example 14: (42 mg, 81%). MS (ES+) C$_{24}$H$_{24}$F$_3$N$_7$O$_3$ requires: 515, found: 516 [M+H]$^+$. $^1$H NMR (600 MHz, DMSO-d$_6$) δ 8.29 (d, J=8.8 Hz, 2H), 7.80 (s, 1H), 7.75 (d, J=7.7 Hz, 1H), 7.45 (t, J=7.7 Hz, 1H), 7.37 (d, J=7.7 Hz, 1H), 7.35 (d, J=8.8 Hz, 2H), 6.98-6.94 (m, 1H), 5.51 (s, 2H), 3.52 (m, 2H), 2.56 (s, 3H), 2.52 (t, J=5.8 Hz, 2H), 2.26 (s, 6H).

EXAMPLE 31

5-(1-((2-(4,4-Dimethylpiperidin-1-yl)pyridin-4-yl)methyl)-5-methyl-1H-1,2,4-triazol-3-yl)-3-(4-(trifluoromethoxy)phenyl)-1,2,4-oxadiazole

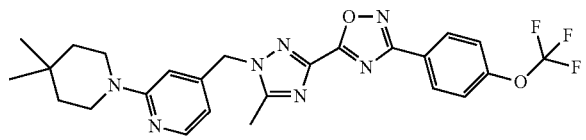 [SMILES: Cc1nc(-c2nc(-c3ccc(OC(F)(F)F)cc3)no2)nn1Cc1ccnc(N2CCC(C)(C)CC2)c1]

Prepared in an analogous manner to Example 10. Purification by prep-HPLC (MeCN/H$_2$O 40%-80% MeCN, containing 0.1% TFA). The product was taken up in EtOAc (10 mL), washed with sat. NaHCO$_3$ (10 mL), dried over Na$_2$SO$_4$, filtered, and concentrated to afford the desired compound (25 mg, 42%). MS (ES+) C$_{25}$H$_{26}$F$_3$N$_7$O$_2$ requires: 513, found 514 [M+H]$^+$; $^1$H NMR (600 MHz, CDCl$_3$) δ 8.31 (d, J=7.7 Hz, 2H), 8.21-8.12 (m, 1H), 7.37 (d, J=7.7 Hz, 2H), 6.45-6.31 (m, 2H), 5.37 (s, 2H), 3.60-3.45 (m, 4H), 2.56 (s, 3H), 1.51-1.39 (m, 4H), 1.01 (s, 6H).

EXAMPLE 32

N-(3-Methoxypropyl)-4-((5-methyl-3-(3-(4-(trifluoromethoxy)phenyl)-1,2,4-oxadiazol-5-yl)-1H-1,2,4-triazol-1-yl)methyl)pyridin-2-amine

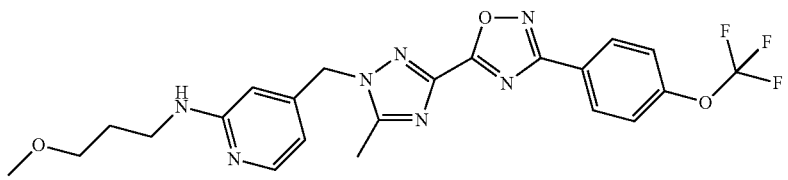 [SMILES: COCCCNc1cc(Cn2nc(-c3nc(-c4ccc(OC(F)(F)F)cc4)no3)nc2C)ccn1]

Prepared in an analogous manner to Example 10. Purification by prep-HPLC (MeCN/H$_2$O 20%-60% MeCN, containing 0.1% TFA). The product was taken up in EtOAc (10 mL), washed with sat. NaHCO$_3$ (10 mL), dried over Na$_2$SO$_4$, filtered, and concentrated to afford the desired compound (4 mg, 7%). MS (ES+) C$_{22}$H$_{22}$F$_3$N$_7$O$_3$ requires: 489, found 490 [M+H]$^+$; $^1$H NMR (600 MHz, CDCl$_3$) δ 8.29 (d, J=8.8 Hz, 2H), 8.06 (d, J=5.3 Hz, 1H), 7.34 (d, J=8.8 Hz, 2H), 6.34 (d, J=5.3 Hz, 1H), 6.10 (s, 1H), 5.33 (s, 2H), 5.00-4.88 (m, 1H), 3.49 (t, J=5.8 Hz, 2H), 3.39-3.33 (m, 2H), 3.33 (s, 3H), 2.54 (s, 3H), 1.90-1.83 (m, 2H).

EXAMPLE 33

5-(1-Benzyl-5-ethyl-1H-1,2,4-triazol-3-yl)-3-(4-(trifluoromethoxy)phenyl)-1,2,4-oxadiazole

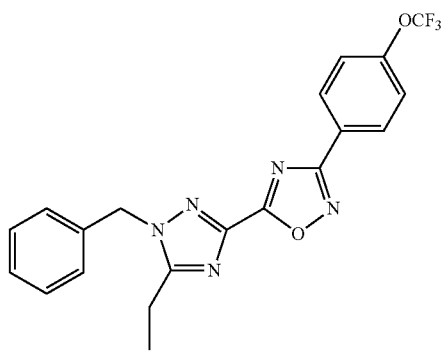 [SMILES: CCc1nc(-c2nc(-c3ccc(OC(F)(F)F)cc3)no2)nn1Cc1ccccc1]

Synthesized in an analogous method to Example 4 (2.8 mg, 7%): $^1$H NMR (600 MHz, CDCl$_3$) δppm 8.23 (d, J=8.8

Hz, 2H), 7.61 (d, J=8.4 Hz, 2H), 7.42-7.32 (m, 3H), 7.30 (d, J=7.3 Hz, 2H), 5.58 (s, 2H), 2.92 (q, J=7.5 Hz, 2H), 1.25 (t, J=7.5 Hz, 3H); MS (ES+) C$_{20}$H$_{16}$F$_3$N$_5$O$_2$ requires: 415, found: 416 [M+H]+.

EXAMPLE 34

5-(1-Benzyl-5-cyclopropyl-1H-1,2,4-triazol-3-yl)-3-(4-(trifluoromethoxy)phenyl)-1,2,4-oxadiazole

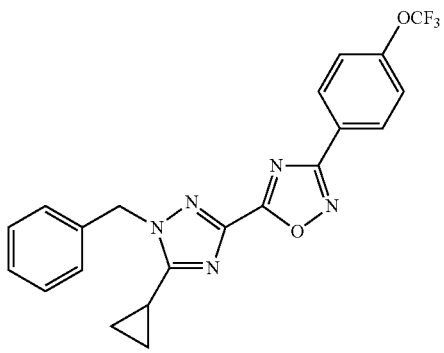 [SMILES: FC(F)(F)Oc1ccc(-c2noc(-c3nc(C4CC4)n(Cc4ccccc4)n3)n2)cc1]

Synthesized in an analogous method to Example 4 (1.2 mg, 2%): $^1$H NMR (600 MHz, CDCl$_3$) δppm 8.25 (d, J=8.1 Hz, 2H), 7.39-7.29 (m, 5H), 7.27 (d, J=7.5 Hz, 2H), 5.55 (s, 2H), 1.92-1.85 (m, 1H), 1.25-1.20 (m, 2H), 1.11 (d, J=7.0 Hz, 2H); MS (ES+) C$_{21}$H$_{16}$F$_3$N$_5$O$_2$ requires: 427, found: 428 [M+H]+.

EXAMPLE 35

4-((5-Methyl-3-(3-(4-(trifluoromethoxy)phenyl)-1,2,4-oxadiazol-5-yl)-1H-1,2,4-triazol-1-yl)methyl)-N-(2-morpholinoethyl)pyridin-2-amine

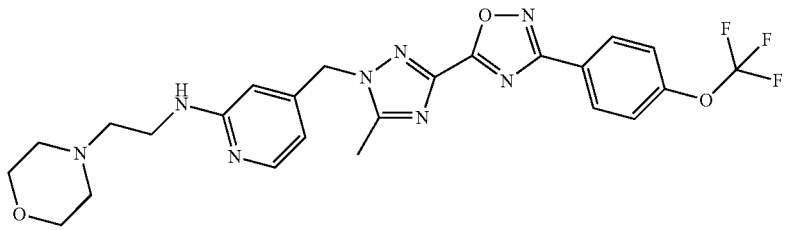 [SMILES: Cc1nc(-c2nc(-c3ccc(OC(F)(F)F)cc3)no2)nn1Cc1ccnc(NCCN2CCOCC2)c1]

Prepared in an analogous manner to Example 10. Purification by prep-HPLC (MeCN/H$_2$O 20%-50% MeCN, containing 0.1% TFA). The product was taken up in EtOAc (10 mL), washed with sat. NaHCO$_3$ (10 mL), dried over Na$_2$SO$_4$, filtered, and concentrated to afford the desired compound (1.9 mg, 4%). MS (ES+) C$_{24}$H$_{25}$F$_3$N$_8$O$_3$ requires: 530, found 531 [M+H]$^+$; $^1$H NMR (600 MHz, CDCl$_3$) δ 8.29 (d, J=8.5 Hz, 2H), 8.08 (d, J=5.3 Hz, 1H), 7.34 (d, J=8.5 Hz, 2H), 6.38 (d, J=5.3 Hz, 1H), 6.09 (s, 1H), 5.34 (s, 2H), 5.24-5.13 (m, 1H), 3.74-3.65 (m, 4H), 3.36-3.26 (m, 2H), 2.65-2.56 (m, 2H), 2.55 (s, 3H), 2.52-2.38 (m, 4H).

EXAMPLE 36

N-Methyl-4-((5-methyl-3-(3-(4-(trifluoromethoxy)phenyl)-1,2,4-oxadiazol-5-yl)-1H-1,2,4-triazol-1-yl)methyl)pyridin-2-amine

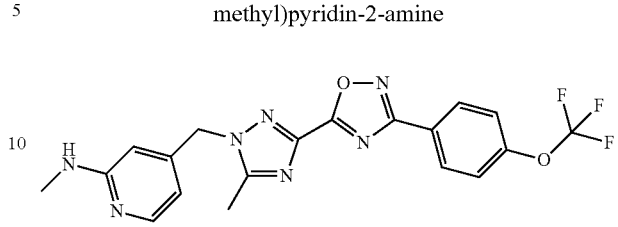

Prepared in an analogous manner to Example 10. Purification by prep-HPLC (MeCN/H$_2$O 20%-50% MeCN, containing 0.1% TFA). The product was taken up in EtOAc (10 mL), washed with sat. NaHCO$_3$ (10 mL), dried over Na$_2$SO$_4$, filtered, and concentrated to afford the desired compound (6 mg, 15%). MS (ES+) C$_{19}$H$_{16}$F$_3$N$_7$O$_2$ requires: 431, found 432 [M+H]$^+$; $^1$H NMR (600 MHz, CDCl$_3$) δ 8.29 (d, J=8.1 Hz, 2H), 8.08 (d, J=5.2 Hz, 1H), 7.34 (d, J=8.1 Hz, 2H), 6.37 (d, J=5.2 Hz, 1H) 6.10 (s, 1H), 5.35 (s, 2H), 4.69-4.58 (m, 1H), 2.89 (d, J=4.9 Hz, 3H), 2.54 (s, 3H).

EXAMPLE 37

N,N-Dimethyl-4-((5-methyl-3-(3-(4-(trifluoromethoxy)phenyl)-1,2,4-oxadiazol-5-yl)-1H-1,2,4-triazol-1-yl)methyl)pyridin-2-amine

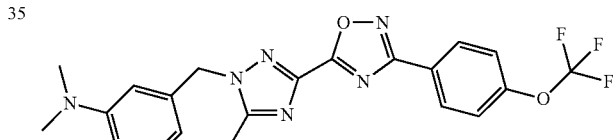

Prepared in an analogous manner to Example 10. Purification by prep-HPLC (MeCN/H$_2$O 20%-60% MeCN, containing 0.1% TFA). The product was taken up in EtOAc (10 mL), washed with sat. NaHCO$_3$ (10 mL), dried over Na$_2$SO$_4$, filtered, and concentrated to afford the desired compound (16 mg, 39%). MS (ES+) C$_{20}$H$_{18}$F$_3$N$_7$O$_2$ requires: 445, found 446 [M+H]$^+$; $^1$H NMR (600 MHz, CDCl$_3$) δ 8.29 (d, J=7.7 Hz, 2H), 8.19-8.12 (m, 1H), 7.34 (d, J=7.7 Hz, 2H), 6.36-6.29 (m, 1H), 6.24 (s, 1H), 5.36 (s, 2H), 3.06 (s, 6H), 2.54 (s, 3H).

EXAMPLE 38

1-(4-(4-((5-Methyl-3-(3-(4-(trifluoromethoxy)phenyl)-1,2,4-oxadiazol-5-yl)-1H-1,2,4-triazol-1-yl)methyl)pyridin-2-yl)piperazin-1-yl)ethanone

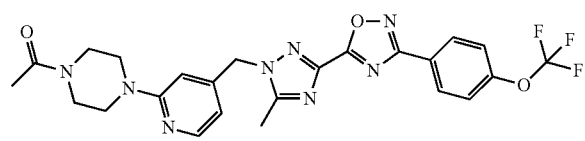 [SMILES: CC(=O)N1CCN(c2cc(Cn3nc(-c4nc(-c5ccc(OC(F)(F)F)cc5)no4)nc3C)ccn2)CC1]

Prepared in an analogous manner to Example 10. Purification by prep-HPLC (MeCN/H$_2$O 20%-50% MeCN, containing 0.1% TFA). The product was taken up in EtOAc (10 mL), washed with sat. NaHCO$_3$ (10 mL), dried over Na$_2$SO$_4$, filtered, and concentrated to afford the desired compound (11 mg, 23%). MS (ES+) C$_{24}$H$_{23}$F$_3$N$_8$O$_3$ requires: 528, found 529 [M+H]$^+$; $^1$H NMR (600 MHz, CDCl$_3$) δ 8.29 (d, J=8.1 Hz, 2H), 8.18 (d, J=4.3 Hz, 1H), 7.35 (d, J=8.1 Hz, 2H), 6.45 (d, J=4.3 Hz, 1H), 6.40 (s, 1H), 5.38 (s, 2H), 3.77-3.46 (m, 8H), 2.55 (s, 3H), 2.13 (s, 3H).

EXAMPLE 39

N-(2-Hydroxyethyl)-3-((5-methyl-3-(3-(4-(trifluoromethoxy)phenyl)-1,2,4-oxadiazol-5-yl)-1H-1,2,4-triazol-1-yl)methyl)benzamide Synthesized in an analogous method to Example 14: (41 mg, 84%). MS (ES+) C$_{22}$H$_{19}$F$_3$N$_6$O$_4$ requires: 488, found: 489 [M+H]$^+$. $^1$H NMR (600 MHz, DMSO-d$_6$) δ 8.50 (t, J=5.6 Hz, 1H), 8.22 (d, J=8.8 Hz, 2H), 7.84 (d, J=7.6 Hz, 1H), 7.81 (s, 1H), 7.60 (d, J=8.3 Hz, 2H), 7.49 (t, J=7.6 Hz, 1H), 7.46 (d, J=7.7 Hz, 1H), 5.62 (s, 2H), 4.72 (t, J=5.6 Hz, 1H), 3.50 (m, 2H), 3.32 (m, 2H), 2.60 (s, 3H).

EXAMPLE 40

N,N-Dimethyl-3-((5-methyl-3-(3-(4-(trifluoromethoxy)phenyl)-1,2,4-oxadiazol-5-yl)-1H-1,2,4-triazol-1-yl)methyl)benzamide

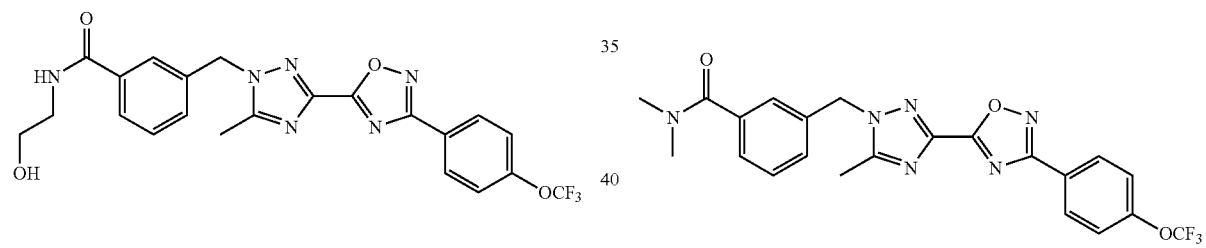

Step 1

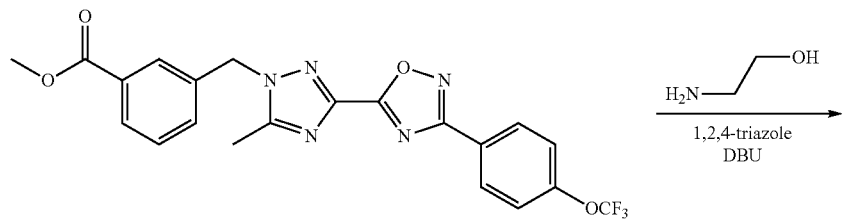

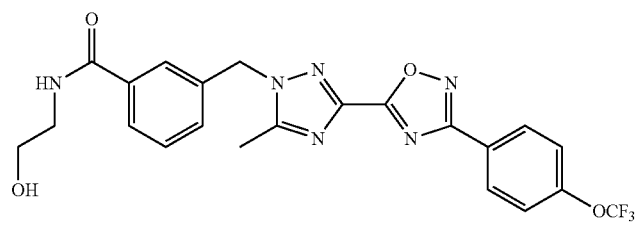 [SMILES: Cc1nc(-c2nc(-c3ccc(OC(F)(F)F)cc3)no2)nn1Cc1cccc(C(=O)NCCO)c1]

Step 1
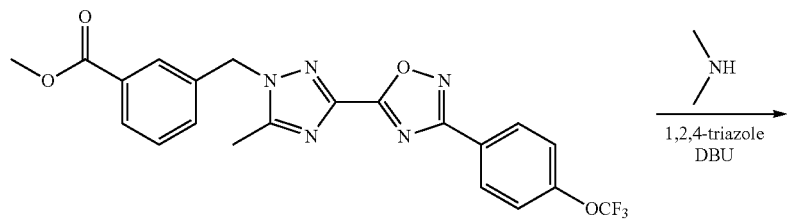
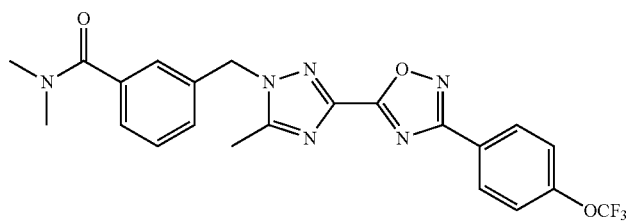 [SMILES: Cc1nc(-c2nc(-c3ccc(OC(F)(F)F)cc3)no2)nn1Cc1cccc(C(=O)N(C)C)c1]
Synthesized in an analogous method to Example 14: (18 mg, 38%). MS (ES+) $C_{22}H_{19}F_3N_6O_3$ requires: 472, found: 473 [M+H]$^+$. $^1$H NMR (600 MHz, CDCl$_3$) δ 8.29 (d, J=8.8 Hz, 2H), 7.43 (t, J=7.7 Hz, 1H), 7.40 (d, J=7.6 Hz, 1H), 7.35 (s, 1H), 7.35-7.33 (m, 2H), 7.29 (d, J=7.3 Hz, 1H), 5.48 (s, 2H), 3.10 (s, 3H), 2.95 (s, 3H), 2.56 (s, 3H).
EXAMPLE 41
N-(3-Methoxypropyl)-4-((5-methyl-3-(3-(4-(trifluoromethoxy)phenyl)-1,2,4-oxadiazol-5-yl)-1H-1,2,4-triazol-1-yl)methyl)benzamide
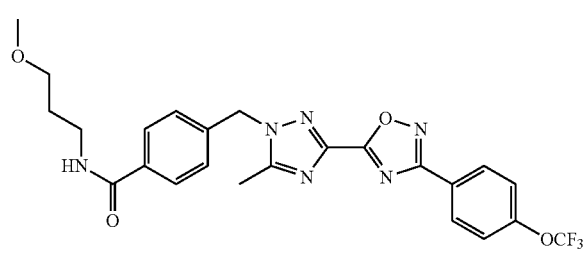 [SMILES: COCCCNC(=O)c1ccc(Cn2nc(-c3nc(-c4ccc(OC(F)(F)F)cc4)no3)nc2C)cc1]
Step 1
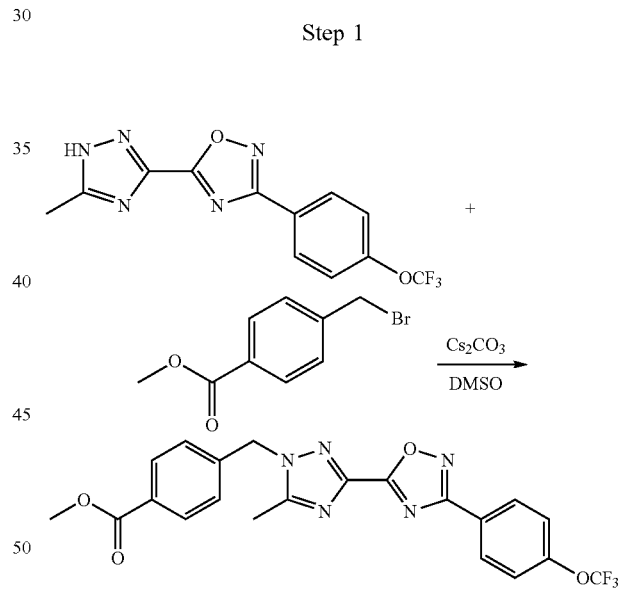
Synthesized in an analogous method to Example 12: (312 mg, 68%). MS (ES+) $C_{21}H_{16}F_3N_5O_4$ requires: 459, found: 460[M+H]$^+$.
Step 2
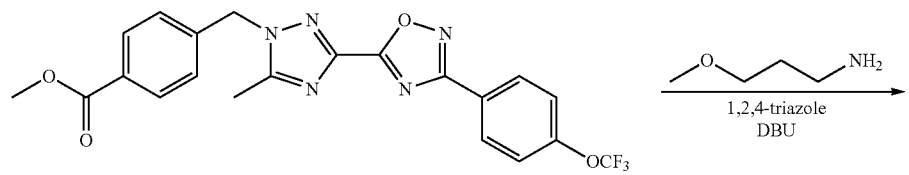

-continued

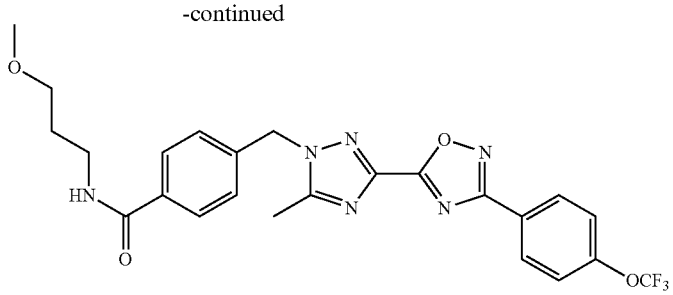

Synthesized in an analogous method to Example 14: (45 mg, 87%). MS (ES+) $C_{24}H_{23}F_3N_6O_4$ requires: 516, found: 517 [M+H]$^+$. $^1$H NMR (600 MHz, CDCl$_3$) δ 8.29 (d, J=8.8 Hz, 2H), 7.77 (d, J=8.4 Hz, 2H), 7.34 (d, J=8.2 Hz, 2H), 7.30 (d, J=8.4 Hz, 2H), 7.03-6.98 (m, 1H), 5.50 (s, 2H), 3.59-3.55 (m, 4H), 3.38 (s, 3H), 2.53 (s, 3H), 1.91-1.86 (m, 2H).

EXAMPLE 42

(4-((5-Methyl-3-(3-(4-(trifluoromethoxy)phenyl)-1,2,4-oxadiazol-5-yl)-1H-1,2,4-triazol-1-yl)methyl)phenyl)(4-methylpiperazin-1-yl)methanone

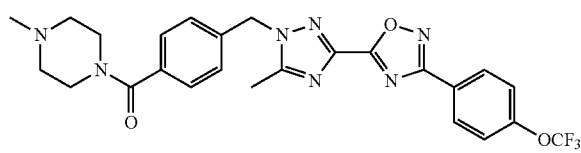 [SMILES: Cc1nc(-c2nc(-c3ccc(OC(F)(F)F)cc3)no2)nn1Cc1ccc(C(=O)N2CCN(C)CC2)cc1]

Step 1

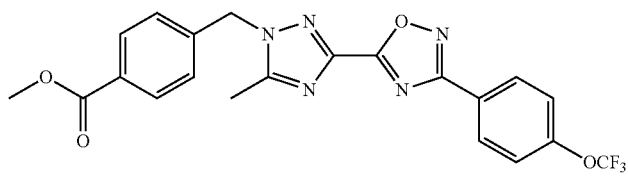

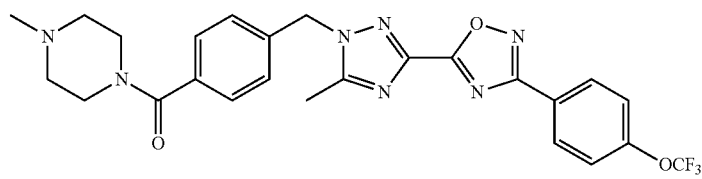

Synthesized in an analogous method to Example 14: (34 mg, 65%). MS (ES+) $C_{25}H_{24}F_3N_7O_3$ requires: 527, found: 528 [M+H]$^+$. $^1$H NMR (600 MHz, CDCl$_3$) δ 8.29 (d, J=8.6 Hz, 2H), 7.43 (d, J=8.0 Hz, 2H), 7.35 (d, J=8.4 Hz, 2H), 7.29 (d, J=8.0 Hz, 2H), 5.48 (s, 2H), 3.87-3.72 (m, 2H), 3.45-3.35 (m, 2H), 2.56 (s, 3H), 2.52-2.44 (m, 2H), 2.38-2.30 (m, 2H), 2.31 (s, 3H).

EXAMPLE 43

2-(1,1-Dioxidothiomorpholino)-4-((5-methyl-3-(3-(4-(trifluoromethoxy)phenyl)-1,2,4-oxadiazol-5-yl)-1H-1,2,4-triazol-1-yl)methyl)pyridin-1-ium trifluoroacetate

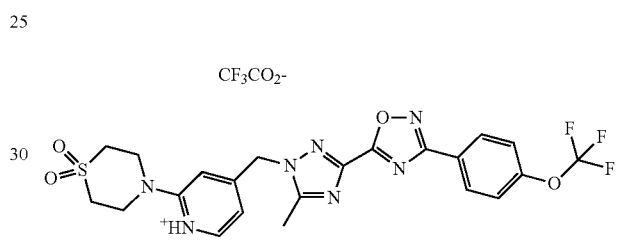

Prepared in an analogous manner to Example 10. Purification by prep-HPLC (MeCN/H$_2$O 30%-70% MeCN, containing 0.1% TFA) to afford the desired compound (2.5 mg, 5%). MS (ES+) $C_{22}H_{20}F_3N_7O_4S$ requires: 535, found 536 [M+H]$^+$; $^1$H NMR (600 MHz, CDCl$_3$) δ 8.28-8.23 (m, 3H), 7.36 (d, J=8.3 Hz, 2H) 6.72-6.68 (m, 2H), 5.44 (s, 2H), 4.20-4.15 (m, 4H), 3.17-3.12 (m, 4H), 2.62 (s, 3H).

EXAMPLE 44

4-(3-((5-Methyl-3-(3-(4-(trifluoromethoxy)phenyl)-1,2,4-oxadiazol-5-yl)-1H-1,2,4-triazol-1-yl)methyl)phenyl)morpholine

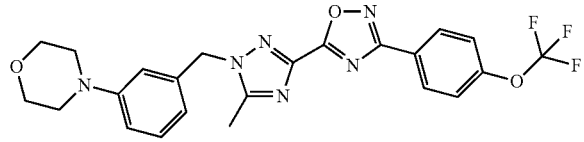 [SMILES: Cc1nc(-c2nc(-c3ccc(OC(F)(F)F)cc3)no2)nn1Cc1cccc(N2CCOCC2)c1]

Prepared in an analogous manner to Example 11. Purification by prep-HPLC (MeCN/H$_2$O 40%-80% MeCN, containing 0.1% TFA). The product was taken up in EtOAc (10 mL), washed with sat. NaHCO$_3$ (10 mL), dried over Na$_2$SO$_4$, filtered, and concentrated to afford the desired compound (8 mg, 20%). MS (ES+) C$_{23}$H$_{21}$F$_3$N$_6$O$_3$ requires: 486, found 487 [M+H]$^+$; $^1$H NMR (600 MHz, CDCl$_3$) δ 8.31-8.27 (m, 2H), 7.34 (d, J=8.1 Hz, 2H), 7.32-7.27 (m, 1H), 6.95-6.91 (m, 1H), 6.86-6.82 (m, 1H), 6.80-6.75 (m, 1H), 5.42 (s, 2H), 3.89-3.84 (m, 4H), 3.19-3.14 (m, 4H), 2.54 (s, 3H).

EXAMPLE 45

N1,N1-Dimethyl-N2-(4-((5-methyl-3-(3-(4-(trifluoromethoxy)phenyl)-1,2,4-oxadiazol-5-yl)-1H-1,2,4-triazol-1-yl)methyl)pyridin-2-yl)ethane-1,2-diamine

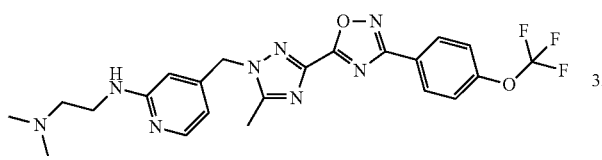

Prepared in an analogous manner to Example 10. Purification by prep-HPLC (MeCN/H$_2$O 20%-50% MeCN, containing 0.1% TFA). The product was taken up in EtOAc (10 mL), washed with sat. NaHCO$_3$ (10 mL), dried over Na$_2$SO$_4$, filtered, and concentrated to afford the desired compound (12 mg, 27%). MS (ES+) C$_{22}$H$_{23}$F$_3$N$_8$O$_2$ requires: 488, found 489 [M+H]$^+$; $^1$H NMR (600 MHz, CDCl$_3$) δ 8.32-8.27 (m, 2H), 8.06 (d, J=5.3 Hz, 1H), 7.34 (d, J=8.1 Hz, 2H), 6.37-6.34 (m, 1H), 6.12 (s, 1H), 5.32 (s, 2H), 5.32-5.23 (m, 1H), 3.41-3.33 (m, 2H), 2.63-2.55 (m, 2H), 2.54 (s, 3H), 2.30 (s, 6H).

EXAMPLE 46

4-((5-Methyl-3-(3-(4-(trifluoromethoxy)phenyl)-1,2,4-oxadiazol-5-yl)-1H-1,2,4-triazol-1-yl)methyl)-N-(2-(pyrrolidin-1-yl)ethyl)pyridin-2-amine

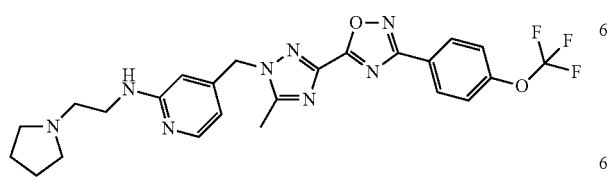

Prepared in an analogous manner to Example 10. Purification by prep-HPLC (MeCN/H$_2$O 20%-50% MeCN, containing 0.1% TFA). The product was taken up in EtOAc (10 mL), washed with sat. NaHCO$_3$ (10 mL), dried over Na$_2$SO$_4$, filtered, and concentrated to afford the desired compound (13 mg, 28%). MS (ES+) C$_{24}$H$_{25}$F$_3$N$_8$O$_2$ requires: 514, found 515 [M+H]$^+$; $^1$H NMR (600 MHz, CDCl$_3$) δ 8.31-8.27 (m, 2H), 8.06 (d, J=5.3 Hz, 1H), 7.34 (d, J=8.1 Hz, 2H), 6.37-6.33 (m, 1H), 6.09 (s, 1H), 5.32 (s, 2H), 5.28-5.18 (m, 1H), 3.39-3.31 (m, 2H), 2.70 (t, J=5.9 Hz, 2H), 2.54 (s, 3H), 2.59-2.47 (m, 4H), 1.81-1.72 (m, 4H).

EXAMPLE 47

5-(1-((5-Chlorothiophen-2-yl)methyl)-5-methyl-1H-1,2,4-triazol-3-yl)-3-(4-(trifluoromethoxy)phenyl)-1,2,4-oxadiazole

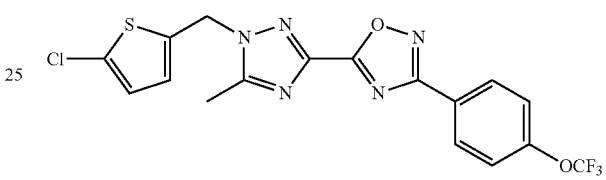

Step 1

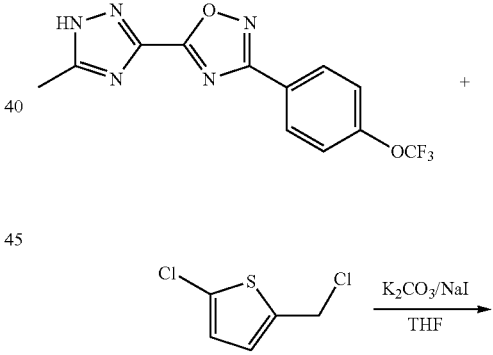

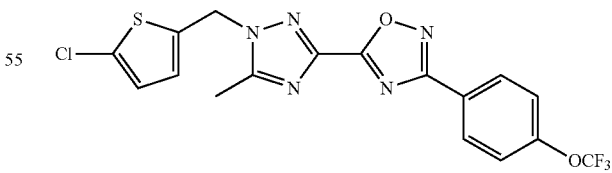

Synthesized in an analogous method to Example 17: (28 mg, 64%). MS (ES+) C$_{17}$H$_{11}$F$_3$N$_5$ClO$_2$S requires: 441, 443 found: 442, 444 [M+H]$^+$; $^1$H NMR (600 MHz, DMSO-d$_6$) δ 8.22 (d, J=8.7 Hz, 2H), 7.61 (d, J=8.4 Hz, 2H), 7.14 (d, J=3.8 Hz, 1H), 7.07 (d, J=3.8 Hz, 1H), 5.73 (s, 2H), 2.62 (s, 3H).

EXAMPLE 48

5-(1-((1,3-Dimethyl-1H-pyrazol-5-yl)methyl)-5-methyl-1H-1,2,4-triazol-3-yl)-3-(4-(trifluoromethoxy)phenyl)-1,2,4-oxadiazole

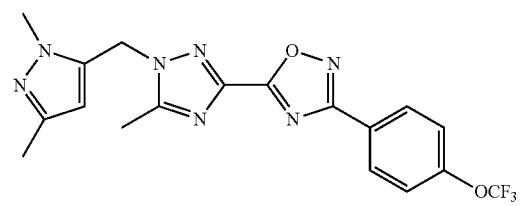 [SMILES: Cc1cc(Cn2nc(-c3nc(-c4ccc(OC(F)(F)F)cc4)no3)nc2C)n(C)n1]

Step 1

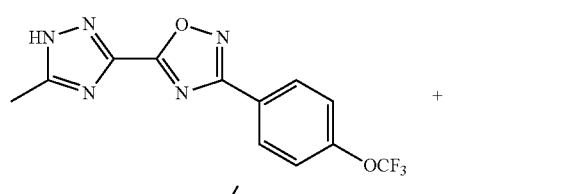

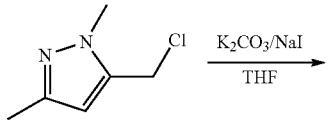

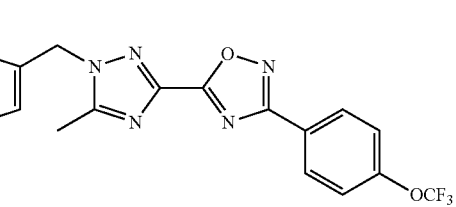

Synthesized in an analogous method to Example 17: (18 mg, 43%). MS (ES+) $C_{18}H_{16}F_3N_7O_2$ requires: 419, found: 420[M+H]$^+$; $^1$H NMR (600 MHz, DMSO-d$_6$) δ 8.22 (d, J=8.7 Hz, 2H), 7.61 (d, J=8.4 Hz, 2H), 6.03 (s, 1H), 5.40 (s, 2H), 3.67 (s, 3H), 2.59 (s, 3H), 2.21 (s, 3H).

EXAMPLE 49

7-((5-Methyl-3-(3-(4-(trifluoromethoxy)phenyl)-1,2,4-oxadiazol-5-yl)-1H-1,2,4-triazol-1-yl)methyl)-5H-thiazolo[3,2-a]pyrimidin-5-one

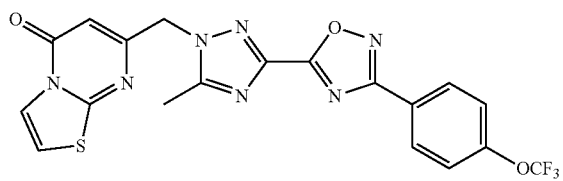 [SMILES: Cc1nc(-c2nc(-c3ccc(OC(F)(F)F)cc3)no2)nn1Cc1cc(=O)n2ccsc2n1]

Step 1

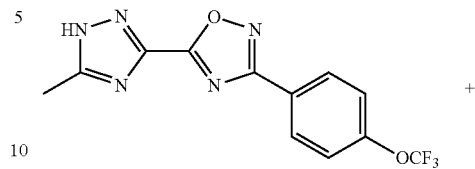

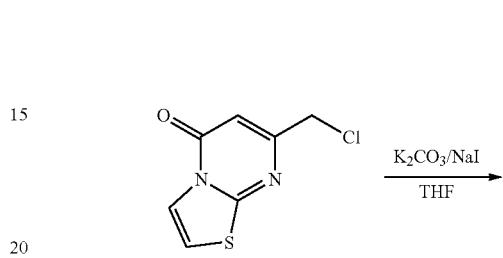

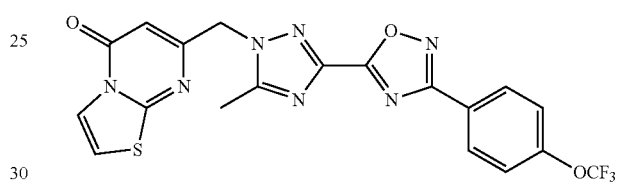

Synthesized in an analogous method to Example 17: (33 mg, 69%). MS (ES+) $C_{19}H_{12}F_3N_7O_3S$ requires: 475, found: 476[M+H]$^+$; $^1$H NMR (600 MHz, DMSO-d$_6$) δ 8.22 (d, J=8.8 Hz, 2H), 8.06 (d, J=4.9 Hz, 1H), 7.61 (d, J=8.4 Hz, 2H), 7.58 (d, J=4.9 Hz, 1H), 6.23 (s, 1H), 5.55 (s, 2H), 2.62 (s, 3H).

EXAMPLE 50

5-(5-Methyl-1-(3-(pyrrolidin-1-yl)benzyl)-1H-1,2,4-triazol-3-yl)-3-(4-(trifluoromethoxy)phenyl)-1,2,4-oxadiazole

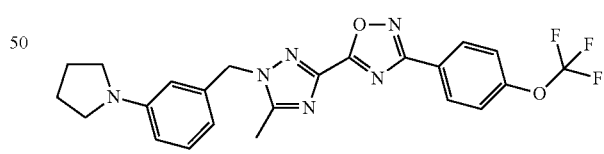

Prepared in an analogous manner to Example 11. Purification by prep-HPLC (MeCN/H$_2$O 50%-90% MeCN, containing 0.1% TFA). The product was taken up in EtOAc (10 mL), washed with sat. NaHCO$_3$ (10 mL), dried over Na$_2$SO$_4$, filtered, and concentrated to afford the desired compound (10 mg, 25%). MS (ES+) $C_{23}H_{21}F_3N_6O_2$ requires: 470, found 471 [M+H]$^+$; $^1$H NMR (600 MHz, CDCl$_3$) δ 8.31-8.26 (m, 2H), 7.34 (d, J=8.2 Hz, 1H), 7.25-7.19 (m, 1H), 6.61-6.57 (m, 1H), 6.55 (d, J=7.6 Hz, 1H), 6.48 (s, 1H), 5.40 (s, 2H), 3.31-3.24 (m, 4H), 2.54 (s, 3H), 2.04-1.98 (m, 4H).

EXAMPLE 51

1-(3-((5-Methyl-3-(3-(4-(trifluoromethoxy)phenyl)-1,2,4-oxadiazol-5-yl)-1H-1,2,4-triazol-1-yl)methyl)phenyl)piperidine-4-carbonitrile

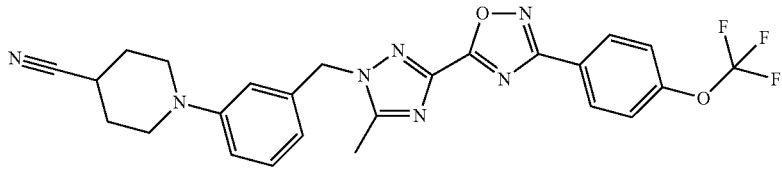

Prepared in an analogous manner to Example 11. Purification by prep-HPLC (MeCN/H$_2$O 40%-80% MeCN, containing 0.1% TFA). The product was taken up in EtOAc (10 mL), washed with sat. NaHCO$_3$ (10 mL), dried over Na$_2$SO$_4$, filtered, and concentrated to afford the desired compound (8 mg, 19%). MS (ES+) C$_{25}$H$_{22}$F$_3$N$_7$O$_2$ requires: 509, found 510 [M+H]$^+$; $^1$H NMR (600 MHz, CDCl$_3$) δ 8.30-8.25 (m, 2H), 7.42-7.37 (m, 1H), 7.35 (d, J=8.1 Hz, 2H), 7.18-7.12 (m, 2H), 6.98 (d, J=7.7 Hz, 1H), 5.44 (s, 2H), 3.53-3.45 (m, 2H), 3.37-3.30 (m, 2H), 2.99-2.92 (m, 1H), 2.57 (s, 3H), 2.32-2.23 (m, 2H), 2.15-2.06 (m, 2H).

EXAMPLE 52

N,N-Dimethyl-3-((5-methyl-3-(3-(4-(trifluoromethoxy)phenyl)-1,2,4-oxadiazol-5-yl)-1H-1,2,4-triazol-1-yl)methyl)aniline

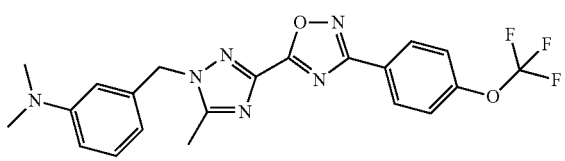 [SMILES: Cc1nc(-c2nc(-c3ccc(OC(F)(F)F)cc3)no2)nn1Cc1cccc(N(C)C)c1]

Prepared in an analogous manner to Example 11 and purified by prep-HPLC (MeCN/H$_2$O 30%-70% MeCN, containing 0.1% TFA). The product was taken up in EtOAc (10 mL), washed with sat. NaHCO$_3$ (10 mL), dried over Na$_2$SO$_4$, filtered, and concentrated to afford the desired compound (6 mg, 16%). MS (ES+) C$_{21}$H$_{19}$F$_3$N$_6$O$_2$ requires: 444, found 445 [M+H]$^+$; $^1$H NMR (600 MHz, CDCl$_3$) δ 8.28 (d, J=8.7 Hz, 2H), 7.39-7.32 (m, 3H), 7.02 (d, J=8.3 Hz, 1H), 7.00 (s, 1H), 6.85 (d, J=7.6 Hz, 1H), 5.44 (s, 2H), 3.03 (s, 6H), 2.56 (s, 3H).

EXAMPLE 53

N-(3-Methoxypropyl)-3-((5-methyl-3-(3-(4-(trifluoromethoxy)phenyl)-1,2,4-oxadiazol-5-yl)-1H-1,2,4-triazol-1-yl)methyl)aniline

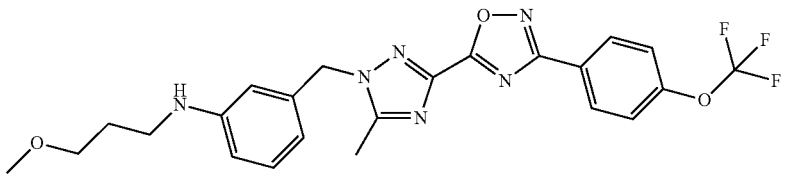

Prepared in an analogous manner to Example 11 and purified by prep-HPLC (MeCN/H$_2$O 30%-70% MeCN, containing 0.1% TFA). The product was taken up in EtOAc (10 mL), washed with sat. NaHCO$_3$ (10 mL), dried over Na$_2$SO$_4$, filtered, and concentrated to afford the desired compound (9 mg, 22%). MS (ES+) C$_{23}$H$_{23}$F$_3$N$_6$O$_3$ requires: 488, found 489 [M+H]$^+$; $^1$H NMR (600 MHz, CDCl$_3$) δ 8.28 (d, J=8.8 Hz, 2H), 7.34 (d, J=8.8 Hz, 2H), 7.25-7.20 (m, 1H), 6.75 (d, J=8.1 Hz, 1H), 6.69 (d, J=8.1 Hz, 1H), 6.67 (s, 1H), 5.39 (s, 2H), 3.54 (t, J=5.7 Hz, 2H), 3.37 (s, 3H), 3.28 (t, J=6.4 Hz, 2H), 2.54 (s, 3H), 1.92-1.85 (m, 2H).

EXAMPLE 54

5-(5-Methyl-1-(pyrazin-2-ylmethyl)-1H-1,2,4-triazol-3-yl)-3-(4-(trifluoromethoxy)phenyl)-1,2,4-oxadiazole

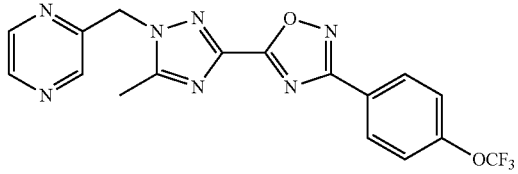 [SMILES: Cc1nc(-c2nc(-c3ccc(OC(F)(F)F)cc3)no2)nn1Cc1cnccn1]

Step 1

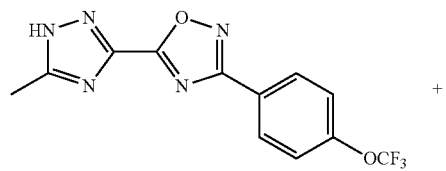

+

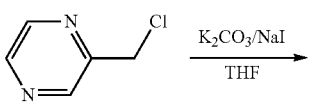

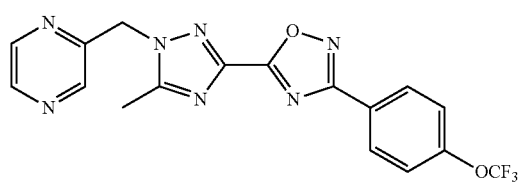

Synthesized in an analogous method to Example 17: (3.5 mg, 9%). MS (ES+) $C_{17}H_{12}F_3N_7O_2$ requires: 403, found: 404[M+H]$^+$; $^1$H NMR (600 MHz, CDCl$_3$) δ 8.69 (d, J=1.3 Hz, 1H), 8.60 (d, J=2.4 Hz, 1H), 8.55 (dd, J=1.4, 2.3 Hz, 1H), 8.27 (d, J=8.8 Hz, 2H), 7.34 (d, J=8.3 Hz, 2H), 5.59 (s, 2H), 2.72 (s, 3H).

EXAMPLE 55

4-(4-((5-Methyl-3-(3-(4-(trifluoromethoxy)phenyl)-1,2,4-oxadiazol-5-yl)-1H-1,2,4-triazol-1-yl)methyl)pyrimidin-2-yl)morpholine

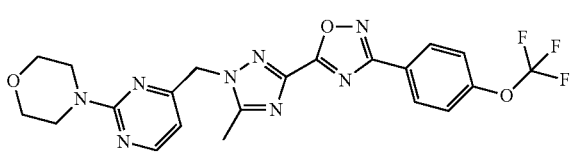 [SMILES: Cc1nc(-c2nc(-c3ccc(OC(F)(F)F)cc3)no2)nn1Cc1ccnc(N2CCOCC2)n1]

Prepared in an analogous manner to Example 20 and purified by prep-HPLC (MeCN/H$_2$O 40%-80% MeCN, containing 0.1% TFA) to afford the desired compound (24 mg, 43%). MS (ES+) $C_{21}H_{19}F_3N_8O_3$ requires: 488, found 489 [M+H]$^+$; $^1$H NMR (600 MHz, CDCl$_3$) δ 8.31 (d, J=5.0 Hz, 1H), 8.28 (d, J=8.8 Hz, 2H), 7.34 (d, J=8.8 Hz, 2H), 6.36 (d, J=5.0 Hz, 1H), 5.34 (s, 2H), 3.75-3.68 (m, 8H), 2.64 (s, 3H).

EXAMPLE 56

3-(5-Methyl-1-(3-(4-methylpiperazin-1-yl)benzyl)-1H-1,2,4-triazol-3-yl)-5-(4-(trifluoromethoxy)phenyl)-1,2,4-oxadiazole

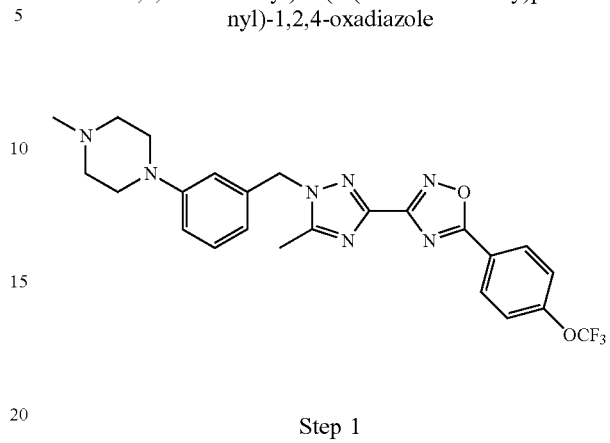

Step 1

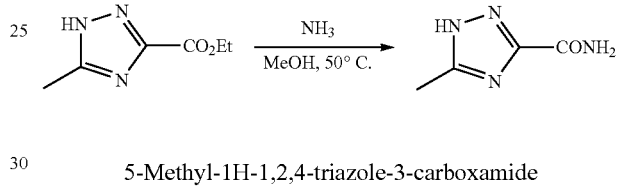

5-Methyl-1H-1,2,4-triazole-3-carboxamide

Ethyl 5-methyl-1H-1,2,4-triazole-3-carboxylate (3.0 g, 19.3 mmol) is placed in a sealed tube that is then charged with a solution of 7N NH$_3$ in MeOH (40 mL). The reaction is stirred at 50° C. for 24 h. The solvent was then removed under reduced pressure and the crude material was used directly for the next step without further purification. MS (ES$^+$) $C_4H_6N_4O$ requires: 126 found: 127 [M+H]$^+$.

Step 2

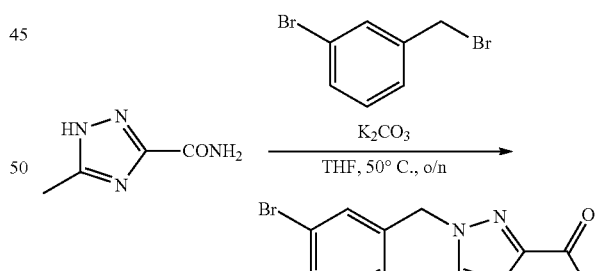

1-(3-Bromobenzyl)-5-methyl-1H-1,2,4-triazole-3-carboxamide

To a solution of 5-methyl-1H-1,2,4-triazole-3-carboxamide (2.5 g, 19.8 mmol) and 1-bromo-3-(bromomethyl)benzene (5.45 g, 21.8 mmol) in THF (99 mL), K$_2$CO$_3$ (5.5 g, 39.6 mmol) was added. The mixture was stirred at 50° C. for 18 h, and then the reaction was filtered under vacuum. The solvent was removed under reduced pressure and the crude product was purified on a Biotage pre-packed silica gel column with a gradient of 0% to 20% MeOH:DCM to afford 1-(3-bromobenzyl)-5-methyl-1H-1,2,4-triazole-3-carboxamide (1.5 g, 26%) as a viscous oil. MS (ES+) $C_{11}H_{11}BrN_4O$ requires: 294, 296 found: 295, 297 $[MH]^+$ (1:1).

Step 3

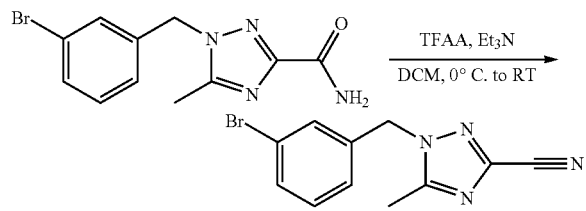

1-(3-Bromobenzyl)-5-methyl-1H-1,2,4-triazole-3-carbonitrile

To a suspension of 1-(3-bromobenzyl)-5-methyl-1H-1,2,4-triazole-3-carboxamide (50 mg, 0.17 mmol) and $Et_3N$ (47 µL, 0.34 mmol) in DCM (2 mL) was slowly added a solution of trifluoroacetic anhydride (29 µL, 0.20 mmol) in DCM (2 mL) at 0° C. The reaction was stirred at 0° C. for 2 h, and was then warmed to RT while stirring overnight. The reaction was then quenched with $H_2O$ (3 mL) and washed with NaOH (1N, 5 mL) and brine (2×5 mL) before being concentrated under reduced pressure. The crude product was purified on a Biotage pre-packed silica gel column with a gradient of 12% to 80% EtOAc:Hexanes to afford 1-(3-bromobenzyl)-5-methyl-1H-1,2,4-triazole-3-carbonitrile (39 mg, 83%) as a viscous oil. MS (ES+) $C_{11}H_9BrN_4$ requires: 276, 278 found: 277, 279 $[M+H]^+$ (1:1).

Step 4

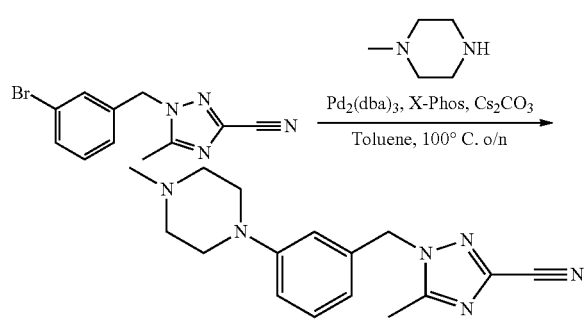

5-Methyl-1-(3-(4-methylpiperazin-1-yl)benzyl)-1H-1,2,4-triazole-3-carbonitrile

A mixture of 1-(3-bromobenzyl)-5-methyl-1H-1,2,4-triazole-3-carbonitrile (198 mg, 0.71 mmol), 1-methylpiperazine (159 µL, 1.4 mmol), $Cs_2CO_3$ (466 mg, 1.4 mmol), dicyclohexyl(2',4',6'-triisopropyl-[1,1'-biphenyl]-2-yl)phosphine (34 mg, 0.07 mmol) and tris(dibenzylideneacetone)dipalladium(0) (65.4 mg, 0.07 mmol) in toluene (3.5 mL) was degassed (freeze-pump-thaw, under $N_2$). The reaction mixture was stirred at 100° C. overnight before being quenched with $H_2O$ (5 mL), taken up in EtOAc (15 mL), washed with $H_2O$ (3×10 mL), brine (2×10 mL), dried with $Na_2SO_4$ and concentrated under reduced pressure. The crude product was purified on a Biotage pre-packed silica gel column with a gradient of 0% to 10% MeOH:DCM to afford 5-methyl-1-(3-(4-methylpiperazin-1-yl)benzyl)-1H-1,2,4-triazole-3-carbonitrile (120 mg, 57%) as a white solid. MS (ES+) $C_{16}H_{20}N_6$ requires: 296 found: 297 $[M+H]^+$.

Step 5

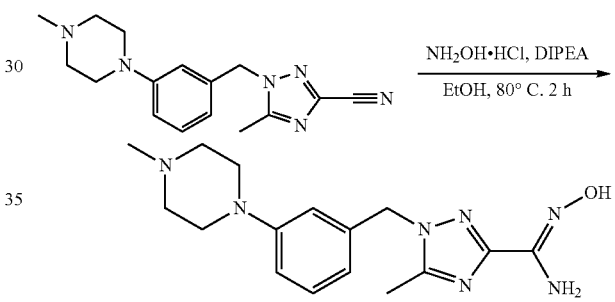

N-Hydroxy-5-methyl-1-(3-(4-methylpiperazin-1-yl)benzyl)-1H-1,2,4-triazole-3-carboximidamide To a solution of 5-methyl-1-(3-(4-methylpiperazin-1-yl)benzyl)-1H-1,2,4-triazole-3-carbonitrile (120 mg, 0.40 mmol) in EtOH (2 mL) was added hydroxylamine hydrochloride (31 mg, 0.44 mmol) and DIPEA (141 µL, 0.81 mmol). The reaction was stirred at 80° C. for 2 h before the solvent was removed under reduced pressure. The crude product was used without further purification. MS (ES+) $C_{16}H_{23}N_7O$ requires: 329 found: 330 $[M+H]^+$.

Step 6

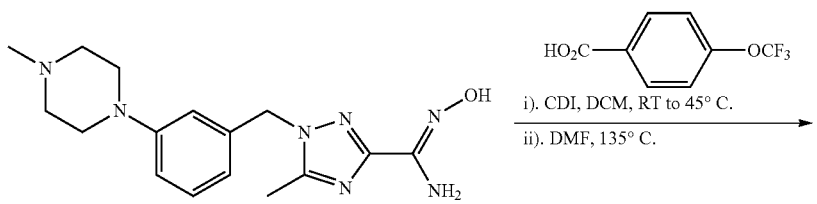

-continued

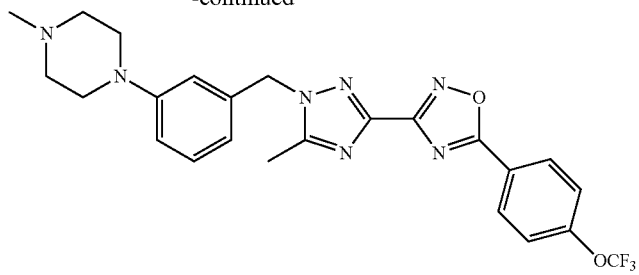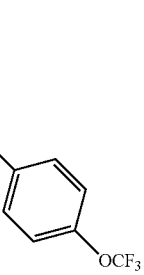

3-(5-Methyl-1-(3-(4-methylpiperazin-1-yl)benzyl)-1H-1,2,4-triazol-3-yl)-5-(4-(trifluoromethoxy)phenyl)-1,2,4-oxadiazole A solution of 4-(trifluoromethoxy)benzoic acid (85 mg, 0.41 mmol) and CDI (66 mg, 0.41 mmol) in DCM (2 mL) was stirred at RT for 4 h before being added to a solution of N-hydroxy-5-methyl-1-(3-(4-methylpiperazin-1-yl)benzyl)-1H-1,2,4-triazole-3-carboximidamide (66 mg, 0.2 mmol) in DCM (1 mL). The reaction was then stirred at 45° C. for 6 h. The solvent was removed under reduced pressure, DMF (2 mL) was added and the reaction was stirred at 135° C. for 2 h. The reaction was then diluted with $H_2O$ (10 mL), extracted with 4:1 $CHCl_3$:iPrOH (3×10 mL), dried with $MgSO_4$ and concentrated under reduced pressure. The crude product was purified by pre-HPLC (Mobile phase: A=0.1% $CF_3CO_2H/H_2O$, B=MeCN; Gradient: B=10%-40% in 30 min; Column: Waters C18) to afford 3-(5-methyl-1-(3-(4-methylpiperazin-1-yl)benzyl)-1H-1,2,4-triazol-3-yl)-5-(4-(trifluoromethoxy)phenyl)-1,2,4-oxadiazole (18 mg, 18%) as a yellow oil. MS (ES+) $C_{24}H_{24}F_3N_7O_2$ requires: 499, found: 500 $[M+H]^+$; $^1$H-NMR (600 MHz, $CDCl_3$) δ ppm 8.34 (d, J=8.4 Hz, 2H), 7.38 (d, J=8.1 Hz, 2H), 7.23 (t, J=7.6 Hz, 1H), 6.86 (d, J=8.1 Hz, 1H), 6.77 (s, 1H), 6.67 (d, J=7.5 Hz, 1H), 5.40 (s, 2H), 3.18 (m, 4H), 2.54 (m, 4H), 2.49 (s, 3H), 2.33 (s, 3H).

EXAMPLE 57

4-(3-((5-Methyl-3-(5-(4-(trifluoromethoxy)phenyl)-1,2,4-oxadiazol-3-yl)-1H-1,2,4-triazol-1-yl)methyl)phenyl)morpholine

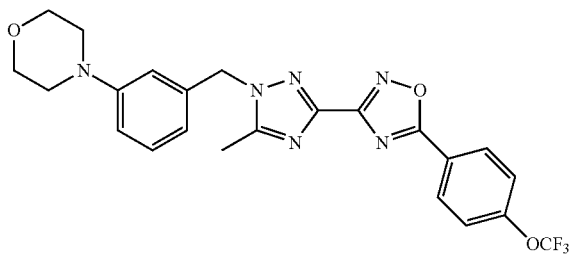 [SMILES: Cc1nc(-c2noc(-c3ccc(OC(F)(F)F)cc3)n2)nn1Cc1cccc(N2CCOCC2)c1]

Prepared in an analogous manner to Example 20. Purification by pre-HPLC (Mobile phase: A=0.1% $CF_3CO_2H/H_2O$, B=MeCN; Gradient: B=40%-80% in 12 min; Column: Waters C18) afforded 4-(3-((5-methyl-3-(5-(4-(trifluoromethoxy)phenyl)-1,2,4-oxadiazol-3-yl)-1H-1,2,4-triazol-1-yl)methyl)phenyl)morpholine (6.8 mg, 7.0%) as a white solid. MS (ES+) $C_{23}H_{21}F_3N_6O_3$ requires: 486, found: 487 $[M+H]^+$; $^1$H-NMR (600 MHz, $CDCl_3$) δ ppm 8.34 (d, J=8.2 Hz, 2H), 7.38 (d, J=8.5 Hz, 2H), 7.25 (t, J=7.2 Hz, 1H), 6.85 (d, J=7.6 Hz, 1H), 6.75 (s, 1H), 6.71 (d, J=7.6 Hz, 1H), 5.40 (s, 2H), 3.82 (m, 4H), 3.12 (m, 4H), 2.49 (s, 3H).

EXAMPLE 58

N,N-Dimethyl-3-((5-methyl-3-(5-(4-(trifluoromethoxy)phenyl)-1,2,4-oxadiazol-3-yl)-1H-1,2,4-triazol-1-yl)methyl)aniline

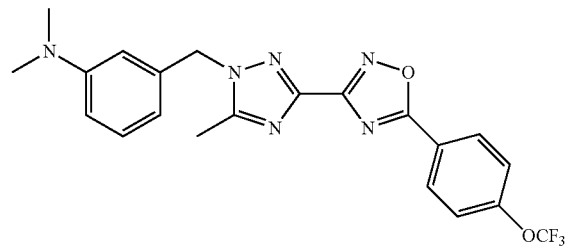 [SMILES: Cc1nc(-c2noc(-c3ccc(OC(F)(F)F)cc3)n2)nn1Cc1cccc(N(C)C)c1]

Prepared in an analogous manner to Example 20. Purification by pre-HPLC (Mobile phase: A=0.1% $CF_3CO_2H/H_2O$, B=MeCN; Gradient: B=40%-80% in 12 min; Column: Waters C18) to afford N,N-dimethyl-3-((5-methyl-3-(5-(4-(trifluoromethoxy)phenyl)-1,2,4-oxadiazol-3-yl)-1H-1,2,4-triazol-1-yl)methyl)aniline (7.0 mg, 7.9%) as a white solid. MS (ES+) $C_{21}H_{19}F_3N_6O_2$ requires: 444, found: 445 $[M+H]^+$; $^1$H-NMR (600 MHz, $CDCl_3$) δ ppm 8.34 (d, J=8.5 Hz, 2H), 7.38 (d, J=8.5 Hz, 2H), 7.20 (t, J=7.8 Hz, 1H), 6.66 (d, J=7.7 Hz, 1H), 6.55 (m, 2H), 5.40 (s, 2H), 2.92 (s, 6H), 2.49 (s, 3H).

EXAMPLE 59

3-((5-Methyl-3-(3-(4-(trifluoromethoxy)phenyl)-1,2,4-oxadiazol-5-yl)-1H-1,2,4-triazol-1-yl)methyl)phenol

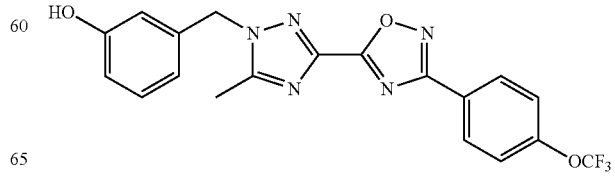

Step 1

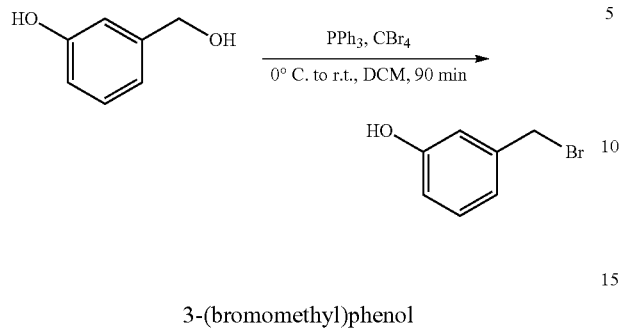

3-(bromomethyl)phenol

To a suspension of 3-hydroxybenzylalcohol (1.0 g, 8.06 mmol) and PPh$_3$ (3.17 g, 12.08 mmol) in DCM (40 mL) at 0° C. was added CBr$_4$ (4.01 g, 12.08 mmol) dropwise. The reaction was warmed to RT over 90 minutes, concentrated under reduced pressure and purified by silica gel chromatography (5% to 50% EtOAc in Hexanes) to give 3-(bromomethyl)phenol as a light brown crystalline solid (1.24 g, 82%).

Step 2

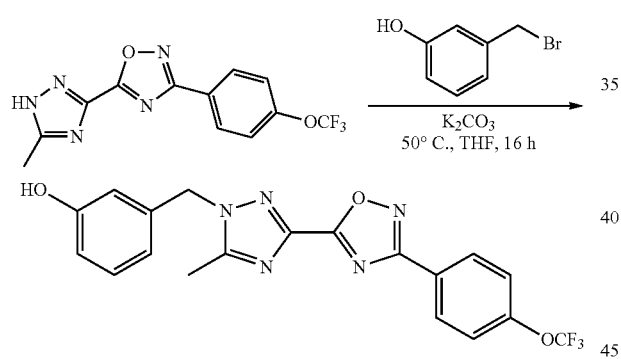

3-((5-methyl-3-(3-(4-(trifluoromethoxy)phenyl)-1,2,4-oxadiazol-5-yl)-1H-1,2,4-triazol-1-yl)methyl)phenol A mixture of K$_2$CO$_3$ (2.63 g, 19.0 mmol), 5-(5-methyl-1H-1,2,4-triazol-3-yl)-3-(4-(trifluoromethoxy)phenyl)-1,2,4-oxadiazole (Intermediate B, 3.70 g, 11.9 mmol) and 3-(bromomethyl)phenol (1.78 g, 9.52 mmol) was dissolved in THF (48 mL) and stirred at 50° C. for 16 h. The reaction mixture was filtered, the solvent was removed under reduced pressure, and the residue was purified by silica gel chromatography (0% to 80% EtOAc in Hexanes) to afford the title compound. MS (ES+) C$_{19}$H$_{14}$F$_3$N$_5$O$_3$ requires: 417, found 418 [M+H]$^+$; $^1$H-NMR (600 MHz, CD$_3$OD) δ ppm 8.22 (d, J=8.8 Hz, 2H), 7.61 (d, J=8.0 Hz, 2H), 7.19 (d, J=7.8 Hz 1H), 6.72 (m, 2H), 6.67 (s, 1H), 5.49 (s, 2H), 2.56 (s, 3H).

EXAMPLE 60

5-(1-{[3-(2-Methoxyethoxy)phenyl]methyl}-5-methyl-1H-1,2,4-triazol-3-yl)-3-[4-(trifluoromethoxy)phenyl]-1,2,4-oxadiazole

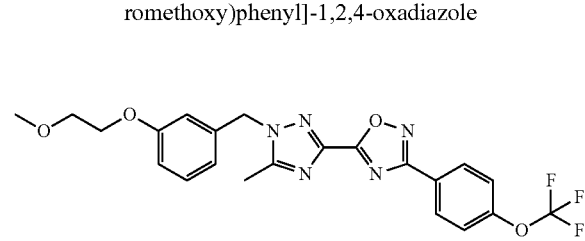

A mixture of K$_2$CO$_3$ (19.9 mg, 0.144 mmol), 3-((5-methyl-3-(3-(4-(trifluoromethoxy)phenyl)-1,2,4-oxadiazol-5-yl)-1H-1,2,4-triazol-1-yl)methyl)phenol (Example 59; 30.0 mg, 0.072 mmol) and 1-bromo-2-methoxyethane (19.9 mg, 0.144 mmol) in DMF (0.36 mL) was stirred at RT for 16 h. The mixture was diluted with H$_2$O and extracted with 4:1 CHCl$_3$:i-PrOH. The organic layer was separated, dried with MgSO$_4$ and concentrated under reduced pressure. The residue was dissolved in DMSO and purified using Prep-HPLC to furnish the title compound. MS (ES+) C$_{22}$H$_{20}$F$_3$N$_5$O$_4$ requires: 475, found 476 [M+H]$^+$; $^1$H-NMR (600 MHz, CD$_3$OD) δ ppm 8.29 (d, J=8.8 Hz, 2H), 7.35 (d, J=8.1 Hz, 2H), 7.28 (m, 1H), 6.91 (m, 1H), 6.83 (d, J=7.6 Hz, 1H), 6.81 (m, 1H), 5.42 (s, 2H), 4.09 (m, 2H), 3.73 (m, 2H), 3.43 (s, 3H), 2.52 (s, 3H).

EXAMPLE 61

2-{3-[(5-Methyl-3-{3-[4-(trifluoromethoxy)phenyl]-124-oxadiazol-5-yl}-1H-124-triazol-1-yl)methyl]phenoxy}acetamide

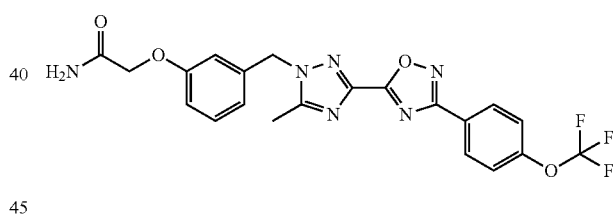

Synthesized in analogous manner to Example 60; MS (ES+) C$_{21}$H$_{17}$F$_3$N$_6$O$_4$ requires: 474, found 475 [M+H]$^+$; $^1$H-NMR (600 MHz, CD$_3$OD) δ ppm 8.27 (d, J=8.8 Hz, 2H), 7.34 (m, 3H), 6.90 (m, 2H), 6.81 (m, 1H), 5.44 (s, 2H), 4.48 (s, 2H), 2.55 (s, 3H).

EXAMPLE 62

N N-Dimethyl-2-{3-[(5-methyl-3-{3-[4-(trifluoromethoxy)phenyl]-124-oxadiazol-5-yl}-1H-124-triazol-1-yl)methyl]phenoxy}acetamide

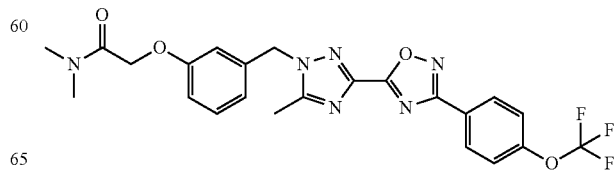

Synthesized in analogous manner to Example 60; MS (ES$^+$) C$_{23}$H$_{21}$F$_3$N$_6$O$_4$ requires: 502, found 503 [M+H]$^+$; $^1$H-NMR (600 MHz, CD$_3$OD) δ ppm 8.28 (d, J=8.8 Hz, 2H), 7.35 (d, J=8.1 Hz, 2H), 7.29 (m, 1H), 6.93 (dd, J=8.2 Hz, J=2.4 Hz, 1H), 6.84 (m, 2H), 5.42 (s, 2H), 4.68 (s, 2H), 3.06 (s, 3H), 2.96 (s, 3H), 2.55 (s, 3H).

EXAMPLE 63

5-(5-Methyl-1-{[3-(propan-2-yloxy)phenyl]methyl}-1H-1,2,4-triazol-3-yl)-3-[4-(trifluoromethoxy)phenyl]-1,2,4-oxadiazole

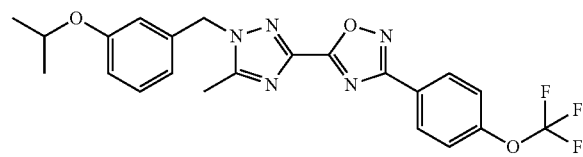 [SMILES: Cc1nc(-c2nc(-c3ccc(OC(F)(F)F)cc3)no2)nn1Cc1cccc(OC(C)C)c1]

Synthesized in analogous manner to Example 60; MS (ES$^+$) C$_{22}$H$_{20}$F$_3$N$_5$O$_3$ requires: 459, found 460 [M+H]$^+$; $^1$H-NMR (600 MHz, CD$_3$OD) δ ppm 8.29 (d, J=8.5 Hz, 2H), 7.35 (d, J=8.4 Hz, 2H), 7.27 (m, 1H), 6.86 (m, 1H), 6.79 (d, J=7.6 Hz, 1H), 6.75 (m, 1H), 5.42 (s, 2H), 4.52 (m, 1H), 2.53 (s, 3H), 1.31 (d, J=6.1 Hz, 6H).

EXAMPLE 64

5-{1-[(3-Ethoxyphenyl)methyl]-5-methyl-1H-1,2,4-triazol-3-yl}-3-[4-(trifluoromethoxy)phenyl]-1,2,4-oxadiazole

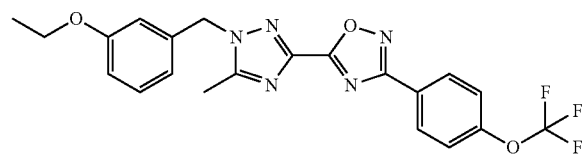 [SMILES: CCOc1cccc(Cn2nc(-c3nc(-c4ccc(OC(F)(F)F)cc4)no3)nc2C)c1]

Synthesized in analogous manner to Example 60; MS (ES$^+$) C$_{21}$H$_{18}$F$_3$N$_5$O$_3$ requires: 445, found 446 [M+H]$^+$; $^1$H-NMR (600 MHz, CD$_3$OD) δ ppm 8.29 (d, J=9.0 Hz, 2H), 7.35 (d, J=8.8 Hz, 2H), 7.27 (m, 1H), 6.87 (m, 1H), 6.81 (d, J=7.7 Hz, 1H), 6.75 (m, 1H), 5.42 (s, 2H), 3.99 (q, J=6.9 Hz, 2H), 2.53 (s, 3H), 1.40 (t, J=6.9 Hz, 3H).

EXAMPLE 65

2-{3-[(5-Methyl-3-{3-[4-(trifluoromethoxy)phenyl]-1,2,4-oxadiazol-5-yl}-1H-1,2,4-triazol-1-yl)methyl]phenoxy}ethan-1-ol

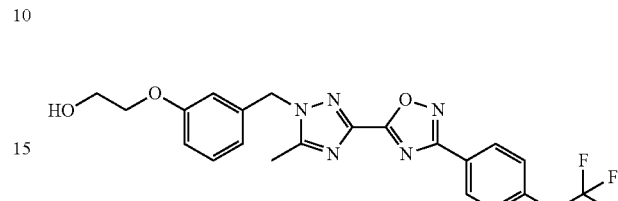

Synthesized in analogous manner to Example 60; MS (ES$^+$) C$_{21}$H$_{18}$F$_3$N$_5$O$_4$ requires: 461, found 462 [M+H]$^+$; $^1$H-NMR (600 MHz, CD$_3$OD) δ ppm 8.29 (d, J=8.8 Hz, 2H), 7.35 (d, J=8.2 Hz, 2H), 7.28 (m, 1H), 6.91 (dd, J=8.2, 2.4 Hz, 1H), 6.85 (d, J=7.8 Hz, 1H), 6.79 (m, 1H), 5.42 (s, 2H), 4.09 (m, 2H), 3.74 (m, 2H), 2.52 (s, 3H).

EXAMPLE 66

2-{3-[(5-Methyl-3-{3-[4-(trifluoromethoxy)phenyl]-1,2,4-oxadiazol-5-yl}-1H-1,2,4-triazol-1-yl)methyl]phenoxy}acetonitrile

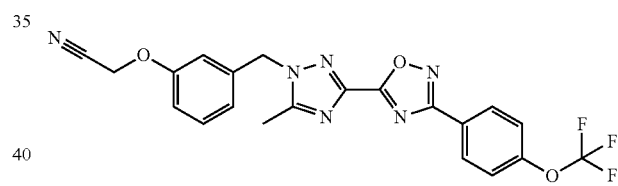

Synthesized in analogous manner to Example 60; MS (ES$^+$) C$_{21}$H$_{15}$F$_3$N$_6$O$_3$ requires: 456, found 457 [M+H]$^+$; $^1$H-NMR (600 MHz, CD$_3$OD) δ ppm 8.27 (d, J=9.0 Hz, 2H), 7.34 (m, 3H), 6.97 (m, 2H), 6.88 (m, 1H), 5.44 (s, 2H), 4.48 (s, 2H), 2.55 (s, 3H).

EXAMPLE 67

Tert-butyl N-(2-{3-[(5-methyl-3-{3-[4-(trifluoromethoxy)phenyl]-1,2,4-oxadiazol-5-yl}-1H-1,2,4-triazol-1-yl)methyl]phenoxy}ethyl)carbamate

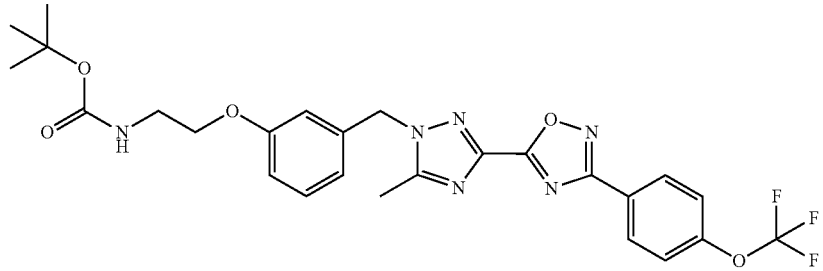 [SMILES: Cc1nc(-c2nc(-c3ccc(OC(F)(F)F)cc3)no2)nn1Cc1cccc(OCCNC(=O)OC(C)(C)C)c1]

Synthesized in analogous manner to Example 60; MS (ES$^+$) C$_{26}$H$_{27}$F$_3$N$_6$O$_5$ requires: 560, found 561 [M+H]$^+$; $^1$H-NMR (600 MHz, CD$_3$OD) δ ppm 8.28 (d, J=8.9 Hz, 2H), 7.35 (d, J=8.1 Hz, 2H), 7.29 (m, 1H), 6.87 (dd, J=8.2, 2.3 Hz, 1H), 6.84 (d, J=7.6 Hz, 1H), 6.76 (m, 1H), 5.43 (s, 2H), 3.98 (m, 2H), 3.52 (m, 2H), 2.54 (s, 3H), 1.44 (s, 9H).

EXAMPLE 68

5-(5-Methyl-1-{[3-(oxetan-3-yloxy)phenyl]methyl}-1H-1,2,4-triazol-3-yl)-3-[4-(trifluoromethoxy)phenyl]-1,2,4-oxadiazole

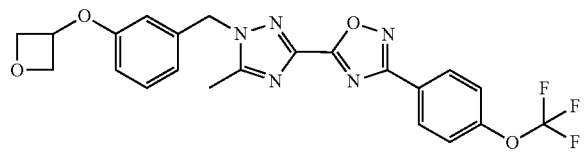 [SMILES: Cc1nc(-c2nc(-c3ccc(OC(F)(F)F)cc3)no2)nn1Cc1cccc(OC2COC2)c1]

A mixture of K$_2$CO$_3$ (19.8 mg, 0.144 mmol), 3-((5-methyl-3-(3-(4-(trifluoromethoxy)phenyl)-1,2,4-oxadiazol-5-yl)-1H-1,2,4-triazol-1-yl)methyl)phenol (Example 59; 30.0 mg, 0.072 mmol), sodium iodide (21.6 mg, 0.144 mmol) and 3-bromooxetane (22 uL, 0.288 mmol) in DMF (0.36 mL) was stirred at 50° C. for 48 h. The crude mixture was diluted with H$_2$O and extracted with 4:1 CHCl$_3$:i-PrOH. The organic layer was dried over MgSO$_4$, concentrated under reduced pressure, and the residue was purified using Prep-HPLC to furnish the title compound; MS (ES$^+$) C$_{22}$H$_{18}$F$_3$N$_5$O$_4$ requires: 473, found 474 [M+H]$^+$; $^1$H-NMR (600 MHz, CD$_3$OD) δ ppm 8.28 (d, J=8.8 Hz, 2H), 7.35 (d, J=8.2 Hz, 2H), 7.28 (m, 1H), 6.86 (d, J=7.8 Hz, 1H), 6.64 (m, 2H), 5.42 (s, 2H), 5.18 (m, 1H), 4.95 (m, 2H), 4.74 (m, 2H), 2.54 (s, 3H).

EXAMPLE 69

5-(5-Methyl-1-{[3-(oxan-4-yloxy)phenyl]methyl}-1H-1,2,4-triazol-3-yl)-3-[4-(trifluoromethoxy)phenyl]-1,2,4-oxadiazole

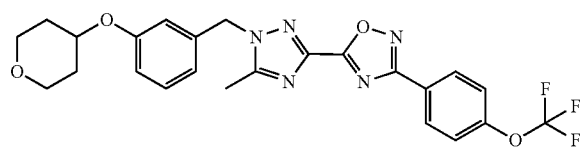 [SMILES: Cc1nc(-c2nc(-c3ccc(OC(F)(F)F)cc3)no2)nn1Cc1cccc(OC2CCOCC2)c1]

A mixture of Cs$_2$CO$_3$ (62.5 mg, 0.192 mmol), 3-((5-methyl-3-(3-(4-(trifluoromethoxy)phenyl)-1,2,4-oxadiazol-5-yl)-1H-1,2,4-triazol-1-yl)methyl)phenol (Example 59; 40.0 mg, 0.096 mmol) and 4-bromotetrahydro-2H-pyran (21.7 uL, 0.192 mmol) in DMF (0.48 mL) was heated at 140° C. for 1 h under microwave irradiation. The mixture was diluted with H$_2$O and extracted with 4:1 CHCl$_3$:i-PrOH. The organic layer was dried over MgSO$_4$ and concentrated under reduced pressure; the residue was dissolved in DMSO and purified using Prep-HPLC to furnish the title compound; MS (ES$^+$) C$_{24}$H$_{22}$F$_3$N$_5$O$_4$ requires: 501, found 502 [M+H]$^+$; $^1$H-NMR (600 MHz, CD$_3$OD) δ ppm 8.29 (d, J=8.8 Hz, 2H), 7.35 (d, J=8.1 Hz, 2H), 7.28 (m, 1H), 6.89 (dd, J=8.1, 2.4 Hz, 1H), 6.80 (m, 2H), 5.41 (s, 2H), 4.47 (m, 1H), 3.95 (m, 2H), 3.57 (m, 2H), 2.54 (s, 3H), 2.01 (m, 2H), 1.75 (m, 2H).

EXAMPLE 70

5-(1-{[3-(2-Aminoethoxy)phenyl]methyl}-5-methyl-1H-1,2,4-triazol-3-yl)-3-[4-(trifluoromethoxy)phenyl]-1,2,4-oxadiazole

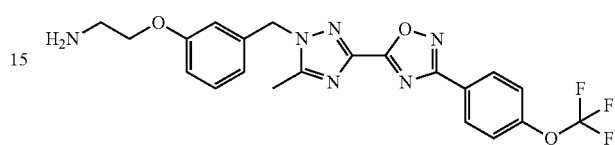

Acetyl chloride (229 uL, 3.21 mmol) was added dropwise to MeOH (1.1 mL) at 0° C., and the resulting mixture was stirred at 0° C. for 1 hr. Tert-butyl (2-(3-((5-methyl-3-(3-(4-(trifluoromethoxy)phenyl)-1,2,4-oxadiazol-5-yl)-1H-1,2,4-triazol-1-yl)methyl)phenoxy)ethyl)carbamate (Example 67; 60.0 mg, 0.107 mmol) was the added in one portion, and the reaction mixture was stirred at RT for 16 h and then concentrated under reduced pressure; the residue was purified using Prep-HPLC to furnish the title compound; MS (ES$^+$) C$_{21}$H$_{19}$F$_3$N$_6$O$_3$ requires: 460, found 461 [M+H]$^+$; $^1$H-NMR (600 MHz, CD$_3$OD) δ ppm 8.17 (d, J=8.6 Hz, 2H), 7.29 (d, J=8.4 Hz, 2H), 7.17 (m, 1H), 6.78 (d, J=7.9 Hz, 1H), 6.73 (d, J=8.2 Hz, 1H), 6.67 (s, 1H), 5.32 (s, 2H), 4.06 (m, 2H), 3.21 (m, 2H), 2.47 (s, 3H).

EXAMPLE 71

3-{3-[(5-Methyl-3-{3-[4-(trifluoromethoxy)phenyl]-1,2,4-oxadiazol-5-yl}-1H-1,2,4-triazol-1-yl)methyl]phenoxy}propan-1-ol

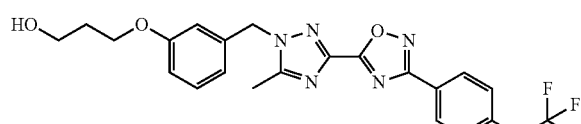

Synthesized in analogous manner to Example 60; MS (ES$^+$) C$_{22}$H$_{20}$F$_3$N$_5$O$_4$ requires: 475, found 476 [M+H]$^+$; $^1$H-NMR (600 MHz, CD$_3$OD) δ ppm 8.28 (d, J=8.8 Hz, 2H), 7.34 (d, J=8.2 Hz, 2H), 7.27 (m, 1H), 6.87 (dd, J=8.2, 2.2 Hz, 1H), 6.82 (d, J=7.8 Hz, 1H) 6.78 (m, 2H), 5.41 (s, 2H), 4.09 (t, J=6.0 Hz, 2H), 3.84 (t, J=5.9 Hz, 2H), 2.54 (s, 3H), 2.02 (m, 2H).

EXAMPLE 72

5-(1-{[3-(3-Methoxy-3-methylbutoxy)phenyl]methyl}-5-methyl-1H-1,2,4-triazol-3-yl)-3-[4-(trifluoromethoxy)phenyl]-1,2,4-oxadiazole

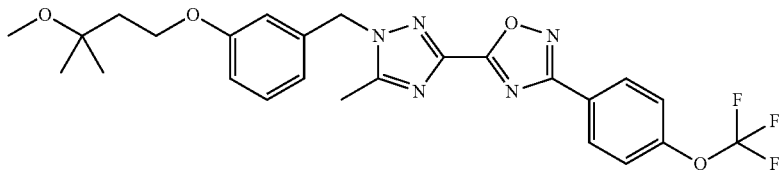 [SMILES: COC(C)(C)CCOc1cccc(Cn2nc(-c3nc(-c4ccc(OC(F)(F)F)cc4)no3)nc2C)c1]

To a solution of 3-((5-methyl-3-(3-(4-(trifluoromethoxy)phenyl)-1,2,4-oxadiazol-5-yl)-1H-1,2,4-triazol-1-yl)methyl)phenol (Example 59; 100 mg, 0.24 mmol), 3-methoxy-3-methylbutan-1-ol (62 uL, 0.48 mmol) and PPh$_3$ (251 mg, 0.96 mmol) in THF (1.2 mL) was added dropwise DEAD (40% by wt in toluene; 125 mg, 0.72 mmol). The reaction was stirred at RT for 72 h. The solvent was removed under reduced pressure, and the residue was purified by Prep-HPLC to furnish the title compound; MS (ES$^+$) C$_{25}$H$_{26}$F$_3$N$_5$O$_4$ requires: 517, found 518 [M+H]$^+$; $^1$H-NMR (600 MHz, CD$_3$OD) δ ppm 8.29 (d, J=8.8 Hz, 2H), 7.35 (d, J=8.5 Hz, 2H), 7.27 (m, 1H), 6.88 (dd, J=8.2, 2.3 Hz, 1H), 6.77 (m, 2H), 5.42 (s, 2H), 4.04 (t, J=7.1 Hz, 2H), 3.20 (s, 3H), 2.53 (s, 3H), 1.97 (t, J=7.2 Hz, 2H), 1.22 (s, 6H).

EXAMPLE 73

1-Methyl-4-{3-[(5-methyl-3-{3-[4-(trifluoromethoxy)phenyl]-1,2,4-oxadiazol-5-yl}-1H-1,2,4-triazol-1-yl)methyl]phenoxy}piperidine

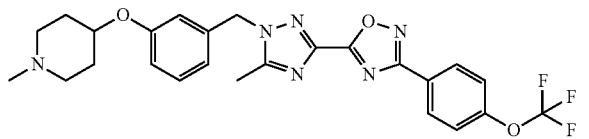 [SMILES: Cc1nc(-c2nc(-c3ccc(OC(F)(F)F)cc3)no2)nn1Cc1cccc(OC2CCN(C)CC2)c1]

Synthesized in analogous manner to Example 72; MS (ES$^+$) C$_{25}$H$_{25}$F$_3$N$_6$O$_3$ requires: 514, found 515 [M+H]$^+$; $^1$H-NMR (600 MHz, CD$_3$OD) δ ppm 8.28 (d, J=8.7 Hz, 2H), 7.34 (m, 3H), 6.89 (m, 2H), 6.76 (s, 1H), 5.42 (s, 2H), 4.69 (m, 1H), 3.45 (m, 2H), 3.12 (m, 2H), 2.83 (m, 3H), 2.55 (s, 3H), 2.34 (m, 2H), 2.16 (m, 2H).

EXAMPLE 74

Dimethyl(3-{3-[(5-methyl-3-{3-[4-(trifluoromethoxy)phenyl]-1,2,4-oxadiazol-5-yl}-1H-1,2,4-triazol-1-yl)methyl]phenoxy}propyl)amine

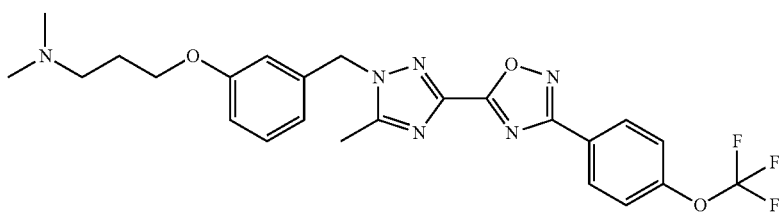 [SMILES: Cc1nc(-c2nc(-c3ccc(OC(F)(F)F)cc3)no2)nn1Cc1cccc(OCCCN(C)C)c1]

Synthesized in analogous manner to Example 60; MS (ES$^+$) C$_{24}$H$_{25}$F$_3$N$_6$O$_3$ requires: 502, found 503 [M+H]$^+$; $^1$H-NMR (600 MHz, CD$_3$OD) δ ppm 8.27 (d, J=8.8 Hz, 2H), 7.34 (d, J=8.2 Hz, 2H), 7.28 (m, 1H), 6.89 (m, 2H), 6.76 (m, 1H), 5.42 (s, 2H), 4.05 (t, J=5.6 Hz, 2H), 3.27 (m, 2H), 2.88 (m, 6H), 2.54 (s, 3H), 2.26 (m, 2H).

EXAMPLE 75

4-[(5-Methyl-3-{3-[4-(trifluoromethoxy)phenyl]-1,2,4-oxadiazol-5-yl}-1H-1,2,4-triazol-1-yl)methyl]-1,2-dihydropyridin-2-one

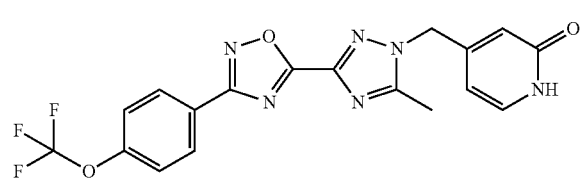 [SMILES: Cc1nc(-c2nc(-c3ccc(OC(F)(F)F)cc3)no2)nn1Cc1cc[nH]c(=O)c1]

Steps 1 to 2

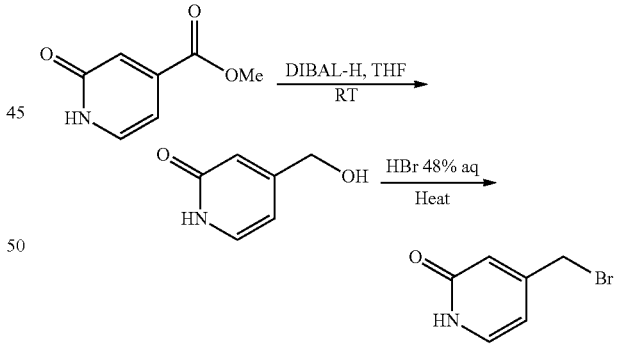

Step 1: 4-(hydroxymethyl)pyridin-2(1H)-one

To a stirred solution of methyl 2-oxo-1,2-dihydropyridine-4-carboxylate (300 mg, 1.96 mmol) in THF (20 mL) was added diisobutylaluminium hydride (1.0 M in THF, 20 mL, 20 mmol). The mixture was stirred at RT for 3 h, then MeOH (2 mL) and H$_2$O (1 mL) were added. The mixture was stirred at RT for 20 minutes and concentrated under reduced pressure. The crude product was purified by silica gel chromatography (DCM:MeOH=8:1) to afford 4-(hydroxymethyl)pyridin-2(1H)-one as a white solid (150 mg, 61.2%). MS (ES+) C$_6$H$_7$NO$_2$ requires: 125, found: 126 [M+H]$^+$.

Step 2: 4-(bromomethyl)pyridin-2(1H)-one

A mixture of 4-(hydroxymethyl)pyridin-2(1H)-one (150 mg, 1.2 mmol) and aqueous hydrogen bromide (48%, 10 mL) was heated to 100° C. for 16 h. The reaction mixture was cooled to RT and concentrated under reduced pressure to afford 4-(bromomethyl)pyridin-2(1H)-one as a brown solid (225 mg, 100%), which was directly used for next step without further purification. MS (ES+) C$_6$H$_6$BrNO requires: 188, found: 189 [M+H]$^+$.

Step 3

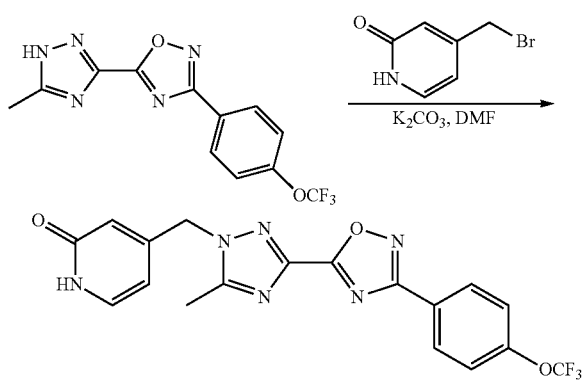

4-((5-methyl-3-(3-(4-(trifluoromethoxy)phenyl)-1,2,4-oxadiazol-5-yl)-1H-1,2,4-riazol-1-yl) methyl)pyridin-2(1H)-one To a solution of 5-(5-methyl-1H-1,2,4-triazol-3-yl)-3-(4-(trifluoromethoxy)phenyl)-1,2,4-oxadiazole (Intermediate B, 340 mg, 1.09 mmol) and 4-(bromomethyl)pyridin-2(1H)-one (225 mg, 1.20 mmol) in DMF (20 mL), was added K$_2$CO$_3$ (453 mg, 3.28 mmol). The mixture was stirred at RT 16 h, then diluted with H$_2$O (20 mL) and extracted with EtOAc (3×20 mL). The combined organic layers were washed with H$_2$O (10 mL), concentrated under reduced pressure and purified by silica gel chromatography (DCM:MeOH=8:1) to afford the title compound; MS (ES+) C$_{18}$H$_{13}$F$_3$N$_6$O$_3$ requires: 418, found: 419 [M+H]$^+$. $^1$H-NMR (500 MHz, CDCl3) δ 12.37 (m, 1H), 8.35-8.20 (m, 2H), 7.42-7.29 (m, 3H), 6.29 (s, 1H), 6.13 (dd, J=6.8, 1.7 Hz, 1H), 5.31 (s, 2H), 2.58 (s, 3H).

EXAMPLE 76

4-[(5-Methyl-3-{3-[4-(trifluoromethoxy)phenyl]-1,2,4-oxadiazol-5-yl}-1H-1,2,4-triazol-1-yl)methyl]-1-(2-methylpropyl)-1,2-dihydropyridin-2-one (Example 76a) and 4-[(5-Methyl-3-{3-[4-(trifluoromethoxy)phenyl]-1,2,4-oxadiazol-5-yl}-1H-1,2,4-triazol-1-yl)methyl]-2-(2-methylpropoxy)pyridine (Example 76b)

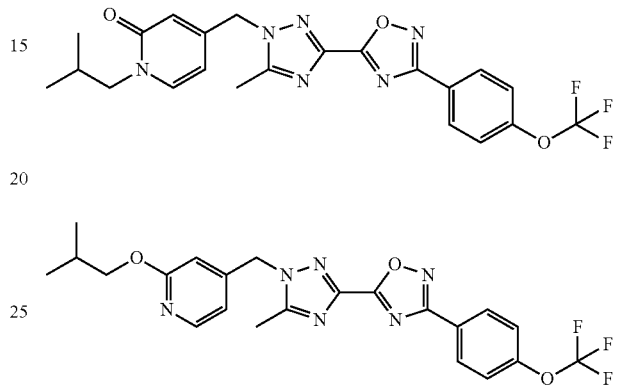

To a mixture of 4-((5-methyl-3-(3-(4-(trifluoromethoxy)phenyl)-1,2,4-oxadiazol-5-yl)-1H-1,2,4-triazol-1-yl)methyl)pyridin-2(1H)-one (Example 75; 100 mg, 0.24 mmol) and K$_2$CO$_3$ (99 mg, 0.72 mmol) in DMF (10 mL), was added 1-bromo-2-methylpropane (1.0 mL, 2.4 mmol). The mixture was stirred at 55° C. for 16 h, then treated with H$_2$O (10 mL) and extracted with EtOAc (3×15 mL). The combined organic layers were concentrated under reduced pressure and the residue was purified by prep-HPLC (Mobile phase: A=0.1% ammonium hydroxide/H$_2$O, B=MeCN; Gradient: B=60%-95% in 18 min; Column: XBridge (C18, 5 um, 30 mm×150 mm) to afford the title compounds as white solids; 1-isobutyl-4-((5-methyl-3-(3-(4-(trifluoromethoxy)phenyl)-1,2,4-oxadiazol-5-yl)-1H-1,2,4-triazol-1-yl)methyl)pyridin-2(1H)-one (Example 76a); MS (ES$^+$) C$_{22}$H$_{21}$F$_3$N$_6$O$_3$ requires: 474, found: 475 [M+H]$^+$; $^1$H NMR (500 MHz, CDCl$_3$) δ 8.29 (d, J=8.0 Hz, 2H), 7.35 (d, J=8.2 Hz, 2H), 7.23 (d, J=7.0 Hz, 1H), 6.33 (s, 1H), 6.01 (dd, J=7.0, 1.9 Hz, 1H), 5.28 (s, 2H), 3.72 (d, J=7.4 Hz, 2H), 2.58 (s, 3H), 2.16 (m, 1H), 0.93 (d, J=6.7 Hz, 6H);

5-(1-((2-isobutoxypyridin-4-yl)methyl)-5-methyl-1H-1,2,4-triazol-3-yl)-3-(4-(trifluoromethoxy)phenyl)-1,2,4-oxadiazole (Example 76b); MS (ES$^+$) C$_{22}$H$_{21}$F$_3$N$_6$O$_3$ requires: 474, found: 475 [M+H]$^+$; $^1$H NMR (500 MHz, CDCl$_3$) δ 8.29 (d, J=8.0 Hz, 2H), 8.14 (d, J=5.3 Hz, 1H), 7.35 (d, J=8.2 Hz, 2H), 6.68 (dd, J=5.3, 1.2 Hz, 1H), 6.49 (s, 1H), 5.41 (s, 2H), 4.05 (d, J=6.7 Hz, 2H), 2.55 (s, 3H), 2.06 (m, 1H), 1.00 (d, J=6.7 Hz, 6H).

EXAMPLE 77

5-[(5-Methyl-3-{3-[4-(trifluoromethoxy)phenyl]-1,2,4-oxadiazol-5-yl}-1H-1,2,4-triazol-1-yl)methyl]-1-(2-methylpropyl)-1,2-dihydropyridin-2-one (Example 77a) and 5-[(5-Methyl-3-{3-[4-(trifluoromethoxy)phenyl]-1,2,4-oxadiazol-5-yl}-1H-1,2,4-triazol-1-yl)methyl]-2-(2-methylpropoxy)pyridine (Example 77b)

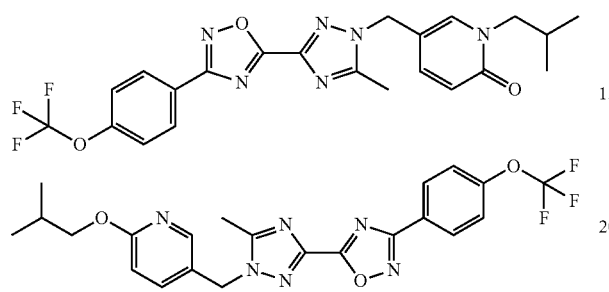

To a mixture of 5-((5-methyl-3-(3-(4-(trifluoromethoxy)phenyl)-1,2,4-oxadiazol-5-yl)-1H-1,2,4-triazol-1-yl)methyl)pyridin-2(1H)-one (prepared as described for Example 75, using 5-(bromomethyl)pyridin-2(1H)-one instead of 4-(bromomethyl)pyridin-2(1H)-one; 100 mg, 0.24 mmol) and K₂CO₃ (99 mg, 0.72 mmol) in DMF (10 mL) was added 1-bromo-2-methylpropane (1.0 mL, 2.4 mmol). The mixture was stirred at 55° C. for 16 h, then treated with H₂O (10 mL) and extracted with EtOAc (3×15 mL). The combined organic layers were concentrated under reduced pressure to afford the crude product, which was purified by prep-HPLC (Mobile phase: A=0.1% ammonium hydroxide/H₂O, B=MeCN; Gradient: B=60%-95% in 18 min; Column: XBridge (C18, 5 um, 30 mm×150 mm) to afford the two products as white solids; 1-isobutyl-5-((5-methyl-3-(3-(4-(trifluoromethoxy)phenyl)-1,2,4-oxadiazol-5-yl)-1H-1,2,4-triazol-1-yl)methyl)pyridin-2(1H)-one (Example 77a); MS (ES⁺) C₂₂H₂₁F₃N₆O₃ requires: 474, found: 475 [M+H]⁺; ¹H NMR (500 MHz, CDCl₃) δ 8.28 (d, J=8.8 Hz, 2H), 7.35 (d, J=8.3 Hz, 2H), 7.32 (m, 1H), 7.30 (s, 1H), 6.58 (m, 1H), 5.17 (s, 2H), 3.74 (d, J=7.4 Hz, 2H), 2.62 (s, 3H), 2.17 (m, 1H), 0.94 (d, J=6.7 Hz, 6H); 5-(1-((6-isobutoxypyridin-3-yl)methyl)-5-methyl-1H-1,2,4-triazol-3-yl)-3-(4-(trifluoromethoxy)phenyl)-1,2,4-oxadiazole (Example 77b); MS (ES+) C₂₂H₂₁F₃N₆O₃ requires: 474, found: 475 [M+H]⁺; ¹H NMR (500 MHz, CDCl₃) δ 8.28 (d, J=8.9 Hz, 2H), 8.13 (m, 1H), 7.56 (m, 1H), 7.36-7.32 (m, 2H), 6.76 (m, 1H), 5.36 (s, 2H), 4.06 (d, J=6.7 Hz, 2H), 2.58 (s, 3H), 2.07 (m, 1H), 1.00 (d, J=6.7 Hz, 6H).

EXAMPLE 78

3-[(5-Methyl-3-{3-[4-(trifluoromethoxy)phenyl]-1,2,4-oxadiazol-5-yl}-1H-1,2,4-triazol-1-yl)methyl]aniline

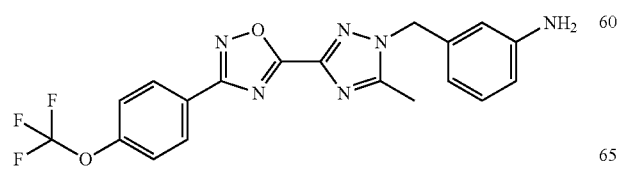

Step 1

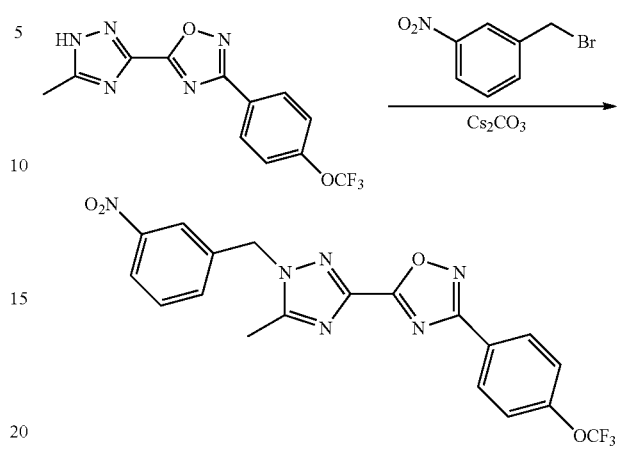

5-(5-methyl-1-(3-nitrobenzyl)-1H-1,2,4-triazol-3-yl)-3-(4-(trifluoromethoxy) phenyl)-1,2,4-oxadiazole A mixture of 5-(5-methyl-1H-1,2,4-triazol-3-yl)-3-(4-(trifluoromethoxy)phenyl)-1,2,4-oxadiazole (Intermediate B, 2 g, 6.43 mmol), 1-(bromomethyl)-3-nitrobenzene (1.39 g, 6.43 mmol) and Cs₂CO₃ (4.2 g, 12.9 mmol) in DMF (40 mL) was stirred at RT for 16 h. The mixture was then diluted with H₂O and extracted with EtOAc (3×200 mL). The combined organic extracts were washed with H₂O (20 mL) and brine (20 mL), dried (Na₂SO₄), and concentrated under reduced pressure to afford the title compound as a yellow solid (1.8 g, 56.4%). LC-MS (ES⁺) C₁₉H₁₃F₃N₆O₄ requires: 446, found: 447 (M+H)⁺.

Step 2

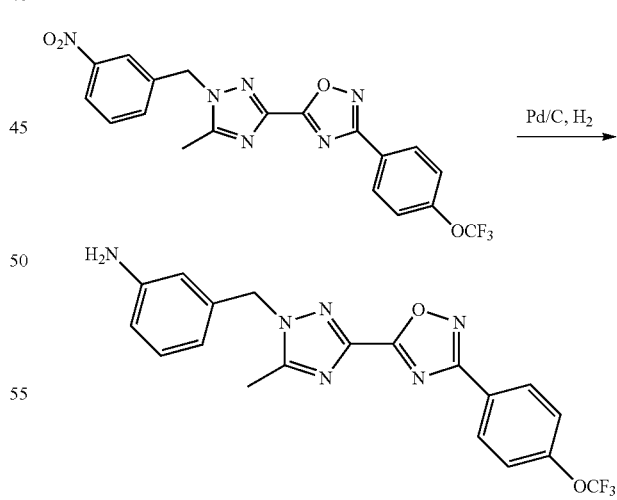

3-((5-methyl-3-(3-(4-(trifluoromethoxy)phenyl)-1,2,4-oxadiazol-5-yl)-1H-1,2,4-triazol-1-yl)methyl)benzenamine A mixture of 5-(5-methyl-1-(3-nitrobenzyl)-1H-1,2,4-triazol-3-yl)-3-(4-(trifluoromethoxy)phenyl)-1,2,4-oxadiazole (100 mg, 0.231 mmol) and Pd/C (10% w, 10 mg) in EtOH (10 mL) was stirred at RT for 2 h under hydrogen atmosphere. The reaction mixture was then filtered and concentrated under reduced pressure, and the residue was purified by prep-HPLC (Mobile phase: A=0.1% formic acid/H$_2$O, B=MeCN; Gradient: B=36%-95% in 18 min; Column: XBridge C18, 5 um, 30 mm×150 mm) to give the title compound as a white solid; MS (ES$^+$) C$_{19}$H$_{13}$ClF$_3$N$_5$O$_4$S requires: 416, found: 417 (M+H)+; $^1$H NMR (500 MHz, DMSO-d$_6$) δ ppm 8.31-8.28 (m, 2H), 7.34 (m, 2H), 7.26 (s, 1H), 7.14 (m, 1H), 6.63 (m, 1H), 6.51 (m, 1H), 5.36 (s, 2H), 2.52 (s, 3H).

EXAMPLE 79

1-Methyl-4-{3-[(5-methyl-3-{3-[4-(trifluoromethoxy)phenyl]-1,2,4-oxadiazol-5-yl}-1H-1,2,4-triazol-1-yl)methyl]benzenesulfonyl}piperazine

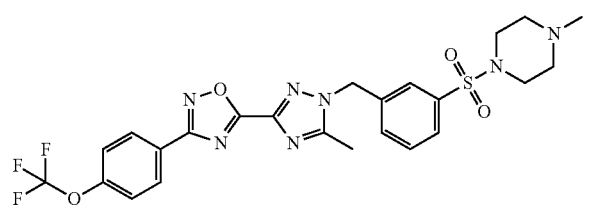 [SMILES: Cc1nc(-c2nc(-c3ccc(OC(F)(F)F)cc3)no2)nn1Cc1cccc(S(=O)(=O)N2CCN(C)CC2)c1]

Step 1

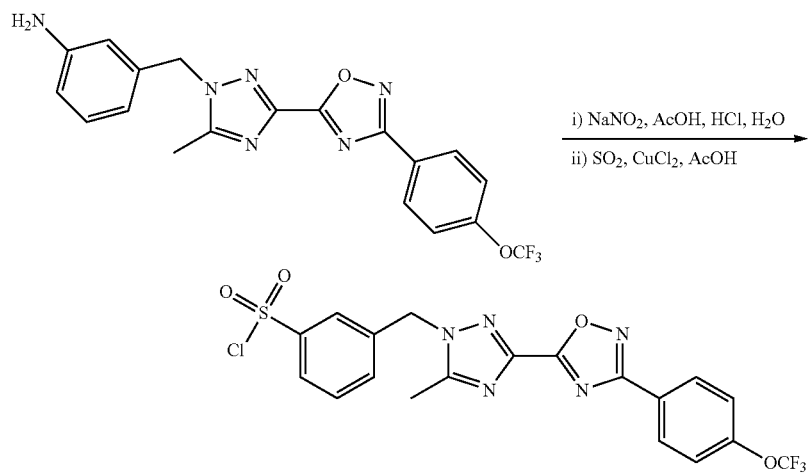

3-((5-methyl-3-(3-(4-(trifluoromethoxy)phenyl)-1,2,4-oxadiazol-5-yl)-1H-1,2,4-triazol-1-yl)methyl)benzene-1-sulfonyl chloride To a solution of 3-((5-methyl-3-(3-(4-(trifluoromethoxy)phenyl)-1,2,4-oxadiazol-5-yl)-1H-1,2,4-triazol-1-yl)methyl)benzenamine (Example 78, 100 mg, 0.24 mmol) in acetic acid (4 mL) and hydrochloric acid (37% aq., 0.5 mL) at 0° C., was added a solution of sodium nitrite (33 mg, 0.48 mmol) in H$_2$O (1 mL) and the resulting mixture was stirred for 1 h at 0° C. Sulfur dioxide (0.9 M solution in AcOH 4 mL) and CuCl$_2$ (20 mg, 0.20 mmol) were then added at 0° C., and the resulting mixture was stirred at RT for 16 h. The mixture was poured onto H$_2$O (50 mL) and extracted with EtOAc (50 mL). The organic phase was washed with aq. sodium bicarbonate and brine, dried (Na$_2$SO$_4$), filtered and concentrated under reduced pressure to afford the title compound as a yellow solid (72 mg, 69.3%). LC-MS (ES$^+$) C$_{19}$H$_{13}$ClF$_3$N$_5$O$_4$S requires: 499, found: 500 (M+H)$^+$.

Step 2

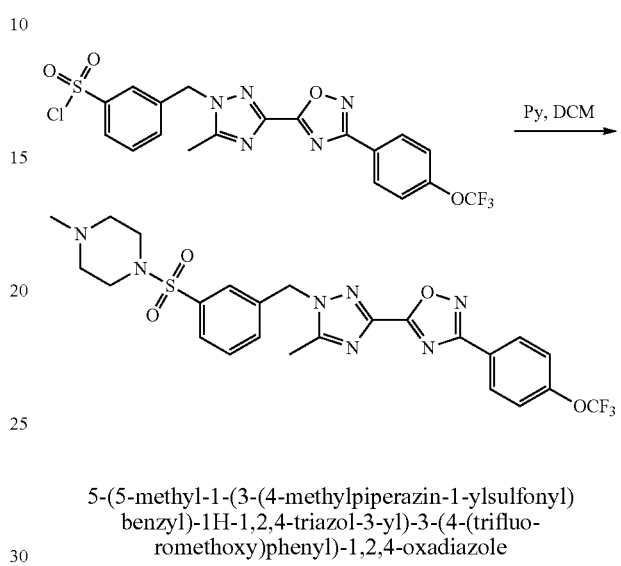

5-(5-methyl-1-(3-(4-methylpiperazin-1-ylsulfonyl)benzyl)-1H-1,2,4-triazol-3-yl)-3-(4-(trifluoromethoxy)phenyl)-1,2,4-oxadiazole To a solution of 3-((5-methyl-3-(3-(4-(trifluoromethoxy)phenyl)-1,2,4-oxadiazol-5-yl)-1H-1,2,4-triazol-1-yl)methyl)benzene-1-sulfonyl chloride (50 mg, 0.1 mmol) in DCM (5 mL) were added pyridine (0.05 ml) and 1-methylpiperazine (20 mg, 0.2 mmol). The mixture was stirred at RT for 1 h, then diluted with DCM and washed with H$_2$O (100 mL). The aqueous layer was separated and extracted with DCM (2×100 mL), the combined organic layers were washed with brine (100 mL), dried (Na$_2$SO$_4$) and concentrated under reduced pressure. The residue was purified by prep-HPLC (Mobile phase: A=0.1% formic acid/H$_2$O, B=MeCN; Gradient: B=36%-95% in 18 min; Column: XBridge C18, 5 um, 30 mm×150 mm) to give the title compound as a white solid; MS (ES$^+$) C$_{21}$H$_{19}$F$_3$N$_6$O$_4$S requires: 508, found: 509 (M+H)$^+$; $^1$H NMR (500 MHz, DMSO-d6) δ ppm 8.28 (d, J=8 Hz, 2H), 7.86 (bs, 1H), 7.84 (m, 1H), 7.64 (m, 2H), 7.50 (d, J=7.5 Hz, 2H), 5.67 (s, 2H), 3.98 (m, 2H), 3.61 (m, 2H), 3.26 (m, 2H), 2.90 (s, 3H), 2.74 (m, 2H), 2.69 (s, 3H).

EXAMPLE 80

4-Methanesulfonyl-1-{3-[(5-methyl-3-{3-[4-(trifluoromethoxy)phenyl]-1,2,4-oxadiazol-5-yl}-1H-1,2,4-triazol-1-yl)methyl]phenyl}piperidine

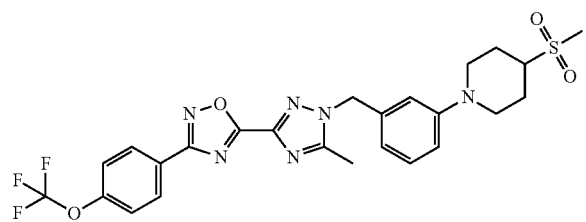 [SMILES: Cc1nc(-c2nc(-c3ccc(OC(F)(F)F)cc3)no2)nn1Cc1cccc(N2CCC(S(C)(=O)=O)CC2)c1]

A mixture of 5-(1-(3-bromobenzyl)-5-methyl-1H-1,2,4-triazol-3-yl)-3-(4-(trifluoromethoxy)phenyl)-1,2,4-oxadiazole (Example 11, Step 1; 165 mg, 0.34 mmol), 4-(methylsulfonyl)piperidine (62 mg, 0.38 mmol), and Cs$_2$CO$_3$ (224 mg, 0.69 mmol) in toluene (2 mL) was degassed with argon for 5 min. Pd$_2$(dba)$_3$ (0.15 mg, 0.017 mmol) and dicyclohexyl(2',4',6'-triisopropyl-[1,1'-biphenyl]-2-yl)phosphine (33 mg, 069 mmol) were added and the reaction mixture was degassed a second time with argon for 5 min, then heated to 140° C. for 18 h. The mixture was then cooled to RT, diluted with EtOAc (15 mL), filtered through a pad of Celite, and concentrated under reduced pressure. The crude product was purified by prep-HPLC (Mobile phase: A=0.1% TFA/H$_2$O, B=0.1% TFA/MeCN; Gradient: B=40%-80% in 12 min; Column: C18) to give the title compound as a white solid; MS (ES$^+$) C$_{25}$H$_{25}$F$_3$N$_6$O$_4$S requires: 562, found: 563 [M+H]$^+$; $^1$H NMR (600 MHz, DMSO-d$_6$) δ 8.22 (d, J=8.8 Hz, 2H), 7.61 (d, J=8.2 Hz, 2H), 7.21 (t, J=7.9 Hz, 1H), 6.97 (bs, 1H), 6.94 (dd, J=8.3, 2.4 Hz, 1H), 6.64 (d, J=7.5 Hz, 1H), 5.48 (s, 2H), 3.86 (bd, J=13.4 Hz, 2H), 3.28 (m, 1H), 2.94 (s, 3H), 2.76 (m, 2H), 2.57 (s, 3H), 2.06 (bd, J=13.4 Hz, 2H), 1.68 (ddd, J=16.5, 12.5, 4.1 Hz, 2H); $^{19}$F NMR (282 MHz, DMSO-d$_6$) δ −56.6.

EXAMPLE 81

1-{3-[(5-Methyl-3-{3-[4-(trifluoromethoxy)phenyl]-1,2,4-oxadiazol-5-yl}-1H-1,2,4-triazol-1-yl)methyl]phenyl}piperazine

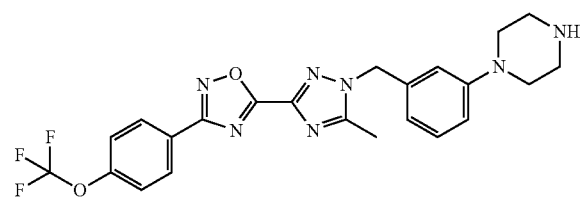 [SMILES: Cc1nc(-c2nc(-c3ccc(OC(F)(F)F)cc3)no2)nn1Cc1cccc(N2CCNCC2)c1]

To a solution of 5-(1-(3-bromobenzyl)-5-methyl-1H-1,2,4-triazol-3-yl)-3-(4-(trifluoromethoxy)phenyl)-1,2,4-oxadiazole (Example 11, Step 1; 500 mg, 1.04 mmol) in toluene (10 mL) were added piperazine (86 mg, 1.04 mmol), t-BuONa (290 mg, 3 mmol), Ruphos (46 mg, 0.1 mmol) and Pd$_2$(dba)$_3$ (90 mg, 0.1 mmol). The reaction mixture was then heated in a sealed vial at 110° C. under inert atmosphere for 12 h. The resulting mixture was cooled, diluted with H$_2$O (30 mL) and extracted with EtOAc (2×20 mL). The combined organic layers were washed with H$_2$O (10 mL) and brine (10 mL), dried over Na$_2$SO$_4$, filtered and concentrated under reduced pressure. The residue was purified by silica gel chromatography (PE:EA=3:1 to 1:1) to give the title compound as a white solid; MS (ES$^+$) C$_{23}$H$_{22}$F$_3$N$_7$O$_2$ requires: 485, found: 486 [M+H]$^+$; $^1$H NMR (500 MHz, DMSO-d$_6$) δ 8.78 (br s, 1H), 8.22 (d, J=9 Hz, 2H), 7.61 (d, J=9 Hz, 2H), 7.27 (m, 1H), 6.97 (m, 2H), 6.76 (d, J=7.5 Hz, 1H), 5.50 (s, 2H), 3.32 (m, 2H), 3.23 (m, 4H), 2.58 (s, 3H), 2.50 (m, 2H).

EXAMPLE 82

1-Methanesulfonyl-4-{3-[(5-methyl-3-{3-[4-(trifluoromethoxy)phenyl]-1,2,4-oxadiazol-5-yl}-1H-1,2,4-triazol-1-yl)methyl]phenyl}piperazine

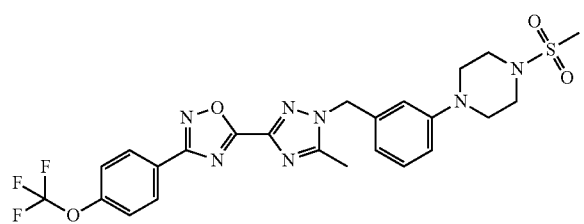 [SMILES: Cc1nc(-c2nc(-c3ccc(OC(F)(F)F)cc3)no2)nn1Cc1cccc(N2CCN(S(C)(=O)=O)CC2)c1]

To a solution of 5-(5-methyl-1-(3-(piperazin-1-yl)benzyl)-1H-1,2,4-triazol-3-yl)-3-(4-(trifluoromethoxy)phenyl)-1,2,4-oxadiazole (Example 81; 110 mg, 0.23 mmol) and Et$_3$N (70 mg, 0.69 mmol) in DCM (5 mL) at 0° C. was added methanesulfonyl chloride (34 mg, 0.30 mmol). The reaction mixture was allowed to warm to RT over 2 h, then diluted with H$_2$O (10 mL) and extracted with EtOAc (2×10 mL). The combined organic layers were washed with H$_2$O (10 mL) and brine (10 mL), dried over Na$_2$SO$_4$, filtered and concentrated under reduced pressure; the residue was purified by prep-HPLC (10% to 30% MeCN/H$_2$O containing 0.1% trifluoroacetic acid) to give the title compound as an off-white solid; MS (ES$^+$) C$_{24}$H$_{24}$F$_3$N$_7$O$_4$S requires: 563, found: 564 [M+H]$^+$; $^1$H-NMR (500 MHz, DMSO-d$_6$) δ 8.22 (d, J=8.5 Hz, 2H), 7.61 (d, J=8.5 Hz, 2H), 7.24 (m, 1H), 6.96 (m, 2H), 6.70 (d, J=7.5 Hz, 1H), 5.49 (s, 2H), 3.98 (m, 4H), 3.25 (m, 4H), 2.92 (s, 3H), 2.58 (s, 3H).

EXAMPLE 83

2-Hydroxy-1-(4-{3-[(5-methyl-3-{3-[4-(trifluoromethoxy)phenyl]-1,2,4-oxadiazol-5-yl}-1H-1,2,4-triazol-1-yl)methyl]phenyl}piperazin-1-yl)ethan-1-one

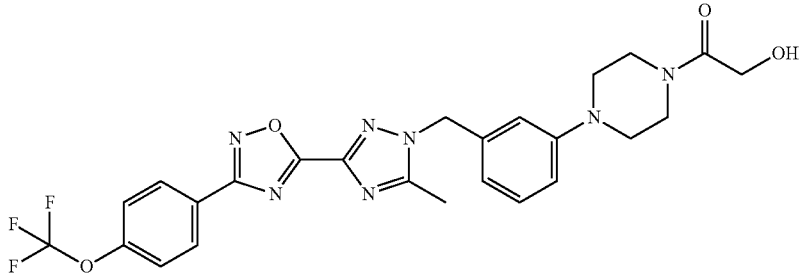 [SMILES: Cc1nc(-c2nc(-c3ccc(OC(F)(F)F)cc3)no2)nn1Cc1cccc(N2CCN(C(=O)CO)CC2)c1]

To a solution of 5-(5-methyl-1-(3-(piperazin-1-yl)benzyl)-1H-1,2,4-triazol-3-yl)-3-(4-(trifluoromethoxy)phenyl)-1,2,4-oxadiazole (Example 81; 110 mg, 0.23 mmol), 2-hydroxyacetic acid (21 mg, 0.28 mmol) and DIPEA (89 mg, 0.69 mmol) in DMF (5 mL) was added HATU (106 mg, 0.28 mmol). The resulting mixture was stirred at room temperature for 3 h, diluted with $H_2O$ (10 mL) and extracted with EtOAc (2×10 mL). The combined organic layers were washed with $H_2O$ (10 mL) and brine (10 mL), dried over $Na_2SO_4$, filtered and concentrated under reduced pressure; the residue was purified by prep-HPLC (20% to 50% MeCN/$H_2O$ containing 0.1% trifluoroacetic acid) to give the title compound as a white solid; MS (ES$^+$) $C_{25}H_{24}F_3N_7O_4$ requires: 543, found: 544 [M+H]$^+$; $^1$H-NMR (500 MHz, DMSO-$d_6$) δ 8.23 (d, J=8.5 Hz, 2H), 7.62 (d, J=8.5 Hz, 2H), 7.24 (m, 1H), 6.95 (m, 2H), 6.69 (d, J=7.5 Hz, 1H), 5.49 (s, 2H), 4.12 (s, 2H), 3.56 (m, 2H), 3.15 (m, 4H), 2.58 (s, 3H), 2.50 (m, 2H).

EXAMPLE 84

5-{1-[(3-Ethenylphenyl)methyl]-5-methyl-1H-1,2,4-triazol-3-yl}-3-[4-(trifluoromethoxy)phenyl]-1,2,4-oxadiazole

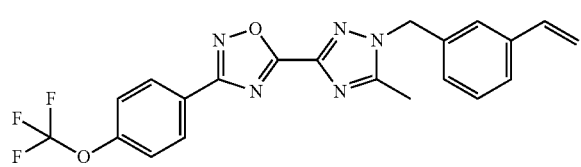 [SMILES: C=Cc1cccc(Cn2nc(-c3nc(-c4ccc(OC(F)(F)F)cc4)no3)nc2C)c1]

To a mixture of 5-(1-(3-bromobenzyl)-5-methyl-1H-1,2,4-triazol-3-yl)-3-(4-(trifluoromethoxy)phenyl)-1,2,4-oxadiazole (Example 11, Step 1; 200 mg, 0.42 mmol), tributyl(vinyl)stannane (159 mg, 0.50 mmol) and $K_2CO_3$ (174 mg, 1.26 mmol) in 1,4-dioxane (5 mL), was added Pd(PPh$_4$)$_3$ (28 mg, 0.025 mmol). The reaction mixture was heated in a sealed vial at 110° C. under inert atmosphere for 12 h, cooled to RT, diluted with $H_2O$ (30 mL) and extracted with EtOAc (2×20 mL). The combined organic layers were washed with $H_2O$ (10 mL) and brine (10 mL), dried over $Na_2SO_4$, filtered and concentrated under reduced pressure; the residue was purified by prep-HPLC to give the title compound as a white solid; MS (ES$^+$) $C_{21}H_{16}F_3N_5O_2$ requires: 427, found: 428 [M+H]$^+$; $^1$H-NMR (500 MHz, DMSO-$d_6$) δ 8.22 (d, J=9 Hz, 2H), 7.61 (d, J=9 Hz, 2H), 7.48 (d, J=7 Hz, 1H), 7.43 (s, 1H), 7.38 (m, 1H), 7.21 (d, J=7 Hz, 1H), 6.76 (m, 1H), 5.87 (d, J=17.5 Hz, 1H), 5.57 (s, 2H), 5.31 (d, J=11.5 Hz, 1H), 2.60 (s, 3H).

EXAMPLE 85

1-{3-[(5-Methyl-3-{3-[4-(trifluoromethoxy)phenyl]-1,2,4-oxadiazol-5-yl}-1H-1,2,4-triazol-1-yl)methyl]phenyl}ethane-1,2-diol

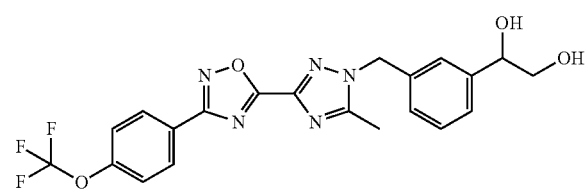 [SMILES: Cc1nc(-c2nc(-c3ccc(OC(F)(F)F)cc3)no2)nn1Cc1cccc(C(O)CO)c1]

To a solution of 5-(5-methyl-1-(3-vinylbenzyl)-1H-1,2,4-triazol-3-yl)-3-(4-(trifluoromethoxy)phenyl)-1,2,4-oxadiazole (Example 84; 110 mg, 0.26 mmol) in t-BuOH (5 mL), were added N-methylmorpholine-N-oxide (152 mg, 1.3 mmol) and OsO$_4$ (10 mg, 0.04 mmol). The reaction mixture was stirred at RT for 24 h, diluted with $H_2O$ (20 mL) and extracted with EtOAc (2×10 mL). The combined organic layers were washed with $H_2O$ (10 mL) and brine (10 mL), dried over $Na_2SO_4$, filtered and concentrated under reduced pressure; the residue was purified by prep-HPLC (10% to 40% MeCN/$H_2O$ containing 0.1% trifluoroacetic acid) to give the title compound as a white solid; MS (ES$^+$) $C_{21}H_{18}F_3N_5O_4$ requires: 461, found: 462 [M+H]$^+$; $^1$H-NMR (500 MHz, DMSO-$d_6$) δ 8.23 (d, J=8.5 Hz, 2H), 7.61 (d, J=8.5 Hz, 2H), 7.33-7.30 (m, 3H), 7.17 (d, J=7 Hz, 1H), 5.56 (s, 2H), 4.54-4.51 (m, 1H), 3.44-3.40 (m, 4H), 2.57 (s, 3H).

EXAMPLE 86

3-{3-[(5-methyl-3-{3-[4-(trifluoromethoxy)phenyl]-1,2,4-oxadiazol-5-yl}-1H-1,2,4-triazol-1-yl)methyl]phenoxy}propane-1,2-diol

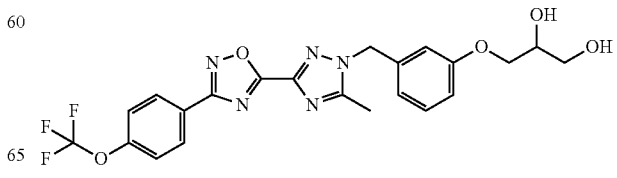

Step 1

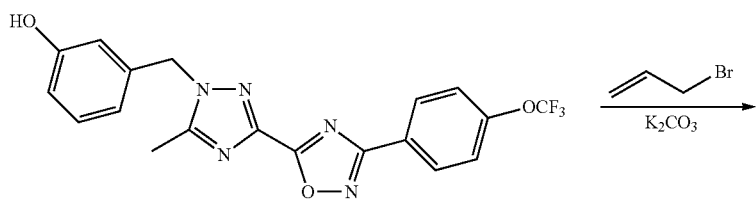

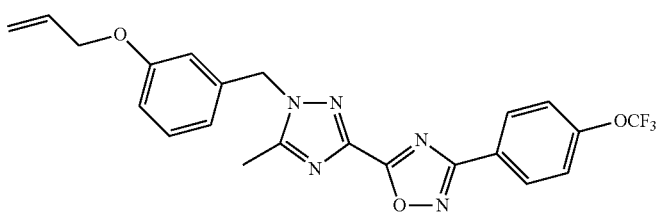

5-(1-(3-(allyloxy)benzyl)-5-methyl-1H-1,2,4-triazol-3-yl)-3-(4-(trifluoromethoxy)phenyl)-1,2,4-oxadiazole A solution of 3-((5-methyl-3-(3-(4-(trifluoromethoxy)phenyl)-1,2,4-oxadiazol-5-yl)-1H-1,2,4-triazol-1-yl)methyl)phenol (Example 59; 140 mg, 0.33 mmol) in DCM (5 mL), was added to a mixture of 3-bromoprop-1-ene (60 mg, 0.5 mmol), $K_2CO_3$ (138 mg, 1.0 mmol) and t-$Bu_4NHSO_4$ (113 mg, 0.33 mmol) in $H_2O$ (5 mL). The mixture was stirred at RT for 16 h, then diluted with $H_2O$ (50 mL) and extracted with EtOAc (3×30 mL). The combined organic layers were washed with brine (20 mL), dried over $Na_2SO_4$, filtered and concentrated under reduced pressure; the residue was purified by silica gel chromatography (Petroleum ether:EtOAc=5:1 to 2:1) to give the title compound (140 mg, 91%) as a white solid. MS (ES$^+$) $C_{22}H_{18}F_3N_5O_3$ requires: 457, found: 458 [M+H]$^+$.

Step 2

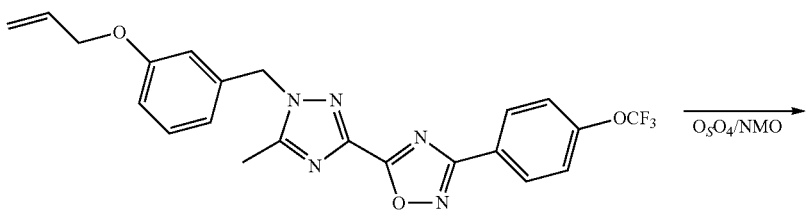

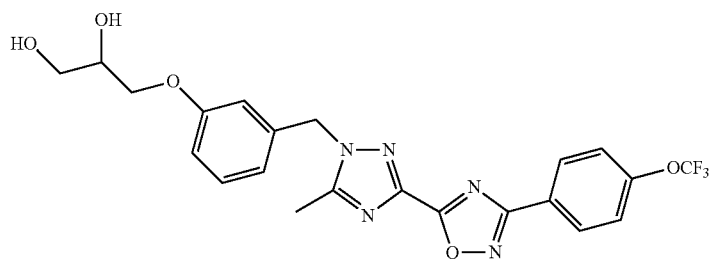

3-(3-((5-methyl-3-(3-(4-(trifluoromethoxy)phenyl)-1,2,4-oxadiazol-5-yl)-1H-1,2,4-triazol-1-yl)methyl)phenoxy)propane-1,2-diol To a solution of 5-(1-(3-(allyloxy)benzyl)-5-methyl-1H-1,2,4-triazol-3-yl)-3-(4-(trifluoromethoxy)phenyl)-1,2,4-oxadiazole (150 mg, 0.33 mmol) and N-methylmorpholin-N-oxide (77 mg, 0.7 mmol) in acetone (2 mL) and $H_2O$ (2 mL) was added $OsO_4$ (17 mg, 0.07 mmol). The mixture was stirred at RT overnight, then diluted with $H_2O$ (50 mL) and extracted with DCM/MeOH (10/1 v/v, 3×30 mL). The combined organic layers were washed with brine (20 mL), dried over $Na_2SO_4$, filtered and concentrated under reduced pressure; the residue was purified by prep-HPLC (Mobile phase: A=0.1% $NH_3.H_2O/H_2O$, B=MeCN; Gradient: B=5%-95% in 8 min; Column: XBridge C18, 5 um, 30 mm×150 mm) to afford the title compound as an off-white solid; MS (ES$^+$) $C_{22}H_{20}F_3N_5O_5$ requires: 491, found: 492 [M+H]$^+$; $^1$H NMR (500 MHz, DMSO-d$_6$) δ 8.22 (d, J=9.0 Hz, 2H), 7.60 (d, J=9.0 Hz, 2H), 7.30 (m, 1H), 6.92 (d, J=8.5 Hz, 1H), 6.89 (s, 1H), 6.85 (d, J=8.0 Hz, 1H), 5.54 (s, 2H), 4.95 (d, J=5.5 Hz, 1H), 4.67 (t, J=5.5 Hz, 1H), 4.00 (m, 1H), 3.86 (m, 1H), 3.77 (m, 1H), 3.44 (t, J=5.5 Hz, 2H), 2.58 (s, 3H).

EXAMPLE 87

1-Methyl-4-{4-[(5-methyl-3-{4-[4-(trifluoromethoxy)phenyl]-1,3-thiazol-2-yl}-1H-1,2,4-triazol-1-yl)methyl]pyridin-2-yl}piperazine

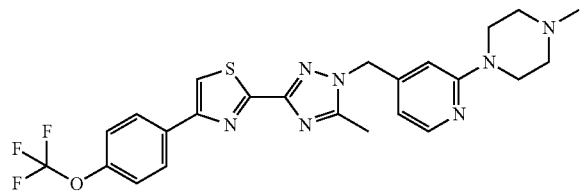 [SMILES: Cc1nc(-c2nc(-c3ccc(OC(F)(F)F)cc3)cs2)nn1Cc1ccnc(N2CCN(C)CC2)c1]

Steps 1 to 4

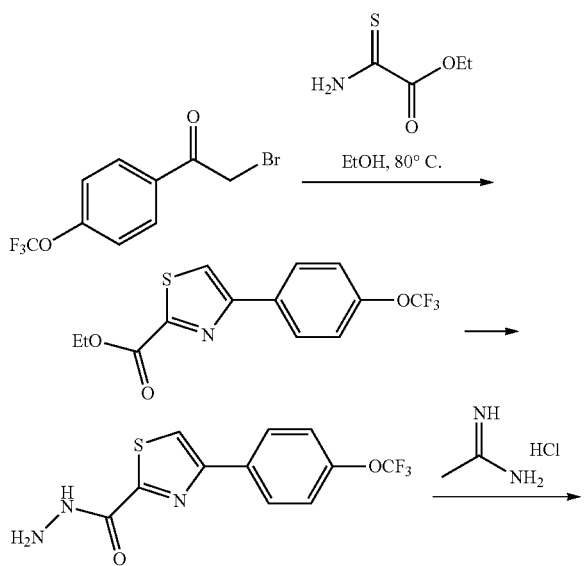

Step 1: Ethyl 4-(4-(trifluoromethoxy)phenyl)thiazole-2-carboxylate

A solution of 2-bromo-1-(4-(trifluoromethoxy)phenyl)ethanone (20.0 g, 71 mmol) and ethyl 2-amino-2-thioxoacetate (9.466 g, 71 mmol) in absolute EtOH (200 mL) was stirred at 80° C. for 16 h. The mixture was concentrated under reduced pressure, diluted with saturated aqueous sodium carbonate (100 mL) and extracted with EtOAc (4×80 mL). The combined organic layers were washed with brine (50 mL), dried over $Na_2SO_4$, filtered and concentrated under reduced pressure, to give the title compound as a white solid (13 g, 57%). MS (ES+) $C_{13}H_{10}F_3NO_3S$ requires: 317, found: 318 [M+H]$^+$.

Step 2 4-(4-(trifluoromethoxy)phenyl)thiazole-2-carbohydrazide

To a solution of ethyl 4-(4-(trifluoromethoxy)phenyl)thiazole-2-carboxylate (10.0 g, 31.5 mmol) in MeOH (80 mL) was added hydrazine hydrate (1.95 g, 33.1 mmol; 85%) dropwise over 15 minutes, and the resulting mixture was stirred for a further 16 h at RT. The mixture was then concentrated under reduced pressure to half volume, and $H_2O$ (30 mL) was added. A white solid precipitated, was filtered, washed with $H_2O$ (3×30 mL) and dried to afford the title compound as a white solid (9.6 g, 100%). MS (ES+) $C_{11}H_8F_3N_3O_2S$ requires: 303, found: 304[M+H]$^+$.

Step 3 N'-(1-iminoethyl)-4-(4-(trifluoromethoxy)phenyl)thiazole-2-carbohydrazide To a solution of 4-(4-(trifluoromethoxy)phenyl)thiazole-2-carbohydrazide (10.0 g, 33.0 mmol) in THF (100 mL) were added acetamidine hydrochloride (62 g, 66 mmol) and sodium hydroxide (4 g, 99 mmol). The mixture was stirred at 100° C. for 16 h, and then concentrated under reduced pressure. The white solid residue was washed with $H_2O$ (30 mL), filtered and dried to afford the title compound as a white solid (10 g, 88%). MS (ES+) $C_{13}H_{11}F_3N_4O_2S$ requires: 344, found: 345 [M+H]$^+$.

Step 4 2-(5-methyl-1H-1,2,4-triazol-3-yl)-4-(4-(trifluoromethoxy)phenyl)thiazole

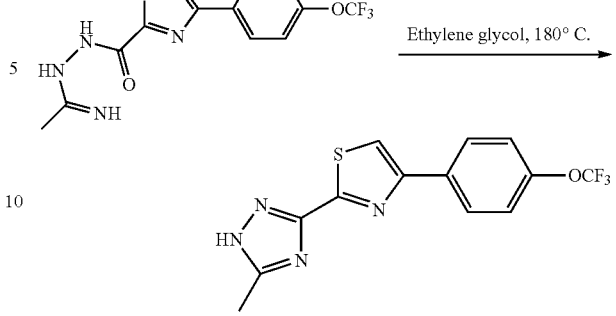

A solution of N'-(1-iminoethyl)-4-(4-(trifluoromethoxy)phenyl)thiazole-2-carbohydrazide (10.0 g, 33.0 mmol) in ethylene glycol (20 mL) was stirred at 180° C. for 2 h. After cooling to RT, $H_2O$ (100 mL) was added and the mixture was extracted with EtOAc (2×100 mL). The combined organic layers were washed with brine (100 mL), dried over Na$_2$SO$_4$, filtered and concentrated under reduced pressure; the residue was purified by silica gel column chromatography (Petroleum ether:EtOAc=5:1) to afford the title compound as a white solid (9.6 g, 100%). MS (ES+) C$_{13}$H$_9$F$_3$N$_4$OS requires: 326, found: 327 [M+H]$^+$; $^1$H NMR (500 MHz, DMSO) 8.27 (s, 1H), 8.15 (d, J=8.5 Hz, 2H), 7.48 (d, J=8.0 Hz, 2H), 2.43 (s, 3H).

Step 5

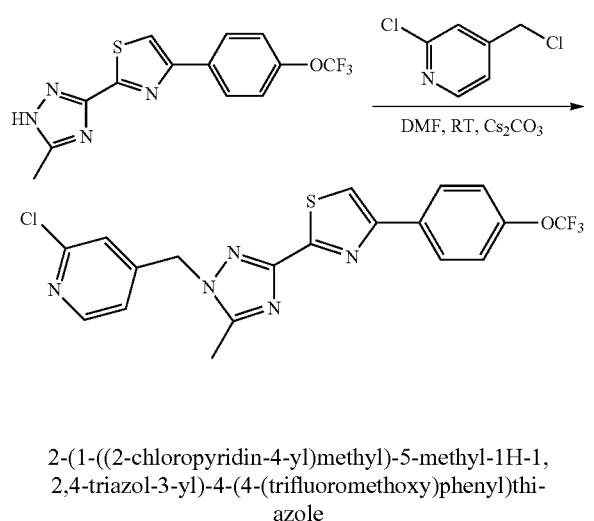

2-(1-((2-chloropyridin-4-yl)methyl)-5-methyl-1H-1, 2,4-triazol-3-yl)-4-(4-(trifluoromethoxy)phenyl)thiazole To a stirred mixture of 2-(5-methyl-1H-1,2,4-triazol-3-yl)-4-(4-(trifluoromethoxy)phenyl)thiazole (3 g, 9.2 mmol) and Cs$_2$CO$_3$ (4.8 g, 13 mmol) in DMF (20 mL) was added 2-chloro-4-(chloromethyl)pyridine (2.1 g, 13 mmol). The mixture was stirred at RT for 16 h, then diluted with H$_2$O (20 mL) and extracted with EtOAc (3×30 mL). The combined organic layers were washed with H$_2$O (20 mL), concentrated under reduced pressure and the residue was purified by silica gel column chromatography (Petroleum ether:EtOAc=4:1) to afford the title compound as an oil (2.1 g, 50.6%).

Step 6

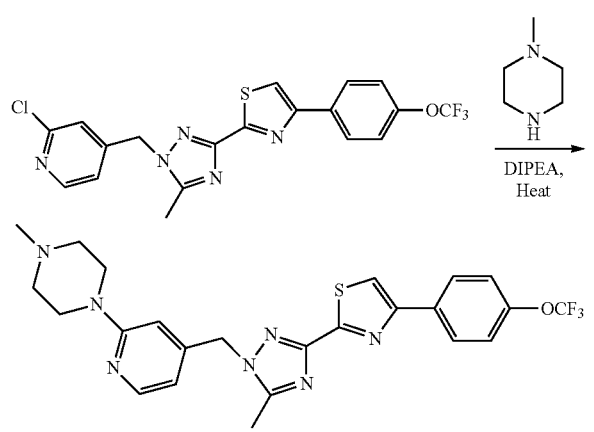

2-(5-methyl-1-((2-(4-methylpiperazin-1-yl)pyridin-4-yl)methyl)-1H-1,2,4-triazol-3-yl)-4-(4-(trifluoromethoxy)phenyl)thiazole To a stirred solution of 2-(1-((2-chloropyridin-4-yl)methyl)-5-methyl-1H-1,2,4-triazol-3-yl)-4-(4-(trifluoromethoxy)phenyl)thiazole (100 mg, 0.22 mmol) in diisopropylethylamine (10 mL) was added 1-methylpiperazine (2 mL, 2.2 mmol). The mixture was stirred at 80° C. for 16 h, then concentrated under reduced pressure. The residue was purified by silica gel column chromatography (Petroleum ether:EtOAc=4:1) to give the title compound as an oil; MS (ES+) C$_{24}$H$_{24}$F$_3$N$_7$OS requires: 515, found: 516. [M+H]$^+$. $^1$H NMR (500 MHz, CDCl$_3$) δ 8.17 (d, J=5.1 Hz, 1H), 8.08 (d, J=8.7 Hz, 2H), 7.58 (s, 1H), 7.29 (d, J=8.1 Hz, 2H), 6.43 (d, J=5.2 Hz, 1H), 6.40 (s, 1H), 5.34 (s, 2H), 3.61-3.49 (m, 4H), 2.57-2.44 (m, 7H), 2.35 (s, 3H).

EXAMPLE 88

1-[(3-Methanesulfonylphenyl)methyl]-5-methyl-3-{4-[4-(trifluoromethoxy)phenyl]-1,3-thiazol-2-yl}-1H-1,2,4-triazole

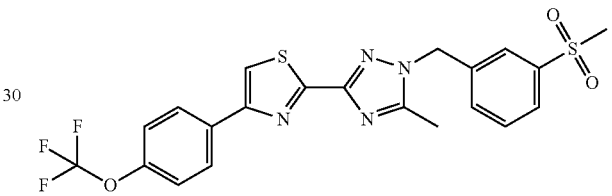

Synthesized in analogous manner to Example 19, using 2-(5-methyl-1H-1,2,4-triazol-3-yl)-4-(4-(trifluoromethoxy)phenyl)thiazole (Example 87, Step 4) instead of 5-(5-methyl-1H-1,2,4-triazol-3-yl)-3-(4-(trifluoromethoxy)phenyl)-1,2,4-oxadiazole; MS (ES$^+$) C$_{21}$H$_{17}$F$_3$N$_4$O$_3$S$_2$ requires: 494, found: 495 [M+H]$^+$; $^1$H-NMR (600 MHz, CDCl$_3$) δ ppm 8.04 (d, J=7.2 Hz, 2H), 7.94 (d, J=7.8 Hz, 2H), 7.88 (s, 1H), 7.59 (t, J=8.0 Hz, 1H), 7.56 (s, 1H), 7.51 (d, J=8.0 Hz, 1H), 7.26 (m, 1H), 5.49 (s, 2H), 3.06 (s, 3H), 2.54 (s, 3H).

EXAMPLE 89

N,N-Dimethyl-3-[(5-methyl-3-{4-[4-(trifluoromethoxy)phenyl]-1,3-thiazol-2-yl}-1H-1,2,4-triazol-1-yl)methyl]benzamide

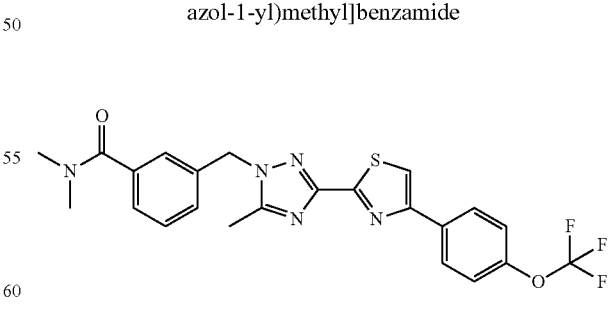

Synthesized in analogous manner to Example 13, using 2-(5-methyl-1H-1,2,4-triazol-3-yl)-4-(4-(trifluoromethoxy)phenyl)thiazole (Example 87, Step 4) instead of 5-(5-Methyl-1H-1,2,4-triazol-3-yl)-3-(4-(trifluoromethoxy)phenyl)-1,2,4-oxadiazole; MS (ES$^+$) C$_{23}$H$_{20}$F$_3$N$_5$O$_2$S requires: 487, found: 488 [M+H]$^+$.

EXAMPLE 90

1-{[3-(2-Methoxyethoxy)phenyl]methyl}-5-methyl-3-{4-[4-(trifluoromethoxy)phenyl]-1,3-thiazol-2-yl}-1H-1,2,4-triazole

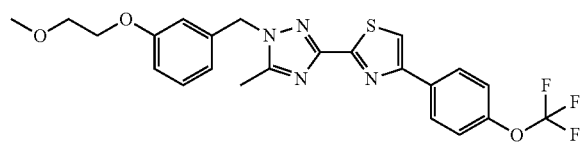 [SMILES: COCCOc1cccc(Cn2nc(-c3nc(-c4ccc(OC(F)(F)F)cc4)cs3)nc2C)c1]

A mixture of 1-bromo-2-methoxyethane (3.2 mg, 0.023 mmol), Cs₂CO₃ (9.4 mg, 0.029 mmol) and 3-((5-methyl-3-(4-(4-(trifluoromethoxy)phenyl)thiazol-2-yl)-1H-1,2,4-triazol-1-yl)methyl)phenol (5.0 mg, 0.012 mmol; synthesized in analogous manner to Example 59, using 2-(5-methyl-1H-1,2,4-triazol-3-yl)-4-(4-(trifluoromethoxy)phenyl)thiazole, Example 87, Step 4) in DMSO (0.2 ml) was stirred at 50° C. for 20 minutes. The mixture was purified by prep-HPLC to give the title compound; MS (ES⁺) C₂₃H₂₁F₃N₄O₃S requires: 474, found: 475 [M+H]⁺.

EXAMPLE 91

2-{3-[(5-Methyl-3-{4-[4-(trifluoromethoxy)phenyl]-1,3-thiazol-2-yl}-1H-1,2,4-triazol-1-yl)methyl]phenoxy}ethan-1-ol

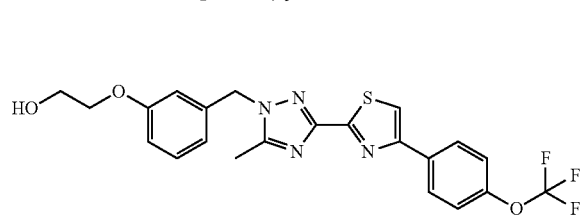

Step 1

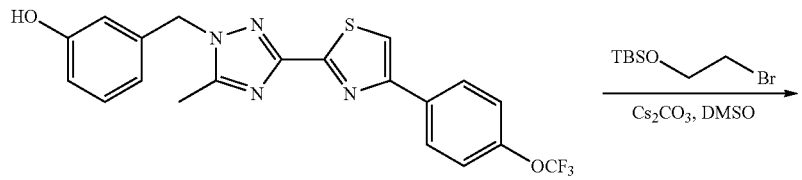

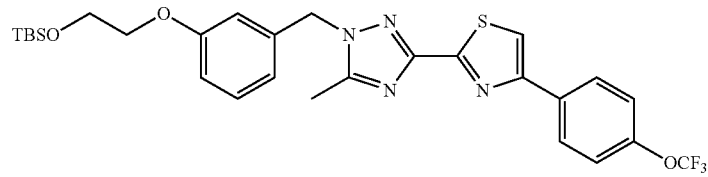

2-(1-(3-(2-((tert-butyldimethylsilyl)oxy)ethoxy)benzyl)-5-methyl-1H-1,2,4-triazol-3-yl)-4-(4-(trifluoromethoxy)phenyl)thiazole A mixture of (2-bromoethoxy)(tert-butyl)dimethylsilane (11.0 mg, 0.046 mmol), Cs₂CO₃ (18.8 mg, 0.058 mmol) and 3-((5-methyl-3-(4-(4-(trifluoromethoxy)phenyl)thiazol-2-yl)-1H-1,2,4-triazol-1-yl)methyl)phenol (10.0 mg, 0.023 mmol; synthesized in analogous manner to Example 59, using 2-(5-methyl-1H-1,2,4-triazol-3-yl)-4-(4-(trifluoromethoxy)phenyl)thiazole, Example 87, Step 4) in DMSO (0.3 ml) was stirred at 50° C. for 30 minutes. The mixture was diluted with EtOAc and washed with H₂O. The organic layer was concentrated under reduced pressure and the residue was used in the following step without further purification. MS (ES⁺) C₂₈H₃₃F₃N₄O₃SSi requires: 590, found: 591 [M+H]⁺.

Step 2

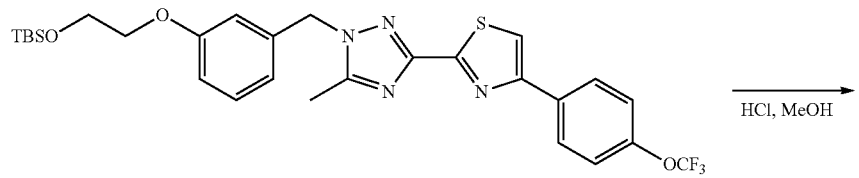

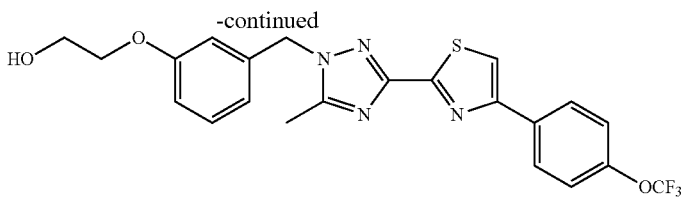

2-(3-((5-methyl-3-(4-(4-(trifluoromethoxy)phenyl)thiazol-2-yl)-1H-1,2,4-triazol-1-yl)methyl)phenoxy)ethanol A mixture of 2-(1-(3-(2-((tert-butyldimethylsilyl)oxy)ethoxy)benzyl)-5-methyl-1H-1,2,4-triazol-3-yl)-4-(4-(trifluoromethoxy)phenyl)thiazole (13.6 mg, 0.023 mmol) and hydrogen chloride (0.096 ml, 1.150 mmol) in MeOH (1 ml) was stirred at RT for 30 minutes. The mixture was then purified by prep HPLC to give the title compound; MS (ES+) C22H19F3N4O3S requires: 476, found: 477 [M+H]+; 1H-NMR (600 MHz, CDCl3) δ ppm 8.06 (d, J=8.7 Hz, 2H), 7.54 (s, 1H), 7.27-7.25 (m, 3H), 6.87 (m, 1H), 6.82 (d, J=7.4 Hz, 1H), 6.77 (s, 1H), 5.37 (s, 2H), 4.04 (m, 2H), 3.94 (m, 2H), 2.47 (s, 3H).

EXAMPLE 92

1-Methyl-4-{4-[(5-methyl-3-{5-[4-(trifluoromethoxy)phenyl]-1,3-oxazol-2-yl}-1H-1,2,4-triazol-1-yl)methyl]pyridin-2-yl}piperazine

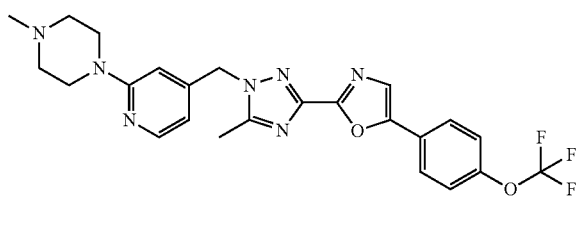 [SMILES: Cc1nc(-c2ncc(-c3ccc(OC(F)(F)F)cc3)o2)nn1Cc1ccnc(N2CCN(C)CC2)c1]

Steps 1 to 4

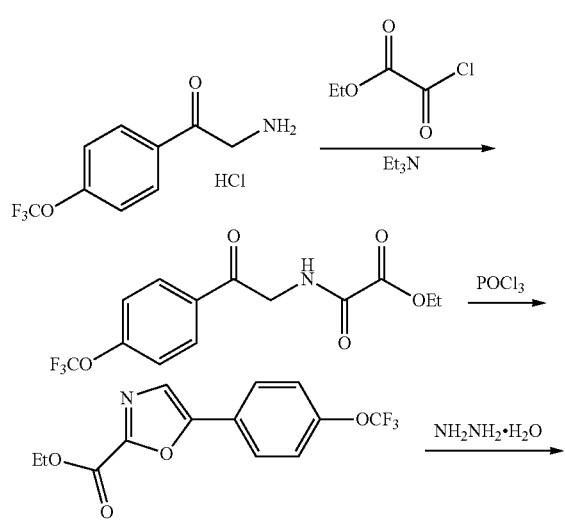

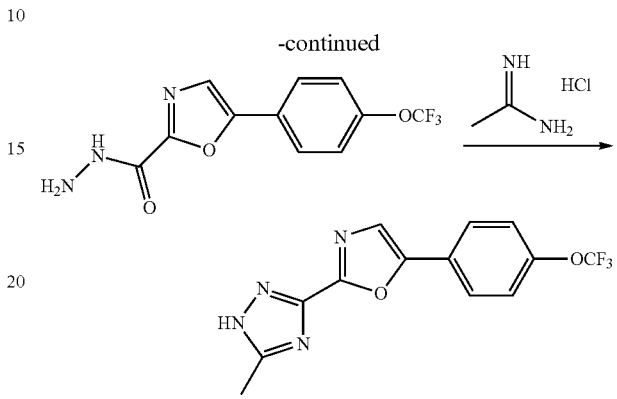

Step 1: Ethyl 2-oxo-2-(2-oxo-2-(4-(trifluoromethoxy)phenyl)ethylamino)acetate To a solution of 2-amino-1-(4-(trifluoromethoxy)phenyl)ethanone hydrochloride (9.5 g, 37 mmol) in DCM (150 mL) at 0° C. was added dropwise ethyl 2-chloro-2-oxoacetate (5.6 g, 41 mmol), followed by Et3N (16 mL, 111 mmol). The mixture was stirred at RT for 16 h and then diluted with H2O (200 mL) and extracted with EtOAc (4×80 mL). The combined organic layers were washed with brine (50 mL), dried over Na2SO4, filtered and concentrated under reduced pressure, and the residue was purified by silica gel column chromatography (Petroleum ether:EtOAc=5:1 to 1:1) to give the title compound as a yellow solid (7.8 g, 66%). MS (ES+) C13H12F3NO5 requires: 319, found: 320 [M+H]+.

Step 2: Ethyl 5-(4-(trifluoromethoxy)phenyl)oxazole-2-carboxylate

A solution of ethyl 2-oxo-2-(2-oxo-2-(4-(trifluoromethoxy)phenyl)ethylamino)acetate (7.8 g, 24.4 mmol) in POCl3 (50 mL) was heated at 110° C. for 3 h, and then cooled to RT. The mixture was concentrated under reduced pressure, diluted with ice—H2O (100 mL) and extracted with EtOAc (3×50 mL). The combined organic layers were washed with H2O (2×50 mL), brine (30 mL), dried over Na2SO4, filtered and concentrated under reduced pressure. The residue was purified by silica gel column chromatography (Petroleum ether:EtOAc=5:1 to 2:1) to give the title compound as a light yellow solid (6.4 g, 87%). MS (ES+) C13H10F3NO4 requires: 301, found: 302 [M+H]+.

Step 3: 5-(4-(trifluoromethoxy)phenyl)oxazole-2-carbohydrazide

To a solution of ethyl 5-(4-(trifluoromethoxy)phenyl)oxazole-2-carboxylate (6.4 g, 21.2 mmol) in EtOH (30 mL), was added dropwise hydrazine hydrate (6 mL, 84% in H2O) while stirring at RT. The mixture was then stirred for further 16 h at RT and then concentrated under reduced pressure to half volume. Upon addition of H₂O (30 mL) a yellow solid precipitated, which was filtered, washed with H₂O (3×30 mL) and dried to afford the title compound as a light yellow solid (4.6 g, 75%). MS (ES⁺) $C_{11}H_8F_3N_3O_3$ requires: 287, found: 288 [M+H]⁺;

Step 4: 2-(5-methyl-1H-1,2,4-triazol-3-yl)-5-(4-(trifluoromethoxy)phenyl)oxazole A mixture of 5-(4-(trifluoromethoxy)phenyl)oxazole-2-carbohydrazide (4.6 g, 16 mmol), acetimidamide hydrochloride (2.27 g, 24 mmol) and NaOH (1.1 g, 27.2 mmol) in dry THF (100 mL) was stirred at reflux for 16 h. The mixture was then cooled to RT, concentrated under reduced pressure and the residue was purified by silica gel column chromatography (Petroleum ether:EtOAc=5:1 to 1:1) to afford the title compound as a yellow solid (4.0 g, 80%). MS (ES⁺) $C_{13}H_9F_3N_4O_2$ requires: 310, found: 311 [M+H]⁺; ¹H NMR (500 MHz, CDCl3) δ 7.78 (d, J=9.0 Hz, 2H), 7.51 (s, 1H), 7.28 (d, J=9.0 Hz, 2H), 3.79 (s, 1H), 2.65 (s, 3H).

Steps 5 to 6

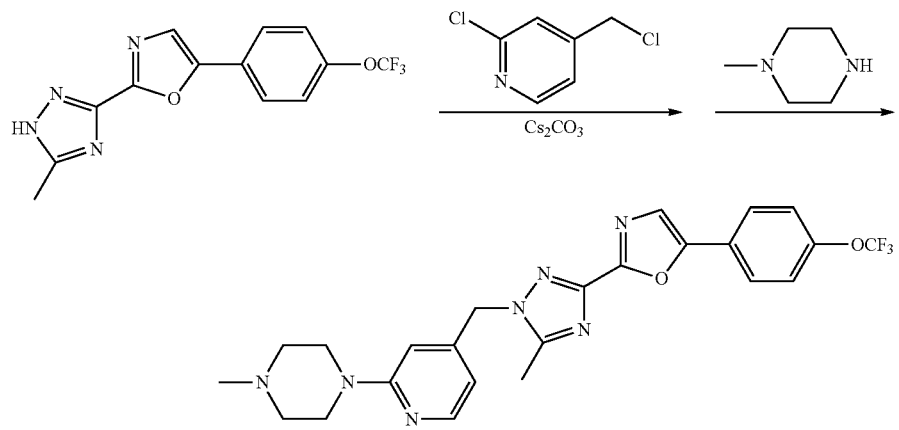

Step 5: 2-(1-((2-chloropyridin-4-yl)methyl)-5-methyl-1H-1,2,4-triazol-3-yl)-5-(4-(trifluoromethoxy)phenyl)oxazole A mixture of 2-(5-methyl-1H-1,2,4-triazol-3-yl)-5-(4-(trifluoromethoxy)phenyl)oxazole (260 mg, 0.83 mmol), 2-chloro-4-(chloromethyl)pyridine (270 mg, 1.66 mmol) and Cs₂CO₃ (820 mg, 2.5 mmol) in dry DMF (5 mL) was stirred at RT for 72 h. The mixture was then diluted with H₂O (50 mL) and extracted with DCM/MeOH (20/1 v/v, 4×50 mL). The combined organic layers were washed with H₂O (3×40 mL), brine (50 mL), dried over Na₂SO₄, filtered and concentrated under reduced pressure to give the crude product, which was purified by silica gel chromatography (DCM:MeOH=20:1 to 15:1) to afford the title compound as a white solid (100 mg, 27%). MS (ES⁺) $C_{19}H_{13}ClF_3N_5O_2$ requires: 435, found: 436 [M+H]⁺.

Step 6: 1-methyl-4-{4-[(5-methyl-3-{5-[4-(trifluoromethoxy)phenyl]-1,3-oxazol-2-yl}-1H-1,2,4-triazol-1-yl)methyl]pyridin-2-yl}piperazine A mixture of 2-(1-((2-chloropyridin-4-yl)methyl)-5-methyl-1H-1,2,4-triazol-3-yl)-5-(4-(trifluoromethoxy)phenyl)oxazole (60 mg, 0.14 mmol) and 1-methyl-piperazine (1 mL) in DMSO (2 mL) was stirred at 140° C. for 16 h under Ar atmosphere. The mixture was then cooled to RT, and purified by prep-HPLC (Mobile phase: A=0.1% TFA/H₂O, B=MeCN; Gradient: B=5%-95% in 8 min; Column: XBridge C18, 5 um, 30 mm×150 mm) to afford the title compound a solid. MS (ES⁺) $C_{24}H_{24}F_3N_7O_2$ requires: 499, found: 500 [M+H]⁺; ¹H NMR (500 MHz, CDCl3) δ 8.18 (d, J=5.0 Hz, 1H), 7.80 (d, J=9.0 Hz, 2H), 7.51 (s, 1H), 7.29 (d, J=9.0 Hz, 2H), 6.48 (d, J=5.0 Hz, 1H), 6.38 (s, 1H), 5.32 (s, 2H), 3.62 (m, 4H), 2.67 (m, 4H), 2.50 (s, 3H).

EXAMPLE 93

4-{4-[(5-methyl-3-{5-[4-(trifluoromethoxy)phenyl]-1,3-oxazol-2-yl}-1H-1,2,4-triazol-1-yl)methyl]pyridin-2-yl}morpholine

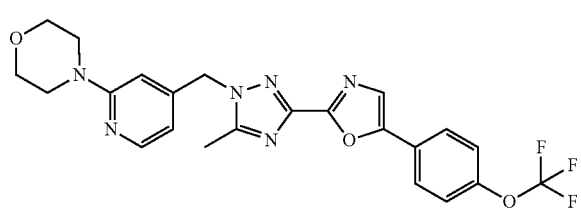 [SMILES: Cc1nc(-c2ncc(-c3ccc(OC(F)(F)F)cc3)o2)nn1Cc1ccnc(N2CCOCC2)c1]

Prepared as described for Example 92; MS (ES⁺) $C_{23}H_{21}F_3N_6O_3$ requires: 486, found: 487 [M+H]⁺; ¹H NMR (500 MHz, CDCl3) δ 8.17 (d, J=5.0 Hz, 1H), 7.80 (d, J=9.0 Hz, 2H), 7.51 (s, 1H), 7.30 (d, J=9.0 Hz, 2H), 6.46 (d, J=5.0 Hz, 1H), 6.35 (s, 1H), 5.33 (s, 2H), 3.78 (m, 4H), 3.47 (m, 4H), 2.50 (s, 3H).

EXAMPLE 94

5-(5-Methyl-1-(3-(4-(methylsulfonyl)piperidin-1-yl)benzyl)-1H-1,2,4-triazol-3-yl)-3-(4-(trifluoromethoxy)phenyl)isoxazole

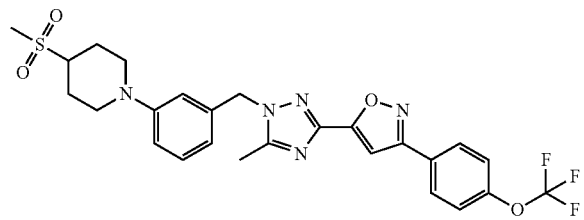 [SMILES: Cc1nc(-c2cc(-c3ccc(OC(F)(F)F)cc3)no2)nn1Cc1cccc(N2CCC(S(C)(=O)=O)CC2)c1]

Steps 1 to 5

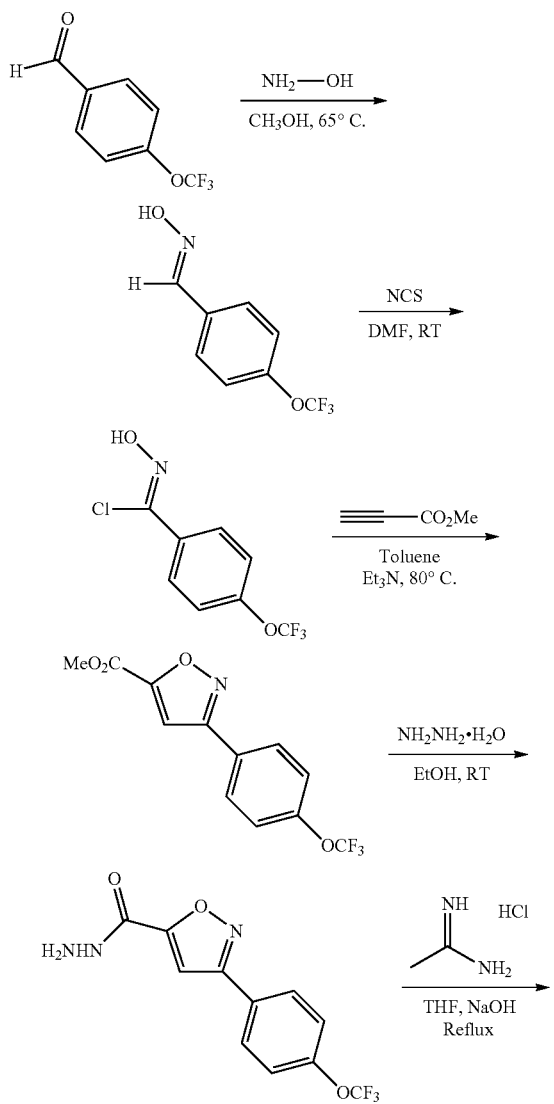

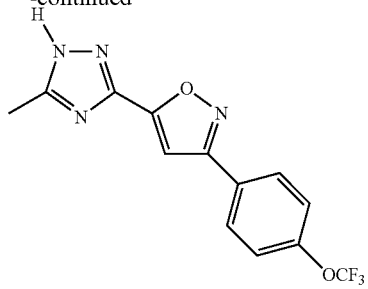

Step 1: (E)-4-(trifluoromethoxy)benzaldehyde oxime

A mixture of 4-(trifluoromethoxy)benzaldehyde (9.5 g, 50 mmol) and hydroxylamine hydrochloride (5.3 g, 75 mmol) in methanol (80 mL) was heated at 65° C. for 2 h. The volatiles were removed under reduced pressure and the residue was dissolved in EtOAc, and washed with H$_2$O, brine. The organic layer was dried over Na$_2$SO$_4$, filtered and concentrated under reduced pressure. The solid thus obtained was then recrystallized from EtOAc and petroleum ether to afford the title compound (9.5 g, 93%) as an off-white solid. $^1$H NMR (500 MHz, CDCl$_3$) δ 8.08 (s, 1H), 7.52 (d, J=7.2 Hz, 2H), 7.15 (d, J=6.8 Hz, 2H).

Step 2: (Z)—N-hydroxy-4-(trifluoromethoxy)benzimidoyl chloride

To a solution of 4-(trifluoromethoxy)benzaldehyde oxime (9.5 g, 46 mmol) in DMF (80 ml) was added N-chlorosuccinimide (8.0 g, 60 mmol) and the resulting mixture was stirred at RT for 5 h. The volatiles were removed under reduced pressure and the residue was dissolved in EtOAc, and washed with H$_2$O, brine. The organic layer was dried over Na$_2$SO$_4$, filtered and concentrated under reduced pressure. The solid residue was used without further purification for the following step. $^1$H NMR (500 MHz, CDCl$_3$) δ 7.78 (d, J=7.2 Hz, 2H), 7.13 (d, J=6.8 Hz, 2H).

Step 3: Methyl 3-(4-(trifluoromethoxy)phenyl)isoxazole-5-carboxylate

To a mixture of N-hydroxy-4-(trifluoromethoxy)benzimidoyl chloride (1.2 g, 5 mmol) and methyl propiolate (0.9 mL, 10 mmol) in toluene (12 mL) was added Et$_3$N (0.73 mL, 5.3 mmol) dropwise over 10 minutes. The resulting reaction mixture was heated at 80° C. for 2.5 h and then diluted with EtOAc (20 mL). The organic layer was washed with 0.1 M aq. HCl, H$_2$O, and brine. The organic layer was dried over anhydrous Na$_2$SO$_4$, filtered and concentrated under reduced pressure. The residue was crystallized from CHCl$_3$ and petroleum ether to afford the title compound (1.1 g, 77%). MS (ES$^+$) C$_{12}$H$_8$F$_3$NO$_4$ requires: 287, found: 288 [M+H]$^+$. $^1$H NMR (500 MHz, CDCl$_3$) δ 7.88 (d, J=6.8 Hz, 2H), 7.33 (d, J=6.8 Hz, 2H), 7.25 (s, 1H).

Step 4: 3-(4-(trifluoromethoxy)phenyl)isoxazole-5-carbohydrazide

To a solution of methyl 3-(4-(trifluoromethoxy)phenyl)isoxazole-5-carboxylate (3.0 g, 10.5 mmol) in EtOH (80 mL) was added NH$_2$NH$_2$.H$_2$O (3.3 mL, 52.3 mmol). The resulting mixture was stirred at RT for 16 h and then concentrated under reduced pressure. The residue was crystallized from CHCl₃ and petroleum ether to afford the title compound (2.7 g, 90%). MS (ES⁺) $C_{11}H_8F_3N_3O_3$ requires: 287, found: 288 [M+H]⁺.

Step 5: 5-(5-methyl-1H-1,2,4-triazol-3-yl)-3-(4-(trifluoromethoxy)phenyl)isoxazole To a mixture of 3-(4-(trifluoromethoxy)phenyl)isoxazole-5-carbohydrazide (2.4 g, 8.5 mmol) and acetimidamide hydrochloride (1.2 g, 12.8 mmol) in dry THF (60 mL), was added NaOH (512 mg, 12.8 mmol). The mixture was then refluxed for 16 h, then cooled to RT and concentrated under reduced pressure. The residue was purified by silica gel chromatography to afford the title compound as a white solid (1.9 g, 71%). ¹H NMR (500 MHz, DMSO-d₆) δ 8.12 (d, J=7.2 Hz, 2H), 7.58 (s, 1H). 7.54 (d, J=6.4 Hz, 2H), 2.46 (s, 3H). MS (ES⁺) $C_{13}H_9F_3N_4O_2$ requires: 310, found: 311 [M+H]⁺.

Step 6

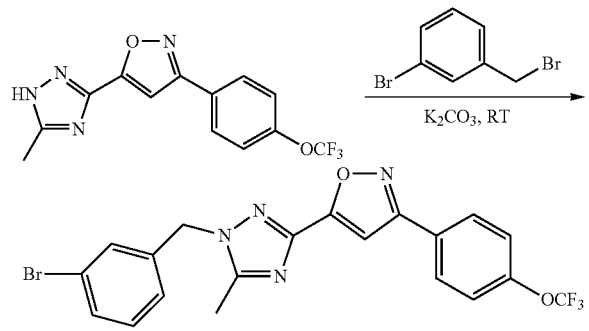

5-(1-(3-bromobenzyl)-5-methyl-1H-1,2,4-triazol-3-yl)-3-(4-(trifluoromethoxy)phenyl)-isoxazole To a solution of 5-(5-methyl-1H-1,2,4-triazol-3-yl)-3-(4-(trifluoromethoxy)phenyl)-isoxazole (257 mg, 0.83 mmol) and 1-bromo-3-(bromomethyl)benzene (206 mg, 0.83 mmol) in DMF (20 mL), was added K₂CO₃ (286 mg, 2.07 mmol). The mixture was stirred at RT for 16 h, then diluted with H₂O (50 mL) and extracted with EtOAc (3×30 mL). The combined organic layers were washed with H₂O (20 mL) and brine (20 mL), dried over Na₂SO₄, filtered and concentrated under reduced pressure; the residue was purified by silica gel chromatography (Petroleum ether: EtOAc=1:1) to give the title compound as a white solid (230 mg, 58%). MS (ES⁺) $C_{20}H_{14}BrF_3N_4O_2$ requires: 478, found: 479 [M+H]⁺.

Step 7

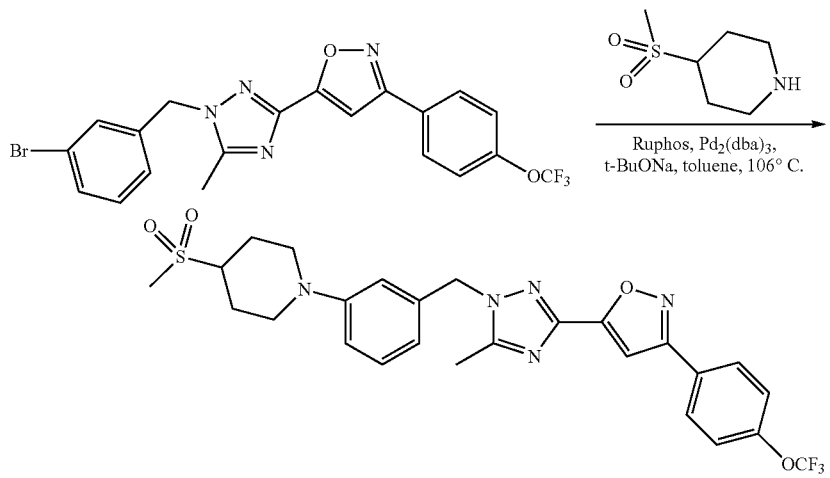

5-(5-methyl-1-(3-(4-(methylsulfonyl)piperidin-1-yl)benzyl)-1H-1,2,4-triazol-3-yl)-3-(4-(trifluoromethoxy)phenyl)isoxazole To a solution of 5-(1-(3-bromobenzyl)-5-methyl-1H-1,2,4-triazol-3-yl)-3-(4-(trifluoromethoxy)phenyl)-isoxazole (48 mg, 0.1 mmol) in toluene (5 ml) were added 4-(methylsulfonyl)-piperidine (33 mg, 0.2 mmol), Ruphos (4.8 mg, 0.01 mmol), Pd₂(dba)₃ (9.2 mg, 0.01 mmol) and t-BuONa (19.2 mg, 0.2 mmol). The mixture was stirred under Ar atmosphere at 106° C. for 16 h, then cooled to RT, diluted with H₂O (20 mL), and extracted with EtOAc (3×10 mL). The combined organic layers were washed with H₂O (10 mL) and brine (10 mL), dried over Na₂SO₄, filtered and concentrated under reduced pressure; the residue was purified by silica gel chromatography (Petroleum ether: EtOAc=1:1) to give the title compound as a white solid; MS (ES⁺) $C_{26}H_{26}F_3N_5O_4S$ requires: 561, found: 562 [M+H]⁺; ¹H NMR (500 MHz, CDCl₃) δ 7.91 (d, J=6.8 Hz, 2H), 7.33 (d, J=6.4 Hz, 2H), 7.25 (m, 1H), 7.10 (s, 1H), 6.89 (d, J=6.4 Hz, 1H), 6.80 (s, 1H), 6.72 (d, J=6.0 Hz, 1H), 5.34 (s, 2H), 3.82 (bd, J=10.0 Hz, 2H), 2.96 (m, 1H), 2.86 (s, 3H), 2.77 (m, 2H), 2.50 (s, 3H), 2.24 (bd, J=10.0 Hz, 2H), 1.95 (m, 2H).

EXAMPLE 95

5-(5-Methyl-1-((2-(4-(methylsulfonyl)piperidin-1-yl)pyridin-4-yl)methyl)-1H-1,2,4-triazol-3-yl)-3-(4-(trifluoromethoxy)phenyl)isoxazole

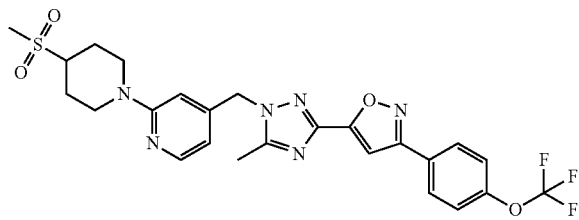

(161 mg, 1.0 mmol) in DMF (20 mL), was added $K_2CO_3$ (345 mg, 2.5 mmol). The mixture was stirred at RT for 16 h, then diluted with $H_2O$ (50 mL) and extracted with EtOAc (3×30 mL). The combined organic layers were washed with $H_2O$ (20 mL) and brine (20 mL), dried over $Na_2SO_4$, filtered and concentrated under reduced pressure. The residue was purified by silica gel chromatography (Petroleum ether: EtOAc=1:1) to give the title compound as a white solid (225 mg, 52%). $^1$H NMR (500 MHz, CDCl$_3$) δ 8.41 (d, J=4.0 Hz, 1H), 7.91 (d, J=6.8 Hz, 2H), 7.33 (d, J=6.4 Hz, 2H), 7.15 (s, 1H), 7.13 (s, 1H), 7.05 (d, J=4.0 Hz, 1H), 5.40 (s, 2H), 2.53 (s, 3H). MS (ES$^+$) $C_{19}H_{13}ClF_3N_5O_2$ requires: 435, found: 436 [M+H]$^+$.

Step 2

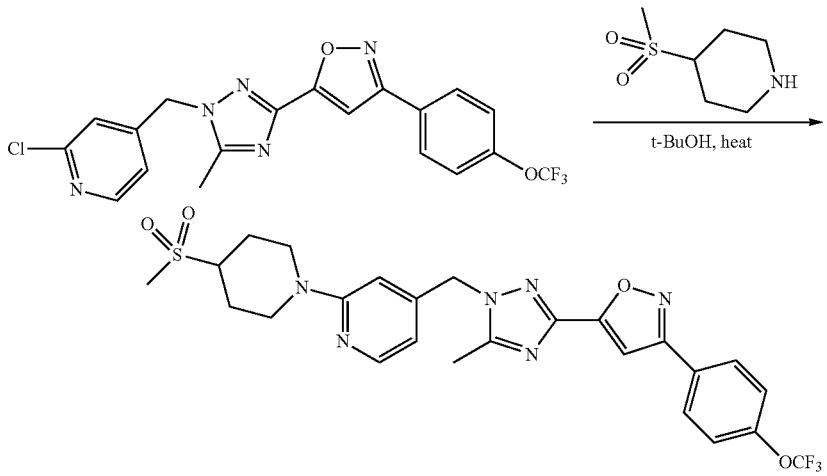

Step 1

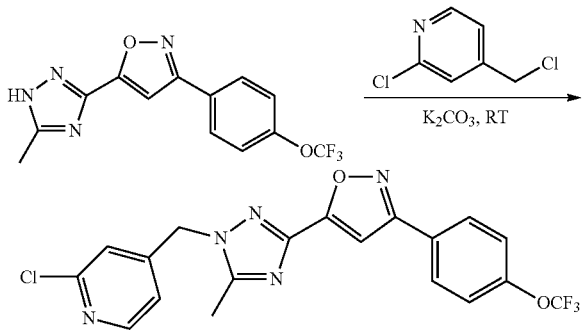

5-(1-(2-chloropyridin-4-yl)methyl)-5-methyl-1H-1,2,4-triazol-3-yl)-3-(4-(trifluoromethoxy)phenyl)-isoxazole To a solution of 5-(5-methyl-1H-1,2,4-triazol-3-yl)-3-(4-(trifluoromethoxy)phenyl)-isoxazole (Example 94, Step 5, 310 mg, 1.0 mmol) and 2-chloro-4-(chloromethyl)pyridine 5-(5-methyl-1-((2-(4-(methylsulfonyl)piperidin-1-yl)pyridin-4-yl)methyl)-1H-1,2,4-triazol-3-yl)-3-(4-(trifluoromethoxy)phenyl)isoxazole To a solution of 5-(1-(2-chloropyridin-4-yl)methyl)-5-methyl-1H-1,2,4-triazol-3-yl)-3-(4-(trifluoromethoxy)phenyl)-isoxazole (50 mg, 0.11 mmol) in t-BuOH (0.5 mL) was added 4-(methylsulfonyl)-piperidine (33 mg, 0.2 mmol). The mixture was stirred at 140° C. for 16 h, then cooled to RT, diluted with $H_2O$ (20 mL), and extracted with EtOAc (3×10 mL). The combined organic layers were washed with $H_2O$ (10 mL) and brine (10 mL), dried over $Na_2SO_4$, filtered and concentrated under reduced pressure; the residue was purified by silica gel chromatography (Petroleum ether: EtOAc=1:1) to give the title compound as a white solid; MS (ES$^+$) $C_{25}H_{25}F_3N_6O_4S$ requires: 562, found: 563 [M+H]$^+$; $^1$H NMR (500 MHz, CDCl$_3$) δ 8.16 (d, J=4.0 Hz, 1H), 7.91 (d, J=6.8 Hz, 2H), 7.33 (d, J=6.4 Hz, 2H), 7.12 (s, 1H), 6.44 (s, 1H), 6.43 (d, J=4.0 Hz, 1H), 5.30 (s, 2H), 4.48 (bd, J=10.8 Hz, 2H), 3.08 (m, 1H), 2.91 (m, 2H), 2.85 (s, 3H), 2.51 (s, 3H), 2.21 (bd, J=10.4 Hz, 2H), 1.83 (m, 2H).

EXAMPLE 96

3-(5-Methyl-1-(3-(4-(methylsulfonyl)piperidin-1-yl)benzyl)-1H-1,2,4-triazol-3-yl)-5-(4-(trifluoromethoxy)phenyl)isoxazole

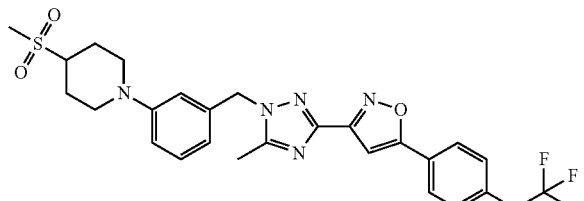

Steps 1 to 4

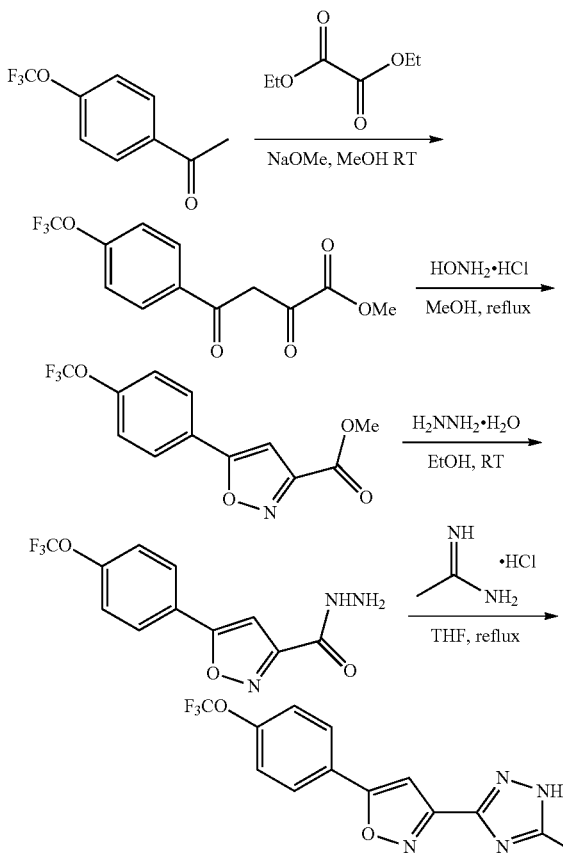

Step 1: Methyl 2,4-dioxo-4-(4-(trifluoromethoxy)phenyl)butanoate

To a solution of 1-(4-(trifluoromethoxy)phenyl)ethanone (5.0 g, 24.5 mmol) and diethyl oxalate (4.3 g, 29.4 mmol) in MeOH (60 mL) was added NaOMe (30% in MeOH, 5.3 g, 29.4 mmol). The mixture was stirred at RT for 4 h and then concentrated under reduced pressure. The residue was treated with 2N aq. HCl (15 mL) and extracted with EtOAc (2×100 mL). The organic layer was washed with brine (100 mL), dried over $Na_2SO_4$, filtered, and concentrated under reduced pressure to afford methyl 2,4-dioxo-4-(4-(trifluoromethoxy)phenyl)butanoate as a brown oil (6.85 g, 96%), which was used in the next step without further purification. MS (ES$^+$) $C_{12}H_9F_3O_5$ requires: 290, found: 291 [M+H]$^+$.

Step 2: Methyl 5-(4-(trifluoromethoxy)phenyl)isoxazole-3-carboxylate

A mixture of methyl 2,4-dioxo-4-(4-(trifluoromethoxy)phenyl)butanoate (6.85 g, 23.6 mmol) and $NH_2OH \cdot HCl$ (4.92 g, 70.8 mmol) in MeOH (120 mL) was refluxed for 4 h. The volatiles were removed under reduced pressure, the residue was taken up in $CHCl_3$ (200 mL) and washed with $H_2O$ (50 mL) and brine (50 mL). The organic layer was dried over $Na_2SO_4$, filtered and concentrated under reduced pressure to give the title compound (6.50 g, 95.6%), which was used in the next step without further purification. MS (ES$^+$) $C_{12}H_8F_3NO_4$ requires: 287, found: 288 [M+H]$^+$.

Step 3: 5-(4-(Trifluoromethoxy)phenyl)isoxazole-3-carbohydrazide

To a solution of methyl 5-(4-(trifluoromethoxy)phenyl)isoxazole-3-carboxylate (6.50 g, 22.6 mmol) in EtOH (200 mL) was added $NH_2NH_2 \cdot H_2O$ (80%, 7 mL, 113 mmol) and the mixture was stirred at RT for 3 h. The mixture was then concentrated under reduced pressure and purified by silica gel chromatography (Petroleum ether:EtOAc=1:2) to give the title compound as a white solid (4.4 g, 67.8%). MS (ES$^+$) $C_{11}H_8F_3N_3O_3$ requires: 287, found: 288 [M+H]$^+$.

Step 4: 3-(5-Methyl-2H-1,2,4-triazol-3-yl)-5-(4-(trifluoromethoxy)phenyl)isoxazole To a solution of 5-(4-(trifluoromethoxy)phenyl)isoxazole-3-carbohydrazide (4.4 g, 15.3 mmol) and acetimidamide hydrochloride (2.2 g, 23.0 mmol) in dry THF (100 mL) was added NaOH (920 mg, 23.0 mmol), and the resulting mixture was refluxed for 16 h. The solution was then cooled to RT and concentrated under reduced pressure, the residue was partitioned between $H_2O$ (80 mL) and EtOAc (2×100 mL). The organic layer was dried over $Na_2SO_4$, filtered and concentrated under reduced pressure. The residue was purified by silica gel chromatography (Petroleum ether:EtOAc=1:2) to afford the title compound as a yellow solid (2.1 g, 44.3%). MS (ES$^+$) $C_{13}H_9F_3N_4O_2$ requires: 310, found: 311 [M+H]$^+$.

Step 5

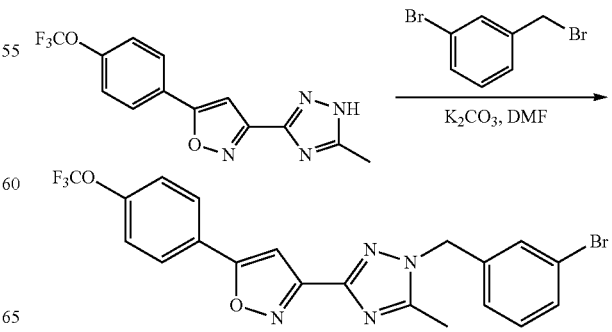

3-(1-(3-Bromobenzyl)-5-methyl-1H-1,2,4-triazol-3-yl)-5-(4-(trifluoromethoxy) phenyl)isoxazole To a suspension of 3-(5-methyl-2H-1,2,4-triazol-3-yl)-5-(4-(trifluoromethoxy)phenyl) isoxazole (400 mg, 1.3 mmol) and $K_2CO_3$ (445 mg, 3.3 mmol) in DMF (5 mL) was added 1-bromo-3-(bromomethyl)benzene (323 mg, 1.3 mmol). The mixture was stirred at RT for 2 h, then diluted with $H_2O$ (30 mL) and extracted with EtOAc (2×40 mL). The combined organic layers were washed with $H_2O$ (20 mL) and concentrated under reduced pressure. The residue was purified by silica gel chromatography (Petroleum ether:EA=1:1) to afford the title compound as a light yellow solid (350 mg, 56.6%). MS (ES$^+$) $C_{20}H_{14}BrF_3N_4O_2$ requires: 478, found: 479 [M+H]$^+$.

Step 6

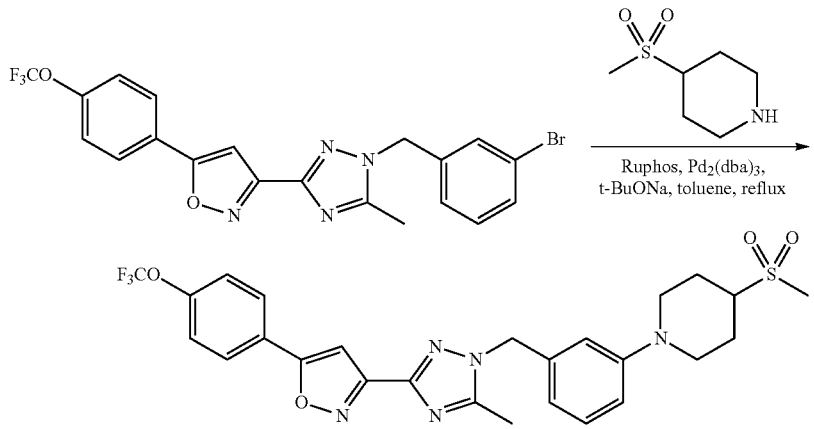

3-(5-Methyl-1-(3-(4-(methylsulfonyl)piperidin-1-yl)benzyl)-1H-1,2,4-triazol-3-yl)-5-(4-(trifluoromethoxy)phenyl)isoxazole To a solution of 3-(1-(3-bromobenzyl)-5-methyl-1H-1,2,4-triazol-3-yl)-5-(4-(trifluoromethoxy)phenyl)isoxazole (100 mg, 0.21 mmol) in toluene (3 mL) were added 2-dicyclohexylphosphino-2',6'-diisopropoxy-1,1'-biphenyl (10 mg, 0.021 mmol), tris(dibenzylideneacetone)dipalladium (19 mg, 0.021 mmol), 4-(methylsulfonyl)piperidine (70 mg, 0.42 mmol) and sodium tert-butoxide (40 mg, 0.42 mmol). The mixture was heated at 100° C. under inert atmosphere for 5 h. The mixture was concentrated under reduced pressure, diluted with $H_2O$ (20 mL) and extracted with EtOAc (3×20 mL). The combined organic layers were washed with $H_2O$ (20 mL) and brine (20 mL), dried over $Na_2SO_4$, filtered, and concentrated under reduced pressure to afford the crude product, which was purified by prep-HPLC (Mobile phase: A=10 mM ammonium bicarbonate/$H_2O$, B=MeCN; Gradient: B=60%-95% in 18 min; Column: XBridge C18, 5 um, 30 mm×150 mm) to afford the title compound as a yellow solid; MS (ES$^+$) $C_{26}H_{26}F_3N_5O_4S$ requires: 561, found: 562 [M+H]$^+$; $^1$H-NMR (500 MHz, CDCl$_3$) δ 7.88 (d, J=8.8 Hz, 2H), 7.34 (d, J=8.3 Hz, 2H), 7.24 (m, 1H), 7.04 (s, 1H), 6.88 (dd, J=8.2, 2.0 Hz, 1H), 6.78 (m, 1H), 6.72 (d, J=7.6 Hz, 1H), 5.34 (s, 2H), 3.81 (bd, J=12.6 Hz, 2H), 2.96 (m, 1H), 2.86 (s, 3H), 2.77 (m, 2H), 2.49 (s, 3H), 2.23 (bd, J=12.7 Hz, 2H), 1.97-1.91 (m, 2H).

EXAMPLE 97

3-(5-Methyl-1-((2-(4-(methylsulfonyl)piperidin-1-yl)pyridin-4-yl)methyl)-1H-1,2,4-triazol-3-yl)-5-(4-(trifluoromethoxy)phenyl)isoxazole

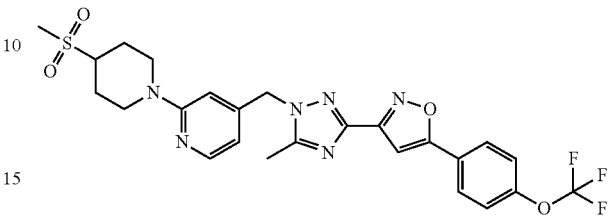

Step 1

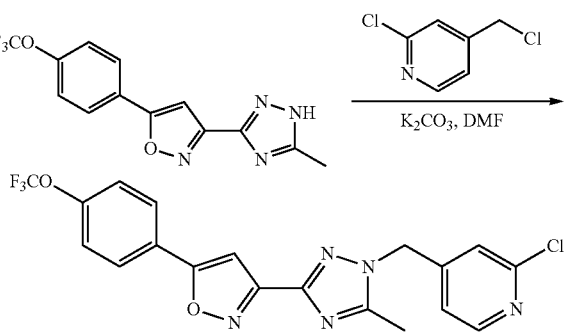

3-(1-((2-Chloropyridin-4-yl)methyl)-5-methyl-1H-1,2,4-triazol-3-yl)-5-(4-(trifluoromethoxy)phenyl)isoxazole To a mixture of 3-(5-methyl-2H-1,2,4-triazol-3-yl)-5-(4-(trifluoromethoxy) phenyl)isoxazole (Example 96, Step 4, 400 mg, 1.3 mmol) and $K_2CO_3$ (445 mg, 3.3 mmol) in DMF (5 mL) was added 2-chloro-4-(chloromethyl)pyridine (210 mg, 1.3 mmol). The mixture was stirred at RT for 2 h, then diluted with $H_2O$ (30 mL) and extracted with EtOAc (2×40 mL). The combined organic layers were washed with $H_2O$ (20 mL) and concentrated under reduced pressure to afford the crude product, which was purified by silica gel chromatography (Petroleum ether:EA=1:3) to give the title compound as a light yellow solid (300 mg, 53.3%). MS (ES$^+$) $C_{19}H_{13}ClF_3N_5O_2$ requires: 435, found: 436 [M+H]$^+$.

Step 2

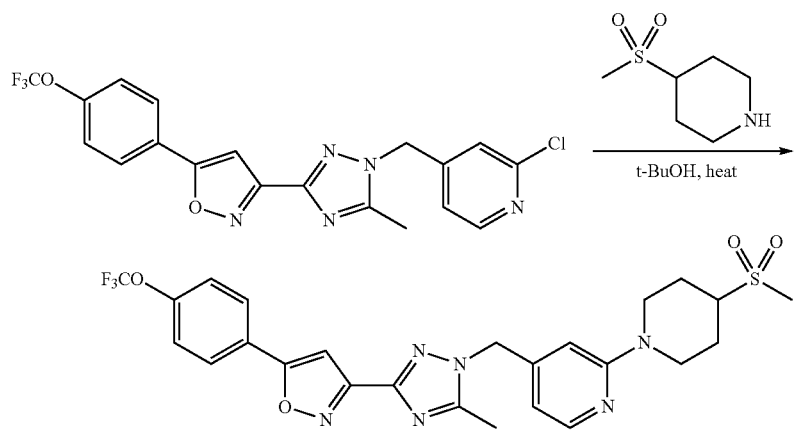

3-(5-methyl-1-((2-(4-(methylsulfonyl)piperidin-1-yl) pyridin-4-yl)methyl)-1H-1,2,4-triazol-3-yl)-5-(4-(trifluoromethoxy)phenyl)isoxazole To a solution of 3-(1-((2-chloropyridin-4-yl)methyl)-5-methyl-1H-1,2,4-triazol-3-yl)-5-(4-(trifluoromethoxy)phenyl)isoxazole (50 mg, 0.12 mmol) in t-BuOH (0.5 mL), was added 4-(methylsulfonyl)piperidine (75 mg, 0.46 mmol). The mixture was stirred at 140° C. for 16 h, then cooled to RT and purified by prep-HPLC (Mobile phase: A=10 mM ammonium bicarbonate/H$_2$O, B=MeCN; Gradient: B=60%- 95% in 18 min; Column: XBridge C18, 5 um, 30 mm×150 mm) to give the title compound as a white solid; MS (ES$^+$) C$_{25}$H$_{25}$F$_3$N$_6$O$_4$S requires: 562, found: 563 [M+H]$^+$; $^1$H NMR (500 MHz, CDCl$_3$) δ 8.16 (d, J=5.0 Hz, 1H), 7.88 (d, J=8.7 Hz, 2H), 7.34 (d, J=8.3 Hz, 2H), 7.03 (s, 1H), 6.43 (m, 2H), 5.30 (s, 2H), 4.47 (bd, J=13.4 Hz, 2H), 3.07 (m, 1H), 2.97-2.81 (m, 5H), 2.50 (s, 3H), 2.20 (bd, J=12.4 Hz, 2H), 1.86-1.79 (m, 2H).

The following compounds in Table 1 were synthesized and tested, and may generally be made by methods disclosed herein, and by methods known in the art.

TABLE 1

| Ex. No. | Structure | Name | MWt | [M + H] | Ex. Method |
|---|---|---|---|---|---|
| 98 | 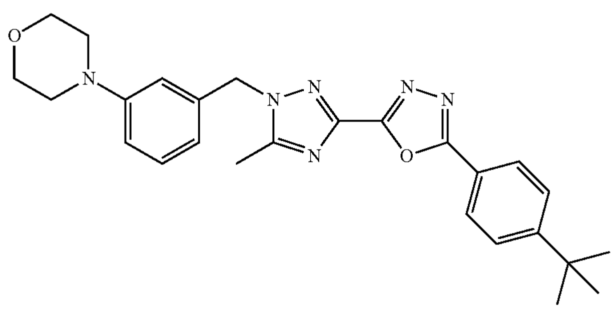 [SMILES: Cc1nc(-c2nnc(-c3ccc(C(C)(C)C)cc3)o2)nn1Cc1cccc(N2CCOCC2)c1] | 4-(3-((3-(5-(4-(tert-butyl)phenyl)-1,3,4-oxadiazol-2-yl)-5-methyl-1H-1,2,4-triazol-1-yl)methyl)phenyl)morpholine | 458 | 459 | 6 |
| 99 | 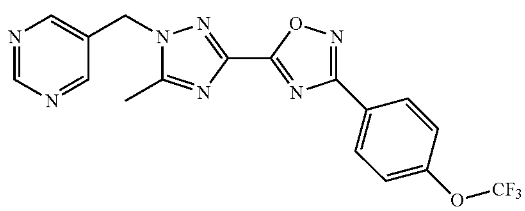 [SMILES: Cc1nc(-c2nc(-c3ccc(OC(F)(F)F)cc3)no2)nn1Cc1cncnc1] | 5-(5-methyl-1-(pyrimidin-5-ylmethyl)-1H-1,2,4-triazol-3-yl)-3-(4-(trifluoromethoxy)phenyl)-1,2,4-oxadiazole | 403 | 404 | 17 |
| 100 | 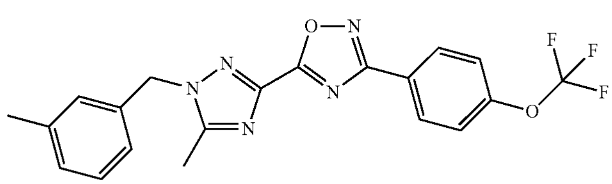 [SMILES: Cc1cccc(Cn2nc(-c3nc(-c4ccc(OC(F)(F)F)cc4)no3)nc2C)c1] | 5-(5-methyl-1-(3-methylbenzyl)-1H-1,2,4-triazol-3-yl)-3-(4-(trifluoromethoxy) | 415 | 416 | 17 |

| Ex. No. | Structure | Name | MWt | [M + H] | Ex. Method |
|---|---|---|---|---|---|
| | | phenyl)-1,2,4-oxadiazole | | | |
| 101 | 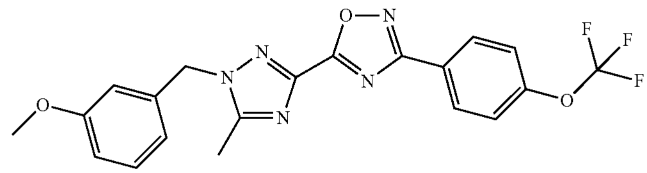 | 5-(1-(3-methoxy-benzyl)-5-methyl-1H-1,2,4-triazol-3-yl)-3-(4-(trifluoro-methoxy)phenyl)-1,2,4-oxadiazole | 431 | 432 | 17 |
| 102 | 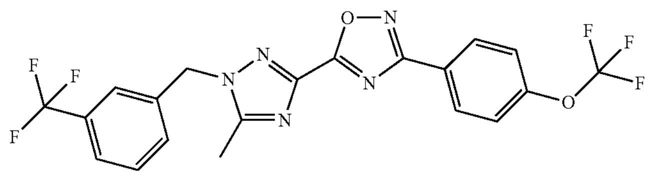 [SMILES: Cc1nc(-c2nc(-c3ccc(OC(F)(F)F)cc3)no2)nn1Cc1cccc(C(F)(F)F)c1] | 5-(5-methyl-1-(3-(trifluoro-methyl)benzyl)-1H-1,2,4-triazol-3-yl)-3-(4-(trifluoro-methoxy)phenyl)-1,2,4-oxadiazole | 469 | 470 | 17 |
| 103 | 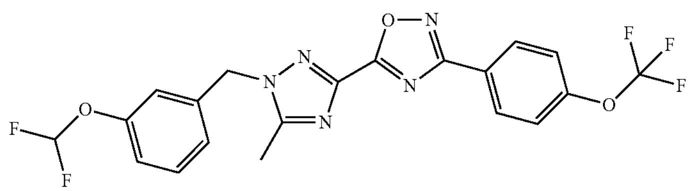 [SMILES: Cc1nc(-c2nc(-c3ccc(OC(F)(F)F)cc3)no2)nn1Cc1cccc(OC(F)F)c1] | 5-(1-(3-(difluoro-methoxy)benzyl)-5-methyl-1H-1,2,4-triazol-3-yl)-3-(4-(trifluoro-methoxy)phenyl)-1,2,4-oxadiazole | 467 | 468 | 19 |
| 104 | 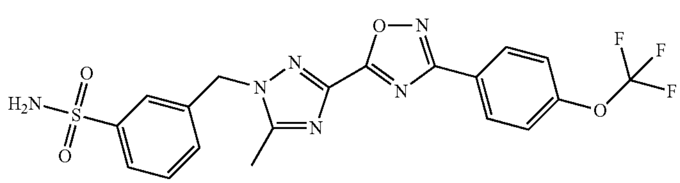 [SMILES: Cc1nc(-c2nc(-c3ccc(OC(F)(F)F)cc3)no2)nn1Cc1cccc(S(N)(=O)=O)c1] | 3-((5-methyl-3-(3-(4-(trifluoro-methoxy)phenyl)-1,2,4-oxadiazol-5-yl)-1H-1,2,4-triazol-1-yl)methyl)benzene-sulfonamide | 480 | 481 | 19 |
| 105 | 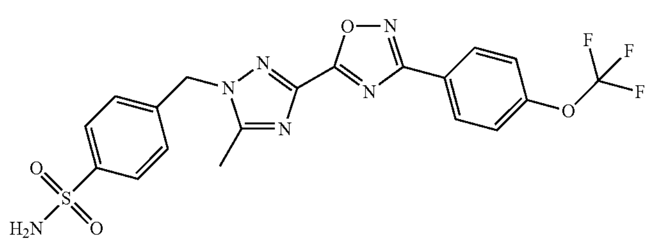 [SMILES: Cc1nc(-c2nc(-c3ccc(OC(F)(F)F)cc3)no2)nn1Cc1ccc(S(N)(=O)=O)cc1] | 4-((5-methyl-3-(3-(4-(trifluoro-methoxy)phenyl)-1,2,4-oxadiazol-5-yl)-1H-1,2,4-triazol-1-yl)methyl)benzene-sulfonamide | 480 | 481 | 19 |

TABLE 1-continued

| Ex. No. | Structure | Name | MWt | [M + H] | Ex. Method |
|---|---|---|---|---|---|
| 106 | 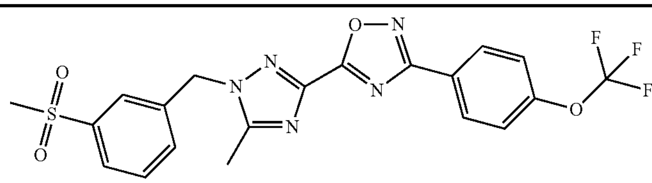 | 5-(5-methyl-1-(3-(methyl-sulfonyl)benzyl)-1H-1,2,4-triazol-3-yl)-3-(4-(trifluoro-methoxy)phenyl)-1,2,4-oxadiazole | 479 | 480 | 19 |
| 107 | 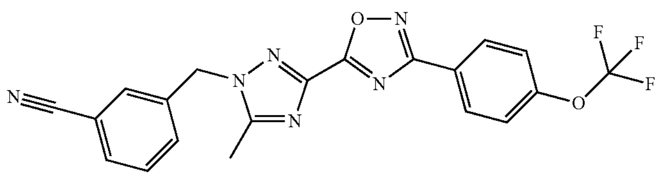 [SMILES: Cc1nc(-c2nc(-c3ccc(OC(F)(F)F)cc3)no2)nn1Cc1cccc(C#N)c1] | 3-((5-methyl-3-(3-(4-(trifluoro-methoxy)phenyl)-1,2,4-oxadiazol-5-yl)-1H-1,2,4-triazol-1-yl)methyl)benzonitrile | 426 | 427 | 19 |
| 108 | 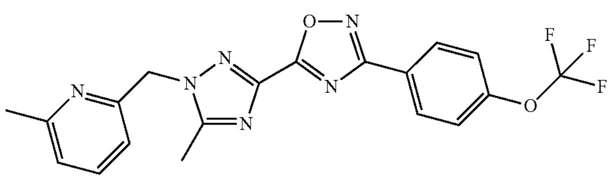 [SMILES: Cc1cccc(Cn2nc(-c3nc(-c4ccc(OC(F)(F)F)cc4)no3)nc2C)n1] | 5-(5-methyl-1-((6-methyl-pyridin-2-yl)methyl)-1H-1,2,4-triazol-3-yl)-3-(4-(trifluoro-methoxy)phenyl)-1,2,4-oxadiazole | 416 | 417 | 19 |
| 109 | 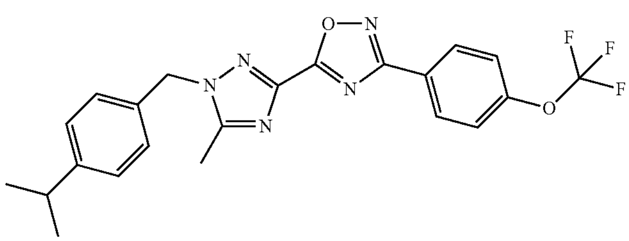 [SMILES: Cc1nc(-c2nc(-c3ccc(OC(F)(F)F)cc3)no2)nn1Cc1ccc(C(C)C)cc1] | 5-(1-(4-isopropyl-benzyl)-5-methyl-1H-1,2,4-triazol-3-yl)-3-(4-(trifluoro-methoxy)phenyl)-1,2,4-oxadiazole | 443 | 444 | 19 |
| 110 | 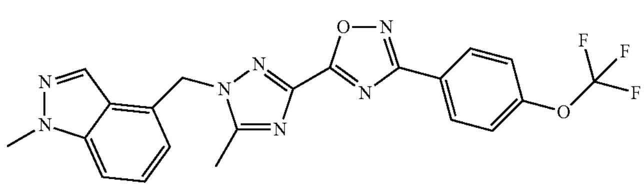 [SMILES: Cc1nc(-c2nc(-c3ccc(OC(F)(F)F)cc3)no2)nn1Cc1cccc2c1cnn2C] | 5-(5-methyl-1-((1-methyl-1H-indazol-4-yl)methyl)-1H-1,2,4-triazol-3-yl)-3-(4-(trifluoro-methoxy)phenyl)-1,2,4-oxadiazole | 455 | 456 | 19 |
| 111 | 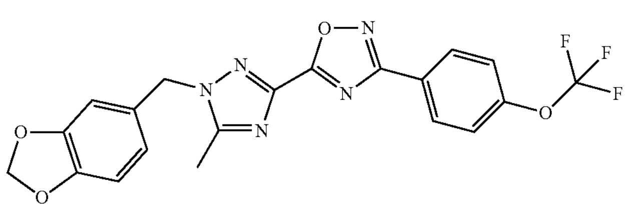 [SMILES: Cc1nc(-c2nc(-c3ccc(OC(F)(F)F)cc3)no2)nn1Cc1ccc2c(c1)OCO2] | 5-(1-(benzo[d][1,3]dioxol-5-ylmethyl)-5-methyl-1H-1,2,4-triazol-3-yl)-3-(4-(trifluoro-methoxy)phenyl)-1,2,4-oxadiazole | 445 | 446 | 19 |

TABLE 1-continued

| Ex. No. | Structure | Name | MWt | [M + H] | Ex. Method |
|---|---|---|---|---|---|
| 112 | 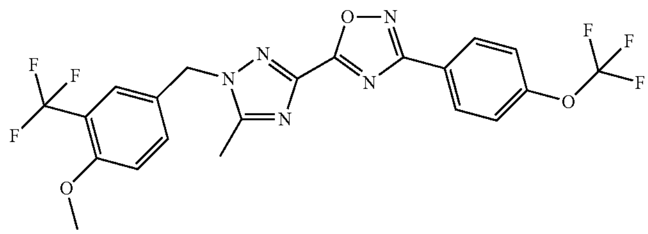 [SMILES: COc1ccc(Cn2nc(-c3nc(-c4ccc(OC(F)(F)F)cc4)no3)nc2C)cc1C(F)(F)F] | 5-(1-(4-methoxy-3-(trifluoromethyl)benzyl)-5-methyl-1H-1,2,4-triazol-3-yl)-3-(4-(trifluoromethoxy)phenyl)-1,2,4-oxadiazole | 499 | 500 | 19 |
| 113 | 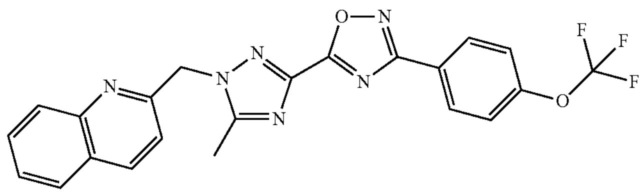 [SMILES: Cc1nc(-c2nc(-c3ccc(OC(F)(F)F)cc3)no2)nn1Cc1ccc2ccccc2n1] | 5-(5-methyl-1-(quinolin-2-ylmethyl)-1H-1,2,4-triazol-3-yl)-3-(4-(trifluoromethoxy)phenyl)-1,2,4-oxadiazole | 452 | 453 | 19 |
| 114 | 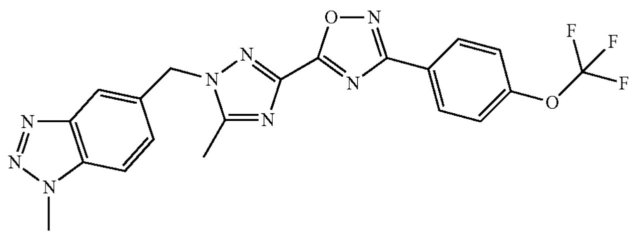 [SMILES: Cc1nc(-c2nc(-c3ccc(OC(F)(F)F)cc3)no2)nn1Cc1ccc2c(c1)nnn2C] | 5-(5-methyl-1-((1-methyl-1H-benzo[d][1,2,3]triazol-5-yl)methyl)-1H-1,2,4-triazol-3-yl)-3-(4-(trifluoromethoxy)phenyl)-1,2,4-oxadiazole | 456 | 457 | 19 |
| 115 | 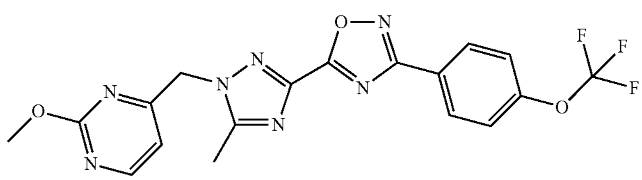 [SMILES: COc1nccc(Cn2nc(-c3nc(-c4ccc(OC(F)(F)F)cc4)no3)nc2C)n1] | 5-(1-((2-methoxypyrimidin-4-yl)methyl)-5-methyl-1H-1,2,4-triazol-3-yl)-3-(4-(trifluoromethoxy)phenyl)-1,2,4-oxadizole | 433 | 434 | 19 |
| 116 | 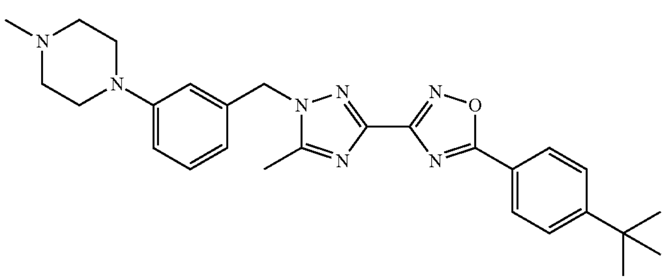 [SMILES: Cc1nc(-c2noc(-c3ccc(C(C)(C)C)cc3)n2)nn1Cc1cccc(N2CCN(C)CC2)c1] | 5-(4-(tert-butyl)phenyl)-3-(5-methyl-1-(3-(4-methylpiperazin-1-yl)benzyl)-1H-1,2,4-triazol-3-yl)-1,2,4-oxadiazole | 471 | 472 | 56 |
| 117 | 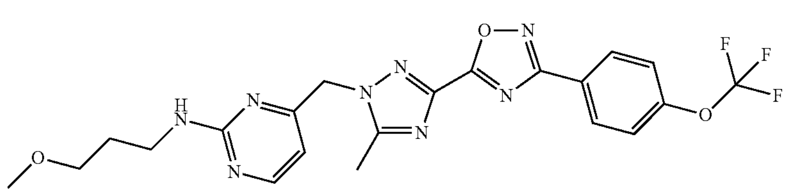 | N-(3-methoxypropyl)-4-((5-methyl-3-(3-(4-(trifluoromethoxy)phenyl)-1,2,4- | 490 | 491 | 20 |

TABLE 1-continued

| Ex. No. | Structure | Name | MWt | [M + H] | Ex. Method |
|---|---|---|---|---|---|
| | | oxadiazol-5-yl)-1H-1,2,4-triazol-1-yl)methyl)pyrimidin-2-amine | | | |
| 118 | 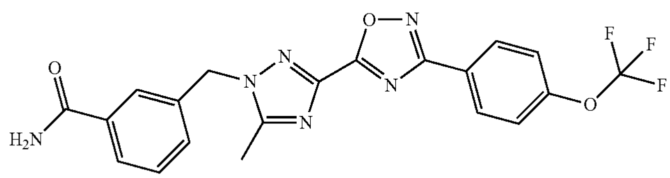 [SMILES: Cc1nc(-c2nc(-c3ccc(OC(F)(F)F)cc3)no2)nn1Cc1cccc(C(N)=O)c1] | 3-((5-methyl-3-(3-(4-(trifluoromethoxy)phenyl)-1,2,4-oxadiazol-5-yl)-1H-1,2,4-triazol-1-yl)methyl)benzamide | 444 | 445 | 13 |
| 119 | 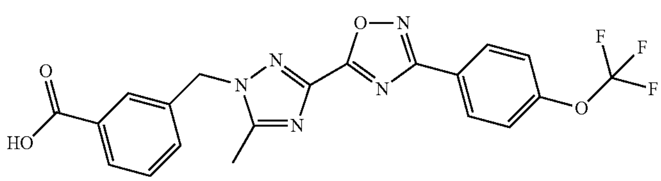 [SMILES: Cc1nc(-c2nc(-c3ccc(OC(F)(F)F)cc3)no2)nn1Cc1cccc(C(=O)O)c1] | 3-((5-methyl-3-(3-(4-(trifluoromethoxy)phenyl)-1,2,4-oxadiazol-5-yl)-1H-1,2,4-triazol-1-yl)methyl)benzoic acid | 445 | 446 | 19 |
| 120 | 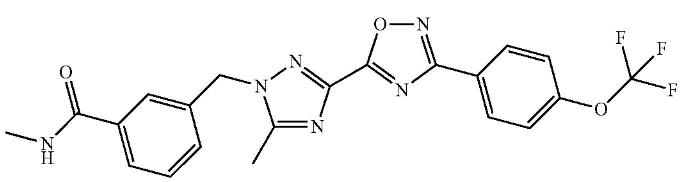 [SMILES: CNC(=O)c1cccc(Cn2nc(-c3nc(-c4ccc(OC(F)(F)F)cc4)no3)nc2C)c1] | N-methyl-3-[(5-methyl-3-{3-[4-(trifluoromethoxy)phenyl]-1,2,4-oxadiazol-5-yl}-1H-1,2,4-triazol-1-yl)methyl]benzamide | 458 | 459 | 13 |
| 121 | 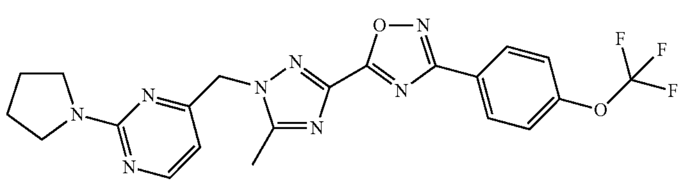 [SMILES: Cc1nc(-c2nc(-c3ccc(OC(F)(F)F)cc3)no2)nn1Cc1ccnc(N2CCCC2)n1] | 4-[(5-methyl-3-{3-[4-(trifluoromethoxy)phenyl]-1,2,4-oxadiazol-5-yl}-1H-1,2,4-triazol-1-yl)methyl]-2-(pyrrolidin-1-yl)pyrimidine | 472 | 473 | 20 |
| 122 | 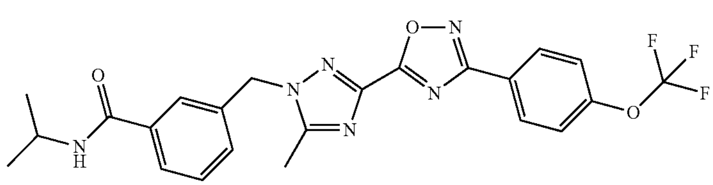 [SMILES: Cc1nc(-c2nc(-c3ccc(OC(F)(F)F)cc3)no2)nn1Cc1cccc(C(=O)NC(C)C)c1] | 3-[(5-methyl-3-{3-[4-(trifluoromethoxy)phenyl]-1,2,4-oxadiazol-5-yl}-1H-1,2,4-triazol-1-yl)methyl]-N-(propan-2-yl)benzamide | 486 | 487 | 13 |

TABLE 1-continued

| Ex. No. | Structure | Name | MWt | [M + H] | Ex. Method |
|---|---|---|---|---|---|
| 123 | 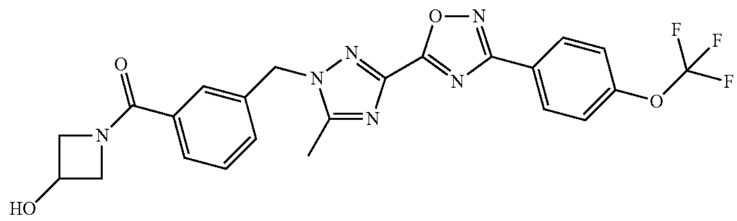 [SMILES: Cc1nc(-c2nc(-c3ccc(OC(F)(F)F)cc3)no2)nn1Cc1cccc(C(=O)N2CC(O)C2)c1] | 1-{3-[(5-methyl-3-{3-[4-(trifluoromethoxy)phenyl]-1,2,4-oxadiazol-5-yl}-1H-1,2,4-triazol-1-yl)methyl]benzoyl}azetidin-3-ol | 500 | 501 | 13 |
| 124 | 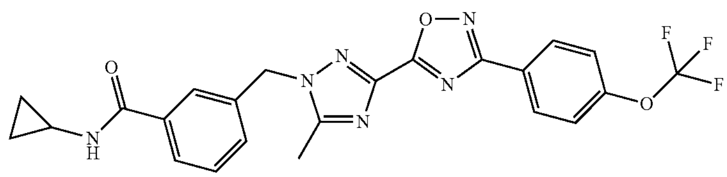 [SMILES: Cc1nc(-c2nc(-c3ccc(OC(F)(F)F)cc3)no2)nn1Cc1cccc(C(=O)NC2CC2)c1] | N-cyclopropyl-3-[(5-methyl-3-{3-[4-(trifluoromethoxy)phenyl]-1,2,4-oxadiazol-5-yl}-1H-1,2,4-triazol-1-yl)methyl]benzamide | 484 | 485 | 13 |
| 125 | 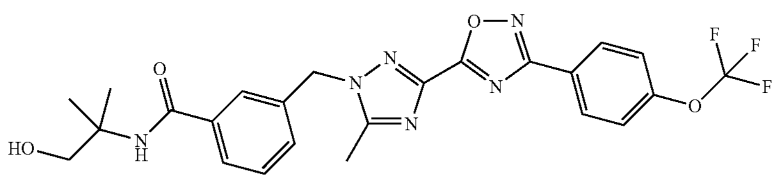 [SMILES: Cc1nc(-c2nc(-c3ccc(OC(F)(F)F)cc3)no2)nn1Cc1cccc(C(=O)NC(C)(C)CO)c1] | N-(1-hydroxy-2-methylpropan-2-yl)-3-[(5-methyl-3-{3-[4-(trifluoromethoxy)phenyl]-1,2,4-oxadiazol-5-yl}-1H-1,2,4-triazol-1-yl)methyl]benzamide | 516 | 517 | 13 |
| 126 | 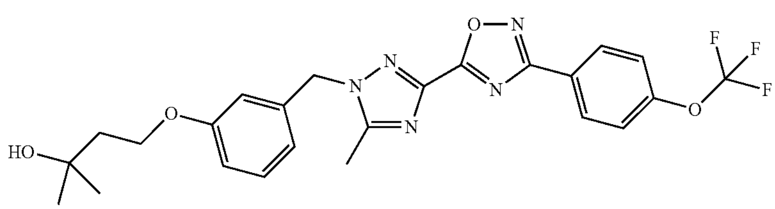 [SMILES: Cc1nc(-c2nc(-c3ccc(OC(F)(F)F)cc3)no2)nn1Cc1cccc(OCCC(C)(C)O)c1] | 2-methyl-4-{3-[(5-methyl-3-{3-[4-(trifluoromethoxy)phenyl]-1,2,4-oxadiazol-5-yl}-1H-1,2,4-triazol-1-yl)methyl]phenoxy}butan-2-ol | 503 | 504 | 60 |
| 127 | 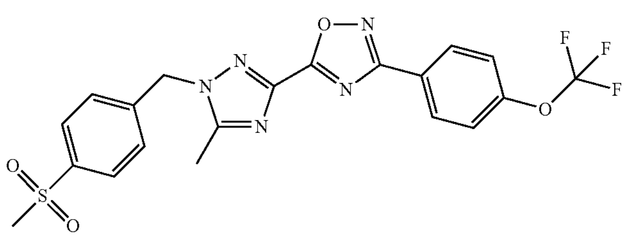 [SMILES: Cc1nc(-c2nc(-c3ccc(OC(F)(F)F)cc3)no2)nn1Cc1ccc(S(C)(=O)=O)cc1] | 5-{1-[(4-methanesulfonylphenyl)methyl]-5-methyl-1H-1,2,4-triazol-3-yl}-3-[4-(trifluoromethoxy)phenyl]-1,2,4-oxadiazole | 479 | 480 | 19 |

TABLE 1-continued

| Ex. No. | Structure | Name | MWt | [M + H] | Ex. Method |
|---|---|---|---|---|---|
| 128 | 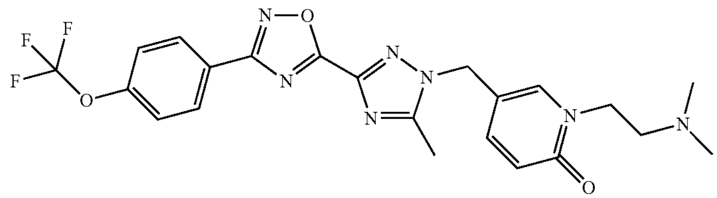 | 1-[2-(dimethyl-amino)ethyl]-5-[(5-methyl-3-{3-[4-(trifluoro-methoxy)phenyl]-1,2,4-oxadiazol-5-yl}-1H-1,2,4-triazol-1-yl)methyl]-1,2-dihydro-pyridin-2-one | 489 | 490 | 77a |
| 129 | 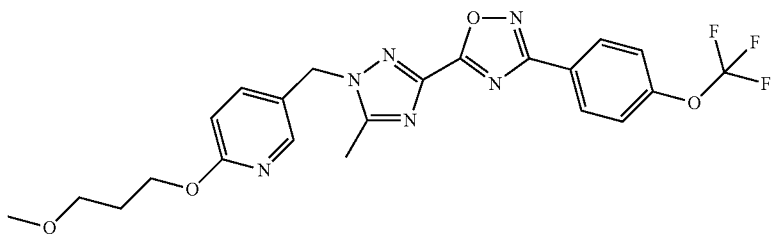 [SMILES: COCCCOc1ccc(Cn2nc(-c3nc(-c4ccc(OC(F)(F)F)cc4)no3)nc2C)cn1] | 2-(3-methoxy-propoxy)-5-[(5-methyl-3-{3-[4-(trifluoro-methoxy)phenyl]-1,2,4-oxadiazol-5-yl}-1H-1,2,4-triazol-1-yl)methyl]pyridine | 490 | 491 | 77b |
| 130 | 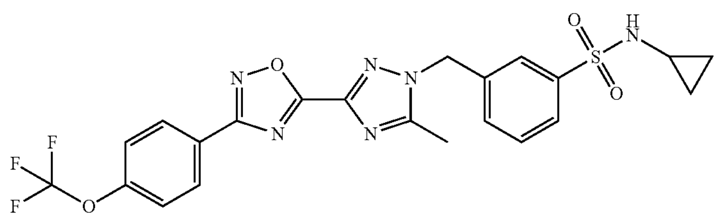 [SMILES: Cc1nc(-c2nc(-c3ccc(OC(F)(F)F)cc3)no2)nn1Cc1cccc(S(=O)(=O)NC2CC2)c1] | N-cyclopropyl-3-[(5-methyl-3-{3-[4-(trifluoro-methoxy)phenyl]-1,2,4-oxadiazol-5-yl}-1H-1,2,4-triazol-1-yl)methyl]benzene-1-sulfonamide | 520 | 521 | 79 |
| 131 | 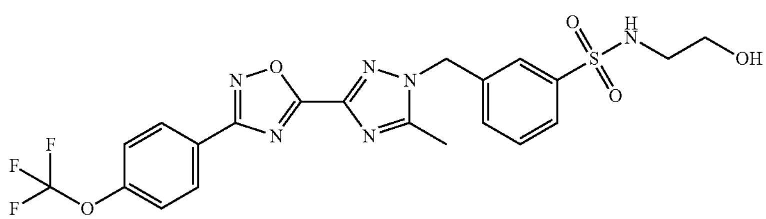 [SMILES: Cc1nc(-c2nc(-c3ccc(OC(F)(F)F)cc3)no2)nn1Cc1cccc(S(=O)(=O)NCCO)c1] | 2-hydroxy-S-(3-[(5-methyl-3-{3-[4-(trifluoro-methoxy)phenyl]-1,2,4-oxadiazol-5-yl}-1H-1,2,4-triazol-1-yl)methyl]phenyl}ethane-1-sulfonamido | 524 | 525 | 79 |
| 132 | 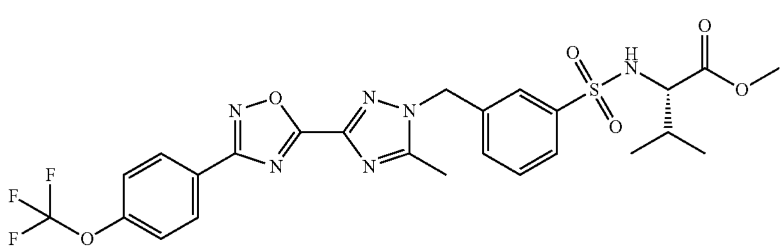 [SMILES: COC(=O)[C@@H](NS(=O)(=O)c1cccc(Cn2nc(-c3nc(-c4ccc(OC(F)(F)F)cc4)no3)nc2C)c1)C(C)C] | methyl (2S)-3-methyl-2-{3-[(5-methyl-3-{3-[4-(trifluoro-methoxy)phenyl]-1,2,4-oxadiazol-5-yl}-1H-1,2,4- | 594 | 595 | 79 |

TABLE 1-continued

| Ex. No. | Structure | Name | MWt | [M + H] | Ex. Method |
|---|---|---|---|---|---|
| | | triazol-1-yl)methyl]benzene-sulfonamido}butanoate | | | |
| 133 | 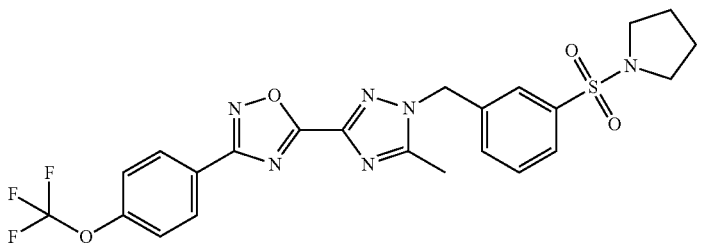 [SMILES: Cc1nc(-c2nc(-c3ccc(OC(F)(F)F)cc3)no2)nn1Cc1cccc(S(=O)(=O)N2CCCC2)c1] | 5-(5-methyl-1-{[3-(pyrrolidine-1-sulfonyl)phenyl]methyl}-1H-1,2,4-triazol-3-yl)-3-[4-(trifluoromethoxy)phenyl]-1,2,4-oxadiazole | 534 | 535 | 79 |
| 134 | 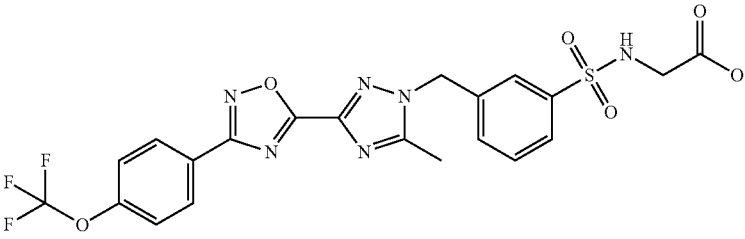 | methyl 2-{3-[(5-methyl-3-{3-[4-(trifluoromethoxy)phenyl]-1,2,4-oxadiazol-5-yl}-1H-1,2,4-triazol-1-yl)methyl]benzene-sulfonamido}acetate | 552 | 553 | 79 |
| 135 | 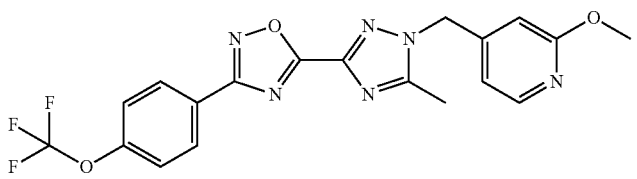 [SMILES: COc1cc(Cn2nc(-c3nc(-c4ccc(OC(F)(F)F)cc4)no3)nc2C)ccn1] | 2-methoxy-4-[(5-methyl-3-{3-[4-(trifluoromethoxy)phenyl]-1,2,4-oxadiazol-5-yl}-1H-1,2,4-triazol-1-yl)methyl]pyridine | 432 | 433 | 76b |
| 136 | 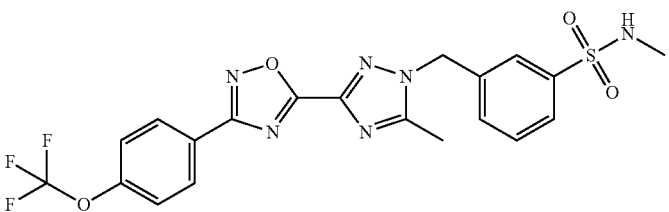 [SMILES: CNS(=O)(=O)c1cccc(Cn2nc(-c3nc(-c4ccc(OC(F)(F)F)cc4)no3)nc2C)c1] | N-methyl-3-[(5-methyl-3-{3-[4-(trifluoromethoxy)phenyl]-1,2,4-oxadiazol-5-yl}-1H-1,2,4-triazol-1-yl)methyl]benzene-1-sulfonamide | 494 | 495 | 79 |
| 137 | 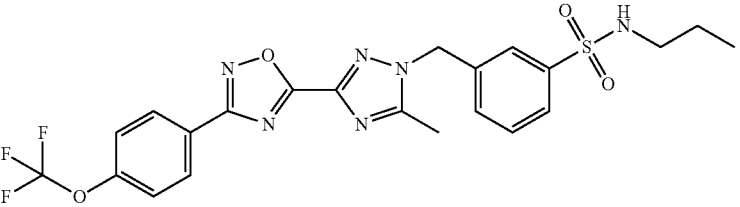 [SMILES: CCCNS(=O)(=O)c1cccc(Cn2nc(-c3nc(-c4ccc(OC(F)(F)F)cc4)no3)nc2C)c1] | 3-[(5-methyl-3-{3-[4-(trifluoromethoxy)phenyl]-1,2,4-oxadiazol-5-yl}-1H-1,2,4-triazol-1-yl)methyl]-N-propylbenzene-1-sulfonamide | 522 | 523 | 79 |

TABLE 1-continued

| Ex. No. | Structure | Name | MWt | [M + H] | Ex. Method |
|---|---|---|---|---|---|
| 138 | 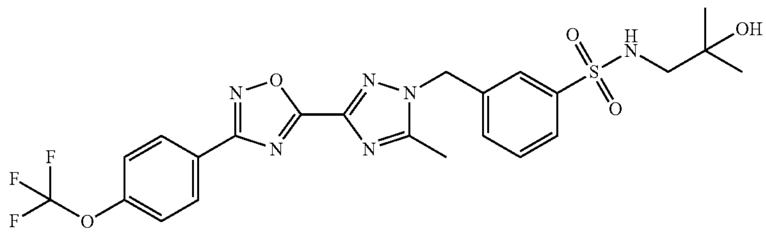 [SMILES: Cc1nc(-c2nc(-c3ccc(OC(F)(F)F)cc3)no2)nn1Cc1cccc(S(=O)(=O)NCC(C)(C)O)c1] | 2-hydroxy-2-methyl-S-{3-[(5-methyl-3-{3-[4-(trifluoromethoxy)phenyl]-1,2,4-oxadiazol-5-yl}-1H-1,2,4-triazol-1-yl)methyl]phenyl}propane-1-sulfonamido | 552 | 553 | 79 |
| 139 | 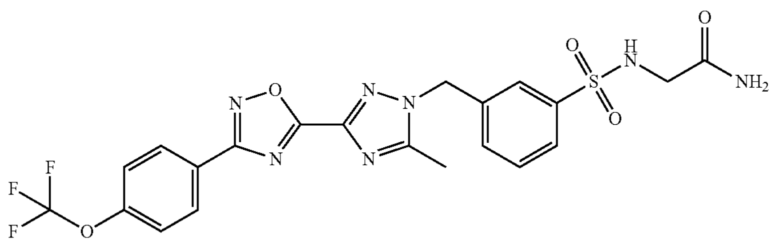 [SMILES: Cc1nc(-c2nc(-c3ccc(OC(F)(F)F)cc3)no2)nn1Cc1cccc(S(=O)(=O)NCC(N)=O)c1] | 2-{3-[(5-methyl-3-{3-[4-(trifluoromethoxy)phenyl]-1,2,4-oxadiazol-5-yl}-1H-1,2,4-triazol-1-yl)methyl]benzenesulfonamido}acetamide | 537 | 538 | 79 |
| 140 | 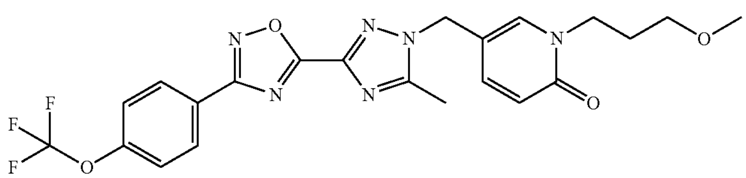 [SMILES: COCCCn1cc(Cn2nc(-c3nc(-c4ccc(OC(F)(F)F)cc4)no3)nc2C)ccc1=O] | 1-(3-methoxypropyl)-5-[(5-methyl-3-{3-[4-(trifluoromethoxy)phenyl]-1,2,4-oxadiazol-5-yl}-1H-1,2,4-triazol-1-yl)methyl]-1,2-dihydropyridin-2-one | 490 | 491 | 77a |
| 141 | 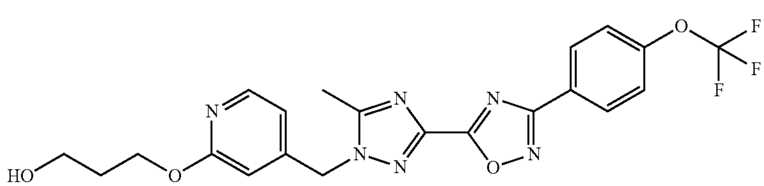 [SMILES: Cc1nc(-c2nc(-c3ccc(OC(F)(F)F)cc3)no2)nn1Cc1ccnc(OCCCO)c1] | 3-({4-[(5-methyl-3-{3-[4-(trifluoromethoxy)phenyl]-1,2,4-oxadiazol-5-yl}-1H-1,2,4-triazol-1-yl)methyl]pyridin-2-yl}oxy)propan-1-ol | 476 | 477 | 76b |

TABLE 1-continued

| Ex. No. | Structure | Name | MWt | [M + H] | Ex. Method |
|---|---|---|---|---|---|
| 142 | 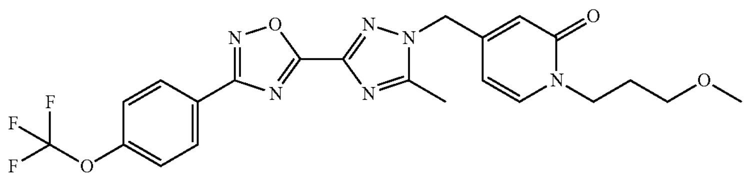 [SMILES: COCCCn1ccc(Cn2nc(-c3nc(-c4ccc(OC(F)(F)F)cc4)no3)nc2C)cc1=O] | 1-(3-methoxy-propyl)-4-[(5-methyl-3-{3-[4-(trifluoro-methoxy)phenyl]-1,2,4-oxadiazol-5-yl}-1H-1,2,4-triazol-1-yl)methyl]-1,2-dihydro-pyridin-2-one | 490 | 491 | 76a |
| 143 | 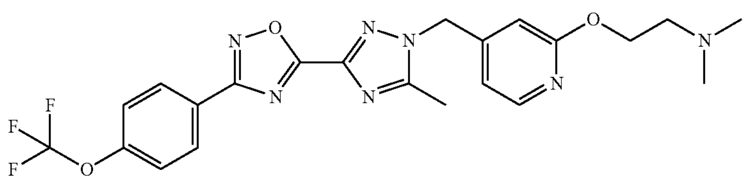 [SMILES: Cc1nc(-c2nc(-c3ccc(OC(F)(F)F)cc3)no2)nn1Cc1ccnc(OCCN(C)C)c1] | dimethyl[2-({4-[(5-methyl-3-{3-[4-(trifluoro-methoxy)phenyl]-1,2,4-oxadiazol-5-yl}-1H-1,2,4-triazol-1-yl)methyl]pyridin-2-yl}oxy)ethyl]amine | 489 | 490 | 76b |
| 144 | 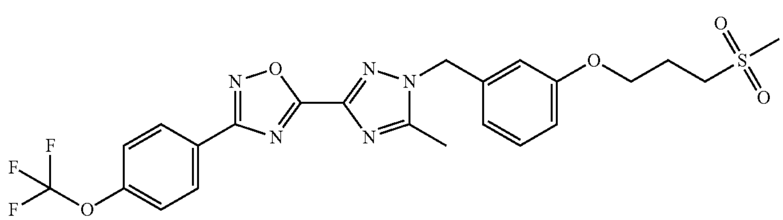 [SMILES: Cc1nc(-c2nc(-c3ccc(OC(F)(F)F)cc3)no2)nn1Cc1cccc(OCCCS(C)(=O)=O)c1] | 5-(1-([3-(3-methane-sulfonyl-propoxy)phenyl]methyl)-5-methyl-1H-1,2,4-triazol-3-yl)-3-[4-(trifluoro-methoxy)phenyl]-1,2,4-oxadiazole | 537 | 538 | 60 |
| 145 | 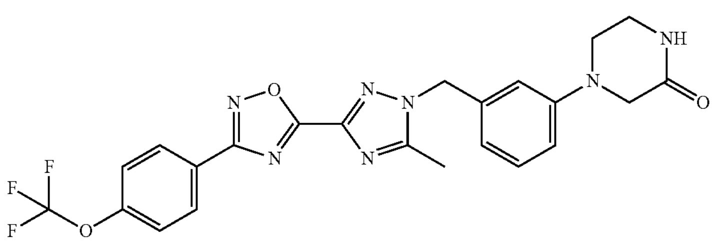 [SMILES: Cc1nc(-c2nc(-c3ccc(OC(F)(F)F)cc3)no2)nn1Cc1cccc(N2CCNC(=O)C2)c1] | 4-{3-[(5-methyl-3-{3-[4-(trifluoro-methoxy)phenyl]-1,2,4-oxadiazol-5-yl}-1H-1,2,4-triazol-1-yl)methyl]phenyl}piperazin-2-one | 499 | 500 | 11 |

TABLE 1-continued

| Ex. No. | Structure | Name | MWt | [M + H] | Ex. Method |
|---|---|---|---|---|---|
| 146 | 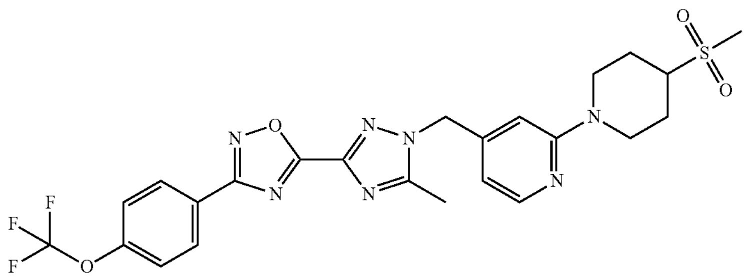 [SMILES: Cc1nc(-c2nc(-c3ccc(OC(F)(F)F)cc3)no2)nn1Cc1ccnc(N2CCC(S(C)(=O)=O)CC2)c1] | 2-(4-methane-sulfonyl-piperidin-1-yl)-4-[(5-methyl-3-{3-[4-(trifluoro-methoxy)phenyl]-1,2,4-oxadiazol-5-yl}-1H-1,2,4-triazol-1-yl)methyl]pyridine | 563 | 564 | 10 |
| 147 | 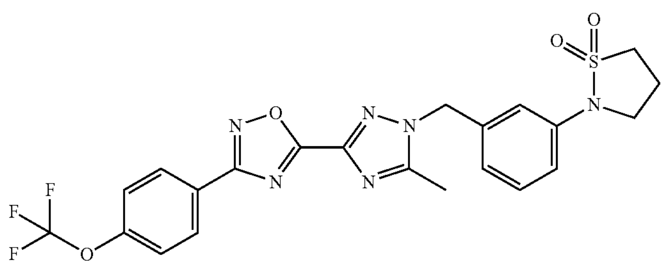 [SMILES: Cc1nc(-c2nc(-c3ccc(OC(F)(F)F)cc3)no2)nn1Cc1cccc(N2CCCS2(=O)=O)c1] | 2-(3-((5-methyl-3-(3-(4-(trifluoro-methoxy)phenyl)-1,2,4-oxadiazol-5-yl)-1H-1,2,4-triazol-1-yl)methyl)phenyl)isothiazolidine 1,1-dioxide | 520 | 521 | 11 |
| 148 | 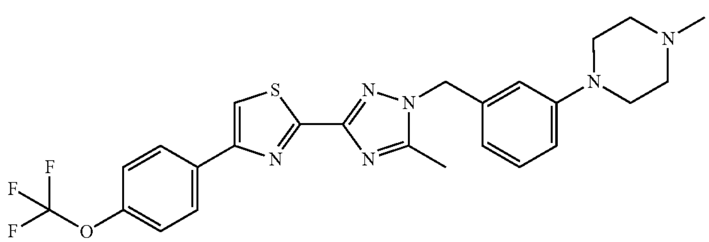 [SMILES: Cc1nc(-c2nc(-c3ccc(OC(F)(F)F)cc3)cs2)nn1Cc1cccc(N2CCN(C)CC2)c1] | 1-methyl-4-{3-[(5-methyl-3-{4-[4-(trifluoro-methoxy)phenyl]-1,3-thiazol-2-yl}-1H-1,2,4-triazol-1-yl)methyl]phenyl}piperazine | 514 | 515 | 87; 11 |
| 149 | 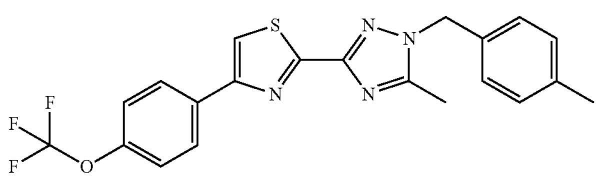 [SMILES: Cc1ccc(Cn2nc(-c3nc(-c4ccc(OC(F)(F)F)cc4)cs3)nc2C)cc1] | 5-methyl-1-[(4-methyl-phenyl)methyl]-3-{4-[4-(trifluoro-methoxy)phenyl]-1,3-thiazol-2-yl}-1H-1,2,4-triazole | 430 | 431 | 88 |
| 150 | 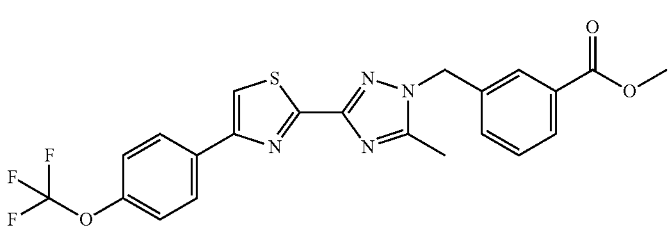 [SMILES: COC(=O)c1cccc(Cn2nc(-c3nc(-c4ccc(OC(F)(F)F)cc4)cs3)nc2C)c1] | methyl 3-[(5-methyl-3-{4-[4-(trifluoro-methoxy)phenyl]-1,3-thiazol-2-yl}-1H-1,2,4-triazol-1-yl)methyl]benzoate | 474 | 475 | 88 |

TABLE 1-continued

| Ex. No. | Structure | Name | MWt | [M + H] | Ex. Method |
|---|---|---|---|---|---|
| 151 | 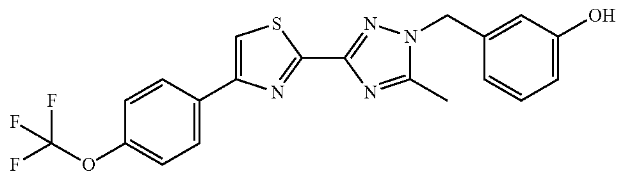 [SMILES: Cc1nc(-c2nc(-c3ccc(OC(F)(F)F)cc3)cs2)nn1Cc1cccc(O)c1] | 3-[(5-methyl-3-{4-[4-(trifluoromethoxy)phenyl]-1,3-thiazol-2-yl}-1H-1,2,4-triazol-1-yl)methyl]phenol | 432 | 433 | 88 |
| 152 | 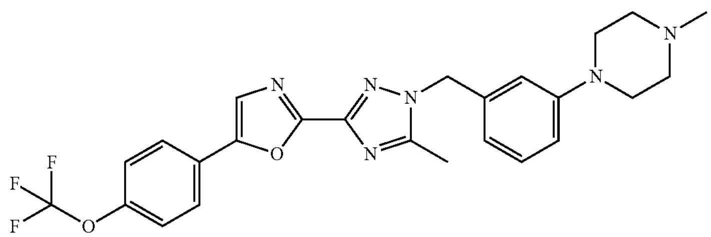 [SMILES: Cc1nc(-c2ncc(-c3ccc(OC(F)(F)F)cc3)o2)nn1Cc1cccc(N2CCN(C)CC2)c1] | 1-methyl-4-{3-[(5-methyl-3-{5-[4-(trifluoromethoxy)phenyl]-1,3-oxazol-2-yl}-1H-1,2,4-triazol-1-yl)methyl]phenyl}piperazine | 498 | 499 | 92; 11 |
| 153 | 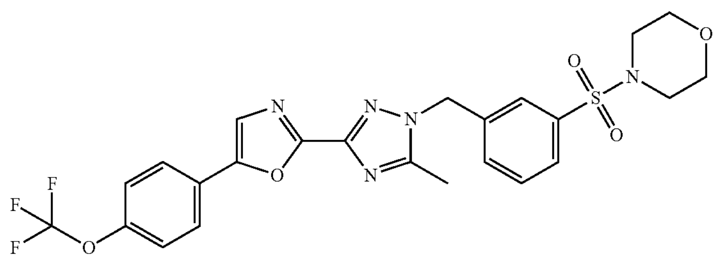 [SMILES: Cc1nc(-c2ncc(-c3ccc(OC(F)(F)F)cc3)o2)nn1Cc1cccc(S(=O)(=O)N2CCOCC2)c1] | 4-{3-[(5-methyl-3-{5-[4-(trifluoromethoxy)phenyl]-1,3-oxazol-2-yl}-1H-1,2,4-triazol-1-yl)methyl]benzenesulfonyl}morpholine | 549 | 550 | 92; 79 |
| 154 | 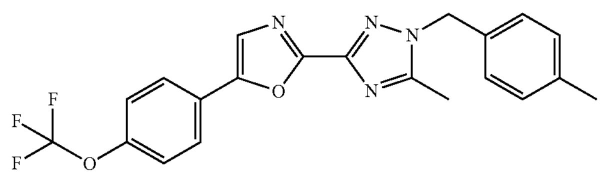 [SMILES: Cc1ccc(Cn2nc(-c3ncc(-c4ccc(OC(F)(F)F)cc4)o3)nc2C)cc1] | 5-methyl-1-[(4-methylphenyl)methyl]-3-{5-[4-(trifluoromethoxy)phenyl]-1,3-oxazol-2-yl}-1H-1,2,4-triazole | 414 | 415 | 92; 17 |
| 155 | 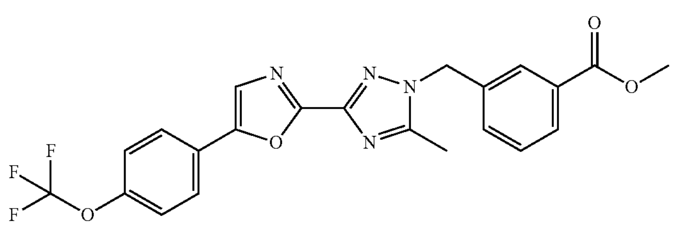 [SMILES: COC(=O)c1cccc(Cn2nc(-c3ncc(-c4ccc(OC(F)(F)F)cc4)o3)nc2C)c1] | methyl 3-[(5-methyl-3-{5-[4-(trifluoromethoxy)phenyl]-1,3-oxazol-2-yl}-1H-1,2,4-triazol-1-yl)methyl]benzoate | 458 | 459 | 92; 17 |
| 156 | 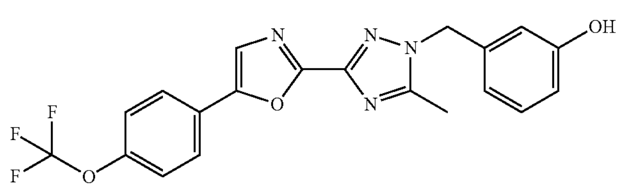 [SMILES: Cc1nc(-c2ncc(-c3ccc(OC(F)(F)F)cc3)o2)nn1Cc1cccc(O)c1] | 3-[(5-methyl-3-{5-[4-(trifluoromethoxy)phenyl]-1,3-oxazol-2-yl}-1H-1,2,4-triazol-1-yl)methyl]phenol | 416 | 417 | 92; 17 |

TABLE 1-continued

| Ex. No. | Structure | Name | MWt | [M + H] | Ex. Method |
|---|---|---|---|---|---|
| 157 | 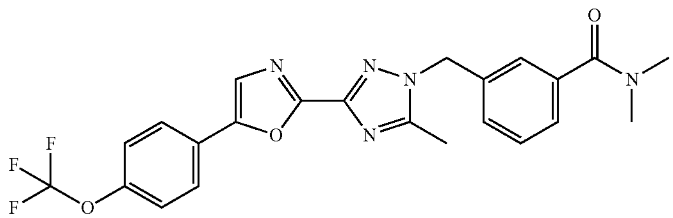 [SMILES: Cc1nc(-c2ncc(-c3ccc(OC(F)(F)F)cc3)o2)nn1Cc1cccc(C(=O)N(C)C)c1] | N,N-dimethyl-3-[(5-methyl-3-{5-[4-(trifluoromethoxy)phenyl]-1,3-oxazol-2-yl}-1H-1,2,4-triazol-1-yl)methyl]benzamide | 471 | 472 | 92; 13 |
| 158 | 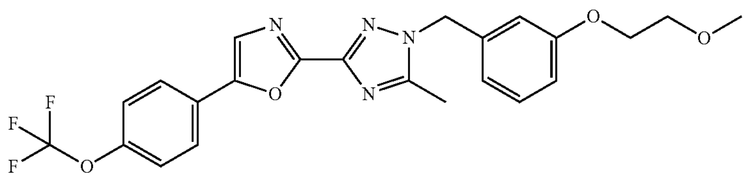 [SMILES: COCCOc1cccc(Cn2nc(-c3ncc(-c4ccc(OC(F)(F)F)cc4)o3)nc2C)c1] | 1-{[3-(2-methoxyethoxy)phenyl]methyl}-5-methyl-3-{5-[4-(trifluoromethoxy)phenyl]-1,3-oxazol-2-yl}-1H-1,2,4-triazole | 474 | 475 | 92; 60 |
| 159 | 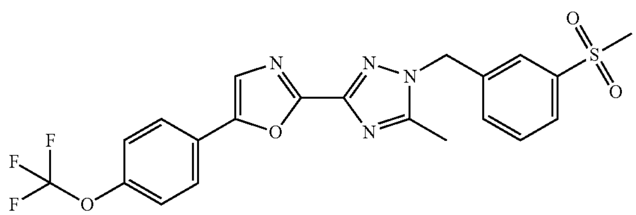 [SMILES: Cc1nc(-c2ncc(-c3ccc(OC(F)(F)F)cc3)o2)nn1Cc1cccc(S(C)(=O)=O)c1] | 1-[(3-methanesulfonylphenyl)methyl]-5-methyl-3-{5-[4-(trifluoromethoxy)phenyl]-1,3-oxazol-2-yl}-1H-1,2,4-triazole | 478 | 479 | 92; 17 |
| 160 | 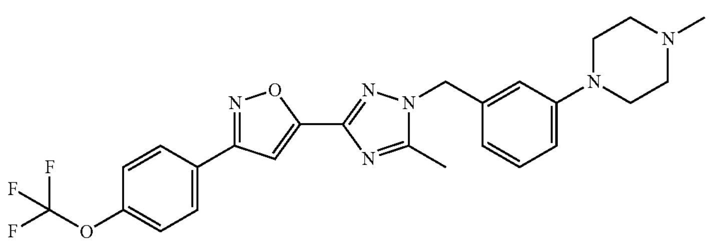 [SMILES: Cc1nc(-c2cc(-c3ccc(OC(F)(F)F)cc3)no2)nn1Cc1cccc(N2CCN(C)CC2)c1] | 1-methyl-4-{3-[(5-methyl-3-{3-[4-(trifluoromethoxy)phenyl]-1,2-oxazol-5-yl}-1H-1,2,4-triazol-1-yl)methyl]phenyl}piperazine | 498 | 499 | 94 |
| 161 | 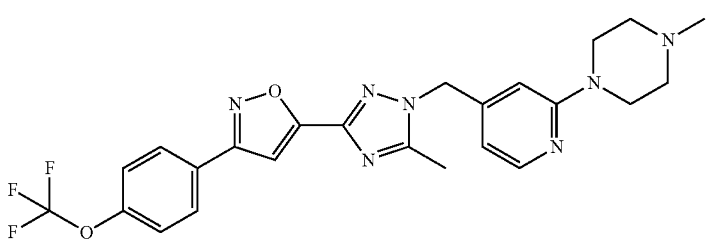 [SMILES: Cc1nc(-c2cc(-c3ccc(OC(F)(F)F)cc3)no2)nn1Cc1ccnc(N2CCN(C)CC2)c1] | 1-methyl-4-{4-[(5-methyl-3-{3-[4-(trifluoromethoxy)phenyl]-1,2-oxazol-5-yl}-1H-1,2,4-triazol-1-yl)methyl]pyridin-2-yl}piperazine | 499 | 500 | 95 |

TABLE 1-continued

| Ex. No. | Structure | Name | MWt | [M + H] | Ex. Method |
|---|---|---|---|---|---|
| 162 | 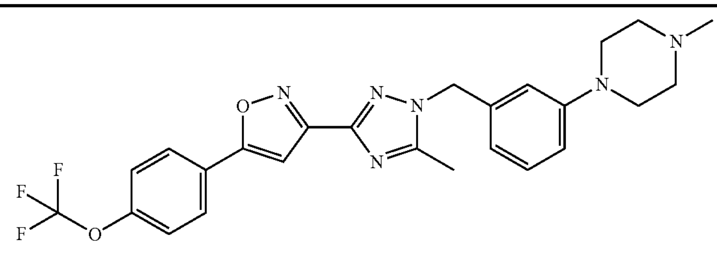 | 1-methyl-4-{3-[(5-methyl-3-{5-[4-(trifluoromethoxy)phenyl]-1,2-oxazol-3-yl}-1H-1,2,4-triazol-1-yl)methyl]phenyl}piperazine | 498 | 499 | 96 |
| 163 | 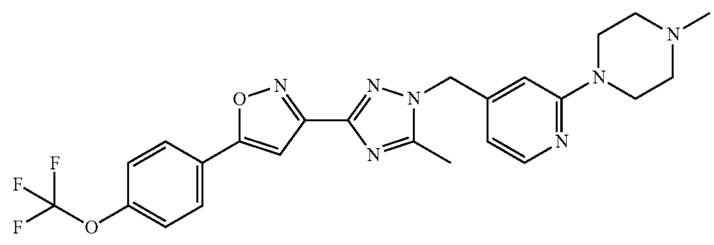 [SMILES: Cc1nc(-c2cc(-c3ccc(OC(F)(F)F)cc3)on2)nn1Cc1ccnc(N2CCN(C)CC2)c1] | 1-methyl-4-{4-[(5-methyl-3-{5-[4-(trifluoromethoxy)phenyl]-1,2-oxazol-3-yl}-1H-1,2,4-triazol-1-yl)methyl]pyridin-2-yl}piperazine | 499 | 500 | 97 |

Cell-Based Reporter Assay for $IC_{50}$ Determinations

293T-HRE-GFP-luc cells were routinely maintained in DMEM media (high glucose version with GlutaMAX and HEPES, Gibco, catalog #10564) supplemented with 10% fetal bovine serum and 2 μg/mL puromycin (Invitrogen, catalog #A11138-03) using a humidified incubator (normoxia conditions consisting of 37° C., 5% $CO_2$ and ambient $O_2$).

In preparation for the reporter assay, cells were harvested and resuspended in DMEM media (high glucose version with GlutaMAX and HEPES) supplemented with 10% fetal bovine serum. Cells were inoculated into 384-well white Culturplates (Perkin Elmer catalog #6007680) at a density of 12,000 cells/well in a volume of 30 μL. The microplates were incubated overnight (approximately 17-19 hours) at 37° C. with 5% $CO_2$ and ambient $O_2$. Stock solutions of the test compounds were prepared in DMSO (Sigma, Catalog #D2650) and serially diluted 1:3 using DMSO. Compounds were additionally diluted (1:50) with culturemedium and 10 μL were added per well to the Culturplate. Following a 30 min. incubation under normoxia conditions, the plates were incubated in hypoxia for 6 hrs. (37° C., 5% $CO_2$ and 1% $O_2$). Steadylite Plus (Perkin Elmer, catalog #6016751) was then added (40 μL/well), the plates were mixed on an orbital shaker at room temperature in the dark for 15 min., and luminescence was measured using an Envision plate reader (Perkin Elmer). $IC_{50}$ values were calculated using a four-parameter logistic curve fit. Results are shown below in Table 2; ND indicates no data.

TABLE 2

| Example No. | Classification: A = <100 nM B = 100-1000 nM C = 1-10 uM |
|---|---|
| 1 | B |
| 2 | A |
| 3 | C |
| 4 | A |
| 5 | C |
| 6 | A |
| 7 | B |
| 8 | A |
| 9 | A |
| 10 | A |
| 11 | C |
| 12 | A |
| 13 | A |
| 14 | A |
| 15 | A |
| 16 | B |
| 17 | C |
| 18 | C |
| 19 | C |
| 20 | A |
| 21 | C |
| 22 | B |
| 23 | B |
| 24 | B |
| 25 | A |
| 26 | A |
| 27 | A |
| 28 | A |
| 29 | C |
| 30 | A |
| 31 | A |
| 32 | A |
| 33 | C |
| 34 | C |
| 35 | A |
| 36 | A |
| 37 | A |
| 38 | A |
| 39 | B |
| 40 | A |
| 41 | B |
| 42 | B |
| 43 | B |
| 44 | A |
| 45 | C |

TABLE 2-continued

| Example No. | Classification:<br>A = <100 nM<br>B = 100-1000 nM<br>C = 1-10 uM |
|---|---|
| 46 | C |
| 47 | B |
| 48 | B |
| 49 | B |
| 50 | B |
| 51 | A |
| 52 | A |
| 53 | A |
| 54 | C |
| 55 | A |
| 56 | A |
| 57 | A |
| 58 | B |
| 59 | B |
| 60 | A |
| 61 | A |
| 62 | A |
| 63 | A |
| 64 | A |
| 65 | A |
| 66 | B |
| 67 | A |
| 68 | A |
| 69 | A |
| 70 | B |
| 71 | A |
| 72 | A |
| 73 | A |
| 74 | A |
| 75 | B |
| 76a | B |
| 76b | B |
| 77a | A |
| 77b | B |
| 78 | A |
| 79 | A |
| 80 | A |
| 81 | A |
| 82 | A |
| 83 | A |
| 84 | B |
| 85 | A |
| 86 | A |
| 87 | A |
| 88 | B |
| 89 | B |
| 90 | B |
| 91 | B |
| 92 | A |
| 93 | B |
| 94 | A |
| 95 | A |
| 96 | A |
| 97 | B |
| 98 | A |
| 99 | C |
| 100 | C |
| 101 | B |
| 102 | C |
| 103 | B |
| 104 | B |
| 105 | B |
| 106 | A |
| 107 | B |
| 108 | C |
| 109 | B |
| 110 | B |
| 111 | B |
| 112 | C |
| 113 | A |
| 114 | B |
| 115 | C |
| 116 | A |
| 117 | B |
| 118 | A |
| 119 | B |
| 120 | A |
| 121 | B |
| 122 | A |
| 123 | A |
| 124 | A |
| 125 | A |
| 126 | A |
| 127 | B |
| 128 | B |
| 129 | B |
| 130 | A |
| 131 | A |
| 132 | B |
| 133 | A |
| 134 | A |
| 135 | B |
| 136 | A |
| 137 | A |
| 138 | A |
| 139 | B |
| 140 | B |
| 141 | A |
| 142 | B |
| 143 | B |
| 144 | A |
| 145 | A |
| 146 | A |
| 147 | A |
| 148 | A |
| 149 | A |
| 150 | B |
| 151 | B |
| 152 | A |
| 153 | B |
| 154 | B |
| 155 | B |
| 156 | C |
| 157 | B |
| 158 | A |
| 159 | B |
| 160 | A |
| 161 | A |
| 162 | A |
| 163 | A |

Diffuse Large B-Cell Lymphoma (DLBCL) Assay

Equal number of TMD8 cells were plated and treated with varying concentrations of the compound of Example 80 for 7 days. Percent of viable cells was determined using Guava ViaCount reagents (EMD Millipore cat #4000-0040) that contains proprietary dyes that enable the determination of the number of live and dead cells in a sample (FIG. 1). TMD8 cells respond robustly to the compound of Example 80, indicating the effectiveness of the compound as an anti-tumor agent in DLBCL.

Acute Myeloid Leukemia

Figure 9:
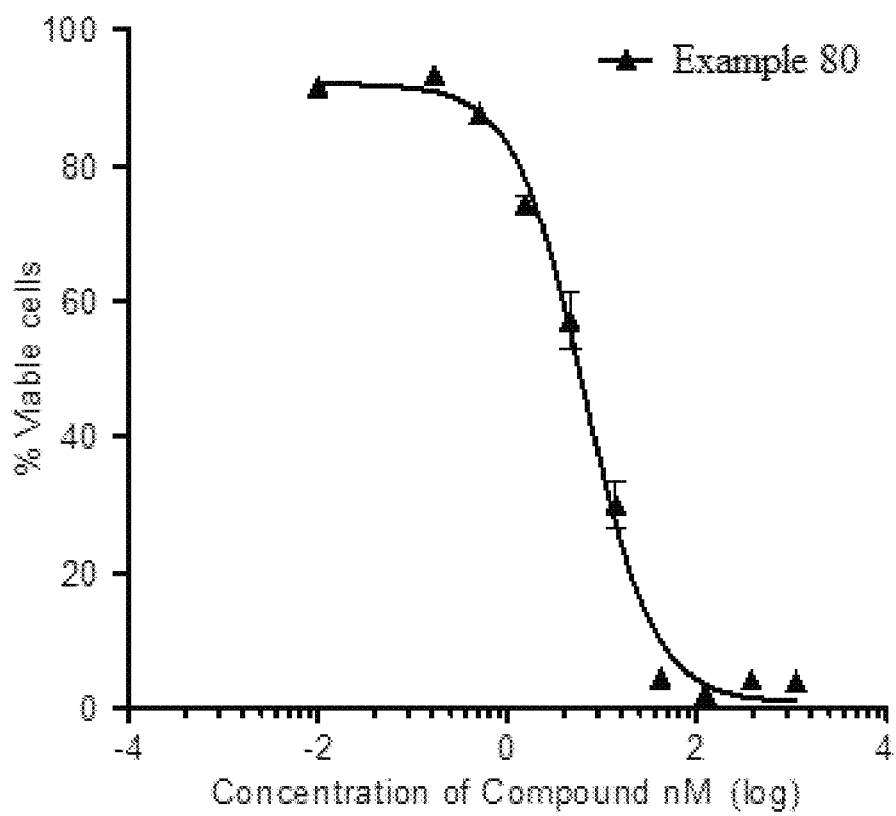
FIG. 9—Compounds of this invention inhibit the growth of leukemia OCI-AML3 cells as shown by reduced number of viable cells following treatment with Example 80.
Figure 10:
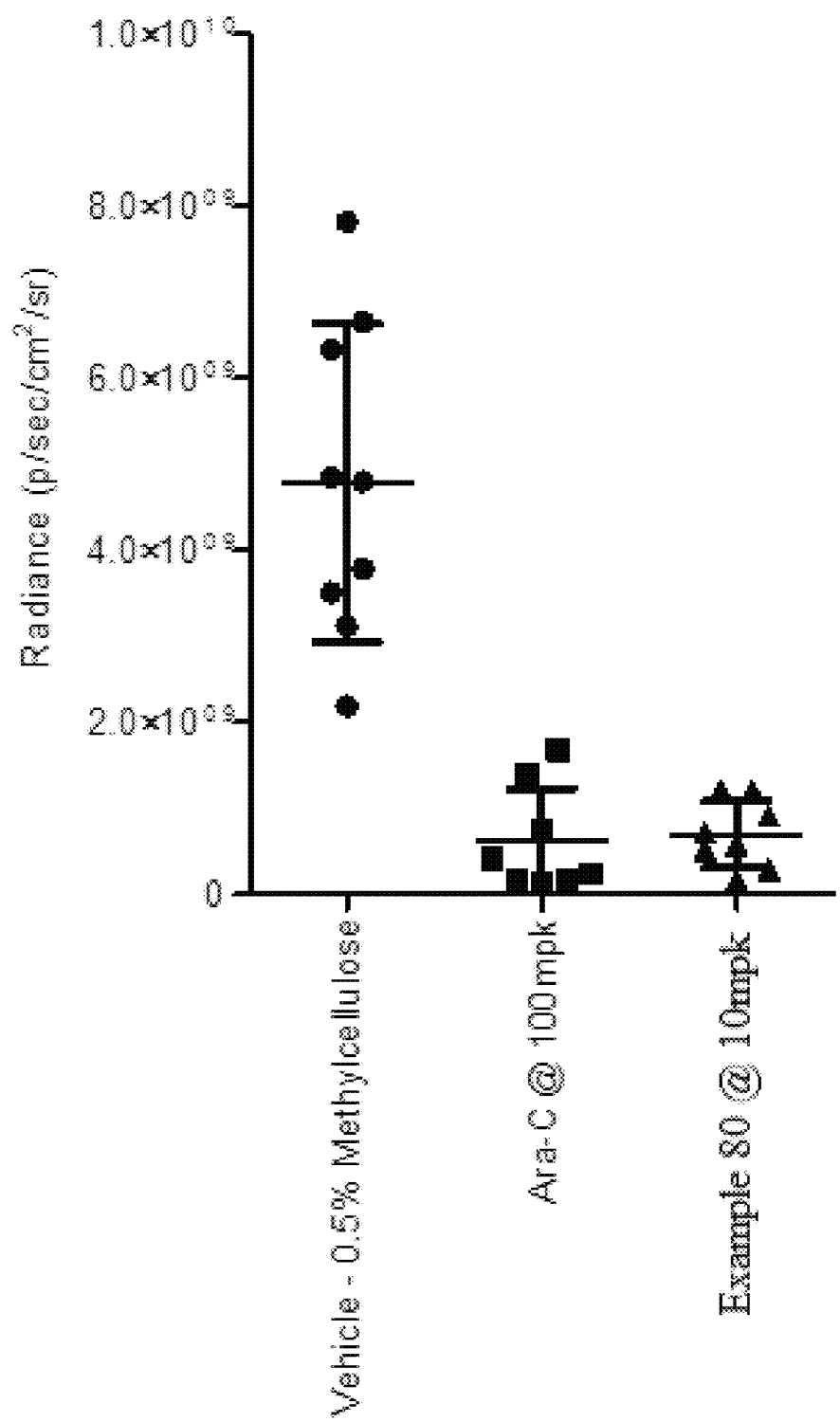
FIG. 10—Compounds of this invention reduce disease burden in human leukemia model, daily oral treatment with 10 mg/kg of Example 80 reduces disease burden in OCI-AML3 models in NSG mice as measured by IVIS imaging.
Figure 11:
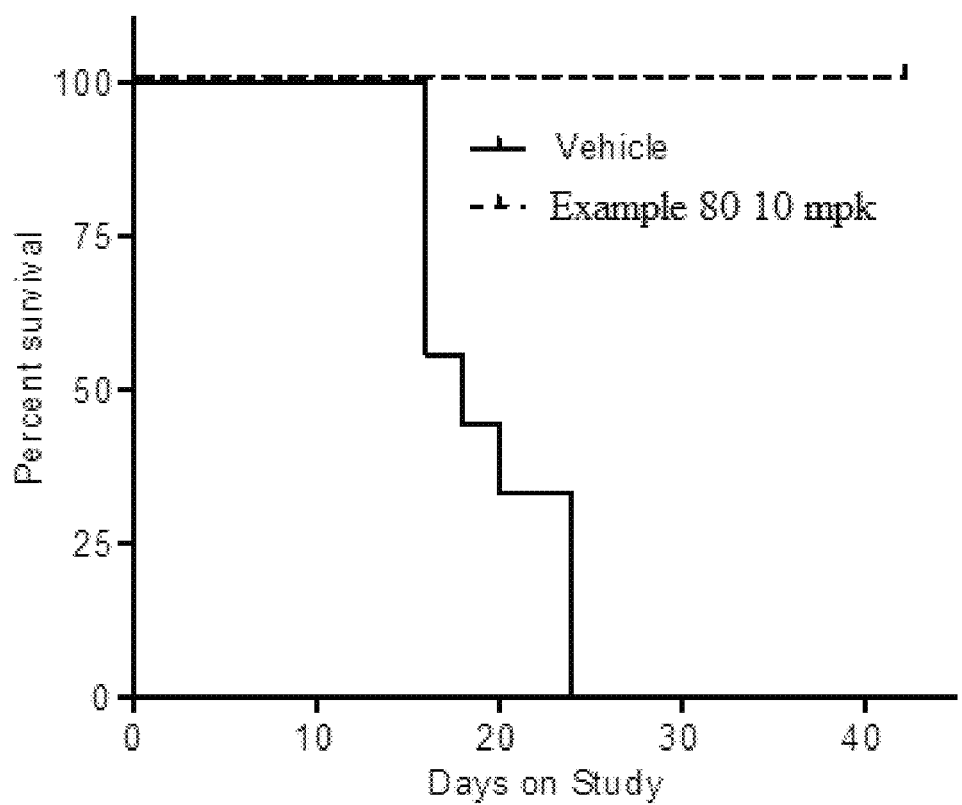
FIG. 11—Compounds of this invention prolong the survival in human leukemia model, daily oral treatment with 10 mg/kg of Example 80 extends survival in OCI-AML3 models in NSG mice.

The OCI-AML3 cell line was treated with various concentrations of compound for 2 days and the percent of viable cells normalized to control cells treated with DMSO (FIG. 9). OCI-AML3 cells constitutively expressing luciferase were tail vein injected in NSG nude mice. 17 days after cell injection, luciferin was injected into animals and luciferase signal was measured using an IVIS imaging system to determine tumor burden and for randomization of subjects into study groups. On day 18, animals began receiving daily oral doses of vehicle or 10 mpk of the compound of Example 80 which continued throughout the study. On day 28, imaging was performed again to determine tumor burden (FIG. 10). Treatment of tumor cell bearing animals with the compound of Example 80 significantly increased their survival relative to vehicle treated animals (FIG. 11).

Neuroblastoma and Glioblastoma Cellular Assay and Xenograft Model

Figure 3:
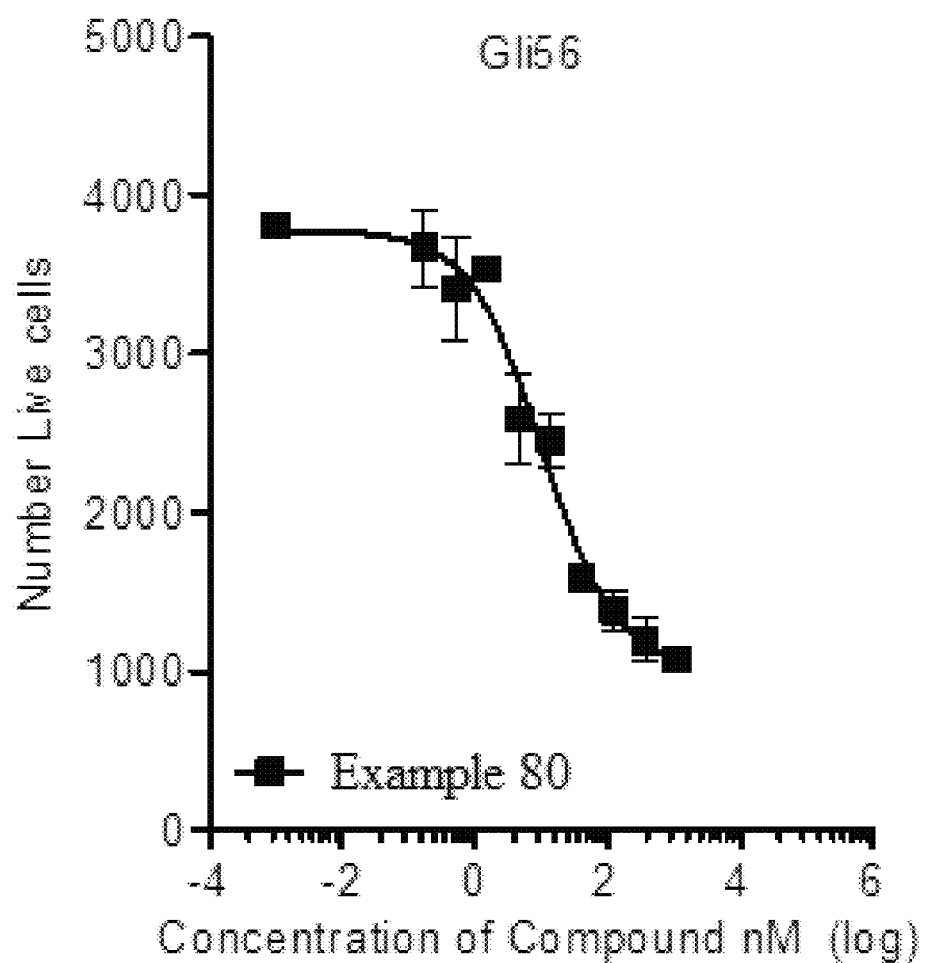
FIG. 3—Compounds of this invention inhibit the growth of glioblastoma Gli56 cells as shown by reduced number of viable cells following treatment with Example 80.

Cellular Assays:
NB-1, Gli56, and D423 cell lines are deleted for ENO-1 (GLI56 and D423) or PGD, which renders them with reduced glycolytic capacity (Muller, F. et al., Nature, 2012, 488, 337-42). When these cell lines are treated with various concentrations of the compounds of Example 2 and Example 80, cell numbers are significantly reduced with cell death readily apparent in NB-1 and Gli56 (FIG. 2-4).

Figure 5:
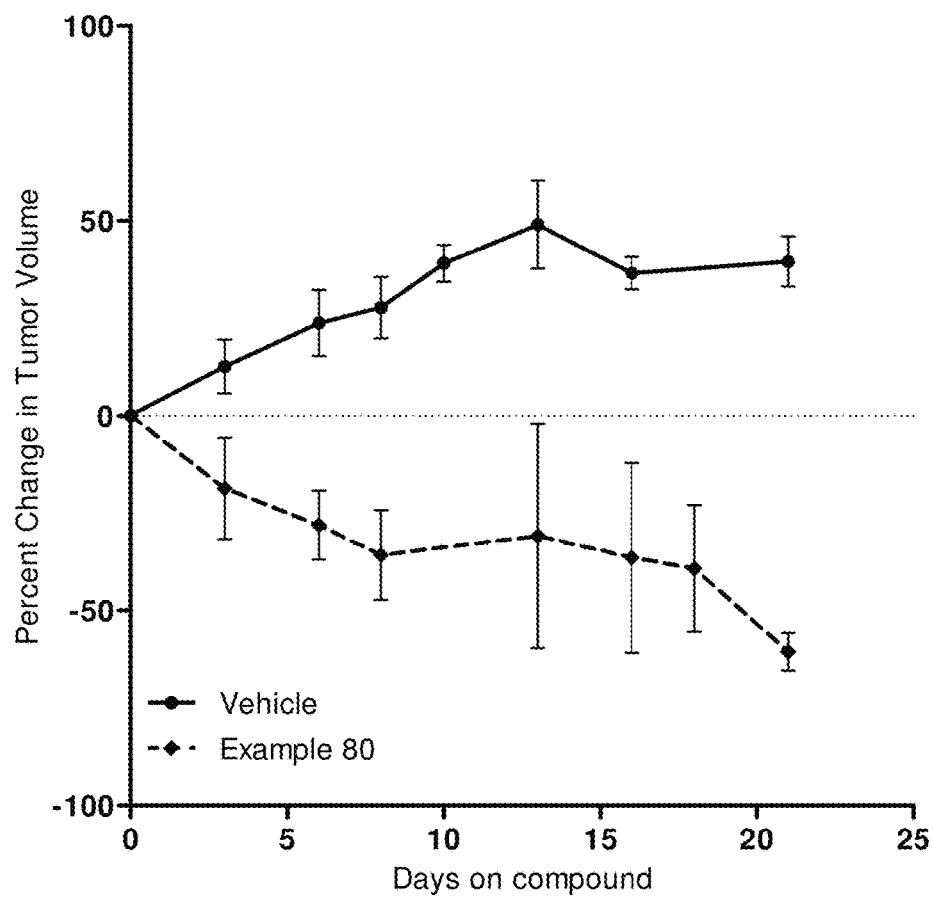
FIG. 5—Compounds of this invention inhibit the growth of NB-1 xenografts in vivo, daily oral treatment with 10 mg/kg of Example 80 reduces the tumor growth.

Xenograft Model:
To establish activity and provide in vivo proof of concept, NB-1 cells were implanted into CD-1 nude mice and treated with 40 mpk of the compound of Example 80 po or vehicle daily when tumors reached 400-500 mm$^3$. Tumor size was measured 3×/week using caliper measurements (FIG. 5).

In Vivo Murine Xenograft Models for Tumor Growth Inhibition

The compounds disclosed herein have been evaluated in vivo and shown to inhibit the growth of human cancer xenografts in nude mice.

Figure 6:
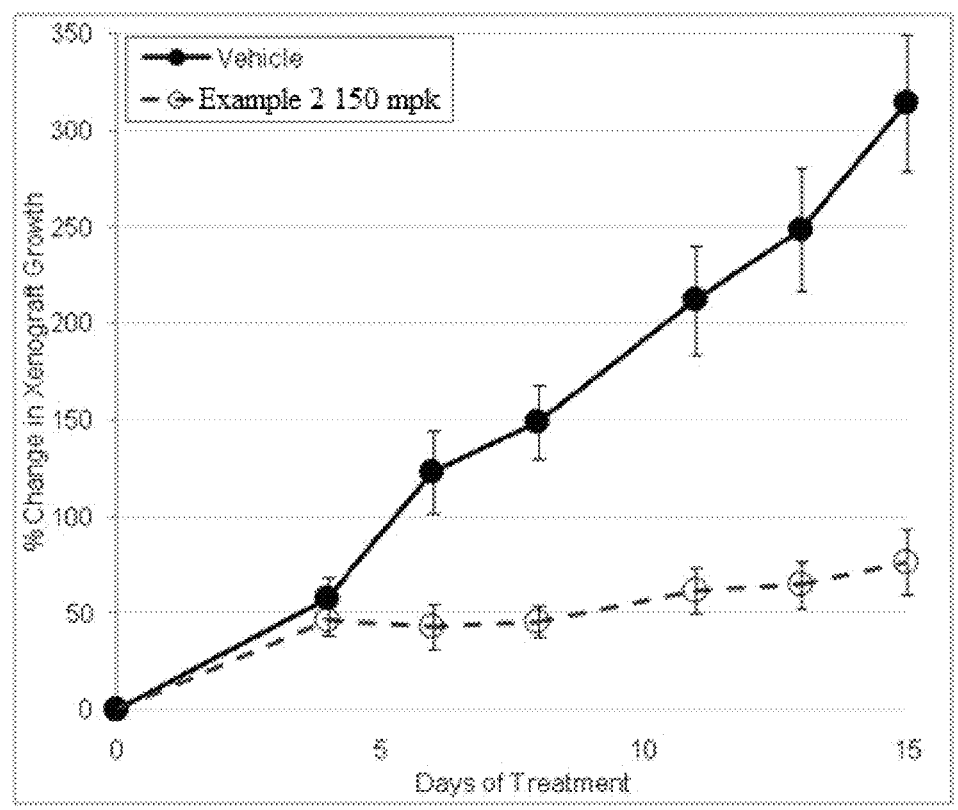
FIG. 6—Compounds of this invention inhibit the growth of H460 xenografts in vivo, daily oral treatment with 150 mg/kg of Example 2 reduces the tumor growth.
Figure 7:
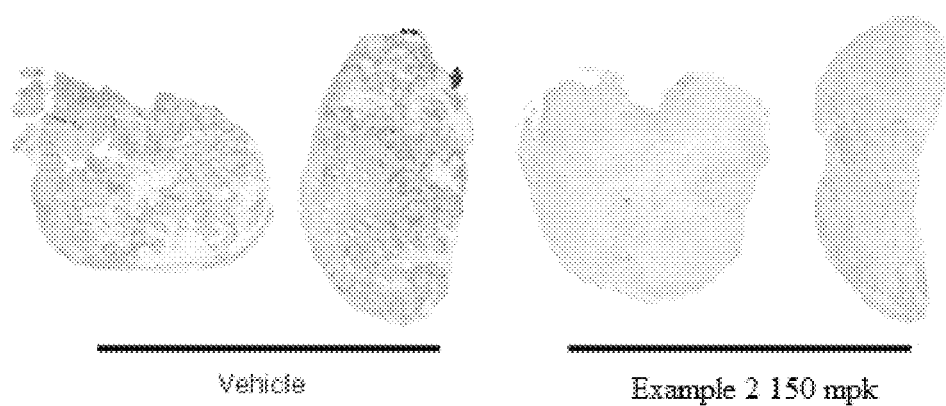
FIG. 7—Compounds of this invention reduce the level of hypoxia in H460 xenografts, daily oral treatment with 150 mg/kg of Example 2 reduce the level of hypoxia as measure by hypoxyprobe.
Figure 8:
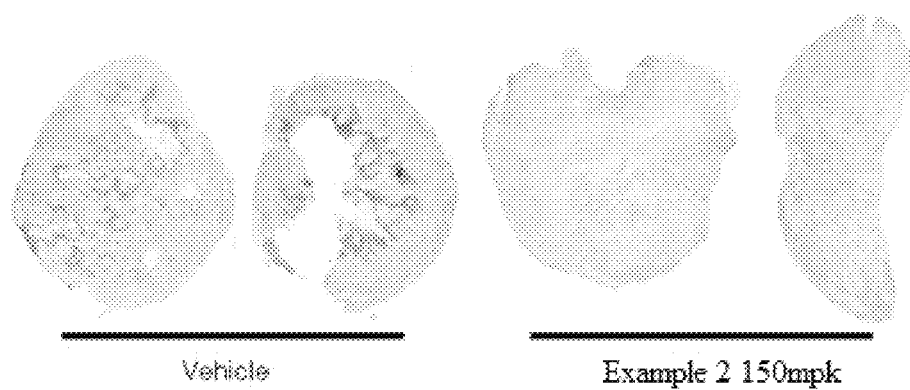
FIG. 8—Compounds of this invention reduce the level of the HIF regulated gene carbonic anhydrase IX in H460 xenografts, daily oral treatment with 150 mg/kg of Example 2 reduce the level of CAIX as shown by IHC.

Non-Small Cell Lung Cancer:
H460 cells were implanted subcutaneously in CD-1 nude mice and treated with 150 mpk qdx14 PO of the compound of Example 2 delivered by oral gavage for 14 days. Animals were randomized into study groups and the study initiated when the average tumor volume was 400 mm$^3$. During treatment, tumor volume was measured three times per week to determine tumor growth over the course of the study (FIG. 6). Nine tumor bearing mice were included in each group. On day 15, 3 hours prior to take down, hypoxyprobe (Hypoxyprobe, Inc. cat # HP3) was injected into mice. Tumor sections were stained (dark areas) for the level of hypoxia utilizing an anti-hypoxyprobe antibody and standard IHC methods (FIG. 7). The same tumors were stained for the expression of HIF regulated gene carbonic anhydrase IX (CA9) using standard IHC methods (FIG. 8). Treatment of the mice with the compound of Example 2 inhibited the growth of the H460 xenografts over the course of the study, establishing the anti-tumor activity of the compound. Target engagement, as measured by elimination of hypoxia and CA9 protein expression in the tumor, was achieved establishing that at the anti-tumor activity level, the compound of Example 2 is inhibiting HIF pathway activity.

Head and Neck Cancer:
In one example of an in vivo study, HN5 head and neck cells are injected intramuscularly into CD-1 nude mice. Upon tumors reaching 8.5 mm in diameter, animals are enrolled in the study and received either vehicle or test compound with or without a 4 Gy dose 6 hours after test compound on days 1-5 of the study. Tumor size is measured every other day to determine the rate of growth.

Further examples of xenograft models are given below for glioblastoma cancer.

Glioblastoma Cancer.
In one example of a typical protocol, female athymic nu/nu nude mice, 5 to 6 weeks-old (approx. 18-22 g) may be obtained, for example from Harland Sprague-Dawley, Inc. Nude mice are inoculated with tumor cells. U251, U87-EGFRviii or other human cancer cells, at a concentration of about $1-5\times10^6$ in 0.15 ml solution mixed with matrigel and DMEM medium are injected subcutaneously into the right flank of each mouse. When tumor volume reaches around 200 or 600 mm$^3$, animal are randomly assigned to three groups (or more, depending on the umber of dose levels of a compound to be evaluated) and treatment started with test article (for example, at 5 mg/kg/day or 10 mg/kg/day) delivered via oral gavage for up to 21 days. Animals in control group receive the vehicle alone under identical conditions. Tumor volumes are measured by a digital caliper and calculated using the formula (L×W×H)×0.5236. Significant differences are expected to be observed compared with control group ($P<0.05$, using ANOVA). Animal weight is monitored throughout the experiment. It is expected that no significant difference will be observed between control and treated groups, which further indicates the test article is non-toxic in tumor-bearing nude mice at doses used for inhibiting tumor growth.

The foregoing protocols are versatile, and may be modified to substitute virtually any type of human cancer cell line. Examples include the breast cancer cell lines AG11132A, MCF-7, and T47-D; estrogen, progesterone, and HER-2/neu receptor positive breast cancer cell lines HCC-1428 and ZR-75; estrogen, progesterone, and HER-2/neu receptors negative breast cancer cell lines MDA-231 and BT20; prostate cancer cell lines LNCaP, PC-3, and DU145; colon cancer cell lines DLD-1 and LoVo; ovarian cancer cell lines OVCAR-3 and SK-OV-3; lung cancer cell lines H69AR, NCI-H23, and A549; and pancreatic cancer cell lines Capan-1 and BxPC-3. Additionally, the protocol may be altered to assay the prevention of tumor development by pre-treating with test compound. Combinations of compounds may be tested, and dosing schedules altered to deliver compound in other ways, i.e., by oral gavage, or to skip days of treatment to reduce any toxic signals. Those skilled in the art will recognize and appropriately apply the multitude of variations available.

REFERENCES

Bardella, C., P. J. Pollard, and I. Tomlinson. 2011. SDH mutations in cancer. *Biochim Biophys Acta.* 1807:1432-1443.

Ebos, J. M., C. R. Lee, W. Cruz-Munoz, G. A. Bjarnason, J. G. Christensen, and R. S. Kerbel. 2009. Accelerated metastasis after short-term treatment with a potent inhibitor of tumor angiogenesis. *Cancer Cell.* 15:232-239.

Gill, A. J. 2012. Succinate dehydrogenase (SDH) and mitochondrial driven neoplasia. *Pathology.* 44:285-292.

Harada, H., M. Inoue, S. Itasaka, K. Hirota, A. Morinibu, K. Shinomiya, L. Zeng, G. Ou, Y. Zhu, M. Yoshimura, W. G. McKenna, R. J. Muschel, and M. Hiraoka. 2012. Cancer cells that survive radiation therapy acquire HIF-1 activity and translocate towards tumour blood vessels. *Nat Commun.* 3:783.

Isaacs, J. S., Y. J. Jung, D. R. Mole, S. Lee, C. Torres-Cabala, Y. L. Chung, M. Merino, J. Trepel, B. Zbar, J. Toro, P. J. Ratcliffe, W. M. Linehan, and L. Neckers. 2005. HIF overexpression correlates with biallelic loss of fumarate hydratase in renal cancer: novel role of fumarate in regulation of HIF stability. *Cancer Cell.* 8:143-153.

Jones, D. T., and A. L. Harris. 2012. Small-molecule inhibitors of the HIF pathway and synthetic lethal interactions. *Expert Opin Ther Targets.*

Kaelin, W. G., Jr. 2011. Cancer and altered metabolism: potential importance of hypoxia-inducible factor and 2-oxoglutarate-dependent dioxygenases. *Cold Spring Harb Symp Quant Biol.* 76:335-345.

Kaelin, W. G., Jr., and P. J. Ratcliffe. 2008. Oxygen sensing by metazoans: the central role of the HIF hydroxylase pathway. *Mol Cell.* 30:393-402.

Kim, W. Y., and W. G. Kaelin. 2004. Role of VHL gene mutation in human cancer. *J Clin Oncol.* 22:4991-5004.

Klein, T. J., and P. M. Glazer. 2010. The tumor microenvironment and DNA repair. *Semin Radiat Oncol.* 20:282-287.

Koi, M., and C. R. Boland. 2011. Tumor hypoxia and genetic alterations in sporadic cancers. *J Obstet Gynaecol Res.* 37:85-98.

Li, L., X. Lin, M. Stayer, A. Shoemaker, D. Semizarov, S. W. Fesik, and Y. Shen. 2005. Evaluating hypoxia-inducible factor-1alpha as a cancer therapeutic target via inducible RNA interference in vivo. *Cancer Res.* 65:7249-7258.

Maxwell, P. H., M. S. Wiesener, G. W. Chang, S. C. Clifford, E. C. Vaux, M. E. Cockman, C. C. Wykoff, C. W. Pugh, E. R. Maher, and P. J. Ratcliffe. 1999. The tumour suppressor protein VHL targets hypoxia-inducible factors for oxygen-dependent proteolysis. *Nature.* 399:271-275.

Mazure, N. M., and J. Pouyssegur. 2010. Hypoxia-induced autophagy: cell death or cell survival? *Curr Opin Cell Biol.* 22:177-180.

Onnis, B., A. Rapisarda, and G. Melillo. 2009. Development of HIF-1 inhibitors for cancer therapy. *J Cell Mol Med.* 13:2780-2786.

Paez-Ribes, M., E. Allen, J. Hudock, T. Takeda, H. Okuyama, F. Vinals, M. Inoue, G. Bergers, D. Hanahan, and O. Casanovas. 2009. Antiangiogenic therapy elicits malignant progression of tumors to increased local invasion and distant metastasis. *Cancer Cell.* 15:220-231.

Pollard, P. J., J. J. Briere, N. A. Alam, J. Barwell, E. Barclay, N. C. Wortham, T. Hunt, M. Mitchell, S. Olpin, S. J. Moat, I. P. Hargreaves, S. J. Heales, Y. L. Chung, J. R. Griffiths, A. Dalgleish, J. A. McGrath, M. J. Gleeson, S. V. Hodgson, R. Poulsom, P. Rustin, and I. P. Tomlinson. 2005. Accumulation of Krebs cycle intermediates and over-expression of HIF1alpha in tumours which result from germline FH and SDH mutations. *Hum Mol Genet.* 14:2231-2239.

Poon, E., A. L. Harris, and M. Ashcroft. 2009. Targeting the hypoxia-inducible factor (HIF) pathway in cancer. *Expert Rev Mol Med.* 11:e26.

Rohwer, N., and T. Cramer. 2011. Hypoxia-mediated drug resistance: novel insights on the functional interaction of HIFs and cell death pathways. *Drug Resist Updat.* 14:191-201.

Semenza, G. L. 2012a. Hypoxia-inducible factors in physiology and medicine. *Cell.* 148:399-408.

Semenza, G. L. 2012b. Hypoxia-inducible factors: mediators of cancer progression and targets for cancer therapy. *Trends Pharmacol Sci.* 33:207-214.

Wilson, W. R., and M. P. Hay. 2011. Targeting hypoxia in cancer therapy. *Nat Rev Cancer.* 11:393-410.

Wouters, B. G., and M. Koritzinsky. 2008. Hypoxia signalling through mTOR and the unfolded protein response in cancer. *Nat Rev Cancer.* 8:851-864.

All references, patents or applications, U.S. or foreign, cited in the application are hereby incorporated by reference as if written herein in their entireties. Where any inconsistencies arise, material literally disclosed herein controls.

What is claimed is:
1. A compound having structural Formula II

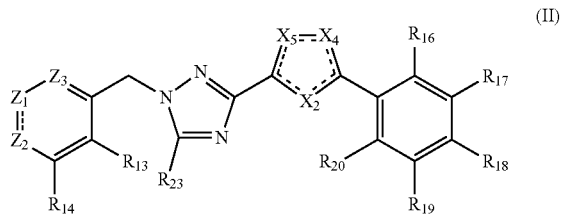

or a salt thereof, wherein:

$X_2$, $X_4$, and $X_5$ are independently selected from the group consisting of $CR_{21}$, N, O, and S, and wherein $X_2$, $X_4$, and $X_5$, taken together, form a 5-membered heteroaryl;

two of $X_2$, $X_4$, and $X_5$ are N; and one of $X_2$, $X_4$, and $X_5$ is O; or one of $X_2$, $X_4$, and $X_5$ is N; one of $X_2$, $X_4$, and $X_5$ is O; and one of $X_2$, $X_4$, and $X_5$ is CH;

$Z_1$ and $Z_2$ are independently selected from the group consisting of N, $NR_1$, C=O, and $CR_1$;

at least one of $Z_1$ or $Z_2$ is $CR_1$;

$Z_3$ is selected from the group consisting of N, $NR_{12}$, C=O, and $CR_{12}$;

$R_1$ is selected from the group consisting of hydrogen, deuterium, fluorine, bromine, cyano, methyl, isopropyl,

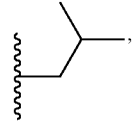 [SMILES: *CC(C)C]

ethylene,

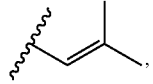 [SMILES: *C=C(C)C]

trifluoromethyl, bromomethyl, hydroxymethyl, difluoromethoxy, methoxy, ethoxy, isopropoxy, hydroxy, nitro, acetyl, carboxyl, —CO$_2$CH$_3$,

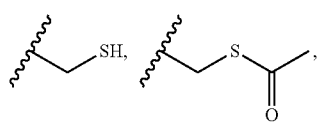

—SO$_2$CH$_3$, —SO$_2$CH$_2$CH$_3$, SO$_2$CH$_2$CH$_2$CH$_3$, —SO$_2$NH$_2$,

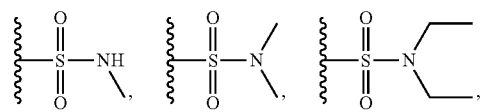

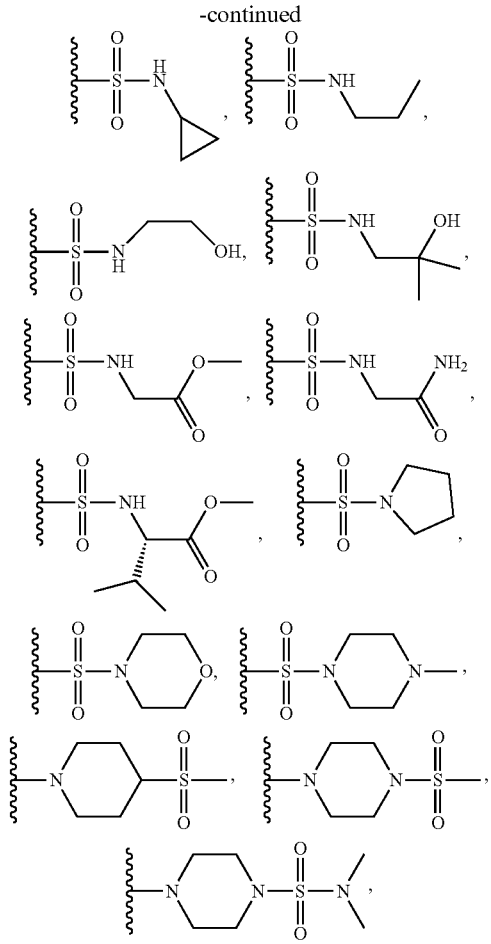
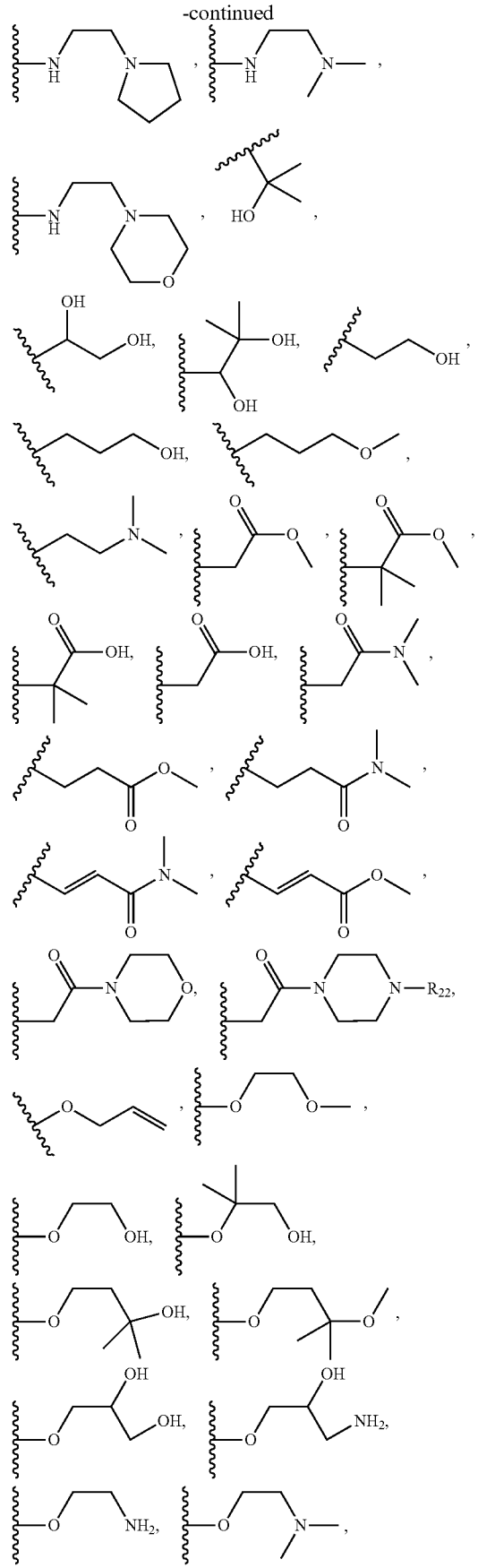
amino, methylamino, dimethylamino,

-continued

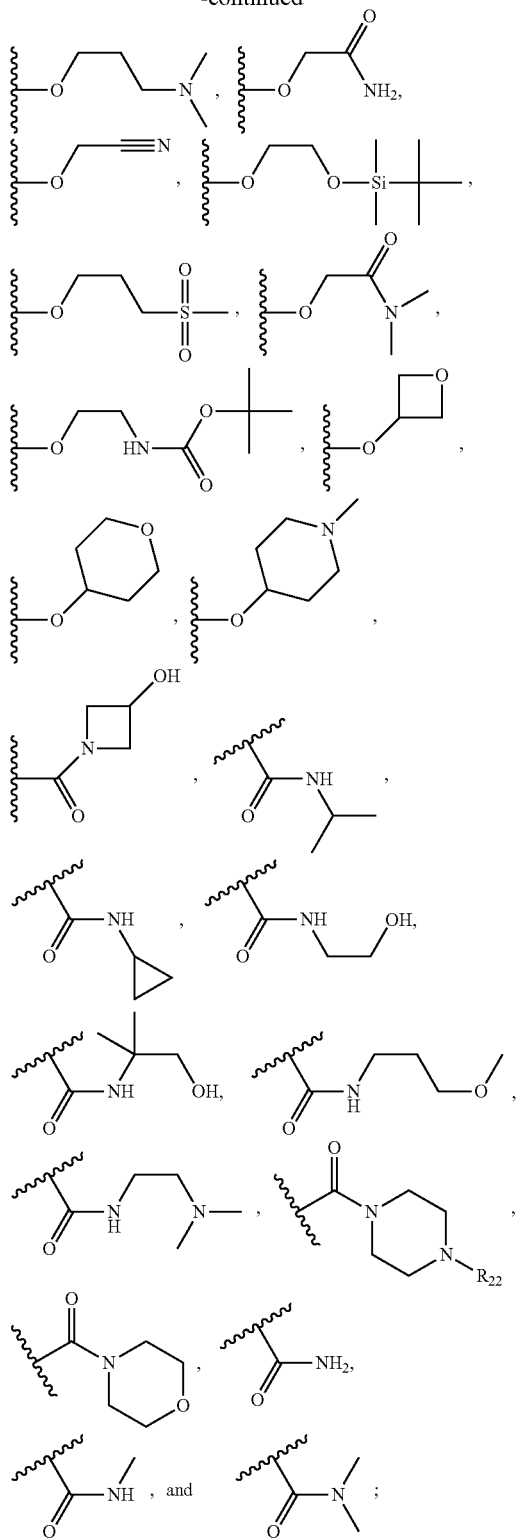

$R_{12}$, $R_{13}$, and $R_{14}$ are hydrogen;
$R_{16}$, $R_{19}$, and $R_{20}$ are hydrogen;
$R_{17}$ is hydrogen;
$R_{18}$ is selected from the group consisting of hydrogen, deuterium, halogen, methyl, isopropyl, tert-butyl, cyclopropyl, cyclohexyl, acetyl, hydroxymethyl, methoxymethyl, methoxy, isopropoxy, methylamino, dimethylamino, methylthio, cyanomethyl, cyanomethylthio, cyano, —SO$_2$CH$_3$, —SO$_2$CH(CH$_3$)$_2$, —SO$_2$CH$_2$CH(CH$_3$)$_2$, —SO$_2$NHCH$_2$CH$_2$CH$_3$, —SO$_2$CHF$_2$, —SO$_2$CF$_3$,

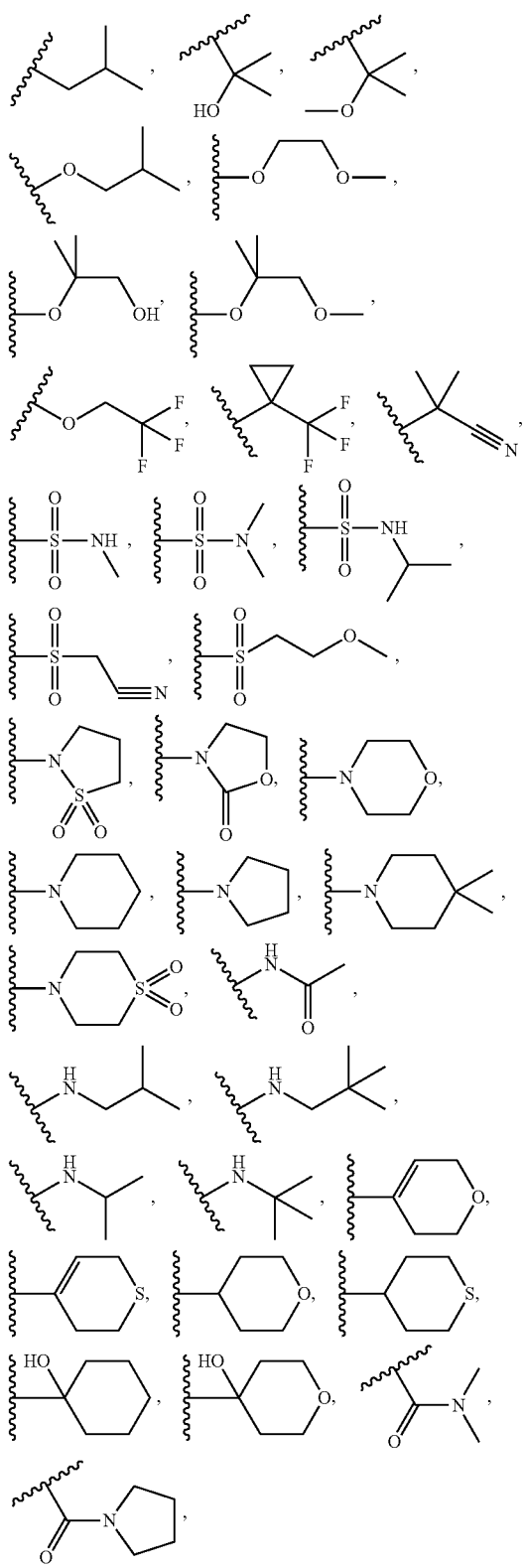

trifluoromethyl, trifluoromethylthio, difluoromethoxy, and trifluoromethoxy;

$R_{21}$ is selected from the group consisting of null, hydrogen, deuterium, halogen, and alkyl;

$R_{22}$ is selected from the group consisting of hydrogen, deuterium, methyl, acetyl,

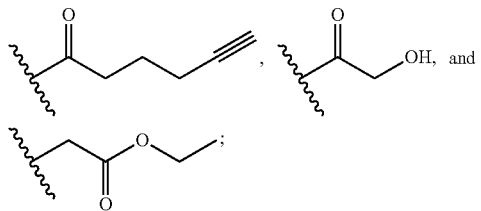

and $R_{23}$ is selected from the group consisting of hydrogen, deuterium, methyl, ethyl, 3-pyridyl, and cyclopropyl.

2. The compound as recited in claim 1 wherein:

$R_1$ is selected from the group consisting of hydrogen, halogen, cyano, methyl, isopropyl,

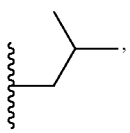

ethylene, trifluoromethyl, difluoromethoxy, methoxy, ethoxy, isopropoxy, hydroxy, carboxyl, —$CO_2CH_3$, —$SO_2CH_3$, —$SO_2NH_2$,

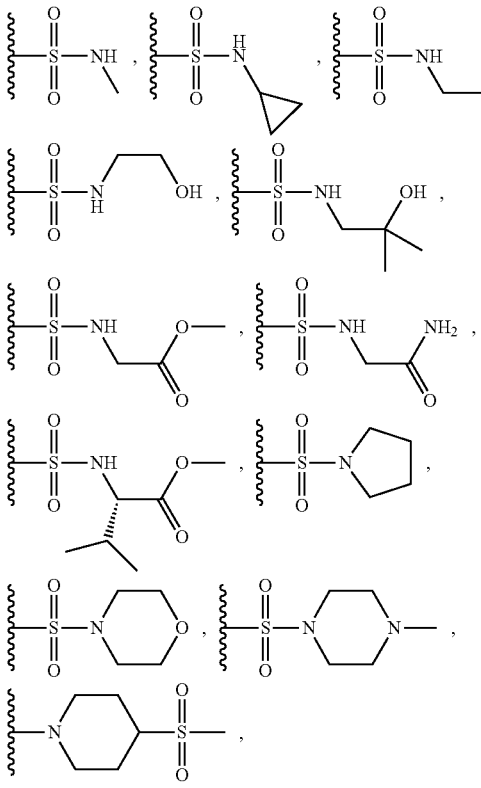

amino, methylamino, dimethylamino,

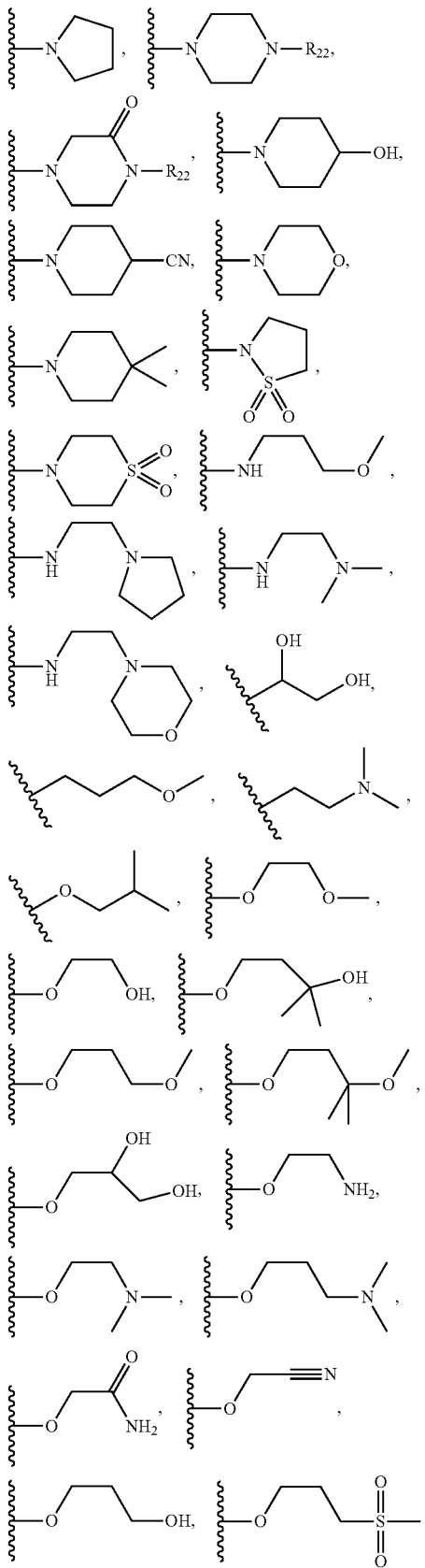

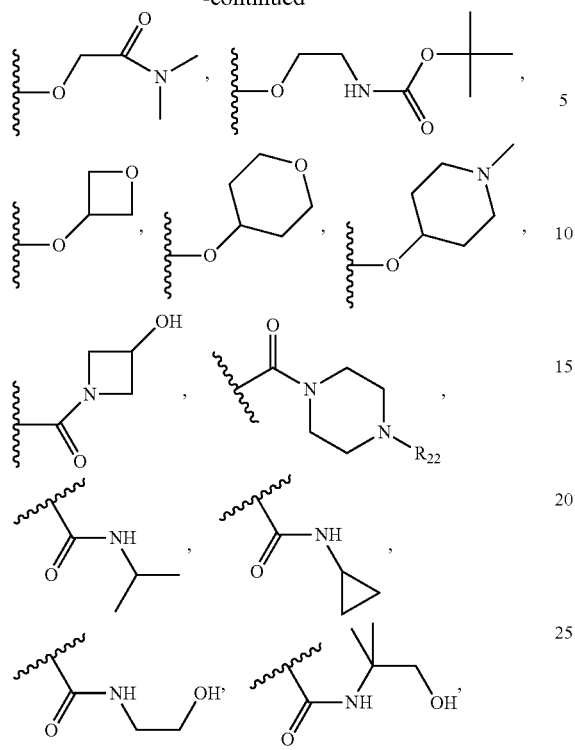
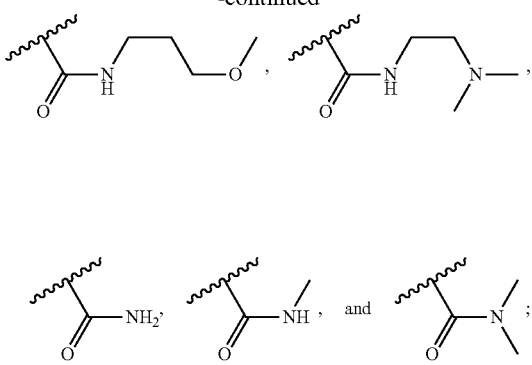
and
R$_{23}$ is methyl.
3. The compound as recited in claim 2 wherein two of X$_2$, X$_4$, and X$_5$ are N; and one of X$_2$, X$_4$, and X$_5$ is O.
4. The compound as recited in claim 2 wherein one of X$_2$, X$_4$, and X$_5$ is N; one of X$_2$, X$_4$, and X$_5$ is O; and one of X$_2$, X$_4$, and X$_5$ is CH.
5. A compound selected from the group consisting of Examples 11, 12, 15, 21, 22, 24, 32-37, 39-42, 45, 46, 52, 53, 55, 58, 59, 61-67, 70, 73, 74, 76a, 77a, 78, 84-86, 92, 93, 100-109, 112, 115, 118-121, 123-128, 130-132, 134-140, 142, 143, 145, 152-159:
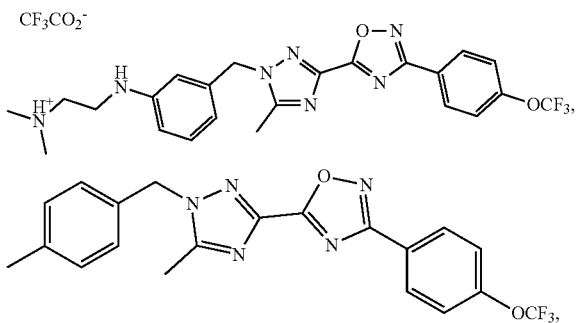
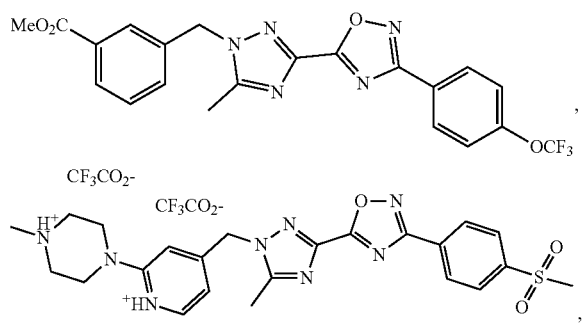
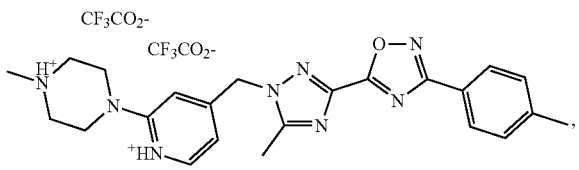
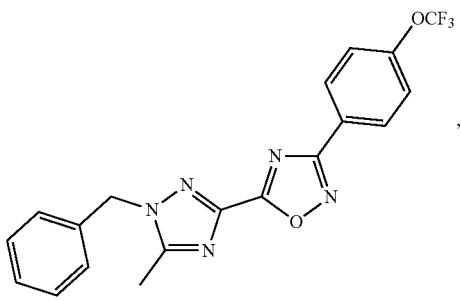
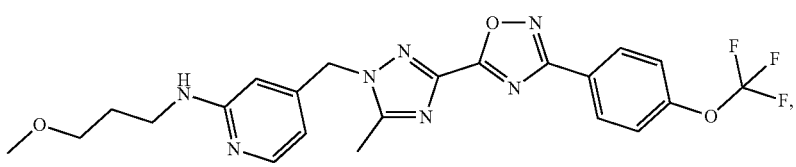

231 232
-continued
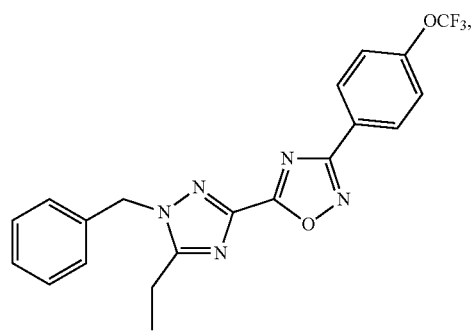
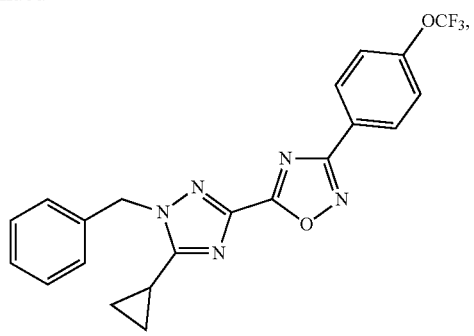
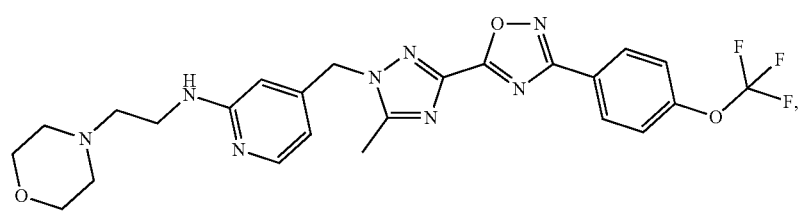
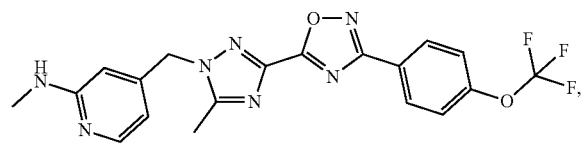
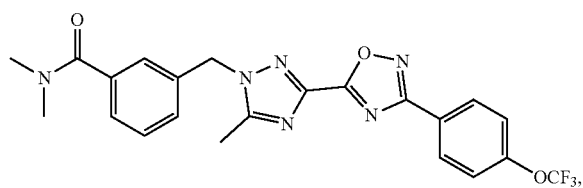
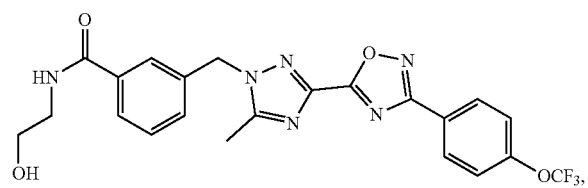
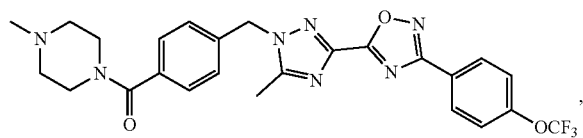
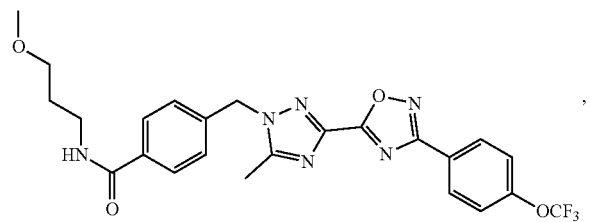
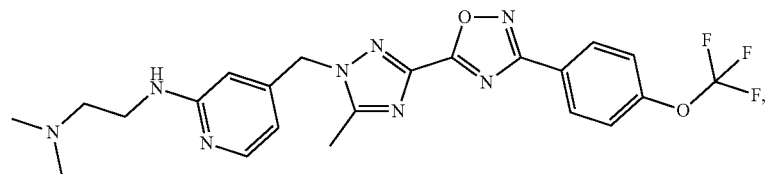
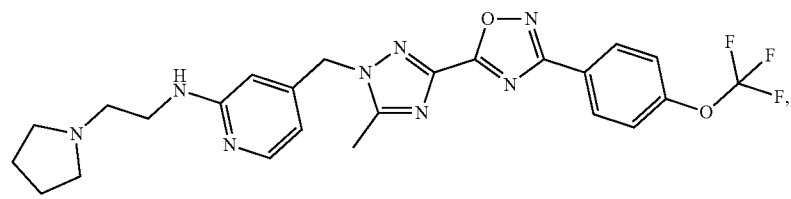
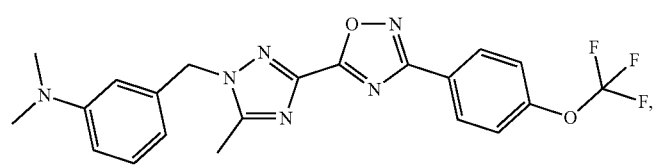

-continued
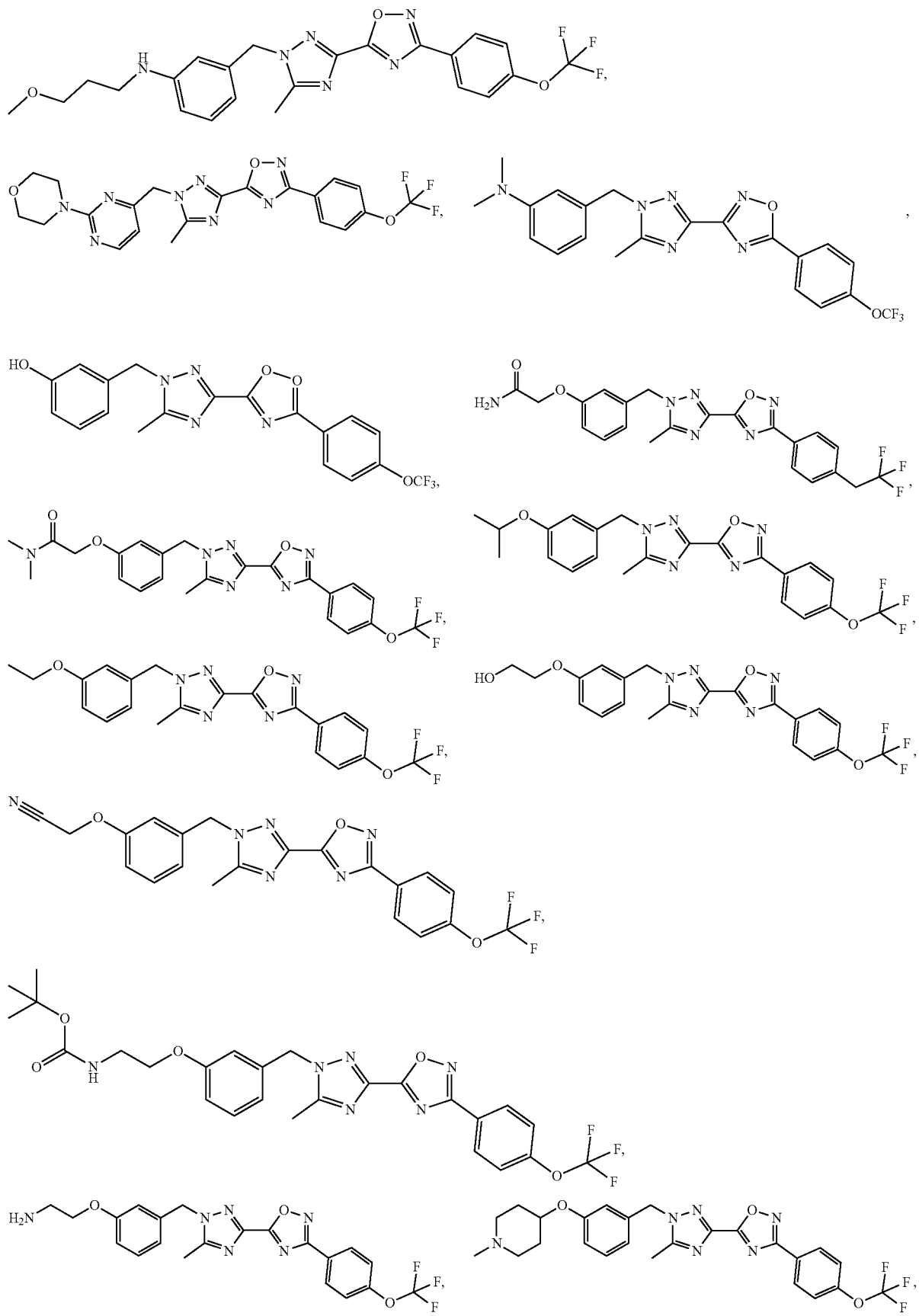

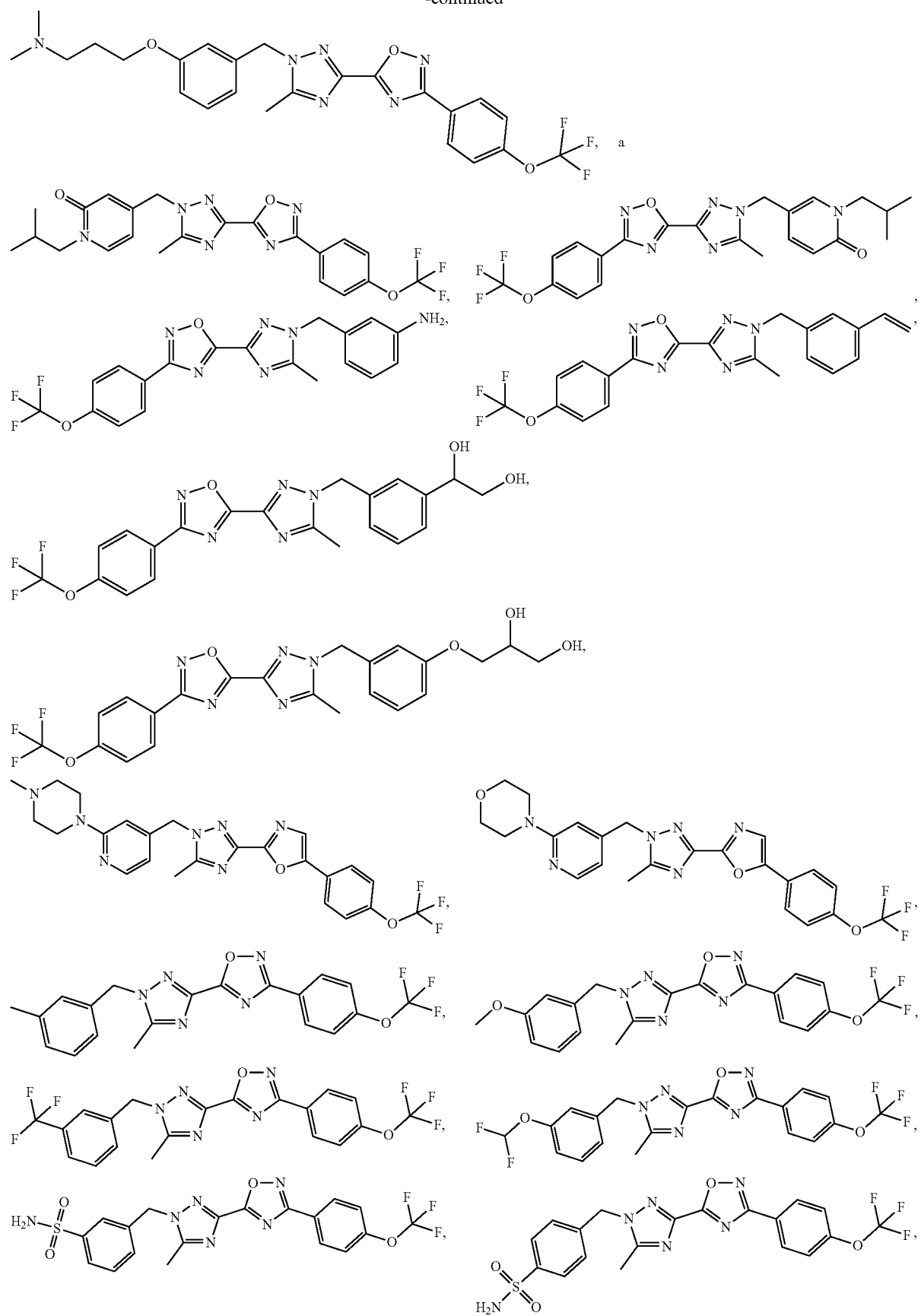

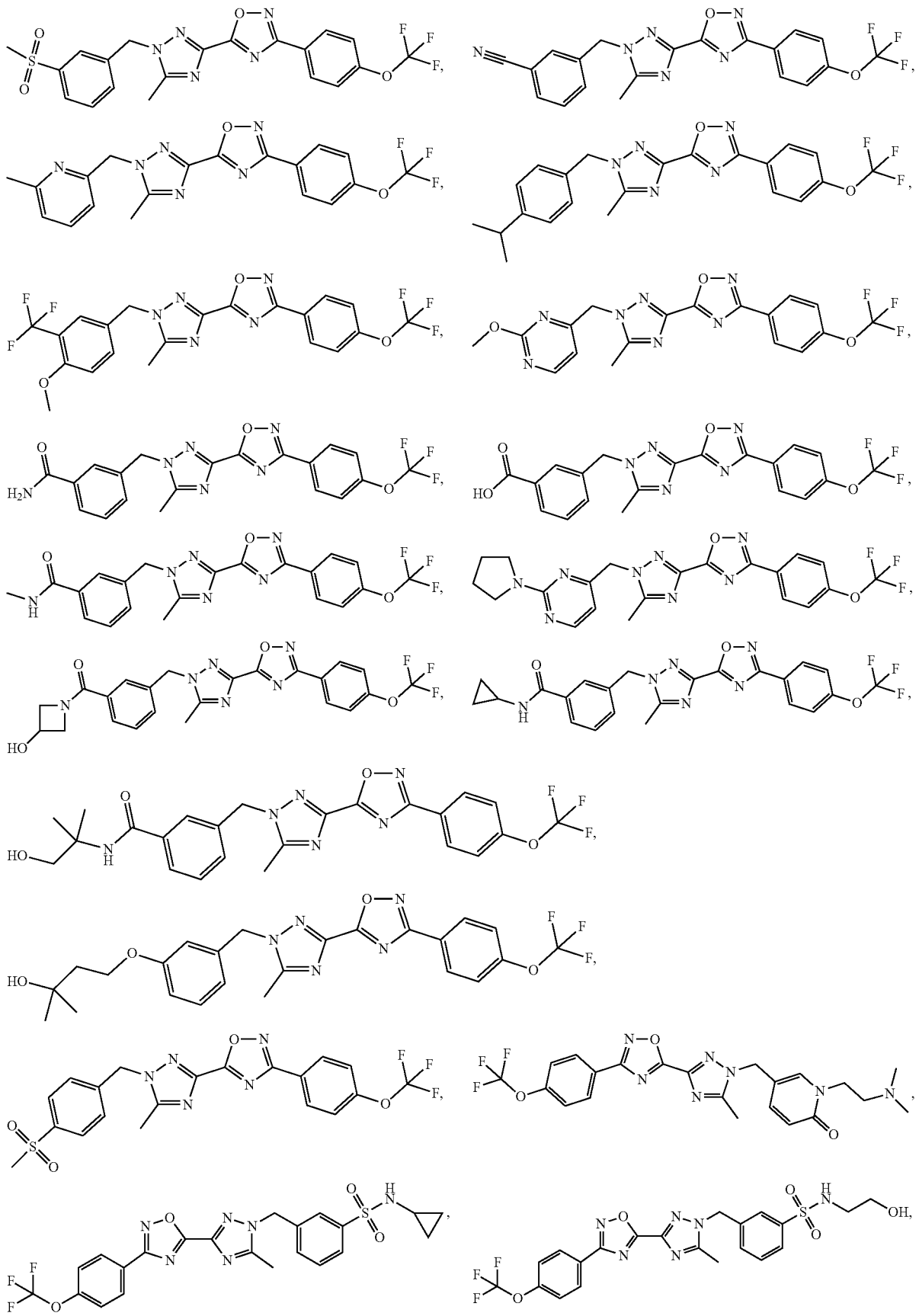

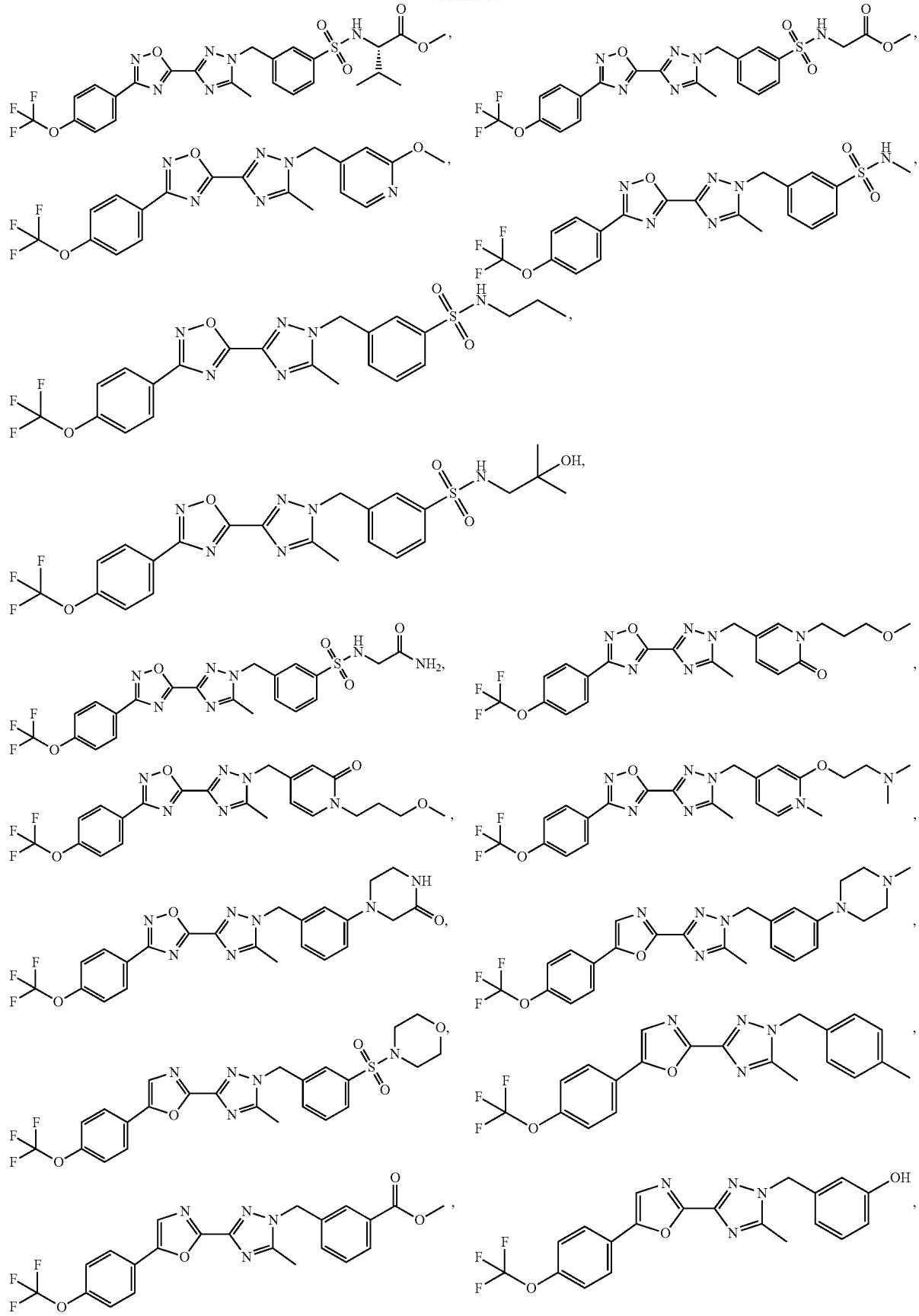

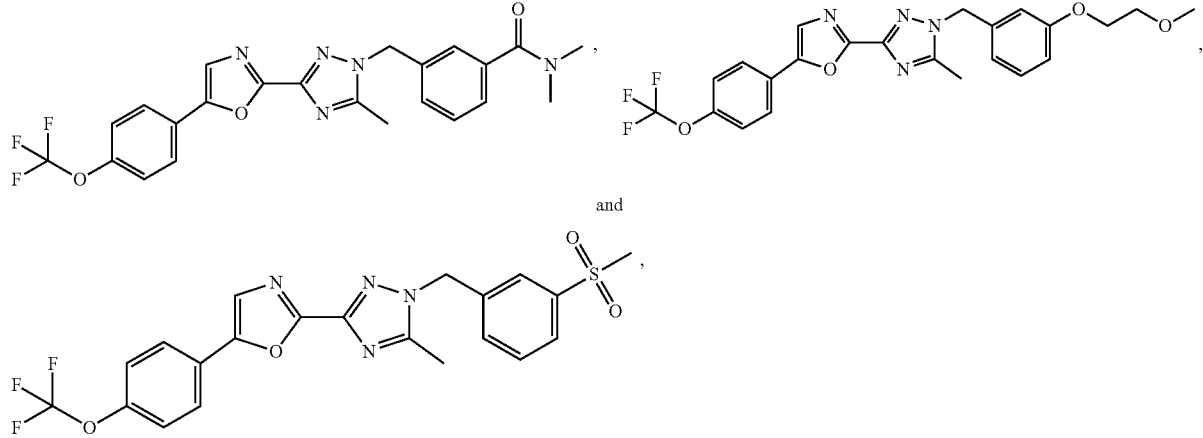
or a salt thereof.
6. A pharmaceutical composition comprising a compound as recited in claim 1 together with a pharmaceutically acceptable carrier.
* * * * *